US010407683B2

(12) United States Patent
Nelson et al.

(10) Patent No.: US 10,407,683 B2
(45) Date of Patent: Sep. 10, 2019

(54) CIRCULAR POLYNUCLEOTIDES

(71) Applicant: ModernaTX, Inc., Cambridge, MA (US)

(72) Inventors: Jennifer Nelson, Brookline, MA (US); Andrew W. Fraley, Arlington, MA (US); Amy Rhoden Smith, Watertown, MA (US)

(73) Assignee: ModernaTX, Inc., Cambridge, MA (US)

( * ) Notice: Subject to any disclaimer, the term of this patent is extended or adjusted under 35 U.S.C. 154(b) by 10 days.

(21) Appl. No.: 15/326,059

(22) PCT Filed: Jul. 16, 2015

(86) PCT No.: PCT/US2015/040691
§ 371 (c)(1),
(2) Date: Jan. 13, 2017

(87) PCT Pub. No.: WO2016/011222
PCT Pub. Date: Jan. 21, 2016

(65) Prior Publication Data
US 2017/0204422 A1 Jul. 20, 2017

Related U.S. Application Data

(60) Provisional application No. 62/045,425, filed on Sep. 3, 2014, provisional application No. 62/025,390, filed on Jul. 16, 2014.

(51) Int. Cl.
C12N 15/64 (2006.01)
C07H 21/02 (2006.01)
A61K 48/00 (2006.01)
C07K 14/535 (2006.01)
C12N 15/10 (2006.01)

(52) U.S. Cl.
CPC .......... C12N 15/64 (2013.01); A61K 48/0066 (2013.01); C07H 21/02 (2013.01); C07K 14/535 (2013.01); C12N 15/10 (2013.01)

(58) Field of Classification Search
CPC ...... C12N 15/64; C12N 15/10; C07K 14/535; A61K 48/0066; C07H 21/02
See application file for complete search history.

(56) References Cited

U.S. PATENT DOCUMENTS

| 5,426,180 A | 6/1995 | Kool |
| 5,489,677 A | 2/1996 | Sanghvi et al. |
| 5,512,439 A | 4/1996 | Hornes et al. |
| 5,591,722 A | 1/1997 | Montgomery et al. |
| 5,637,459 A | 6/1997 | Burke et al. |
| 5,639,873 A | 6/1997 | Barascut et al. |
| 5,789,578 A | 8/1998 | Burton et al. |
| 5,808,039 A | 9/1998 | Reddy et al. |
| 5,989,911 A | 11/1999 | Fournier et al. |
| 6,022,715 A | 2/2000 | Merenkova et al. |
| 6,248,268 B1 | 6/2001 | Cook |
| 6,303,378 B1 | 10/2001 | Bridenbaugh et al. |
| 6,423,492 B1 | 7/2002 | Harbron |
| 6,511,832 B1 | 1/2003 | Guarino et al. |
| 6,521,411 B2 | 2/2003 | Hecker et al. |
| 7,691,569 B2 | 4/2010 | Wohlgemuth et al. |
| 8,093,367 B2 | 1/2012 | Kore et al. |
| 8,664,194 B2 | 3/2014 | de Fougerolles et al. |
| 8,680,069 B2 | 3/2014 | de Fougerolles et al. |
| 8,710,200 B2 | 4/2014 | Schrum et al. |
| 8,716,465 B2 | 5/2014 | Rossi et al. |
| 8,802,438 B2 | 8/2014 | Rossi et al. |
| 8,822,663 B2 | 9/2014 | Schrum et al. |
| 8,883,506 B2 | 11/2014 | Rossi et al. |
| 8,898,864 B1 | 12/2014 | Porter |
| 8,980,864 B2 | 3/2015 | Hoge et al. |
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 9,751,925 B2 | 9/2017 | Hoge et al. |
| 9,803,177 B2 | 10/2017 | Rossi et al. |
| 9,872,900 B2 | 1/2018 | Ciaramella et al. |
| 10,022,435 B2 | 7/2018 | Ciaramella et al. |
| 10,064,935 B2 | 9/2018 | Ciaramella et al. |

(Continued)

FOREIGN PATENT DOCUMENTS

| CA | 2028849 A1 | 9/1991 |
| CA | 2473135 A1 | 6/2003 |

(Continued)

OTHER PUBLICATIONS

Lietard, J., "New strategies for cyclization and bicyclization of oligonucleotides by click chemistry assisted by microwaves." The Journal of organic chemistry 73.1 (2008): 191-200.*

Anderson et al., "Incorporation of pseudouridine into mRNA enhances translation by diminishing PKR activation," Nucleic Acids Res. 38(17):5884-92 (2010).

Anderson et al., "Nucleoside modifications in RNA limit activation of 2'-5'-oligoadenylate synthetase and increase resistance to cleavage by RNase L," Nucleic Acids Res. 39(21): 9329-38 (2011) (10 pages).

(Continued)

Primary Examiner — John M Mauro
(74) Attorney, Agent, or Firm — Clark & Elbing LLP

(57) ABSTRACT

The invention relates to compositions and methods for the preparation, manufacture and therapeutic use of circular polynucleotides.

21 Claims, 13 Drawing Sheets
Specification includes a Sequence Listing.

(56) References Cited

U.S. PATENT DOCUMENTS

| | | |
|---|---|---|
| 10,072,057 B2 | 9/2018 | Hoge et al. |
| 2001/0025097 A1 | 9/2001 | Sheridan et al. |
| 2002/0001812 A1 | 1/2002 | Smith et al. |
| 2002/0016450 A1 | 2/2002 | Laugharn et al. |
| 2002/0114784 A1 | 8/2002 | Li et al. |
| 2002/0130430 A1 | 9/2002 | Castor |
| 2002/0153312 A1 | 10/2002 | Gjerde et al. |
| 2003/0120035 A1 | 6/2003 | Gao et al. |
| 2003/0170876 A1 | 9/2003 | Widner et al. |
| 2003/0170891 A1 | 9/2003 | McSwiggen |
| 2003/0180754 A1 | 9/2003 | Bergholtz et al. |
| 2003/0180779 A1 | 9/2003 | Lofton-Day et al. |
| 2004/0038278 A1 | 2/2004 | Tzertzinis et al. |
| 2004/0142433 A1 | 7/2004 | Padgett et al. |
| 2004/0220127 A1 | 11/2004 | Sternberg et al. |
| 2004/0259097 A1 | 12/2004 | De Backer et al. |
| 2005/0003496 A1 | 1/2005 | McGall et al. |
| 2005/0130196 A1 | 6/2005 | Hofstadler et al. |
| 2006/0058266 A1 | 3/2006 | Manoharan et al. |
| 2006/0121441 A1 | 6/2006 | Spira |
| 2006/0223081 A1 | 10/2006 | Jarrell et al. |
| 2007/0020678 A1 | 1/2007 | Ault-Riche et al. |
| 2007/0037148 A1 | 2/2007 | Fong et al. |
| 2007/0037770 A1 | 2/2007 | Gryaznov et al. |
| 2007/0244062 A1 | 10/2007 | Laux et al. |
| 2007/0281336 A1 | 12/2007 | Jendrisak et al. |
| 2008/0076910 A1 | 3/2008 | Takkellapati et al. |
| 2008/0171711 A1 | 7/2008 | Hoerr et al. |
| 2008/0274463 A1 | 11/2008 | Chen et al. |
| 2008/0311140 A1 | 12/2008 | Lee et al. |
| 2009/0215125 A1 | 8/2009 | Reed et al. |
| 2009/0264511 A1 | 10/2009 | de Fougerolles et al. |
| 2009/0286852 A1 | 11/2009 | Kariko et al. |
| 2010/0015232 A1 | 1/2010 | Besenbacher et al. |
| 2010/0047261 A1 | 2/2010 | Hoerr et al. |
| 2010/0178272 A1 | 7/2010 | Hartmann et al. |
| 2010/0183639 A1 | 7/2010 | Uhlmann et al. |
| 2010/0261228 A1 | 10/2010 | Gharib et al. |
| 2010/0261231 A1 | 10/2010 | Kore et al. |
| 2010/0317532 A1 | 12/2010 | Liu et al. |
| 2011/0130440 A1 | 6/2011 | Manoharan et al. |
| 2011/0143397 A1 | 6/2011 | Kariko et al. |
| 2011/0218170 A1 | 9/2011 | Thottassery et al. |
| 2011/0244026 A1 | 10/2011 | Guild et al. |
| 2011/0281938 A1 | 11/2011 | Schaub et al. |
| 2012/0046346 A1 | 2/2012 | Rossi et al. |
| 2012/0100136 A1 | 4/2012 | Patel et al. |
| 2012/0129261 A1 | 5/2012 | Eberwine et al. |
| 2012/0251618 A1 | 10/2012 | Schrum et al. |
| 2013/0046083 A1 | 2/2013 | Brown et al. |
| 2013/0046084 A1 | 2/2013 | Brown et al. |
| 2013/0052721 A1 | 2/2013 | Hollander et al. |
| 2013/0058894 A1 | 3/2013 | Maldonado et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0197068 A1 | 8/2013 | Kariko et al. |
| 2013/0203115 A1 | 8/2013 | Schrum et al. |
| 2013/0244282 A1 | 9/2013 | Schrum et al. |
| 2013/0245103 A1 | 9/2013 | de Fougerolles et al. |
| 2013/0245106 A1 | 9/2013 | de Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0243399 A1 | 8/2014 | Schrum et al. |
| 2014/0273230 A1 | 9/2014 | Chen et al. |
| 2014/0275227 A1 | 9/2014 | Hoge et al. |
| 2014/0343129 A1 | 11/2014 | de Fougerolles et al. |
| 2014/0371302 A1 | 12/2014 | Afeyan et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0050354 A1 | 2/2015 | Bouchon et al. |
| 2015/0050738 A1 | 2/2015 | Ozsolak et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141269 A1 | 5/2015 | Soldatov et al. |
| 2015/0141499 A1 | 5/2015 | Bancel et al. |
| 2015/0166616 A1 | 6/2015 | Bancel et al. |
| 2015/0167017 A1 | 6/2015 | Roy et al. |
| 2015/0211039 A1 | 7/2015 | Wang et al. |
| 2015/0307542 A1 | 10/2015 | Roy et al. |
| 2016/0017313 A1 | 1/2016 | Spivak et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0032273 A1 | 2/2016 | Shahrokh et al. |
| 2016/0038612 A1 | 2/2016 | Hoge et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| EP | 0366400 A2 | 5/1990 |
| EP | 1083232 B1 | 2/2005 |
| EP | 1619254 A1 | 1/2006 |
| EP | 1383556 B9 | 3/2008 |
| EP | 1831160 B1 | 6/2010 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2011-130725 A | 7/2011 |
| RU | 2540017 C2 | 1/2015 |
| WO | WO-91/05058 A1 | 4/1991 |
| WO | WO-93/03052 A1 | 2/1993 |
| WO | WO-93/13121 A1 | 7/1993 |
| WO | WO-97/07825 A1 | 3/1997 |
| WO | WO-01/55306 A2 | 8/2001 |
| WO | WO-02/44399 A2 | 6/2002 |
| WO | WO-02/098443 A2 | 12/2002 |
| WO | WO-03/039523 A2 | 5/2003 |
| WO | WO-03/051881 A1 | 6/2003 |
| WO | WO-2004/020575 A2 | 3/2004 |
| WO | WO-2004/064782 A2 | 8/2004 |
| WO | WO-2006/015445 A1 | 2/2006 |
| WO | WO-2007/024708 A2 | 3/2007 |
| WO | WO-2007/024798 A2 | 3/2007 |
| WO | WO-2007/089607 A2 | 8/2007 |
| WO | WO-2007/120863 A2 | 10/2007 |
| WO | WO-2008/039669 A1 | 4/2008 |
| WO | WO-2008/045505 A2 | 4/2008 |
| WO | WO-2008/083949 A2 | 7/2008 |
| WO | WO-2008/120016 A1 | 10/2008 |
| WO | WO-2009/042971 A2 | 4/2009 |
| WO | WO-2009/051451 A2 | 4/2009 |
| WO | WO-2009/127060 A1 | 10/2009 |
| WO | WO-2009/127230 A1 | 10/2009 |

(56) References Cited

FOREIGN PATENT DOCUMENTS

| | | |
|---|---|---|
| WO | WO-2009/147519 A1 | 12/2009 |
| WO | WO-2009/149253 A2 | 12/2009 |
| WO | WO-2010/014895 A2 | 2/2010 |
| WO | WO-2010/017510 A1 | 2/2010 |
| WO | WO-2010/109289 A1 | 9/2010 |
| WO | WO-2011/005850 A1 | 1/2011 |
| WO | WO-2011/012316 A3 | 2/2011 |
| WO | WO-2011/068810 A1 | 6/2011 |
| WO | WO-2011/071931 A2 | 6/2011 |
| WO | WO-2011/127933 A1 | 10/2011 |
| WO | WO-2011/130624 A2 | 10/2011 |
| WO | WO-2011/133868 A2 | 10/2011 |
| WO | WO-2011/140627 A1 | 11/2011 |
| WO | WO-2012/019168 A2 | 2/2012 |
| WO | WO-2012/135805 A2 | 10/2012 |
| WO | WO-2012/138530 A1 | 10/2012 |
| WO | WO-2012/158736 A1 | 11/2012 |
| WO | WO-2012/164565 A1 | 12/2012 |
| WO | WO-2013/039857 A1 | 3/2013 |
| WO | WO-2013/039861 A2 | 3/2013 |
| WO | WO-2013/052523 A1 | 4/2013 |
| WO | WO-2013/090186 A1 | 6/2013 |
| WO | WO-2013/090294 A1 | 6/2013 |
| WO | WO-2013/090648 A1 | 6/2013 |
| WO | WO-2013/090897 A1 | 6/2013 |
| WO | WO-2013/096709 A2 | 6/2013 |
| WO | WO-2013/101690 A1 | 7/2013 |
| WO | WO-2013/113326 A1 | 8/2013 |
| WO | WO-2013/113501 A1 | 8/2013 |
| WO | WO-2013/113502 A1 | 8/2013 |
| WO | WO-2013/130161 A1 | 9/2013 |
| WO | WO-2013/151663 A1 | 10/2013 |
| WO | WO-2013/151664 A1 | 10/2013 |
| WO | WO-2013/151665 A2 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151669 A1 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/184976 A2 | 12/2013 |
| WO | WO-2013/185069 A1 | 12/2013 |
| WO | WO-2014/028429 A2 | 2/2014 |
| WO | WO-2014/081507 A1 | 5/2014 |
| WO | WO-2014/093574 A1 | 6/2014 |
| WO | WO-2014/093622 A2 | 6/2014 |
| WO | WO-2014/093924 A1 | 6/2014 |
| WO | WO-2014/113089 A2 | 7/2014 |
| WO | WO-2014/144039 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/160243 A1 | 10/2014 |
| WO | WO-2014/160284 A1 | 10/2014 |
| WO | WO-2014/164253 A1 | 10/2014 |
| WO | WO-2015/006747 A2 | 1/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/051214 A1 | 4/2015 |
| WO | WO-2015/058069 A1 | 4/2015 |
| WO | WO-2015/070413 A1 | 5/2015 |
| WO | WO-2015/085318 A2 | 6/2015 |
| WO | WO-2015/089511 A2 | 6/2015 |
| WO | WO-2015/101416 A1 | 7/2015 |
| WO | WO-2015/105926 A1 | 7/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/010840 A1 | 1/2016 |
| WO | WO-2016/011222 A2 | 1/2016 |
| WO | WO-2016/011226 A1 | 1/2016 |
| WO | WO-2016/034620 A1 | 3/2016 |
| WO | WO-2016/036902 A1 | 3/2016 |
| WO | WO-2016/077125 A1 | 5/2016 |
| WO | WO-2016/118724 A1 | 7/2016 |
| WO | WO-2016/118725 A1 | 7/2016 |

OTHER PUBLICATIONS

Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).

Derrigo et al., "RNA-protein interactions in the control of stability and localization of messenger RNA (review)," Int J Mol Med. 5(2):111-23 (2000).

Extended European Search Report for European Application No. 15822055.8, dated Oct. 11, 2017 (8 pages).

Fath et al., "Multiparameter RNA and codon optimization: a standardized tool to assess and enhance autologous mammalian gene expression," PLoS One 6(3):e17596 (2011) (14 pages).

Grosjean, Modification and editing of RNA: historical overview and important facts to remember. *Fine-Tuning of RNA Functions by Modification and Editing*. Grosjean H, 1-22 (2005).

Hansen et al., "Circular RNA and miR-7 in Cancer," Cancer Res. 73(18):5609-12 (2013).

Hansen et al., "Natural RNA circles function as efficient microRNA sponges," Nature. 495(7441):384-8 (2013) (7 pages).

Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).

International Search Report and Written Opinion for International Application No. PCT/US15/40691, dated Jan. 20, 2016 (29 pages).

Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).

Jani et al., "In vitro transcription and capping of Gaussia luciferase mRNA followed by HeLa cell transfection," J Vis Exp. 61:e3702 (2012) (9 pages).

Karikó et al., "Incorporation of pseudouridine into mRNA yields superior nonimmunogenic vector with increased translational capacity and biological stability." Mol Ther. 16(11):1833-40 (2008).

Karikó et al., "mRNA is an endogenous ligand for Toll-like receptor 3," J Biol Chem. 279(13): 12542-50 (2004).

Karikó et al., "Suppression of RNA recognition by Toll-like receptors: the impact of nucleoside modification and the evolutionary origin of RNA," Immunity. 23(2):165-75 (2005).

Kluiver et al., "Rapid generation of MicroRNA Sponges for MicroRNA Inhibition ," PLoS One. 7(1):E29275(2012) (8 pages).

Kore et al., "Synthesis and application of 2'-fluoro-substituted cap analogs." Bioorg Med Chem Letters. 17:5295-9 (2007).

Kormann et al., "Expression of therapeutic proteins after delivery of chemically modified mRNA in mice," Nat Biotechnol. 29(2):154-7 (2011) (6 pages).

Kumar et al., "Template-directed oligonucleotide strand ligation, covalent intramolecular DNA circularization and catenation using click chemistry," J Am Chem Soc. 129(21):6859-64 (2007).

Kuwahara et al., "Molecular evolution of functional nucleic acids with chemical modifications," Molecules. 15(8):5423-44 (2010).

Melton et al., "Efficient in vitro synthesis of biologically active RNA and RNA hybridization probes from plasmids containing a bacteriophage SP6 promoter," Nucleic Acids Res. 12(18):7035-56 (1984).

(56) References Cited

OTHER PUBLICATIONS

Memczak et al., "Circular RNAs are a large class of animal RNAs with regulatory potency," Nature. 495(7441):333-8 (2013) (10 pages).

Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).

Qiu et al., "Creating a flexible multiple microRNA expression vector by linking precursor microRNAs," Biochem Biophys Res Commun. 411(2):276-80 (2011).

Semple et al., "Rational design of cationic lipids for siRNA delivery," Nat Biotechnol. 28(2):172-6 (2010) (26 pages).

Tavernier et al., "mRNA as gene therapeutic: how to control protein expression," J Control Release. 150(3):238-47 (2011).

Valadi et al., "Exosome-mediated transfer of mRNAs and microRNAs is a novel mechanism of genetic exchange between cells," Nat Cell Biol. 9(6):654-9 (2007) (17 pages).

Warren et al., "Highly efficient reprogramming to pluripotency and directed differentiation of human cells with synthetic modified mRNA," Cell Stem Cell. 7(5):618-30 (2010).

Yamamoto et al., "Current prospects for mRNA gene delivery," Eur J Pharm Biopharm. 71(3):484-9 (2009).

Applied Biosystems DNA Synthesizer model 380B operation manual, 2001 (327 pages).

Aviv et al., "Purification of Biologically Active Globin Messenger RNA by Chromatography on Oligothymidylic acid-Cellulose," Proc Nat Acad Sci USA 69(6):1408-1412 (1972).

Gilham, "The Synthesis of Polynucleotide-Celluloses and Their Use in the Fractionation of Polynucleotides," J Am Chem Soc 86(22):4982-4985 (1964).

Gustafsson et al., "Codon bias and heterologous protein expression," Trends Biotechnol. 22(7):346-353 (2004).

Henke et al., "microRNA-122 stimulates translation of hepatitis C virus RNA," Embo J. 27(24):3300-10 (2008).

Li et al., "Effects of chemically modified messenger RNA on protein expression," Bioconjug Chem. 27(3):849-53 (2016).

Meyer et al., "Combinatorial recombination of gene fragments to construct a library of chimeras," Curr Protoc Protein Sci. Chapter 26:Unit 26.2 (2006) (17 pages).

Miyoshi-Akiyama et al., "Complete genome sequence of *Streptococcus pyogenes* M1 476, isolated from a patient with streptococcal toxic shock syndrome," J Bacteriology. 194(19):5466 (2012).

Moretti et al., "Mechanism of translational regulation by miR-2 from sites in the 5' untranslated region or the open reading frame," RNA. 16(12):2493-502 (2010).

Motorin, "RNA modification," eLS. John Wiley & Sons, DOI:10.1002/9780470015902.a000528.pub3 (2015) (18 pages).

Nakazato et al., "Purification of messenger RNA and heterogeneous nuclear RNA containing poly(A) sequences," Methods Enzymol. 29:431-443 (1974).

Nielsen et al., "An mRNA is capped by a 2',5' lariat catalyzed by a group I-like ribozyme," Science. 309(5740):1584-7 (2005).

Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).

Rodriguez et al., "Magnetic poly (styrene/divinylbenzene/acrylic acid)-based hybrid microspheres for bio-molecular recognition," Micro Nano Lett. 6(6):349-352 (2011).

Stewart et al., "Effect of azide position on the rate of azido glucose-cyclooctyne cycloaddition," Journal of Carbohydrate Chemistry. 33(7-8):408-19 (2014).

Takita et al., "Precise sequential DNA ligation on a solid substrate: solid-based rapid sequential ligation of multiple DNA molecules," DNA Res. 20(6):583-92 (2013).

Virnekäs et al., "Trinucleotide phosphoramidites: ideal reagents for the synthesis of mixed oligonucleotides for random mutagenesis," Nucleic Acids Res. 22(25):5600-7 (1994).

\* cited by examiner

SEQUENCE LISTING

```
<160> NUMBER OF SEQ ID NOS: 50

<210> SEQ ID NO 1
<211> LENGTH: 47
<212> TYPE: DNA
<213> ORGANISM: Homo sapiens

<400> SEQUENCE: 1
gggaaataag agagaaaaga agagtaagaa gaaatataag agccacc          47

<210> SEQ ID NO 2
<211> LENGTH: 47
<212> TYPE: DNA
<213> ORGANISM: Homo sapiens

<400> SEQUENCE: 2
gggagatcag agagaaaaga agagtaagaa gaaatataag agccacc          47

<210> SEQ ID NO 3
<211> LENGTH: 145
<212> TYPE: DNA
<213> ORGANISM: Homo sapiens

<400> SEQUENCE: 3
ggaataaaag tctcaacaca acatatacaa aacaaacgaa tctcaagcaa tcaagcattc   60
tacttctatt gcagcaattt aaatcatttc ttttaaagca aaagcaattt tctgaaaatt  120
ttcaccattt acgaacgata gcaac                                        145

<210> SEQ ID NO 4
<211> LENGTH: 42
<212> TYPE: RNA
<213> ORGANISM: Homo sapiens
```

```
<400> SEQUENCE: 4
gggagacaag cuuggcauuc cgguacuguu gguaaagcca cc                42

<210> SEQ ID NO 5
<211> LENGTH: 371
<212> TYPE: DNA
<213> ORGANISM: Homo sapiens

<400> SEQUENCE: 5
gcgcctgccc acctgccacc gactgctgga acccagccag tgggagggcc tggcccacca    60
gagtcctgct ccctcactcc tcgccccgcc ccctgtccca gagtcccacc tgggggctct   120
ctccacccct ctcagagttc cagtttcaac cagagttcca accaatgggc tccatcctct   180
ggattctggc caatgaaata tctccctggc agggtcctct tctttcccca gagctccacc   240
ccaaccagga gctctagtta atggagagct cccagcacac tcggagcttg tgctttgtct   300
ccacgcaaag cgataaataa aagcattggt ggcctttggt ctttgaataa agcctgagta   360
ggaagtctag a                                                        371

<210> SEQ ID NO 6
<211> LENGTH: 568
<212> TYPE: DNA
<213> ORGANISM: Homo sapiens

<400> SEQUENCE: 6
gcccctgccg ctcccacccc cacccatctg gccccgggt tcaagagaga gcggggtctg     60
atctcgtgta gccatataga gtttgcttct gagtgtctgc tttgtttagt agaggtgggc   120
aggaggagct gaggggctgg ggctggggtg ttgaagttgg ctttgcatgc ccagcgatgc   180
gcctccctgt gggatgtcat caccctggga accgggagtg gcccttggct cactgtgttc   240
tgcatggttt ggatctgaat taattgtcct ttcttctaaa tcccaaccga acttcttcca   300
acctccaaac tggctgtaac cccaaatcca agccattaac tacacctgac agtagcaatt   360
gtctgattaa tcactggccc cttgaagaca gcagaatgtc cctttgcaat gaggaggaga   420
tctgggctgg gcgggccagc tggggaagca tttgactatc tggaacttgt gtgtgcctcc   480
tcaggtatgg cagtgactca cctggtttta ataaacaac ctgcaacatc tcatggtctt    540
tgaataaagc ctgagtagga agtctaga                                      568

<210> SEQ ID NO 7
<211> LENGTH: 289
<212> TYPE: DNA
<213> ORGANISM: Homo sapiens

<400> SEQUENCE: 7
acacactcca cctccagcac gcgacttctc aggacgacga atcttctcaa tggggggcg     60 gctgagctcc agccaccccg cagtcacttt ctttgtaaca acttccgttg ctgccatcgt   120
aaactgacac agtgtttata acgtgtacat acattaactt attacctcat tttgttattt   180
ttcgaaacaa agccctgtgg aagaaaatgg aaaacttgaa gaagcattaa agtcattctg   240
ttaagctgcg taaatggtct ttgaataaag cctgagtagg aagtctaga                289

<210> SEQ ID NO 8
<211> LENGTH: 379
<212> TYPE: DNA
<213> ORGANISM: Homo sapiens

<400> SEQUENCE: 8
```

```
catcacattt aaaagcatct cagcctacca tgagaataag agaaagaaaa tgaagatcaa      60
aagcttattc atctgttttt cttttcgtt ggtgtaaagc caacaccctg tctaaaaaac     120
ataaatttct ttaatcattt tgcctctttt ctctgtgctt caattaataa aaaatggaaa     180
gaatctaata gagtggtaca gcactgttat ttttcaaaga tgtgttgcta tcctgaaaat     240
tctgtaggtt ctgtggaagt tccagtgttc tctcttattc cacttcggta gaggatttct     300
agtttcttgt gggctaatta aataaatcat taatactctt ctaatggtct ttgaataaag     360
cctgagtagg aagtctaga                                                  379

<210> SEQ ID NO 9
<211> LENGTH: 118
<212> TYPE: DNA
<213> ORGANISM: Mus sp.

<400> SEQUENCE: 9
gctgccttct gcggggcttg ccttctggcc atgcccttct tctctcccctt gcacctgtac     60 ctcttggtct ttgaataaag cctgagtagg aaggcggccg ctcgagcatg catctaga     118

<210> SEQ ID NO 10
<211> LENGTH: 908
<212> TYPE: DNA
<213> ORGANISM: Homo sapiens

<400> SEQUENCE: 10
gccaagccct ccccatccca tgtatttatc tctatttaat atttatgtct atttaagcct      60
catatttaaa gacagggaag agcagaacgg agccccaggc ctctgtgtcc ttccctgcat     120
ttctgagttt cattctcctg cctgtagcag tgagaaaaag ctcctgtcct cccatcccct     180
ggactgggag gtagataggt aaataccaag tatttattac tatgactgct ccccagccct     240
ggctctgcaa tgggcactgg gatgagccgc tgtgagcccc tggtcctgag gtccccacc     300 tgggacccctt gagagtatca ggtctcccac gtgggagaca agaaatccct gtttaatatt     360
taaacagcag tgttccccat ctgggtcctt gcacccctca ctctggcctc agccgactgc     420
acagcggccc ctgcatcccc ttggctgtga ggcccctgga caagcagagg tggccagagc     480
tgggaggcat ggccctgggg tcccacgaat ttgctgggga atctcgtttt tcttcttaag     540
acttttggga catggtttga ctcccgaaca tcaccgacgc gtctcctgtt tttctgggtg     600
gcctcgggac acctgccctg cccccacgag ggtcaggact gtgactcttt ttagggccag     660
gcaggtgcct ggacatttgc cttgctgac ggggactggg gatgtgggag ggagcagaca     720
ggaggaatca tgtcaggcct gtgtgtgaaa ggaagctcca ctgtcaccct ccacctcttc     780 acccccact caccagtgtc ccctccactg tcacattgta actgaacttc aggataataa     840
agtgtttgcc tccatggtct ttgaataaag cctgagtagg aaggcggccg ctcgagcatg     900
catctaga                                                              908

<210> SEQ ID NO 11
<211> LENGTH: 835
<212> TYPE: DNA
<213> ORGANISM: Homo sapiens

<400> SEQUENCE: 11
actcaatcta aattaaaaaa gaaagaaatt tgaaaaaact ttctctttgc catttcttct      60
tcttcttttt taactgaaag ctgaatccctt ccatttcttc tgcacatcta cttgcttaaa    120
```

```
ttgtgggcaa aagagaaaaa gaaggattga tcagagcatt gtgcaataca gtttcattaa      180
ctccttcccc cgctccccca aaaatttgaa ttttttttc aacactctta cacctgttat      240
ggaaaatgtc aacctttgta agaaaccaa ataaaaatt gaaaaataaa aaccataaac      300
atttgcacca cttgtggctt ttgaatatct tccacagagg gaagtttaaa acccaaactt      360
ccaaaggttt aaactacctc aaaacacttt cccatgagtg tgatccacat tgttaggtgc      420
tgacctagac agagatgaac tgaggtcctt gttttgtttt gttcataata caaaggtgct      480
aattaatagt atttcagata cttgaagaat gttgatggtg ctagaagaat tgagaagaa      540
atactcctgt attgagttgt atcgtgtggt gtattttta aaaatttga tttagcattc      600
atattttcca tcttattccc aattaaaagt atgcagatta tttgcccaaa tcttcttcag      660
attcagcatt tgttctttgc cagtctcatt ttcatcttct tccatggttc cacagaagct      720
ttgtttcttg ggcaagcaga aaaattaaat tgtacctatt ttgtatatgt gagatgttta      780
aataaattgt gaaaaaatg aaataaagca tgtttggttt tccaaaagaa catat           835
```

```
<210> SEQ ID NO 12
<211> LENGTH: 297
<212> TYPE: DNA
<213> ORGANISM: Homo sapiens

<400> SEQUENCE: 12
```

```
cgccgccgcc cgggccccgc agtcgagggt cgtgagccca ccccgtccat ggtgctaagc       60
gggcccgggt cccacacggc cagcaccgct gctcactcgg acgacgccct gggcctgcac      120
ctctccagct cctcccacgg ggtccccgta gcccggccc ccgcccagcc ccaggtctcc      180
ccaggccctc cgcaggctgc ccggcctccc tccccctgca gccatcccaa ggctcctgac      240
ctacctggcc cctgagctct ggagcaagcc ctgacccaat aaaggctttg aacccat        297
```

```
<210> SEQ ID NO 13
<211> LENGTH: 602
<212> TYPE: DNA
<213> ORGANISM: Homo sapiens

<400> SEQUENCE: 13
```

```
ggggctagag ccctctccgc acagcgtgga gacggggcaa ggagggggt tattaggatt       60
ggtggttttg ttttgctttg tttaaagccg tgggaaaatg gcacaacttt acctctgtgg      120
gagatgcaac actgagagcc aaggggtggg agttgggata attttttatat aaaagaagtt      180
tttccacttt gaattgctaa aagtggcatt tttcctatgt gcagtcactc ctctcatttc      240
taaaatgggg acgtggccag gcacggtggc tcatgcctgt aatcccagca ctttgggagg      300
ccgaggcagg cggctcacga ggtcaggaga tcgagactat cctggctaac acggtaaaac      360
cctgtctcta ctaaaagtac aaaaaattag ctgggcgtgg tggtgggcac ctgtagtccc      420
agctactcgg gaggctgagg caggagaaag gcatgaatcc aagaggcaga gcttgcagtg      480
agctgagatc acgccattgc actccagcct gggcaacagt gttaagactc tgtctcaaat      540
ataaataaat aaataaataa ataaataaat aaataaaaat aaagcgagat gttgccctca      600
aa                                                                      602
```

```
<210> SEQ ID NO 14
<211> LENGTH: 785
<212> TYPE: DNA
<213> ORGANISM: Homo sapiens

<400> SEQUENCE: 14
```

| | |
|---|---|
| ggccctgccc cgtcggactg cccccagaaa gcctcctgcc ccctgccagt gaagtccttc | 60 |
| agtgagcccc tccccagcca gcccttccct ggccccgccg gatgtataaa tgtaaaaatg | 120 |
| aaggaattac attttatatg tgagcgagca agccggcaag cgagcacagt attatttctc | 180 |
| catcccctcc ctgcctgctc cttggcaccc ccatgctgcc ttcagggaga caggcaggga | 240 |
| gggcttgggg ctgcacctcc taccctccca ccagaacgca ccccactggg agagctggtg | 300 |
| gtgcagcctt cccctccctg tataagacac tttgccaagg ctctcccctc tcgcccatc | 360 |
| cctgcttgcc cgctcccaca gcttcctgag ggctaattct gggaagggag agttctttgc | 420 |
| tgcccctgtc tggaagacgt ggctctgggt gaggtaggcg ggaaaggatg gagtgtttta | 480 |
| gttcttgggg gaggccaccc caaacccag ccccaactcc aggggcacct atgagatggc | 540 |
| catgctcaac ccccctccca gacaggccct cctgtctcc agggccccca ccgaggttcc | 600 |
| cagggctgga gacttcctct ggtaaacatt cctccagcct ccctcccct ggggacgcca | 660 |
| aggaggtggg ccacacccag gaagggaaag cgggcagccc cgttttgggg acgtgaacgt | 720 |
| tttaataatt tttgctgaat tcctttacaa ctaaataaca cagatattgt tataaataaa | 780 |
| attgt | 785 |

<210> SEQ ID NO 15
<211> LENGTH: 3001
<212> TYPE: DNA
<213> ORGANISM: Homo sapiens

<400> SEQUENCE: 15

| | |
|---|---|
| atattaagga tcaagctgtt agctaataat gccacctctg cagttttggg aacaggcaaa | 60 |
| taaagtatca gtatacatgg tgatgtacat ctgtagcaaa gctcttggag aaaatgaaga | 120 |
| ctgaagaaag caaagcaaaa actgtataga gagattttc aaaagcagta atccctcaat | 180 |
| tttaaaaaag gattgaaaat tctaaatgtc tttctgtgca tattttttgt gttaggaatc | 240 |
| aaaagtattt tataaaagga gaaagaacag cctcatttta gatgtagtcc tgttggattt | 300 |
| tttatgcctc ctcagtaacc agaaatgttt taaaaaacta agtgtttagg attttcaagac | 360 |
| aacattatac atggctctga aatatctgac acaatgtaaa cattgcaggc acctgcattt | 420 |
| tatgtttttt ttttcaacaa atgtgactaa tttgaaactt ttatgaactt ctgagctgtc | 480 |
| cccttgcaat tcaccgcag tttgaattaa tcatatcaaa tcagttttaa tttttttaaat | 540 |
| tgtacttcag agtctatatt tcaagggcac attttctcac tactatttta atacattaaa | 600 |
| ggactaaata atctttcaga gatgctggaa acaaatcatt tgctttatat gtttcattag | 660 |
| aataccaatg aaacatacaa cttgaaaatt agtaatagta ttttttgaaga tcccatttct | 720 |
| aattggagat ctcttaatt tcgatcaact tataatgtgt agtactatat taagtgcact | 780 |
| tgagtggaat tcaacatttg actaataaaa tgagttcatc atgttggcaa gtgatgtggc | 840 |
| aattatctct ggtgacaaaa gagtaaaatc aaatatttct gcctgttaca aatatcaagg | 900 |
| aagacctgct actatgaaat agatgacatt aatctgtctt cactgtttat aatacggatg | 960 |
| gattttttt caaatcagtg tgtgttttga ggtcttatgt aattgatgac atttgagaga | 1020 |
| aatggtggct ttttttagct acctcttgt tcatttaagc accagtaaag atcatgtctt | 1080 |
| tttatagaag tgtagatttt ctttgtgact ttgctatcgt gcctaaagct ctaaatatag | 1140 |
| gtgaatgtgt gatgaatact cagattattt gtctctctat ataattagtt tggtactaag | 1200 |
| tttctcaaaa aattattaac acatgaaaga caatctctaa accagaaaaa gaagtagtac | 1260 |

```
aaatttgtt actgtaatgc tcgcgtttag tgagtttaaa acacacagta tcttttggtt    1320
ttataatcag tttctatttt gctgtgcctg agattaagat ctgtgtatgt gtgtgtgtgt    1380
gtgtgtgcgt ttgtgtgtta aagcagaaaa gactttttta aaagttttaa gtgataaatg    1440
caatttgtta attgatctta gatcactagt aaactcaggg ctgaattata ccatgtatat    1500
tctattagaa gaaagtaaac accatcttta ttcctgccct ttttcttctc tcaaagtagt    1560
tgtagttata tctagaaaga agcaattttg atttcttgaa aaggtagttc ctgcactcag    1620
tttaaactaa aaataatcat acttggattt tatttatttt tgtcatagta aaaattttaa    1680
tttatatata ttttttattta gtattatctt attctttgct atttgccaat cctttgtcat    1740
caattgtgtt aaatgaattg aaaattcatg ccctgttcat tttattttac tttattggtt    1800
aggatattta aaggattttt gtatatataa tttcttaaat taatattcca aaaggttagt    1860
ggacttagat tataaattat ggcaaaaatc taaaaacaac aaaaatgatt tttatacatt    1920
ctatttcatt attcctcttt ttccaataag tcatacaatt ggtagatatg acttatttta    1980
tttttgtatt attcactata tctttatgat atttaagtat aaataattaa aaaaatttat    2040
tgtaccttat agtctgtcac caaaaaaaaa aaattatctg taggtagtga aatgctaatg    2100
ttgatttgtc tttaagggct tgttaactat cctttatttt ctcatttgtc ttaaattagg    2160
agtttgtgtt taaattactc atctaagcaa aaaatgtata taaatcccat tactgggtat    2220
atacccaaag gattataaat catgctgcta taaagacaca tgcacacgta tgtttattgc    2280
agcactattc acaatagcaa agacttggaa ccaacccaaa tgtccatcaa tgatagactt    2340
gattaagaaa atgtgcacat atacaccatg gaatactatg cagccataaa aaaggatgag    2400
ttcatgtcct ttgtagggac atggataaag ctggaaacca tcattctgag caaactattg    2460
caaggacaga aaaccaaaca ctgcatgttc tcactcatag gtgggaattg aacaatgaga    2520
acacttggac acaaggtggg gaacaccaca caccagggcc tgtcatgggg tgggggagt    2580 ggggagggat agcattagga gatataccta atgtaaatga tgagttaatg ggtgcagcac    2640
accaacatgg cacatgtata catatgtagc aaacctgcac gttgtgcaca tgtaccctag    2700
aacttaaagt ataattaaaa aaaaaagaa aacagaagct atttataaag aagttatttg    2760
ctgaaataaa tgtgatcttt cccattaaaa aaataaagaa attttggggt aaaaaaacac    2820
aatatattgt attcttgaaa aattctaaga gagtggatgt gaagtgttct caccacaaaa    2880
gtgataacta attgaggtaa tgcacatatt aattagaaag attttgtcat tccacaatgt    2940
atatatactt aaaatatgt tatacacaat aaatacatac attaaaaaat aagtaaatgt    3000
a                                                                   3001

<210> SEQ ID NO 16
<211> LENGTH: 1037
<212> TYPE: DNA
<213> ORGANISM: Homo sapiens

<400> SEQUENCE: 16
cccaccctgc acgccggcac caaaccctgt cctcccaccc ctccccactc atcactaaac      60
agagtaaaat gtgatgcgaa ttttcccgac caacctgatt cgctagattt tttttaagga     120
aaagcttgga aagccaggac acaacgctgc tgcctgcttt gtgcagggtc ctccggggct     180
cagccctgag ttggcatcac ctgcgcaggg ccctctgggg gtcagccctg agctagtgtc     240
acctgcacag ggccctctga ggctcagccc tgagctggcg tcacctgtgc agggccctct     300
ggggctcagc cctgagctgg cctcacctgg gttccccacc ccgggctctc ctgccctgcc     360
```

```
ctcctgcccg ccctccctcc tgcctgcgca gctccttccc taggcacctc tgtgctgcat        420
cccaccagcc tgagcaagac gccctctcgg ggcctgtgcc gcactagcct ccctctcctc        480
tgtccccata gctggttttt cccaccaatc ctcacctaac agttacttta caattaaact        540
caaagcaagc tcttctcctc agcttggggc agccattggc ctctgtctcg ttttgggaaa        600
ccaaggtcag gaggccgttg cagacataaa tctcggcgac tcggcccgt ctcctgaggg         660 tcctgctggt gaccggcctg gaccttggcc ctacagccct ggaggccgct gctgaccagc        720
actgaccccg acctcagaga gtactcgcag gggcgctggc tgcactcaag accctcgaga        780
ttaacggtgc taaccccgtc tgctcctccc tcccgcagag actggggcct ggactggaca        840
tgagagcccc ttggtgccac agagggctgt gtcttactag aaacaacgca aacctctcct        900
tcctcagaat agtgatgtgt tcgacgtttt atcaaaggcc ccctttctat gttcatgtta        960
gttttgctcc ttctgtgttt ttttctgaac catatccatg ttgctgactt tccaaataa       1020 aggttttcac tcctctc                                                     1037

<210> SEQ ID NO 17
<211> LENGTH: 577
<212> TYPE: DNA
<213> ORGANISM: Homo sapiens

<400> SEQUENCE: 17
agaggcctgc ctccagggct ggactgaggc ctgagcgctc ctgccgcaga gctggccgcg         60
ccaaataatg tctctgtgag actcgagaac tttcattttt ttccaggctg gttcggattt        120
ggggtggatt ttggttttgt tccctcctc cactctcccc cacccctcc ccgcccttt          180 tttttttttt ttttaaactg gtatttatc tttgattctc cttcagccct cacccctggt        240
tctcatcttt cttgatcaac atcttttctt gcctctgtcc ccttctctca tctcttagct       300
cccctccaac ctgggggggca gtggtgtgga aagccacag gcctgagatt tcatctgctc        360
tccttcctgg agcccagagg agggcagcag aaggggggtgg tgtctccaac cccccagcac      420
tgaggaagaa cggggctctt ctcatttcac ccctcccttt ctccctgcc ccaggactg         480 ggccacttct gggtgggggca gtgggtccca gattggctca cactgagaat gtaagaacta      540
caaacaaaat ttctattaaa ttaaattttg tgtctcc                                577

<210> SEQ ID NO 18
<211> LENGTH: 2212
<212> TYPE: DNA
<213> ORGANISM: Homo sapiens

<400> SEQUENCE: 18
ctccctccat cccaacctgg ctccctccca cccaaccaac tttcccccca acccggaaac         60
agacaagcaa cccaaactga accccctcaa agccaaaaa atgggagaca atttcacatg         120
gactttggaa aatattttt tcctttgcat tcatctctca aacttagttt ttatctttga        180
ccaaccgaac atgaccaaaa accaaaagtg cattcaacct taccaaaaaa aaaaaaaaaa        240
aaagaataaa taaataactt tttaaaaaag gaagcttggt ccacttgctt gaagacccat        300
gcgggggtaa gtccctttct gccgttggg cttatgaaac cccaatgctg cccttctgc         360 tcctttctcc acaccccct tgggggcctcc cctccactcc ttcccaaatc tgtctcccca       420
gaagacacag gaaacaatgt attgtctgcc cagcaatcaa aggcaatgct caaacaccca       480
agtggccccc accctcagcc cgctcctgcc cgcccagcac cccaggcccc tgggggacct      540
```

| | |
|---|---|
| ggggttctca gactgccaaa gaagccttgc catctggcgc tcccatggct cttgcaacat | 600 |
| ctccccttcg tttttgaggg ggtcatgccg ggggagccac cagcccctca ctgggttcgg | 660 |
| aggagagtca ggaagggcca cgacaaagca gaaacatcgg atttggggaa cgcgtgtcaa | 720 |
| tcccttgtgc cgcagggctg ggcgggagag actgttctgt tccttgtgta actgtgttgc | 780 |
| tgaaagacta cctcgttctt gtcttgatgt gtcaccgggg caactgcctg ggggcgggga | 840 |
| tgggggcagg gtggaagcgg ctccccattt tataccaaag gtgctacatc tatgtgatgg | 900 |
| gtggggtggg gagggaatca ctggtgctat agaaattgag atgccccccc aggccagcaa | 960 |
| atgttccttt ttgttcaaag tctatttta ttccttgata ttttctttt tttttttttt | 1020 |
| tttttgtgga tggggacttg tgaattttc taaaggtgct atttaacatg ggaggagagc | 1080 |
| gtgtgcggct ccagcccagc ccgctgctca ctttccaccc tctctccacc tgcctctggc | 1140 |
| ttctcaggcc tctgctctcc gacctctctc ctctgaaacc ctcctccaca gctgcagccc | 1200 |
| atcctcccgg ctccctccta gtctgtcctg cgtcctctgt ccccgggttt cagagacaac | 1260 |
| ttcccaaagc acaaagcagt ttttccccct aggggtggga ggaagcaaaa gactctgtac | 1320 |
| ctattttgta tgtgtataat aatttgagat gttttaatt attttgattg ctggaataaa | 1380 |
| gcatgtggaa atgacccaaa cataatccgc agtggcctcc taatttcctt ctttggagtt | 1440 |
| ggggagggg tagacatggg aaggggctt tggggtgatg ggcttgcctt ccattcctgc | 1500 |
| cctttccctc cccactattc tcttctagat ccctccataa ccccactccc ctttctctca | 1560 |
| cccttcttat accgcaaacc tttctacttc ctctttcatt ttctattctt gcaatttcct | 1620 |
| tgcaccttt ccaaatcctc ttctcccctg caataccata caggcaatcc acgtgcacaa | 1680 |
| cacacacaca cactcttcac atctggggtt gtccaaacct catacccact ccccttcaag | 1740 |
| cccatccact ctccacccc tggatgccct gcacttggtg gcgtgggat gctcatggat | 1800 |
| actgggaggg tgaggggagt ggaacccgtg aggaggacct gggggcctct ccttgaactg | 1860 |
| acatgaaggg tcatctggcc tctgctccct tctcacccac gctgacctcc tgccgaagga | 1920 |
| gcaacgcaac aggagagggg tctgctgagc ctggcgaggg tctgggaggg accaggagga | 1980 |
| aggcgtgctc cctgctcgct gtcctggccc tgggggagtg agggagacag acacctggga | 2040 |
| gagctgtggg gaaggcactc gcaccgtgct cttgggaagg aaggagacct ggccctgctc | 2100 |
| accacggact gggtgcctcg acctcctgaa tccccagaac acaaccccc tgggctgggg | 2160 |
| tggtctgggg aaccatcgtg ccccccgcctc ccgcctactc cttttaagc tt | 2212 |

<210> SEQ ID NO 19
<211> LENGTH: 729
<212> TYPE: DNA
<213> ORGANISM: Homo sapiens

<400> SEQUENCE: 19

| | |
|---|---|
| ttggccaggc ctgaccctct tggacctttc ttctttgccg acaaccactg cccagcagcc | 60 |
| tctgggacct cggggtccca gggaacccag tccagcctcc tggctgttga cttcccattg | 120 |
| ctcttggagc caccaatcaa agagattcaa agagattcct gcaggccaga ggcggaacac | 180 |
| acctttatgg ctggggctct ccgtggtgtt ctggacccag ccctggaga caccattcac | 240 |
| ttttactgct ttgtagtgac tcgtgctctc caacctgtct tcctgaaaaa ccaaggcccc | 300 |
| cttcccccac ctcttccatg gggtgagact tgagcagaac aggggcttcc ccaagttgcc | 360 |
| cagaaagact gtctgggtga aagccatgg ccagagcttc tcccaggcac aggtgttgca | 420 |
| ccagggactt ctgcttcaag ttttgggta aagacacctg gatcagactc caagggctgc | 480 |

```
cctgagtctg ggacttctgc ctccatggct ggtcatgaga gcaaaccgta gtccctggga    540
gacagcgact ccagagaacc tcttgggaga cagaagaggc atctgtgcac agctcgatct    600
tctacttgcc tgtggggagg ggagtgacag gtccacacac cacactgggt caccctgtcc    660
tggatgcctc tgaagagagg gacagaccgt cagaaactgg agagtttcta ttaaaggtca    720
tttaaacca                                                            729

<210> SEQ ID NO 20
<211> LENGTH: 847
<212> TYPE: DNA
<213> ORGANISM: Homo sapiens

<400> SEQUENCE: 20
tcctccggga ccccagccct caggattcct gatgctccaa ggcgactgat gggcgctgga     60
tgaagtggca cagtcagctt ccctgggggc tggtgtcatg ttgggctcct ggggcggggg    120
cacggcctgg catttcacgc attgctgcca cccaggtcc acctgtctcc actttcacag    180
cctccaagtc tgtggctctt cccttctgtc ctccgagggg cttgccttct ctcgtgtcca    240
gtgaggtgct cagtgatcgg cttaacttag agaagcccgc cccctcccct tctccgtctg    300
tcccaagagg gtctgctctg agcctgcgtt cctaggtggc tcggcctcag ctgcctgggt    360
tgtggccgcc ctagcatcct gtatgcccac agctactgga atcccgctg ctgctccggg    420 ccaagcttct ggttgattaa tgagggcatg gggtggtccc tcaagacctt ccctaccttt    480
ttgtggaacc agtgatgcct caaagacagt gtcccctcca cagctgggtg ccaggggcag    540
gggatcctca gtatagccgg tgaaccctga taccaggagc ctgggcctcc ctgaacccct    600
ggcttccagc catctcatcg ccagcctcct cctggacctc ttggccccca gcccttccc    660 cacacagccc cagaagggtc ccagagctga ccccactcca ggacctaggc ccagcccctc    720
agcctcatct ggagccctg aagaccagtc ccacccacct ttctggcctc atctgacact    780
gctccgcatc ctgctgtgtg tcctgttcca tgttccggtt ccatccaaat acactttctg    840
gaacaaa                                                              847

<210> SEQ ID NO 21
<211> LENGTH: 110
<212> TYPE: DNA
<213> ORGANISM: Homo sapiens

<400> SEQUENCE: 21
gctggagcct cggtggccat gcttcttgcc ccttgggcct cccccagcc cctcctcccc     60 ttcctgcacc cgtacccccg tggtctttga ataaagtctg agtgggcggc               110

<210> SEQ ID NO 22
<211> LENGTH: 18
<212> TYPE: DNA
<213> ORGANISM: Unknown
<220> FEATURE:
<223> OTHER INFORMATION: Description of Unknown: Syn5 promoter
      oligonucleotide sequence

<400> SEQUENCE: 22
attgggcacc cgtaaggg                                                   18

<210> SEQ ID NO 23
<211> LENGTH: 758
<212> TYPE: RNA
<213> ORGANISM: Artificial Sequence
```

<220> FEATURE:
<223> OTHER INFORMATION: Description of Artificial Sequence: Synthetic
      polynucleotide

<400> SEQUENCE: 23

| | | | | |
|---|---|---|---|---|
| gggaaauaag agagaaaaga agaguaagaa gaaauauaag agccaccaug gccggucccg | | | | 60 |
| cgacccaaag ccccaugaaa cuuauggccc ugcaguugcu gcuuggcac ucggcccucu | | | | 120 |
| ggacagucca agaagcgacu ccucucggac cugccucauc guugccgcag ucauuccuuu | | | | 180 |
| ugaagugucu ggagcaggug cgaaagauuc agggcgaugg agccgcacuc caagagaagc | | | | 240 |
| ucugcgcgac auacaaacuu ugccaucccg aggagcucgu acugcucggg cacagcuugg | | | | 300 |
| ggauucccug ggcuccucuc ucguccuguc cgucgcaggc uuugcaguug cagggugcc | | | | 360 |
| uuucccagcu ccacuccggu uuguucuugu aucaggacu gcugcaagcc cuugagggaa | | | | 420 |
| ucucgccaga auugggcccg acgcuggaca cguugcagcu cgacguggcg gauucgcaa | | | | 480 |
| caaccaucug gcagcagaug gaggaacugg ggauggcacc cgcgcugcag cccacgcagg | | | | 540 |
| gggcaaugcc ggccuuugcg uccgcguuuc agcgcagggc ggguggaguc cucguagcga | | | | 600 |
| gccaccuuca aucauuuuug gaagucucgu accgggugcu gagacaucuu gcgcagccgu | | | | 660 |
| gaagcgcugc cuucugcggg gcuugccuuc uggccaugcc cuucuucucu cccuugcacc | | | | 720 |
| uguaccucuu ggucuuugaa uaaagccuga guaggaag | | | | 758 |

<210> SEQ ID NO 24
<211> LENGTH: 1512
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | | | | |
|---|---|---|---|---|
| taatacgact cactataggg aaataagaga gaaagaaga gtaagaagaa atataagagg | | | | 60 |
| gtcttctccc tctcgccaaa ggaatgcaag gtctgttgaa tgtcgtgaag gaagcagttc | | | | 120 |
| ctctggaagc ttcttgaaga caaacaacgt ctgtagcgac cctttgcagg cagcggaacc | | | | 180 |
| ccccacctgg cgacaggtgc ctctgcggcc aaaagccacg tgtataagat acacctgcaa | | | | 240 |
| aggcggcaca accccagtgc cacgttgtga gttggatagt tgtggaaaga gtcaaatggc | | | | 300 |
| tcacctcaag cgtattcaac aaggggctga aggatgccca aaggtaccc cattgtatgg | | | | 360 |
| gatctgatct ggggcctcgg tgcacatgct ttacatgtgt ttagtcgagg ttaaaaaacg | | | | 420 |
| tctaggcccc ccgaaccacg gggacgtggt tttccttga aaaacacgat gataatatgg | | | | 480 |
| ccggtcccgc gacccaaagc ccatgaaac ttatggccct gcagttgctg ctttggcact | | | | 540 |
| cggccctctg acagtccaa gaagcgactc ctctcggacc tgcctcatcg ttgccgcagt | | | | 600 |
| cattcctttt gaagtgtctg gagcaggtgc gaaagattca gggcgatgga gccgcactcc | | | | 660 |
| aagagaagct ctgcgcgaca tacaaacttt gccatcccga ggagctcgta ctgctcgggc | | | | 720 |
| acagcttggg gattccctgg gctcctctct cgtcctgtcc gtcgcaggct ttgcagttgg | | | | 780 |
| cagggtgcct ttcccagctc cactccggtt tgttcttgta tcaggactg ctgcaagccc | | | | 840 |
| ttgagggaat ctcgccagaa ttgggcccga cgctggacac gttgcagctc gacgtggcg | | | | 900 |
| atttcgcaac aaccatctgg cagcagatgg aggaactggg gatggcaccc gcgctgcagc | | | | 960 |
| ccacgcaggg ggcaatgccg gccttttgcgt ccgcgtttca gcgcagggcg ggtggagtcc | | | | 1020 |
| tcgtagcgag ccaccttcaa tcattttttgg aagtctcgta ccgggtgctg agacatcttg | | | | 1080 |

```
cgcagccgtg ataataggct ggagcctcgg tggccatgct tcttgcccct tgggcctccc      1140
cccagcccct cctcccctcc ctgcacccgt accccgtgg tctttgaata aagtctgagt      1200
gggcggcaaa aaaaaaaaaa aaaaaaaaaa aaaaaaaaaa aaaaaaaaaa aaaaaaaaaa      1260
aaaaaaaaaa aaaaaaaaaa aaaaaaaggc gcgcctcgtg aggatctatt tccggtgaat      1320
tcctcgagac tagttctaga gcggccgcgg atcccgcccc tctccctccc ccccccctaa      1380
cgttactggc cgaagccgct tggaataagg ccggtgtgcg tttgtctata tgttattttc      1440
caccatattg ccgtcttttg gcaatgtgag ggcccggaaa cctggccctg tcttcttgac      1500
gagcattcct ag                                                         1512
```

<210> SEQ ID NO 25
<211> LENGTH: 1436
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
taatacgact cactataggg aaataagaga gaaagaagaa gtaagaagaa atataagagc       60
cacctcgtga ggatctattt ccggtgaatt cctcgagact agttctagag cggccgcgga      120
tcccgccccc ctccctcccc cccccctaac gttactggcc gaagccgctt ggaataaggc      180
cggtgtgcgt ttgtctatat gttattttcc accatattgc cgtcttttgg caatgtgagg      240
gcccggaaac ctggccctgt cttcttgacg agcattccta ggggtctttc ccctctcgcc      300
aaaggaatgc aaggtctgtt gaatgtcgtg aaggaagcag ttcctctgga gcttcttga      360 agacaaacaa cgtctgtagc gacccttgc aggcagcgga accccccacc tggcgacagg      420
tgcctctgcg gccaaaagcc acgtgtataa gatacacctg caaaggcggc acaacccag      480 tgccacgttg tgagttggat agttgtgaa agagtcaaat ggctcacctc aagcgtattc      540 aacaagggc tgaaggatgc ccagaaggta ccccattgta tgggatctga tctggggcct      600
cggtgcacat gctttacatg tgtttagtcg aggttaaaaa acgtctaggc ccccgaacc      660 acggggacgt ggttttcctt tgaaaaacac gatgataata tggccggtcc cgcgacccaa      720
agccccatga aacttatggc cctgcagttg ctgctttggc actcggccct ctggacagtc      780
caagaagcga ctcctctcgg acctgcctca tcgttgccgc agtcattcct tttgaagtgt      840
ctggagcagg tgcgaaagat tcagggcgat ggagccgcac tccaagagaa gctctgcgcg      900
acatacaaac tttgccatcc cgaggagctc gtactgctcg gcacagcttg gggattccc      960 tgggctcctc tctcgtcctg tccgtcgcag gctttgcagt tggcagggtg cctttcccag      1020
ctccactccg gtttgttctt gtatcaggga ctgctgcaag cccttgaggg aatctcgcca      1080
gaattgggcc cgacgctgga cacgttgcag ctcgacgtgg cggatttcgc aacaaccatc      1140
tggcagcaga tggaggaact ggggatggca cccgcgctgc agcccacgca gggggcaatg      1200
ccggcctttg cgtccgcgtt tcagcgcagg gcgggtggag tcctcgtagc gagccacctt      1260
caatcatttt tggaagtctc gtaccgggtg ctgagacatc ttgcgcagcc gtgataatag      1320
gctggagcct cggtggccat gcttcttgcc ccttgggcct ccccccagcc cctcctcccc      1380
ttcctgcacc cgtaccccg tggtctttga ataaagtctg agtgggcggc tctaga          1436
```

<210> SEQ ID NO 26
<211> LENGTH: 1413
<212> TYPE: RNA

<213> ORGANISM: Artificial Sequence
<220> FEATURE:
<223> OTHER INFORMATION: Description of Artificial Sequence: Synthetic
    polynucleotide

<400> SEQUENCE: 26

| | | | | | |
|---|---|---|---|---|---|
| gggaauuaag | agagaaaaga | agaguaagaa | gaaauauaag | agccaccucg | ugaggaucua | 60 |
| uuuccgguga | auccucgag | acuaguucua | gagcggccgc | ggaucccgcc | ccucucccuc | 120 |
| ccccccccu | aacguuacug | gccgaagccg | cuuggaauaa | ggccggugug | cguuugucua | 180 |
| uauguuauuu | uccaccauau | ugccgucuuu | uggcaaugug | agggcccgga | aaccuggccc | 240 |
| ugucuucuug | acgagcauuc | cuaggggucu | uuccccucuc | gccaaaggaa | ugcaaggucu | 300 |
| guugaauguc | gugaaggaag | caguuccucu | ggaagcuucu | ugaagacaaa | caacgucugu | 360 |
| agcgacccuu | ugcaggcagc | ggaaccccccc | accggcgac | aggugccucu | gcggccaaaa | 420 |
| gccacgugua | uaagauacac | cugcaaaggc | ggcacaaccc | cagugccacg | uugugaguug | 480 |
| gauaguugug | gaaagaguca | aauggcucac | cucaagcgua | uucaacaagg | ggcugaagga | 540 |
| ugcccagaag | guaccccauu | guaugggauc | ugaucugggg | ccucggugca | caugcuuuac | 600 |
| auguguuuag | ucgagguuaa | aaaacgucua | ggccccccga | accacgggga | cgugguuuuc | 660 |
| cuuugaaaaa | cacgaugaua | auauggccgg | uccgcgacc | caaagcccca | ugaaacuuau | 720 |
| ggcccugcag | uugcugcuuu | ggcacucggc | ccucuggaca | guccaagaag | cgacuccucu | 780 |
| cggaccugcc | ucaucguugc | cgcagucauu | ccuuuugaag | ugucuggagc | aggugcgaaa | 840 |
| gauucagggc | gauggagccg | cacuccaaga | gaagcucugc | gcgacauaca | aacuuugcca | 900 |
| ucccgaggag | cucguacugc | ucgggcacag | cuuggggauu | cccugggcuc | cucucucguc | 960 |
| cuguccgucg | caggcuuugc | aguuggcagg | gugccuuucc | cagcuccacu | ccgguuuguu | 1020 |
| cuuguaucag | ggacugcugc | aagcccuuga | gggaaucucg | ccagaauugg | gcccgacgcu | 1080 |
| ggacacguug | cagcucgacg | uggcggauuu | cgcaacaacc | aucggcagc | agauggagga | 1140 |
| acuggggaug | gcacccgcgc | ugcagcccac | gcaggggggca | augccggccu | uugcguccgc | 1200 |
| guuucagcgc | agggcggguc | gaguccucgu | agcgagccac | cuucaaucau | uuuuggaagu | 1260 |
| cucguaccgg | gugcugagac | aucuugcgca | gccgugauaa | uaggcuggag | ccucgguggc | 1320 |
| caugcuucuu | gccccuuggg | ccucccccca | gccccuccuc | cccuuccugc | acccguaccc | 1380 |
| ccgguggucuu | ugaauaaagu | cugaguggggc | ggc | | | 1413 |

<210> SEQ ID NO 27
<211> LENGTH: 1430
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 27

| | | | | | |
|---|---|---|---|---|---|
| taatacgact | cactataggg | aaataagaga | gaaagaaga | gtaagaagaa | atataagatc | 60 |
| gtgaggatct | atttccggtg | aattcctcga | gactagttct | agagcggccg | cggatcccgc | 120 |
| ccctctccct | cccccccccc | taacgttact | ggccgaagcc | gcttggaata | aggccggtgt | 180 |
| gcgtttgtct | atatgttatt | ttccaccata | ttgccgtctt | ttggcaatgt | gagggcccgg | 240 |
| aaacctggcc | ctgtcttctt | gacgagcatt | cctaggggtc | tttcccctct | cgccaaagga | 300 |
| atgcaaggtc | tgttgaatgt | cgtgaaggaa | gcagttcctc | tggaagcttc | ttgaagacaa | 360 |
| acaacgtctg | tagcgaccct | tgcaggcag | cggaaccccc | cacctggcga | caggtgcctc | 420 |

```
tgcggccaaa agccacgtgt ataagataca cctgcaaagg cggcacaacc ccagtgccac    480
gttgtgagtt ggatagttgt ggaaagagtc aaatggctca cctcaagcgt attcaacaag    540
gggctgaagg atgcccagaa ggtaccccat tgtatgggat ctgatctggg gcctcggtgc    600
acatgcttta catgtgttta gtcgaggtta aaaaacgtct aggccccccg aaccacgggg    660
acgtggtttt cctttgaaaa acacgatgat aatatggccg gtcccgcgac ccaaagcccc    720
atgaaactta tggccctgca gttgctgctt tggcactcgg ccctctggac agtccaagaa    780
gcgactcctc tcggacctgc ctcatcgttg ccgcagtcat tccttttgaa gtgtctggag    840
caggtgcgaa agattcaggg cgatggagcc gcactccaag agaagctctg cgcgacatac    900
aaactttgcc atcccgagga gctcgtactg ctcgggcaca gcttggggat tccctgggct    960
cctctctcgt cctgtccgtc gcaggctttg cagttggcag ggtgcctttc ccagctccac   1020
tccggtttgt tcttgtatca gggactgctg caagcccttg agggaatctc gccagaattg   1080
ggcccgacgc tggacacgtt gcagctcgac gtggcggatt tcgcaacaac catctggcag   1140
cagatggagg aactggggat ggcacccgcg ctgcagccca cgcaggggc aatgccggcc    1200 tttgcgtccg cgtttcagcg cagggcgggt ggagtcctcg tagcgagcca ccttcaatca   1260
tttttggaag tctcgtaccg ggtgctgaga catcttgcgc agccgtgata ataggctgga   1320
gcctcggtgg ccatgcttct tgccccttgg gcctccccc agcccctcct ccccttcctg    1380 caccccgtacc cccgtggtct ttgaataaag tctgagtggg cggctctaga              1430
```

<210> SEQ ID NO 28
<211> LENGTH: 1407
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 28

```
gggaaauaag agagaaaaga agaguaagaa gaaauauaag aucgugagga ucuauuccg     60 gugaauuccu cgagacuagu ucuagagcgg ccgcggaucc cgccccucuc ccucccccc    120 cccuaacguu acuggccgaa gccgcuugga auaaggccgg ugugcguuug ucuauauguu   180
auuuuccacc auauugccgu cuuuuggcaa ugugagggcc cggaaaccug gcccugucuu   240
cuugacgagc auuccuaggg gucuuucccc ucucgccaaa ggaaugcaag gucuguugaa   300
ugucgugaag gaagcaguuc cucuggaagc uucuugaaga caaacaacgu cuguagcgac   360
ccuuugcagg cagcggaacc ccccaccugg cgacaggugc cucugcggcc aaaagccacg   420
uguauaagau acaccugcaa aggcggcaca ccccagugc cacguuguga guuggauagu    480
uguggaaaga gucaaauggc ucaccucaag cguauucaac aaggggcuga aggaugccca   540
gaagguaccc cauguauggg aucugaucu ggggccucgg ugcacaugcu uuacaugugu    600
uuagucgagg uuaaaaaacg ucuaggcccc ccgaaccacg gggacguggu uuuccuuuga   660
aaaacacgau gauaauaugg ccgguccccgc gacccaaagc cccaugaaac uuauggcccu   720
gcaguugcug cuuuggcacu cggcccucug gacaguccaa gaagcgacuc ucucggacc    780 ugccucaucg uugccgcagu cauuccuuuu gaaguguucug gagcagguugc gaaagauuca   840 gggcgaugga gccgcacucc aagagaagcu cugcgcgaca uacaaacuuu gccaucccga   900
ggagcucgua cugcucgggc acagcuuggg gauucccugg gcuccucucu cguccugucc   960
gucgcaggcu uugcaguugg cagggugccu uucccagcuc cacuccgguu uguucuugua   1020
```

```
ucagggacug cugcaagccc uugagggaau cucgccagaa uugggcccga cgcuggacac    1080
guugcagcuc gacguggcgg auuucgcaac aaccaucugg cagcagaugg aggaacuggg    1140
gauggcaccc gcgcugcagc ccacgcaggg ggcaaugccg gccuuugcgu ccgcguuuca    1200
gcgcagggcg gguggagucc ucguagcgag ccaccuucaa ucauuuuugg aagucucgua    1260
ccgggugcug agacaucuug cgcagccgug auaauaggcu ggagccucgg uggccaugcu    1320
ucuugcccct ugggccuccc cccagcccct ccucccctct cugcacccgu accccegugg    1380 ucuuugaaua aagucugagu gggcggc                                        1407
```

<210> SEQ ID NO 29
<211> LENGTH: 795
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
taatacgact cactataggg aaataagaga gaaaagaaga gtaagaagaa atataagaat     60
ggccggtccc gcgacccaaa gccccatgaa acttatggcc ctgcagttgc tgctttggca    120
ctcggccctc tggacagtcc aagaagcgac tcctctcgga cctgcctcat cgttgccgca    180
gtcattcctt ttgaagtgtc tggagcaggt gcgaaagatt cagggcgatg gagccgcact    240
ccaagagaag ctctgcgcga catacaaact tgccatccc gaggagctcg tactgctcgg     300
gcacagcttg gggattccct gggctcctct ctcgtcctgt ccgtcgcagg ctttgcagtt    360
ggcagggtgc ctttcccagc tccactccgg tttgttcttg tatcagggac tgctgcaagc    420
ccttgaggga atctcgccag aattgggccc gacgctggac acgttgcagc tcgacgtggc    480
ggatttcgca acaaccatct ggcagcagat ggaggaactg gggatggcac ccgcgctgca    540
gcccacgcag ggggcaatgc cggcctttgc gtccgcgttt cagcgcaggg cgggtggagt    600
cctcgtagcg agccaccttc aatcattttt ggaagtctcg taccgggtgc tgagacatct    660
tgcgcagccg tgataatagg ctggagcctc ggtggccatg cttcttgccc cttgggcctc    720
cccccagccc ctcctcccct tcctgcaccc gtaccccgt ggtctttgaa taaagtctga    780
gtgggcggct ctaga                                                     795
```

<210> SEQ ID NO 30
<211> LENGTH: 772
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 30

```
gggaauaag agagaaaaga agaguaagaa gaaauauaag aauggccggu cccgcgaccc      60
aaagccccau gaaacuuaug gcccugcagu ugcugcuuug gcacucggcc cucuggacag    120
uccaagaagc gacuccucuc ggaccugccu caucguugcc gcagucauuc cuuuugaagu    180
gucuggagca ggugcgaaag auucagggcg auggagccgc acuccaagag aagcucugcg    240
cgacauacaa acuuugccau ccgaggagc ucguacugcu cgggcacagc uuggggauuc     300
ccugggcucc ucucgucc uguccgucgc aggcuuugca guuggcaggg ugccuuuccc     360
agcuccacuc cgguuuguuc uuguaucagg gacugcugca agcccuugag ggaaucucgc    420
```

| | |
|---|---|
| cagaauuggg cccgacgcug acacguugc agcucgacgu ggcggauuuc gcaacaacca | 480 |
| ucuggcagca gauggaggaa cuggggaugg cacccgcgcu gcagcccacg caggggggcaa | 540 |
| ugccggccuu ugcguccgcg uuucagcgca gggcggugg aguccucgua gcgagccacc | 600 |
| uucaaucauu uuuggaaguc ucguaccggg ugcugagaca ucuugcgcag ccgugauaau | 660 |
| aggcuggagc cucgguggcc augcuucuug ccccuugggc cucccccag ccccuccucc | 720 |
| ccuuccugca cccguacccc cguggucuuu gaauaaaguc ugaguggggcg gc | 772 |

<210> SEQ ID NO 31
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

| | |
|---|---|
| taatacgact cactataggg aaataagaga gaaaagaaga gtaagaagaa atataagagc | 60 |
| cacctcgtga ggatctattt ccggtgaatt cctcgagact agttctagag cggccgcgga | 120 |
| tcccgcccct ctccctcccc ccccctaac gttactggcc gaagccgctt ggaataaggc | 180 |
| cggtgtgcgt ttgtctatat gttatttcc accatattgc cgtcttttgg caatgtgagg | 240 |
| gcccggaaac ctggccctgt cttcttgacg agcattccta ggggtctttc cctctcgcc | 300 |
| aaaggaatgc aaggtctgtt gaatgtcgtg aaggaagcag ttcctctgga agcttcttga | 360 |
| agacaaacaa cgtctgtagc gacccttttgc aggcagcgga accccccacc tggcgacagg | 420 |
| tgcctctgcg gccaaaagcc acgtgtataa gatacacctg caaaggcggc acaacccccag | 480 |
| tgccacgttg tgagttggat agttgtggaa agagtcaaat ggctcacctc aagcgtattc | 540 |
| aacaagggc tgaaggatgc ccagaaggta ccccattgta tgggatctga tctggggcct | 600 |
| cggtgcacat gctttacatg tgtttagtcg aggttaaaaa acgtctaggc ccccgaacc | 660 |
| acggggacgt ggttttcctt tgaaaaacac gatgataata tggccggtcc cgcgacccaa | 720 |
| agccccatga aacttatggc cctgcagttg ctgctttggc actcggccct ctggacagtc | 780 |
| caagaagcga ctcctctcgg acctgcctca tcgttgccgc agtcattcct tttgaagtgt | 840 |
| ctggagcagg tgcgaaagat tcagggcgat ggagccgcac tccaagagaa gctctgcgcg | 900 |
| acatacaaac tttgccatcc cgaggagctc gtactgctcg gcacagctt ggggattccc | 960 |
| tgggctcctc tctcgtcctg tccgtcgcag gctttgcagt tggcagggtg ccttcccag | 1020 |
| ctccactccg gtttgttctt gtatcaggga ctgctgcaag cccttgaggg aatctcgcca | 1080 |
| gaattgggcc cgacgctgga cacgttgcag ctcgacgtgg cggatttcgc aacaaccatc | 1140 |
| tggcagcaga tggaggaact ggggatggca cccgcgctgc agcccacgca gggggcaatg | 1200 |
| ccggcctttg cgtccgcgtt tcagcgcagg gcgggtggag tcctcgtagc gagccacctt | 1260 |
| caatcatttt tggaagtctc gtaccggggt ctgagacatc ttgcgcagcc gtgataatag | 1320 |
| gctggagcct cggtggccat gcttcttgcc ccttgggcct cccccagcc cctcctcccc | 1380 |
| ttcctgcacc cgtaccccg tggtctttga ataaagtctg agtgggcggc aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa ggcgcgcc | 1518 |

<210> SEQ ID NO 32
<211> LENGTH: 1493
<212> TYPE: RNA

<213> ORGANISM: Artificial Sequence
<220> FEATURE:
<223> OTHER INFORMATION: Description of Artificial Sequence: Synthetic polynucleotide

<400> SEQUENCE: 32

| | | | | | |
|---|---|---|---|---|---|
| gggaauuaag | agagaaaaga | agaguaagaa | gaaauauaag | agccaccucg | ugaggaucua | 60 |
| uuuccgguga | auccucgag | acuaguucua | gagcggccgc | ggaucccgcc | ccucucccuc | 120 |
| ccccccccu | aacguuacug | gccgaagccg | cuuggaauaa | ggccggugug | cguuugucua | 180 |
| uauguuauuu | uccaccauau | ugccgucuuu | uggcaaugug | agggcccgga | aaccuggccc | 240 |
| ugucuucuug | acgagcauuc | cuaggggucu | uuccccucuc | gccaaaggaa | ugcaaggucu | 300 |
| guugaauguc | gugaaggaag | caguuccucu | ggaagcuucu | ugaagacaaa | caacgucugu | 360 |
| agcgacccuu | ugcaggcagc | ggaaccccc | accggcgac | aggugccucu | gcggccaaaa | 420 |
| gccacgugua | uaagauacac | cugcaaaggc | ggcacaaccc | cagugccacg | uugugaguug | 480 |
| gauaguugug | gaaagaguca | aauggcucac | cucaagcgua | uucaacaagg | ggcugaagga | 540 |
| ugcccagaag | guaccccauu | guaugggauc | ugaucugggg | ccucggugca | caugcuuuac | 600 |
| auguguuuag | ucgagguuaa | aaaacgucua | ggccccccga | accacgggga | cgugguuuuc | 660 |
| cuuugaaaaa | cacgaugaua | auauggccgg | uccgcgacc | caaagcccca | ugaaacuuau | 720 |
| ggcccugcag | uugcugcuuu | ggcacucggc | ccucuggaca | guccaagaag | cgacuccucu | 780 |
| cggaccugcc | ucaucguugc | cgcagucauu | ccuuuugaag | ugucuggagc | aggugcgaaa | 840 |
| gauucagggc | gauggagccg | cacuccaaga | gaagcucugc | gcgacauaca | aacuuugcca | 900 |
| ucccgaggag | cucguacugc | ucgggcacag | cuuggggauu | cccuggcucu | cucucucguc | 960 |
| cuguccgucg | caggcuuugc | aguuggcagg | ugugccuuuccc | cagcuccacu | ccgguuuguu | 1020 |
| cuuguaucag | ggacugcugc | aagcccuuga | gggaaucucg | ccagaauugg | gcccgacgcu | 1080 |
| ggacacguug | cagcucgacg | uggcggauuu | cgcaacaacc | aucuggcagc | agauggagga | 1140 |
| acuggggaug | gcacccgcgc | ugcagcccac | gcaggggggca | augccggccu | uugcguccgc | 1200 |
| guuucagcgc | agggcggguuag | gaguccucgu | agcgagccac | cuucaaucau | uuuuggaagu | 1260 |
| cucguaccgg | gugcugagac | aucuugcgca | gccgugauaa | uaggcuggag | ccucggugge | 1320 |
| caugcuucuu | gccccuuggg | ccuccccca | gccccuccuc | cccuuccugc | acccguaccc | 1380 |
| ccguggucuu | ugaauaaagu | cugagugggc | ggcaaaaaaa | aaaaaaaaaa | aaaaaaaaa | 1440 |
| aaaaaaaaaa | aaaaaaaaaa | aaaaaaaaaa | aaaaaaaaa | aaaaaaaaaa | aaa | 1493 |

<210> SEQ ID NO 33
<211> LENGTH: 1512
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

| | | | | | |
|---|---|---|---|---|---|
| taatacgact | cactataggg | aaataagaga | gaaagaaga | gtaagaagaa | atataagatc | 60 |
| gtgaggatct | atttccggtg | aattcctcga | gactagttct | agagcggccg | cggatcccgc | 120 |
| ccctctccct | cccccccccc | taacgttact | ggccgaagcc | gcttggaata | aggccggtgt | 180 |
| gcgtttgtct | atatgttatt | ttccaccata | ttgccgtctt | ttggcaatgt | gagggcccgg | 240 |
| aaacctggcc | ctgtcttctt | gacgagcatt | cctaggggtc | tttccccctct | cgccaaagga | 300 |
| atgcaaggtc | tgttgaatgt | cgtgaaggaa | gcagttcctc | tggaagcttc | ttgaagacaa | 360 |

```
acaacgtctg tagcgaccct ttgcaggcag cggaaccccc cacctggcga caggtgcctc      420
tgcggccaaa agccacgtgt ataagataca cctgcaaagg cggcacaacc ccagtgccac      480
gttgtgagtt ggatagttgt ggaaagagtc aaatggctca cctcaagcgt attcaacaag      540
gggctgaagg atgcccagaa ggtaccccat tgtatgggat ctgatctggg cctcggtgc       600 acatgcttta catgtgttta gtcgaggtta aaaacgtct aggcccccg aaccacgggg        660 acgtggtttt cctttgaaaa acacgatgat aatatggccg gtcccgcgac ccaaagcccc     720
atgaaactta tggccctgca gttgctgctt tggcactcgg ccctctggac agtccaagaa     780
gcgactcctc tcgacctgc ctcatcgttg ccgcagtcat tccttttgaa gtgtctggag       840
caggtgcgaa agattcaggg cgatggagcc gcactccaag agaagctctg cgcgacatac     900
aaactttgcc atcccgagga gctcgtactg ctcgggcaca gcttgggat tccctgggct      960 cctctctcgt cctgtccgtc gcaggctttg cagttggcag ggtgcctttc ccagctccac    1020 tccggttttgt tcttgtatca gggactgctg caagcccttg agggaatctc gccagaattg   1080
ggcccgacgc tggacacgtt gcagctcgac gtggcggatt cgcaacaac catctggcag     1140 cagatggagg aactggggat ggcacccgcg ctgcagccca gcaggggc aatgccggcc      1200 tttgcgtccg cgtttcagcg cagggcgggt ggagtcctcg tagcgagcca ccttcaatca    1260
tttttggaag tctcgtaccg ggtgctgaga catcttgcgc agccgtgata ataggctgga   1320
gcctcggtgg ccatgcttct tgccccttgg gcctccccc agccctcct ccccttcctg      1380 cacccgtacc cccgtggtct ttgaataaag tctgagtggg cggcaaaaaa aaaaaaaaa     1440 aaaaaaaaaa aaaaaaaaaa aaaaaaaaaa aaaaaaaaaa aaaaaaaaaa aaaaaaaaaa    1500
aaaaggcgcg cc                                                         1512
```

<210> SEQ ID NO 34
<211> LENGTH: 1487
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 34

```
gggaaauaag agagaaaaga agaguaagaa gaaauauaag aucgugagga ucuauuuccg      60
gugaauuccu cgagacuagu ucuagagcgg ccgcggaucc cgcccucuc ccucccccc      120 cccuaacguu acuggccgaa gccgcuugga auaaggccgg ugugcguuug ucuauauguu    180
auuuuccacc auauugccgu cuuuuggcaa ugugagggcc cggaaaccug gcccugucuu    240
cuugacgagc auuccuaggg gucuuucccc ucucgccaaa ggaaugcaag gucuguugaa    300
ugucgugaag gaagcaguuc cucuggaagc uucuugaaga caaacaacgu cuguagcgac    360
ccuuugcagg cagcggaacc ccccaccugg cgacaggugc cucugcggcc aaaagccacg    420
uguauaagau acaccugcaa aggcggcaca accccagugc cacguugug auuggauagu     480 ugugaaaga gucaaauggc ucaccucaag cguauucaac aaggggcuga aggaugccca     540
gaagguaccc cauuguaugg gaucugaucu ggggccucgg ugcacaugcu uuacaugugu    600
uuagucgagg uuaaaaaacg ucuaggcccc ccgaaccacg gggacguggu uuccuuuga    660 aaaacacgau gauaauaugg ccggucccgc gacccaaagc ccaugaaac uauggcccu     720 gcaguugcug cuuuggcacu cggcccucug gacaguccaa gaagcgacuc ucucggacc    780 ugccucaucg uugccgcagu cauuccuuuu gaagugucug gagcaggugc gaaagauuca   840
```

```
gggcgaugga gccgcacucc aagagaagcu cugcgcgaca uacaaacuuu gccaucccga      900
ggagcucgua cugcucgggc acagcuuggg gauucccugg gcuccucucu cguccugucc      960
gucgcaggcu uugcaguugg cagggugccu uucccagcuc cacuccgguu uguucuugua     1020
ucagggacug cugcaagccc uugagggaau cucgccagaa uugggcccga cgcuggacac     1080
guugcagcuc gacguggcgg auuucgcaac aaccaucugg cagcagaugg aggaacuggg     1140
gauggcaccc gcgcugcagc ccacgcaggg ggcaaugccg gccuuugcgu ccgcguuuca     1200
gcgcagggcg gguggaguuc ucguagcgag ccaccuucaa ucauuuuugg aagucucgua     1260
ccgggugcug agacaucuug cgcagccgug auaauaggcu ggagcucgg uggccaugcu      1320 ucuugccccu ugggccuccc cccagcccu ccuccccuuc cugcacccgu accccgugg       1380 ucuuugaaua aagucugagu gggcggcaaa aaaaaaaaaa aaaaaaaaaa aaaaaaaaaa     1440
aaaaaaaaaa aaaaaaaaaa aaaaaaaaaa aaaaaaaaa aaaaaaa                   1487
```

<210> SEQ ID NO 35
<211> LENGTH: 883
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

```
taatacgact cactataggg aaataagaga gaaagaaga gtaagaagaa atataagagc       60
caccatggcc ggtcccgcga cccaaagccc catgaaactt atggccctgc agttgctgct     120
ttggcactcg gccctctgga cagtccaaga agcgactcct ctcggacctg cctcatcgtt     180
gccgcagtca ttccttttga agtgtctgga gcaggtgcga aagattcagg gcgatggagc     240
cgcactccaa gagaagctct gcgcgacata caaactttgc catcccgagg agctcgtact     300
gctcgggcac agcttgggga ttccctgggc tcctctctcg tcctgtccgt cgcaggcttt     360
gcagttggca gggtgccttt cccagctcca ctccggtttg ttcttgtatc agggactgct     420
gcaagccctt gagggaatct cgccagaatt gggcccgacg ctggacacgt tgcagctcga     480
cgtggcggat ttcgcaacaa ccatctggca gcagatggag gaactgggga tggcacccgc     540
gctgcagccc acgcaggggg caatgccggc ctttgcgtcc gcgtttcagc gcagggcggg     600
tggagtcctc gtagcgagcc accttcaatc attttggaa gtctcgtacc gggtgctgag      660
acatcttgcg cagccgtgat aataggctgg agcctcggtg gccatgcttc ttgccccttg     720
ggcctccccc cagcccctcc tccccttcct gcacccgtac ccccgtggtc tttgaataaa     780
gtctgagtgg gcggcaaaaa aaaaaaaaaa aaaaaaaaaa aaaaaaaaaa aaaaaaaaaa     840
aaaaaaaaaa aaaaaaaaaa aaaaaaaaaa aaaaggcgc gcc                       883
```

<210> SEQ ID NO 36
<211> LENGTH: 858
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 36

```
gggaauaag agagaaaga agaguaagaa gaaauauaag agccaccaug gccgguuccg         60
cgacccaaag ccccaugaaa cuuauggccc ugcaguugcu gcuuuggcac ucggcccucu      120
```

```
ggacagucca agaagcgacu ccucucggac cugccucauc guugccgcag ucauuccuuu    180
ugaagugucu ggagcaggug cgaaagauuc agggcgaugg agccgcacuc caagagaagc    240
ucugcgcgac auacaaacuu ugccaucccg aggagcucgu acugcucggg cacagcuugg    300
ggauucccug ggcuccucuc ucguccuguc cgucgcaggc uuugcaguug cagggugcc     360 uuucccagcu ccacuccggu uuguucuugu aucagggacu gcugcaagcc cuugagggaa    420
ucucgccaga auugggcccg acgcuggaca cguugcagcu cgacguggcg gauuucgcaa    480
caaccaucug gcagcagaug gaggaacugg ggauggcacc cgcgcugcag cccacgcagg    540
gggcaaugcc ggccuuugcg uccgcguuuc agcgcagggc ggguggaguc ucguagcga    600 gccaccuuca aucauuuuug gaagucucgu accggggugcu gagacaucuu gcgcagccgu    660
gauaauaggc uggagcccuc guggccaugc uucuugcccc uugggccucc ccccagcccc    720 uccucccuu ccugcacccg uaccccgug gucuuugaau aaagucugag ugggcggcaa     780
aaaaaaaaaa aaaaaaaaaa aaaaaaaaaa aaaaaaaaaa aaaaaaaaaa aaaaaaaaaa    840
aaaaaaaaaa aaaaaaaa                                                  858
```

<210> SEQ ID NO 37
<211> LENGTH: 877
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
taatacgact cactataggg aaataagaga gaaagaaga gtaagaagaa atataagaat     60
ggccggtccc gcgacccaaa gccccatgaa acttatggcc ctgcagttgc tgctttggca    120
ctcggccctc tggacagtcc aagaagcgac tcctctcgga cctgcctcat cgttgccgca    180
gtcattcctt ttgaagtgtc tggagcaggt gcgaaagatt cagggcgatg gagccgcact    240
ccaagagaag ctctgcgcga catacaaact ttgccatccc gaggagctcg tactgctcgg    300
gcacagcttg gggattccct gggctcctct ctcgtcctgt ccgtcgcagg ctttgcagtt    360
ggcagggtgc ctttcccagc tccactccgg tttgttcttg tatcagggac tgctgcaagc    420
ccttgaggga atctcgccag aattgggccc gacgctggac acgttgcagc tcgacgtggc    480
ggatttcgca caaccatct ggcagcagat ggaggaactg gggatggcac ccgcgctgca    540
gcccacgcag ggggcaatgc cggccttgc gtccgcgttt cagcgcaggg cgggtggagt    600
cctcgtagcg agccaccttc aatcattttt ggaagtctcg taccgggtgc tgagacatct    660
tgcgcagccg tgataatagg ctggagcctc ggtggccatg cttcttgccc cttgggcctc    720
cccccagccc ctcctcccct tcctgcaccc gtaccccgt ggtctttgaa taaagtctga    780
gtgggcggca aaaaaaaaa aaaaaaaaaa aaaaaaaaaa aaaaaaaaaa aaaaaaaaaa    840
aaaaaaaaaa aaaaaaaaaa aaaaaaaag gcgcgcc                              877
```

<210> SEQ ID NO 38
<211> LENGTH: 852
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 38

```
gggaaauaag agagaaaaga gaguaagaa gaaauauaag aauggccggu cccgcgaccc    60
```

```
aaagccccau gaaacuuaug gcccugcagu ugcugcuuug gcacucggcc cucuggacag    120
uccaagaagc gacuccucuc ggaccugccu caucguugcc gcagucauuc cuuuugaagu    180
gucuggagca ggugcgaaag auucagggcg auggagccgc acccaagag aagcucugcg     240
```
(Note: checking) 
```
gucuggagca ggugcgaaag auucagggcg auggagccgc acccaagag aagcucugcg     240 cgacauacaa acuuugccau cccgaggagc ucuacugcu cgggcacagc uuggggauuc     300
ccugggcucc ucucucgucc ugccgucgc aggcuuugca guuggcaggg ugccuuuccc    360
agcuccacuc cgguuuguuc uuguaucagg gacugcugca agcccuugag ggaaucucgc    420
cagaauuggg cccgacgcug gacacguugc agcucgacgu ggcggauuuc gcaacaacca    480
ucuggcagca gauggaggaa cugggugauggg caccccgcgcu gcagcccacg caggggggcaa   540 ugccggccuu ugcguccgcg uuucagcgca gggcgggugg aguccucgua gcgagccacc    600
uucaaucauu uuuggaaguc ucguaccggg ugcugagaca ucuugcgcag ccgugauaau    660
aggcuggagc ucggguggcc augcuucuug ccccuugggc cucccccag ccccuccucc     720 ccuuccugca cccguacccc cguggucuuu gaauaaaguc ugagugggcg gcaaaaaaaa    780
aaaaaaaaaa aaaaaaaaaa aaaaaaaaaa aaaaaaaaaa aaaaaaaaaa aaaaaaaaaa    840
aaaaaaaaaa aa                                                       852

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttctctctta tttcccttt tctagagccc gcc                                  33

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tcttttctct cttatttccc tttttctaga gcccgcccac tc                       42

<210> SEQ ID NO 41
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttctctctta tttccgtagg gttggtagac caggttgagc cggcgtcctt gtttattttc    60
tagagcccgc cc                                                        72

<210> SEQ ID NO 42
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 42
uacacacaca cacacu                                            16

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tacacacaca cacact                                            16

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcttttctct cttatttccc agtgtgtgtg tgtgtatttt tctagagccc gcccactc    58

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttctcttatt tcccagtgtg tgtgtgtgta tttttctaga gccgcc              46

<210> SEQ ID NO 46
<211> LENGTH: 579
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 46
gggaaauaag agagaaaaga agaguaagaa gaaauauaag agccaccgca cgagugnccc    60
gcguggungu gguugcugcu gucgcucaaa caccauugnc acacuccagc cugugcuggg   120
ggcaccaccc agauugaucu gcgacuccaa acaccauugu cacacuccau cuugaagcca   180
aagaagccga aaacaucaca accggaugca aacaccauug ucacacucca ugagaacauu   240
acuguaccgg auacaaaggu caauuucuac aaacaccauu gucacacucc aaggacagca   300
ggccgucgaa guguggcagg ggcucgcgcu caaacaccau ugucacacuc cagggucagg   360
cccuccucgu caacucauca cagccguggg acaaacacca uugucacacu ccauaaagcg   420 gugucgggge uccgcagcuu gacgacguug cucaaacacc auugucacac uccacacguu   480
uaggaagcuu uuuagagugu acagcaauuu ccugagaaaa gaagaguaag aagaaauagu   540
ggucuuugaa uaaagucuga gugggcggcu cuagaaaaa                          579

<210> SEQ ID NO 47
<211> LENGTH: 579
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 47
gggaaauaag agagaaaaga agaguaagaa gaaauauaag agccaccgca cgagugcccc    60
gcgugguugu gguugcugcu gucgcucaaa caccauuguc acacuccagc cugugcuggg   120
ggcaccaccc agauugaucu gcgacuccaa acaccauugu cacacuccau cuugaagcca   180
aagaagccga aaacaucaca accggaugca aacaccauug ucacacucca ugagaacauu   240
acuguaccgg auacaaaggu caauuucuac aaacaccauu gucacacucc aaggacagca   300
ggccgucgaa guguggcagg ggcucgcgcu caaacaccau ugucacacuc cagggucagg   360
cccuccucgu caacucauca cagccguggg acaaacacca uugucacacu ccauaaagcg   420
gugucggggc uccgcagcuu gacgacguug cucaaacacc auugucacac uccacacguu   480
uaggaagcuu uuuagagugu acagcaauuu ccugagaaaa gaagaguaag aagaaauagu   540
ggucuuugaa uaaagucuga gugggcggcu cuagaaaaa                          579

<210> SEQ ID NO 48
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(80)
<223> OTHER INFORMATION: May or may not be present

<400> SEQUENCE: 48
aaaaaaaaaa aaaaaaaaaa aaaaaaaaaa aaaaaaaaaa aaaaaaaaaa aaaaaaaaaa    60
aaaaaaaaaa aaaaaaaaaa                                                80

<210> SEQ ID NO 49
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa aaaaaaaaaa aaaaaaaaaa   120

<210> SEQ ID NO 50
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
tttttttttt tttttttttt tttttttttt tttttttttt tttttttttt tttttttttt    60
tttttttttt tttttttttt tttttttttt tttttttttt tttttttttt tttttttttt   120

CIRCULAR POLYNUCLEOTIDES

REFERENCE TO RELATED APPLICATIONS

This application claims priority to U.S. Provisional Patent Application No. 62/025,390, filed Jul. 16, 2014, entitled Circular Polynucleotides, and to U.S. Provisional Patent Application No. 62/045,425, filed Sep. 3, 2014, entitled Circular Polynucleotides the contents of each of which are herein incorporated by reference in its entirety.

SEQUENCE LISTING

The present application is being filed along with a Sequence Listing in electronic format. The information in the electronic format of the sequence listing is incorporated herein by reference in its entirety.

FIELD OF THE INVENTION

The invention relates to compositions, methods, processes, kits and devices for the design, preparation, manufacture and/or formulation of single stranded circular polynucleotides (circP).

BACKGROUND OF THE INVENTION

Circular RNA was first discovered in 1979 by electron microscope (Hsu et al., Nature (1979) 280:339-340; herein incorporated by reference in its entirety). With its 5' and 3' ends joined together, circRNA has no free ends and has extraordinary long half-life (Harland & Misher, Development (1988) 102:837-852; herein incorporated by reference in its entirety). Recent studies have confirmed that circRNA is resistant to digestion with RNase R exonuclease and turns over more slowly than its counterpart linear RNA in vivo (Memczak et al. Nature (2013) 495:333-338; herein incorporated by reference in its entirety). An analysis of circRNA and their associated linear mRNAs revealed that the circRNA isoforms were highly stable, with transcript half-lives exceeding 48 hours, while the associated linear transcripts exhibited half-lives of less than 20 hours (Jeck et al., RNA (2013) 19:141-157; herein incorporated by reference in its entirety).

Since their initial discovery circRNAs have been developed for various uses. In U.S. Pat. No. 5,766,903 to Sarnow et al., herein incorporated by reference in its entirety, circRNAs comprise an internal ribosome entry site (IRES) element that engages a eukaryotic ribosome and an RNA sequence element encoding a polypeptide operatively linked to the IRES. The circRNA described by Sarnow can then be inserted into cells in order to produce a polypeptide of interest. U.S. Pat. No. 5,580,859 to Felgner et al., herein incorporated by reference in its entirety, describes polynucleotide sequences, which may be circularized, which may be administered directly to tissues in order to produce proteins. CircRNAs for vascular disease are described in International Publication No. WO2012050975, herein incorporated by reference in its entirety, where Sharpless et al. described circRNAs comprising one or more ANRIL exons which play an active role in atherosclerotic vascular disease. U.S. Pat. No. 5,426,180 to Kool et al., herein incorporated by reference in its entirety, discloses single-stranded circular oligonucleotides that bind to both single-stranded and double-stranded target nucleic acids.

The production of circRNAs has been attempted by various methods such as the method described in U.S. Pat. No. 6,210,931 to Feldstein et al., herein incorporated by reference in its entirety, which teaches a method of synthesizing circRNAs by inserting DNA fragments into a plasmid containing sequences having the capability of spontaneous cleavage and self-circularization. Another method is described in U.S. Pat. No. 5,773,244 to Ares Jr. et al. which teaches producing circRNAs by making a DNA construct encoding an RNA cyclase ribozyme, expressing the DNA construct as an RNA, and then allowing the RNA to self-splice, which produces a circRNA free from intron in vitro. International Publication No. WO1992001813 to Ruth et al., herein incorporated by reference in its entirety, teaches a process of making single strand circular nucleic acids by synthesizing a linear polynucleotide, combining the linear nucleotide with a complementary linking oligonucleotide under hybridization conditions, and ligating the linear polynucleotide.

However, the synthetic circRNA molecules are still susceptible to the pitfalls of their linear counterparts including, but not limited to, reduced structural and functional integrity and/or triggering bio-responses such as the immune response and/or degradation pathways.

It has been previously shown that certain linear modified mRNA sequences have the potential as therapeutics. Such studies are detailed in International Publication No. WO2012019168, filed Aug. 5, 2011, International Publication No. WO2012045075, filed Oct. 3, 2011, International Publication No. WO2012135805, filed Apr. 2, 2012, International Publication No. WO2012045082, filed Oct. 3, 2011, International Publication No. WO2013052523, filed Oct. 3, 2012, and International Publication No. WO2013090648, filed Dec. 14, 2012, the contents of each of which are herein incorporated by reference in its entirety.

The present invention provides single stranded circular polynucleotides (circP) which may comprise structural and/or chemical features such as, but not limited to, features which are useful for optimizing formulation and delivery of nucleic acid-based therapeutics while retaining structural and functional integrity, overcoming the threshold of expression, improving expression rates, half-life and/or protein concentrations, optimizing protein localization, and avoiding deleterious bio-responses such as the immune response and/or degradation pathways. The circular polynucleotides which may comprise the structural and/or chemical features described herein may have potential in the fields of therapeutics, diagnostics, reagents and for biological assays.

SUMMARY OF THE INVENTION

Described herein are compositions, methods, processes, kits and devices for the design, preparation, manufacture and/or formulation of circular polynucleotides.

In one aspect, a circular polynucleotide (circP) comprises a first region of linked nucleosides, a first flanking region located 5' relative to said first region of linked nucleosides and a second flanking region located 3' relative to said first region of linked nucleosides. The first and/or second flanking region may comprise a first region of polarity.

The circPs of the present invention may comprise at least one modification described herein such as, but not limited to, a structural and/or chemical modification. As a non-limiting example, the chemical modification may be a nucleotide and/or nucleoside modification including a nucleobase modification and/or a sugar modification. Nucleobases include, but are not limited to, cytosine, guanine, adenine, thymine and uracil. As another non-limiting example, the circPs of the present invention comprise at least two modifications. The modifications may be located on one or more nucleosides and/or backbone linkage between the nucleosides. In one aspect, at least one backbone linkage may be replaced with a phophorothioate linkage.

The first region of linked nucleosides of a circP described herein may encode a polypeptide of interest. The polypeptide of interest may be one known in the art and/or described herein. The circPs described herein may also comprise a second region of linked nucleosides which can encode a polypeptide of interest. The second region of linked nucleosides may comprise a third flanking region located 5' relative to the second region of linked nucleosides and a fourth flanking region located 3' relative to the second region of linked nucleosides. The third flanking region and/or the fourth flanking region may comprise a second region of polarity. The second region of polarity may be the same as the first region of polarity, have at least 20% identity with the first region of polarity or may be different than the first region of polarity.

The second region of linked nucleosides may be located within the first region of linked nucleosides. The first region of linked nucleosides and the second region of linked nucleosides may encode the same polypeptides of interest or different polypeptides of interest. In one aspect, the nucleic acid sequence of the first region of linked nucleosides shares at least 20% identity with the nucleic acid sequence of the second region of linked nucleosides.

The circPs of the present invention comprising at least a first region of linked nucleosides may comprise at least one sensor region. The sensor region may be located in any region of the circP including, but not limited to, the first region of linked nucleosides, the first flanking region and the second flanking region. If the circP comprises a second region of linked nucleosides the sensor region may be located in any region of the circP including, but not limited to, first region of linked nucleosides, the second region of linked nucleosides, the first flanking region, the second flanking region, the third flanking region and the fourth flanking region. The at least one sensor region located in the first region of linked nucleosides may be the same and/or different then the at least one sensor region in the second region of linked nucleosides. A non-limiting example of sensor regions include a miR sequence, a miR seed sequence, a miR binding site and a miR sequence without the seed.

Provided herein are compositions comprising the circPs of the present invention. In one aspect, the circP may be formulated where the formulation may be selected from, but is not limited to, nanoparticles, poly(lactic-co-glycolic acid) (PLGA) microspheres, lipidoid, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Compositions of the circPs of the present invention may include pharmaceutically acceptable excipients such as, but not limited to, a solvent, aqueous solvent, non-aqueous solvent, dispersion media, diluent, dispersion, suspension aid, surface active agent, isotonic agent, thickening or emulsifying agent, preservative, lipid, lipidoids liposome, lipid nanoparticle, core-shell nanoparticles, polymer, lipoplex, peptide, protein, cell, hyaluronidase, and mixtures thereof. A non-exhaustive listing of lipids which may be used with the circPs of the present invention include DLin-DMA, DLin-K-DMA, DLin-KC2-DMA, 98N12-5, C12-200, DLin-MC3-DMA, reLNP, PLGA, PEG, PEG-DMA and PEGylated lipids and mixtures thereof.

Provided herein are circular polynucleotide sponges (circ-SPs) comprising a first region of linked nucleosides, a first flanking region located 5' relative to the first region and a second flanking region located 3' relative to the first region. The circSP comprises at least one sensor region and the first flanking region or the second flanking region comprises a first region of polarity. The at least one sensor region may be selected from, but is not limited to, a miR sequence, a miR seed sequence, a miR binding site and a miR sequence without the seed.

In one aspect, the first region of linked nucleosides of the circSP does not encode a polypeptide of interest.

Provided herein are compositions comprising the circSPs of the present invention. In one aspect, the circSP may be formulated where the formulation may be selected from, but is not limited to, nanoparticles, poly(lactic-co-glycolic acid) (PLGA) microspheres, lipidoid, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Compositions of the circSPs of the present invention may include pharmaceutically acceptable excipients such as, but not limited to, a solvent, aqueous solvent, non-aqueous solvent, dispersion media, diluent, dispersion, suspension aid, surface active agent, isotonic agent, thickening or emulsifying agent, preservative, lipid, lipidoids liposome, lipid nanoparticle, core-shell nanoparticles, polymer, lipoplex, peptide, protein, cell, hyaluronidase, and mixtures thereof. A non-exhaustive listing of lipids which may be used with the circSPs of the present invention include DLin-DMA, DLin-K-DMA, DLin-KC2-DMA, 98N12-5, C12-200, DLin-MC3-DMA, reLNP, PLGA, PEG, PEG-DMA and PEGylated lipids and mixtures thereof.

Provided herein are methods for altering the level of a polypeptide of interest in a cell, tissue and/or organism comprising administering a composition comprising the circPs of the present invention. The method may be used to increase, decrease and/or maintain a desired level of a polypeptide of interest in a cell, tissue and/or organism.

In one embodiment, the method described herein may comprise decreasing the level of a polypeptide of interest in a cell, tissue and/or organism comprising administering a composition comprising the circSPs of the present invention.

Administration to a cell, tissue and/or organism includes, but is not limited to, prenatal administration, neonatal administration, postnatal administration, oral, by injection (e.g., intravenous, intraarterial, intraperotoneal, intradermal, subcutaneous and intramuscular), by ophthalmic administration and by intranasal administration. The circPs may be administered at a total daily dose between 1 ug and 150 ug and may be administered in one or more doses.

According to the present invention are provided chimeric polynucleotides encoding a polypeptide which may be circularized to form circular polynucleotides, where the chimeric polynucleotide having a sequence or structure comprising Formula I,

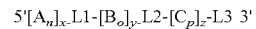  Formula I wherein:

each of A and B independently comprise a region of linked nucleosides;

C is an optional region of linked nucleosides;

at least one of regions A, B, or C is positionally modified, wherein said positionally modified region comprises at least two chemically modified nucleosides of one or more of the same nucleoside type of adenosine, thymidine, guanosine, cytidine, or uridine, and wherein at least two of the chemical modifications of nucleosides of the same type are different chemical modifications;

n, o and p are independently an integer between 15-1000;

x and y are independently 1-20;

z is 0-5;

L1 and L2 are independently optional linker moieties, said linker moieties being either nucleic acid based or non-nucleic acid based; and L3 is an optional conjugate or an optional linker moiety, said linker moiety being either nucleic acid based or non-nucleic acid based.

Also provided are methods of making and using the circular polynucleotides in research, diagnostics and therapeutics.

In another aspect, the invention features a chimeric polynucleotide (e.g., a circular polynucleotide) encoding a polypeptide, wherein the polynucleotide has a sequence including Formula II:

[A$_n$]-L$^1$-[B$_o$]  Formula II wherein each A and B independently includes any nucleoside (e.g., a nucleotide);

n and o are, independently 10 to 10,000, e.g., 10 to 1000 or 10 to 2000; and

L$^1$ has the structure of Formula III:

Formula III

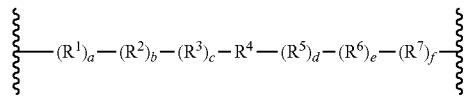

wherein a, b, c, d, e, and f are each, independently, 0 or 1;

each of R$^1$, R$^3$, R$^5$, and R$^7$, is, independently, selected from optionally substituted C$_1$-C$_6$ alkylene, optionally substituted C$_1$-C$_6$ heteroalkylene, O, S, and NR$^8$;

R$^2$ and R$^6$ are each, independently, selected from carbonyl, thiocarbonyl, sulfonyl, or phosphoryl;

R$^4$ is optionally substituted C$_1$-C$_{10}$ alkylene, optionally substituted C$_2$-C$_{10}$ alkenylene, optionally substituted C$_2$-C$_{10}$ alkynylene, optionally substituted C$_2$-C$_9$ heterocyclylene, optionally substituted C$_6$-C$_{12}$ arylene, optionally substituted C$_2$-C$_{100}$ polyethylene glycolene, or optionally substituted C$_1$-C$_{10}$ heteroalkylene, or a bond linking (R$^1$)$_a$—(R$^2$)$_b$—(R$^3$)$_c$ to (R$^5$)$_d$—(R$^6$)$_e$—(R$^7$)$_f$, wherein if a, b, c, d, e, and f are 0, R$^4$ is not a bond; and R$^8$ is hydrogen, optionally substituted C$_1$-C$_4$ alkyl, optionally substituted C$_2$-C$_4$ alkenyl, optionally substituted C$_2$-C$_4$ alkynyl, optionally substituted C$_2$-C$_6$ heterocyclyl, optionally substituted C$_6$-C$_{12}$ aryl, or optionally substituted C$_1$-C$_7$ heteroalkyl;

wherein L$^1$ is attached to [A$_n$] and [B$_o$] at the sugar of one of the nucleosides (e.g., at the 3' position of a five-membered sugar ring or 4' position of a six membered sugar ring of a nucleoside of [A$_n$] and the 5' position of a five-membered sugar ring or 6' position of a six membered sugar ring of a nucleoside of [B$_o$] or at the 5' position of a five-membered sugar ring or 6' position of a six membered sugar ring of a nucleoside of [A$_n$] and the 3' position of a five-membered sugar ring or 4' position of a six membered sugar ring of a nucleoside of [B$_o$]).

In some embodiments, at least one of [A$_n$] and [B$_o$] includes the structure of Formula IV or Formula XVIII:

Formula IV

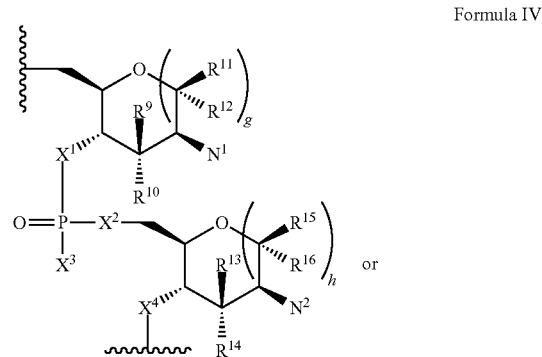

or

Formula XVIII

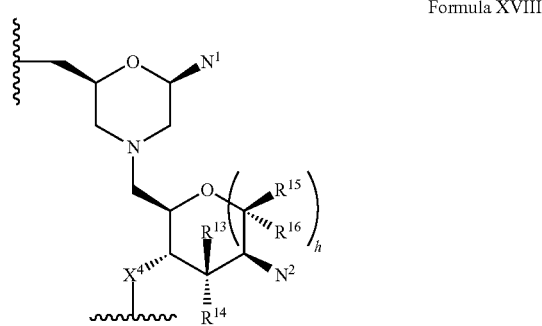

wherein each of N$^1$ and N$^2$ is independently a nucleobase;

each of R$^9$, R$^{10}$, R$^{11}$, R$^{12}$, R$^{13}$, R$^{14}$, R$^{15}$, and R$^{16}$ is, independently, H, halo, hydroxy, thiol, optionally substituted C$_1$-C$_6$ alkyl, optionally substituted C$_1$-C$_6$ heteroalkyl, optionally substituted C$_2$-C$_6$ heteroalkenyl, optionally substituted C$_2$-C$_6$ heteroalkynyl, optionally substituted amino, azido, or optionally substituted C$_6$-C$_{10}$ aryl;

each of g and h is, independently, 0 or 1;

each X$^1$ and X$^4$ is, independently, O, NH, or S;

each X$^2$ is independently O, NH, or S; and each X$^3$ is OH or SH, or a salt thereof.

In some embodiments, h is 0; R$^{13}$ is H; and R$^{14}$ is optionally substituted C$_1$-C$_6$ heteroalkyl.

In other embodiments, the optionally substituted C$_1$-C$_6$ heteroalkyl is methoxy.

In certain embodiments, X$^3$ is SH.

In another aspect, the invention features a circular polynucleotide encoding a polypeptide, wherein the polynucleotide has a sequence including Formula II:

[A$_n$]-L$^1$-[B$_o$]  Formula II wherein each A and B independently includes any nucleoside (e.g., a nucleotide);

n and o are, independently 10 to 10,000, e.g., 10 to 1000 or 10 to 2000; and

L$^1$ is a bond or has the structure of Formula III:

Formula III

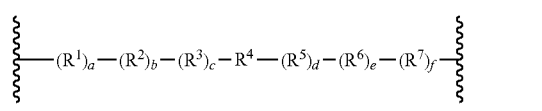

wherein a, b, c, d, e, and f are each, independently, 0 or 1;

each of $R^1$, $R^3$, $R^5$, and $R^7$, is, independently, selected from optionally substituted $C_1$-$C_6$ alkylene, optionally substituted $C_1$-$C_6$ heteroalkylene, O, S, and $NR^8$;

$R^2$ and $R^6$ are each, independently, selected from carbonyl, thiocarbonyl, sulfonyl, or phosphoryl;

$R^4$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_9$ heterocyclylene, optionally substituted $C_6$-$C_{12}$ arylene, optionally substituted $C_2$-$C_{10}$ polyethylene glycolene, or optionally substituted $C_1$-$C_{10}$ heteroalkylene, or a bond linking $(R^1)_a$—$(R^2)_b$—$(R^3)_c$ to $(R^5)_d$—$(R^6)_e$—$(R^7)_f$; and $R^8$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl;

wherein $L^1$ is attached to $[A_n]$ and $[B_o]$ at the sugar of one of the nucleosides (e.g., at the 3' position of a five-membered sugar ring or 4' position of a six membered sugar ring of a nucleoside of $[A_n]$ and the 5' position of a five-membered sugar ring or 6' position of a six membered sugar ring of a nucleoside of $[B_o]$ or at the 5' position of a five-membered sugar ring or 6' position of a six membered sugar ring of a nucleoside of $[A_n]$ and the 3' position of a five-membered sugar ring or 4' position of a six membered sugar ring of a nucleoside of $[B_o]$).

wherein at least one of $[A_n]$ or $[B_o]$ includes the structure of Formula IV or Formula XVIII:

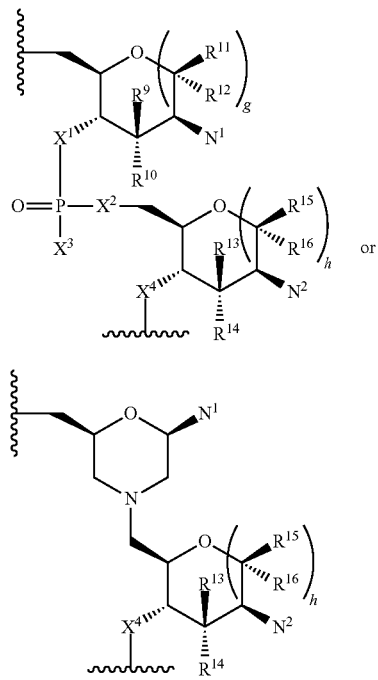

Formula IV

Formula XVIII wherein each of $N^1$ and $N^2$ is independently a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;
each $X^1$ and $X^4$ is, independently, O, NH, or S; and
each $X^2$ is independently O, NH, or S; and
each $X^3$ is OH or SH, or a salt thereof;
wherein, for Formula IV, at least one of $X^1$, $X^2$, or $X^4$ is NH or S.

In some embodiments, $X^1$ is NH. In other embodiments, $X^4$ is NH. In certain embodiments, $X^2$ is S.

In some embodiments, the polynucleotide includes: (a) a coding region; (b) a 5' UTR; and (c) a 3' UTR. In some embodiments, the polynucleotide further includes (d) at least one 5' cap structure. In other embodiments, the polynucleotide further includes (e) a poly-A tail.

In some embodiments, one of the coding region, the 5' UTR, the 3' UTR, the 5' cap structure, or the poly-A tail includes $[A_n]$-$L^1$-$[B_o]$.

In other embodiments, one of the coding region, the 5' UTR, the 3' UTR, the 5' cap structure, or the poly-A tail includes $[A_n]$ and another of the coding region, the 5' UTR, the 3' UTR, the 5' cap structure, or the poly-A tail includes $[B_o]$.

In some embodiments, the 5' UTR includes at least one Kozak sequence.

In certain embodiments, the polynucleotide includes at least one modified nucleoside (e.g., a nucleoside of Table 4).

In some embodiments, $R^4$ is optionally substituted $C_{2-9}$ heterocyclylene, for example, the heterocycle may have the structure:

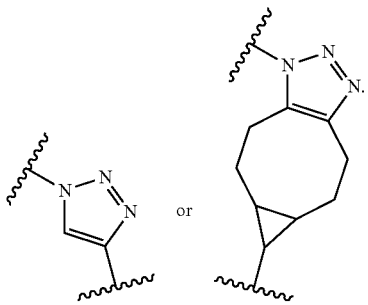 [SMILES: *c1cn(*)nn1 ; "or" ; *C1C2CCc3nnn(*)c3CCC12]

or

In some embodiments, $L^1$ includes the structure:

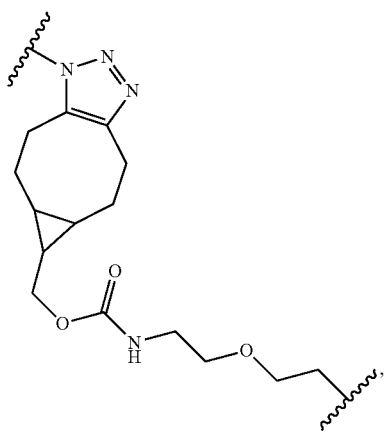

-continued

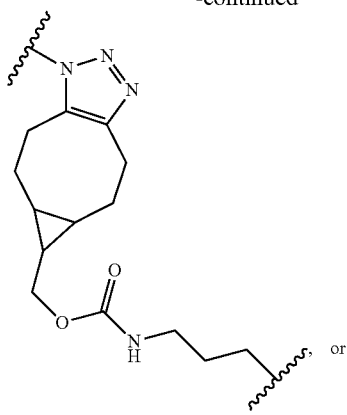

or

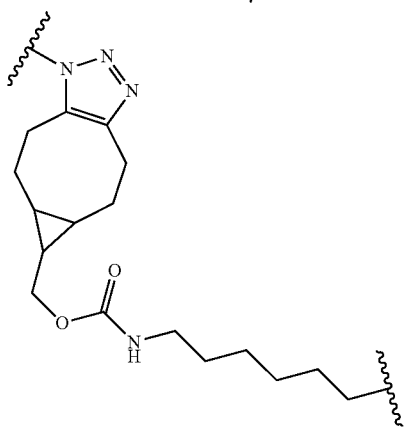

In certain embodiments, $L^1$ is attached to $[A_n]$ at the 3' position of a five-membered sugar ring or 4' position of a six membered sugar ring of one of the nucleosides and to $[B_o]$ at the 5' position of a five-membered sugar ring or 6' position of a six membered sugar ring of one of the nucleosides.

In some embodiments, the polynucleotide is circular.

In certain embodiments, the poly-A tail terminates in the structure of Formula XXI:

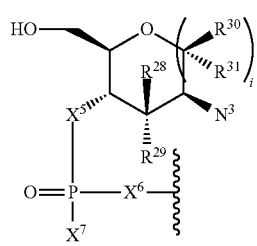

Formula XXI wherein $N^3$ is a nucleobase
each of $R^{28}$, $R^{29}$, $R^{30}$, and $R^{31}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;
i is 0 or 1;
$X^5$ is O, NH, or S; and
$X^6$ is o or S; and
$X^7$ is OH or SH, or a salt thereof.

In some embodiments, the structure of Formula XXI is:

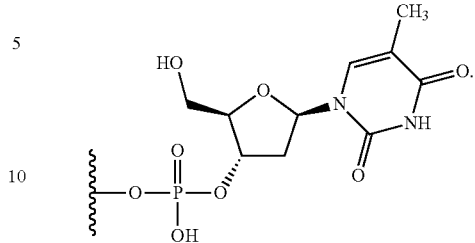

In other embodiments, the poly-A tail has 40 to 80 nucleosides (SEQ ID NO: 48).

In certain embodiments, the structure of Formula XXI is attached to two to four 2'-methoxy-adenosines and/or 2'-fluoro-adenosines.

In some embodiments, the poly-A tail terminates in the structure:

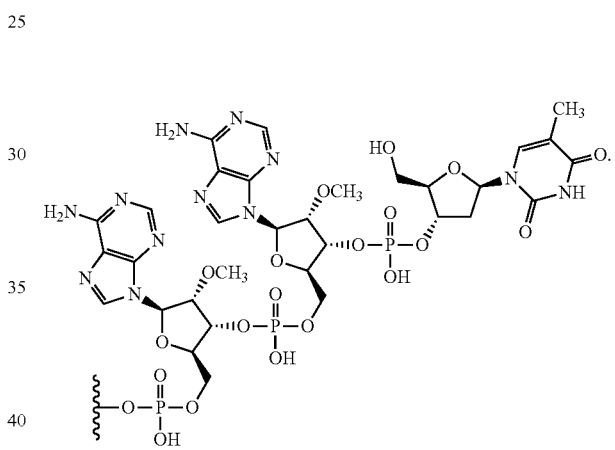

In other embodiments, the poly-A tail terminates in the structure:

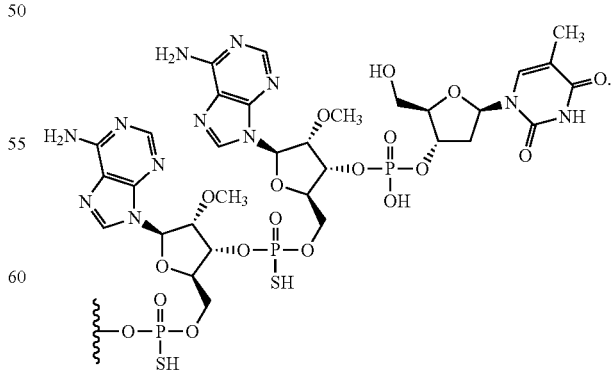

In certain embodiments, the poly-A tail includes the structure:

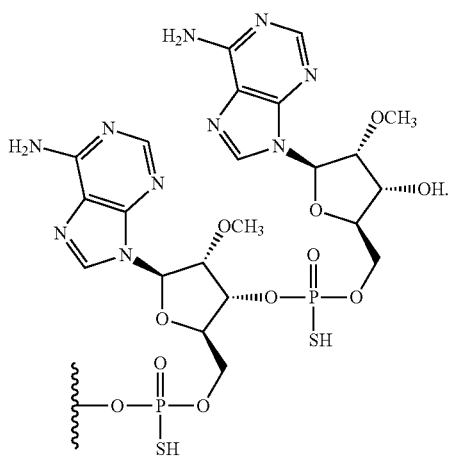 [SMILES: *OP(=O)(S)OC[C@H]1O[C@@H](n2cnc3c(N)ncnc32)[C@H](OC)[C@@H]1OP(=O)(S)OC[C@H]1O[C@@H](n2cnc3c(N)ncnc32)[C@H](OC)[C@@H]1O]

In another aspect, the invention features a method of producing a composition including a chimeric polynucleotide encoding a polypeptide, wherein the polynucleotide includes the structure of Formula Va or Vb:

Formula Va

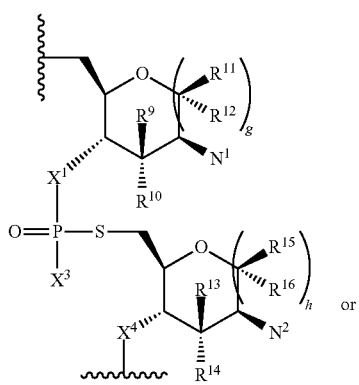

Formula Vb

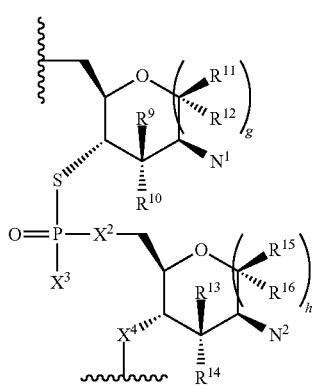

This method includes reacting (e.g., under alkylating conditions) a compound having the structure of Formula VIa or VIb:

Formula VIa

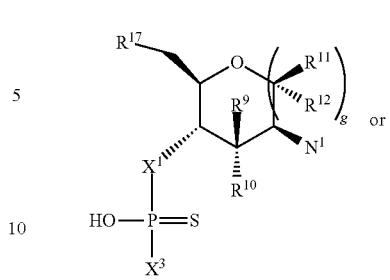

or

Formula VIb

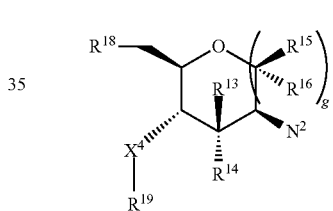

with a compound having the structure of Formula VII:

Formula VII

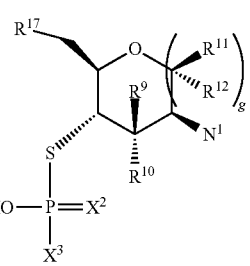

wherein each of $N^1$ and $N^2$ is, independently, a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, O, NH, or S;

each $X^2$ is O or S; and each $X^3$ is independently OH or SH, or a salt thereof;

each of $R^{17}$ and $R^{19}$ is, independently, a region of linked nucleosides; and $R^{18}$ is a halogen, to produce a composition comprising a chimeric polynucleotide encoding a polypeptide, wherein the polynucleotide comprises the structure of Formula Va or Vb.

In another aspect, the invention features a method of producing a composition including a chimeric polynucleotide encoding a polypeptide, wherein the polynucleotide includes the structure of Formula VIIIa or VIIIb:

Formula VIIIa

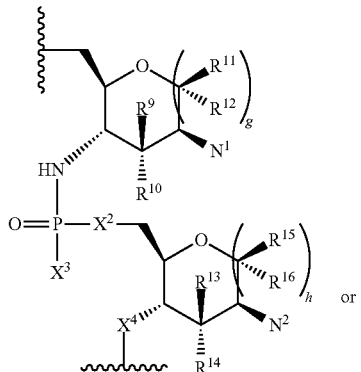

Formula VIIIb

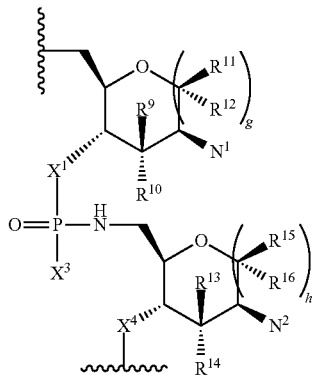

This method includes reacting (e.g., under Staudinger reaction conditions) a compound having the structure of Formula IXa or IXb:

Formula IXa

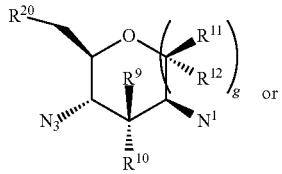

Formula IXb

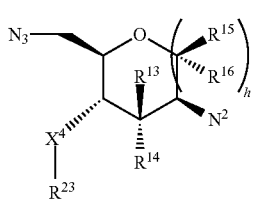

with a compound having the structure of Formula Xa or Xb:

Formula Xa

Formula Xb wherein each of $N^1$ and $N^2$ is, independently, a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^4$ is, independently, O, NH, or S; and each $X^1$ and $X^2$ is independently O or S;

each $X^3$ is independently OH, SH, or a salt thereof;

each of $R^{20}$ and $R^{23}$ is, independently, a region of linked nucleosides; and each of $R^{21}$ and $R^{22}$ is, independently, optionally substituted $C_1$-$C_6$ alkoxy;

to produce a composition comprising a circular polynucleotide encoding a polypeptide, wherein the polynucleotide comprises the structure of Formula VIIIa or VIIIb.

In another aspect, the invention features a method of producing a composition including a circular polynucleotide encoding a polypeptide, wherein the polynucleotide includes the structure of Formula XIa, XIb, XIIa, or XIIb:

Formula XIa

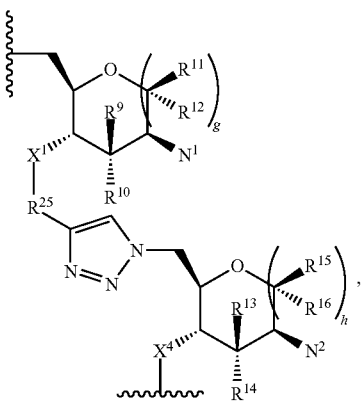

-continued
Formula XIb
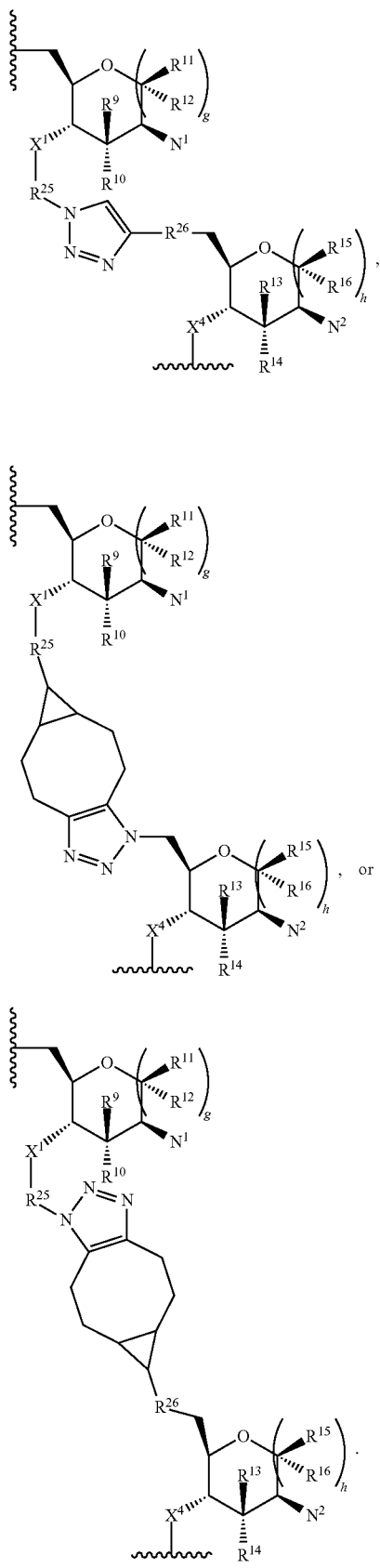
Formula XIIa
Formula XIIb
This method includes reacting (e.g., under [3+2] cycloaddition conditions in the presence or absence of a copper source) a compound having the structure of Formula XIIIa, XIIIb, XIVa, or XIVb:
Formula XIIIa
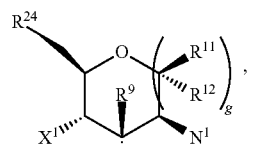
Formula XIIIb
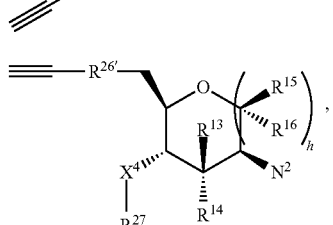
Formula XIVa
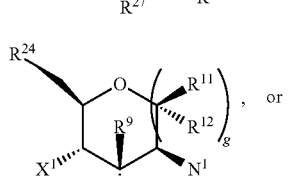, or
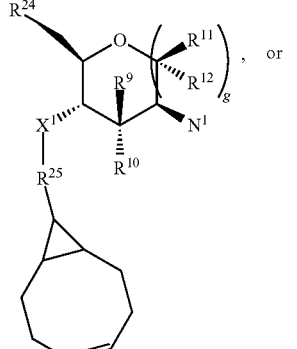
Formula XIVb
with a compound having the structure of Formula XVa or XVb:
Formula XVa
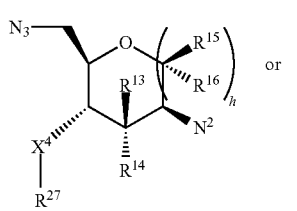 or
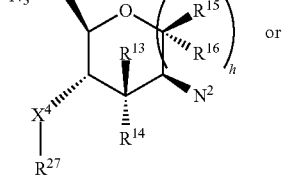

-continued

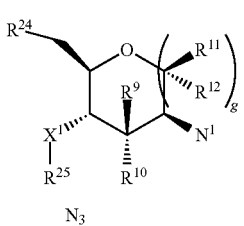

Formula XVb wherein each of $N^1$ and $N^2$ is, independently, a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, absent, O, NH, or S or a salt thereof;

each of $R^{24}$ and $R^{27}$ is, independently, a region of linked nucleosides; and each of $R^{25}$, $R^{25'}$, $R^{26}$, and $R^{26'}$ is absent or optionally substituted $C_1$-$C_6$ alkylene or optionally substituted $C_1$-$C_6$ heteroalkylene or $R^{25'}$ or $R^{26'}$ and the alkynyl group together form optionally substituted cycloalkynyl;

to produce a composition comprising a circular polynucleotide encoding a polypeptide, wherein the polynucleotide comprises the structure of Formula XIa, XIb, XIIa, or XIIb.

In another aspect, the invention features a method of producing a composition including a circular polynucleotide encoding a polypeptide, wherein the polynucleotide has a sequence including Formula II:

$$[A_n]\text{-}L^1\text{-}[B_o],\qquad\text{Formula II}$$

This method includes reacting (e.g., under [3+2] cycloaddition conditions in the presence or absence of a copper source) a compound having the structure of Formula XVI:

$$[A_n]\text{-}(R^1)_a\text{—}(R^2)_b\text{—}(R^3)_c\text{—}N_3\qquad\text{Formula XVI}$$

with a compound having the structure of Formula XVII:

$$R^{27}\text{—}(R^5)_d\text{—}(R^6)_e\text{—}(R^7)_f\text{—}[B_o]\qquad\text{Formula XVII}$$

wherein each A and B is independently any nucleoside;
n and o are, independently 10 to 10,000, e.g., 10 to 1000 or 10 to 2000; and
$L^1$ has the structure of Formula III:

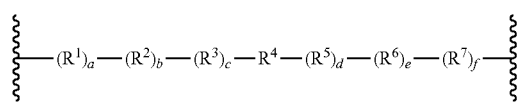

Formula III wherein a, b, c, d, e, and f are each, independently, 0 or 1;

$R^1$, $R^3$, $R^5$, and $R^7$ each, independently, is selected from optionally substituted $C_1$-$C_6$ alkylene, optionally substituted $C_1$-$C_6$ heteroalkylene, O, S, and $NR^8$;

$R^2$ and $R^6$ are each, independently, selected from carbonyl, thiocarbonyl, sulfonyl, or phosphoryl;

$R^4$ is an optionally substituted triazolene; and $R^8$ is hydrogen, optionally substituted $C_1$-$C_4$ alkyl, optionally substituted $C_3$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl; and $R^{27}$ is an optionally substituted $C_2$-$C_3$ alkynyl or an optionally substituted $C_8$-$C_{12}$ cycloalkynyl, wherein $L^1$ is attached to $[A_n]$ and $[B_o]$ at the sugar of one of the nucleosides;

to produce a composition comprising a circular polynucleotide encoding a polypeptide, wherein the polynucleotide has a sequence comprising Formula II.

In some embodiments, the optionally substituted triazolene has the structure:

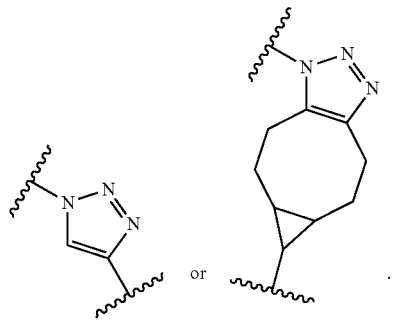 [SMILES: *c1cn(*)nn1 ; *C1C2CCc3nnn(*)c3CCC12]

In another aspect, the invention features a method of producing a composition comprising a circular polynucleotide encoding a polypeptide, wherein the polynucleotide comprises the structure of Formula XVIII:

Formula XVIII

[structure image]

the method comprising reacting (e.g., under reductive amination conditions) a compound having the structure of Formula XIX:

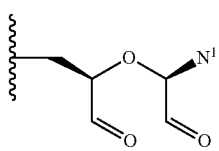

Formula XIX with a compound having the structure of Formula XX:

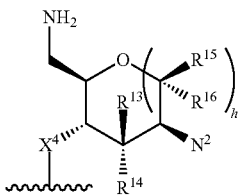

Formula XX wherein each of $N^1$ and $N^2$ is, independently, a nucleobase;

each of $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

h is 0 or 1; and $X^4$ is O, NH, or S;

to produce a composition comprising a circular polynucleotide encoding a polypeptide, wherein the polynucleotide comprises the structure of Formula XVIII.

In some embodiments, the method includes producing a compound of Formula XIX from a compound of Formula XXI:

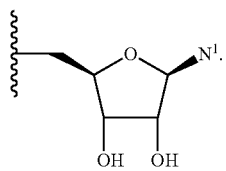

Formula XIX

The details of various embodiments of the invention are set forth in the description below. Other features, objects, and advantages of the invention will be apparent from the description and the drawings, and from the claims.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

Figure 1:
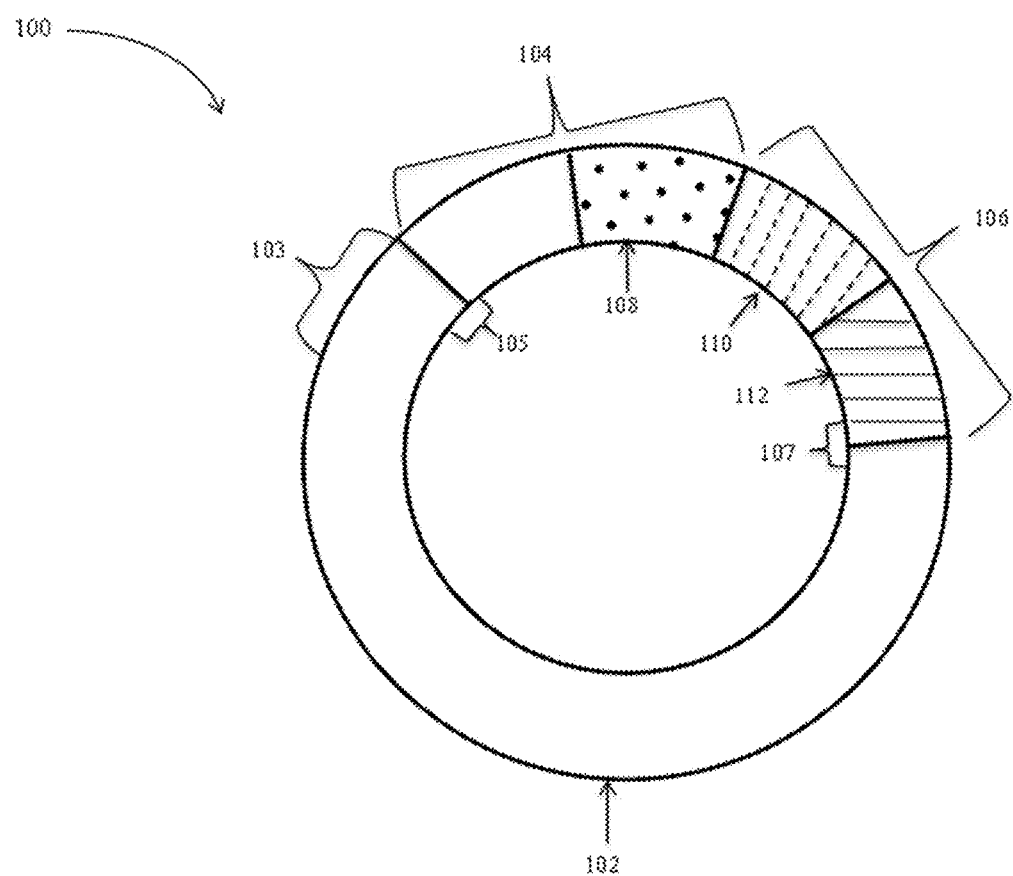
FIG. 1 is a schematic of a circular primary construct of the present invention.

It is of great interest in the fields of therapeutics, diagnostics, reagents and for biological assays to be able to synthesize, modify, and utilize circular polynucleotides (circP).

Described herein are compositions and methods for the design, preparation, manufacture and/or formulation of circular polynucleotides. As used herein, "circular polynucleotides" or "circP" means a single stranded circular polynucleotide which acts substantially like, and has the properties of, an RNA. The term "circular" is also meant to encompass any secondary or tertiary configuration of the circP.

The circPs of the present invention which encode at least one polypeptide of interest are known as circular RNAs or circRNA. As used herein, "circular RNA" or "circRNA" means a circular polynucleotide that can encode at least one polypeptide of interest. It is well known that a nucleic acid, e.g., a messenger ribonucleic acid (mRNA), may be delivered inside a cell, whether in vitro, in vivo, in situ or ex vivo, to cause intracellular translation of the nucleic acid and production of an encoded polypeptide of interest. Because of their unique closed circular structure, circRNAs are more resistant to the degradation by exonuclease and have a longer half-life than their corresponding linear counterparts. As such, it is desirable to develop new and improved circRNAs which are useful in the production of polypeptides of interest.

Described herein are compositions (including pharmaceutical compositions) and methods for the design, preparation, manufacture and/or formulation of circRNA which may encode one or more polypeptides of interest. Also provided are systems, processes, devices and kits for the selection, design and/or utilization of circRNA to modulate cellular processes where no polypeptide is produced.

The circPs of the present invention which comprise at least one sensor sequence and do not encode a polypeptide of interest are known as circular sponges or circSP. As used herein, "circular sponges," "circular polynucleotide sponges" or "circSP" means a circular polynucleotide which comprises at least one sensor sequence and does not encode a polypeptide of interest. As used herein, "sensor sequence" means a receptor or pseudo-receptor for endogenous nucleic acid binding molecules. Non-limiting examples of sensor sequences include, microRNA binding sites, microRNA seed sequences, microRNA binding sites without the seed sequence, transcription factor binding sites and artificial binding sites engineered to act as pseudo-receptors and portions and fragments thereof.

The circPs of the present invention which comprise at least one sensor sequence and encode at least one polypeptide of interest are known as circular RNA sponges or circRNA-SP. As used herein, "circular RNA sponges" or "circRNA-SP" means a circular polynucleotide which comprises at least one sensor sequence and at least one region encoding at least one polypeptide of interest. A circRNA sponge comprises a single-stranded non-coding polynucleotide with repeat copies of at least one specific microRNA binding site to hold microRNA molecules of interest and a region of linked nucleosides encoding at least one polypeptide of interest. This artificial microRNA inhibitor, when expressed in a cell, would decrease the cellular level of the microRNA of interest. The circP, circSP or circRNA-SP of the invention may comprise one or more microRNA target sequences or binding sites for microRNA molecules of interest. In one aspect, circPs, circSPs or circRNA-SPs that act as sponges are able to regulate expression of genes which are regulated by microRNAs.

In some embodiments, the circular polynucleotides of the present invention, including circRNA, circSP and circRNA-SP, comprise at least one modification, as described herein, in order to avoid at least one of the deficiencies of the linear polynucleotides described and/or known in the art. Hence, in some embodiments, the circP, circRNA, circSP and circRNA-SP of the present invention which comprise at least one modification are referred to as modified circular polynucleotides or modified circP, modified circular RNA or modified circRNA, modified circular sponges or modified circSP and modified circular RNA sponges or modified circRNA-SP.

The use of modified polynucleotides, particularly modified linear mRNA, in the fields of antibodies, viruses, veterinary applications and a variety of in vivo settings have been explored previously and these studies are disclosed in for example, co-owned U.S. provisional patent application Ser. Nos. 61/470,451 filed Mar. 31, 2011 teaching in vivo applications of mmRNA; 61/517,784 filed on Apr. 26, 2011 teaching engineered nucleic acids for the production of antibody polypeptides; 61/519,158 filed May 17, 2011 teaching veterinary applications of mmRNA technology; 61/533,537 filed on Sep. 12, 2011 teaching antimicrobial applications of mmRNA technology; 61/533,554 filed on Sep. 12, 2011 teaching viral applications of mmRNA technology, 61/542,533 filed on Oct. 3, 2011 teaching various chemical modifications for use in mmRNA technology; 61/570,690 filed on Dec. 14, 2011 teaching mobile devices for use in making or using mmRNA technology; 61/570,708 filed on Dec. 14, 2011 teaching the use of mmRNA in acute care situations; 61/576,651 filed on Dec. 16, 2011 teaching terminal modification architecture for mmRNA; 61/576,705 filed on Dec. 16, 2011 teaching delivery methods using lipidoids for mmRNA; 61/578,271 filed on Dec. 21, 2011 teaching methods to increase the viability of organs or tissues using mmRNA; 61/581,322 filed on Dec. 29, 2011 teaching mmRNA encoding cell penetrating peptides; and 61/631,729 filed on Jan. 10, 2012 teaching methods of using mmRNA for crossing the blood brain barrier; all of which are herein incorporated by reference in their entirety.

Provided herein, in part, are circP, circRNA, circSP and circRNA-SP which may comprise features to improve one or more of the stability and/or clearance in tissues, receptor uptake and/or kinetics, cellular access by the compositions, engagement with translational machinery, half-life, translation efficiency, immune evasion, protein production capacity, secretion efficiency (when applicable), accessibility to circulation, protein half-life and/or modulation of a cell's status, function and/or activity. Also provided herein, in part, are circPs, circRNA and circRNA-SP which encode at least one polypeptide of interest and may be capable of being translated to produce the encoded polypeptide of interest in vitro, in vivo, in situ or ex vivo.

I. Composition of the Invention (circP, circRNA, circSP and circRNA-SP)

The present invention provides circP, circRNA, circSP and circRNA-SP. The circP, circRNA, circSP and circRNA-SP of the present invention may contain modifications described herein and/or known in the art, but it is not required that the circP, circRNA, circSP and circRNA-SP contain modifications.

In one embodiment, the circP, circRNA or circRNA-SP of the present invention may act as a messenger RNA (mRNA). As used herein, the term "messenger RNA" (mRNA) means a polynucleotide which encodes a polypeptide of interest and which is capable of being translated to produce the encoded polypeptide of interest in vitro, in vivo, in situ or ex vivo.

circP, circRNA, circSP and circRNA-SP Architecture

The circP, circRNA, and circRNA-SP of the present invention are distinguished from wild type linear polynucleotides in their functional and/or structural design features which serve to, as evidenced herein, overcome existing problems of effective polypeptide production using nucleic acid-based methodologies.

In one embodiment, the circP, circRNA, circSP and circRNA-SP may comprise at least one flanking region which may comprise a region of polarity and/or an untranslated region. As a non-limiting example, the region of polarity may be an internal ribosomal entry site (IRES).

In one embodiment, the circP, circRNA, and circRNA-SP may comprise at least one region of linked nucleosides comprising at least one open reading frame (ORF) encoding a polypeptide of interest. The circP, circRNA, and circRNA-SP may also comprise a region of polarity and/or an untranslated region.

In one embodiment, one or more structural and/or chemical modifications or alterations described herein may be incorporated into the circPs, circSPs, circRNAs, and circRNA-SPs. These modifications and/or alteration can impart useful properties to the polynucleotide including, in some embodiments, the lack of a substantial induction of the innate immune response of a cell into which the polynucleotide is introduced. As used herein, a "structural" feature or modification is one in which two or more linked nucleotides are inserted, deleted, duplicated, inverted or randomized in a circPs, circSPs, circRNAs or circRNA-SPs without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCG". Here, the dinucleotide "CC" has been inserted, resulting in a structural modification to the polynucleotide.

Generally, the shortest length of an open reading frame (ORF) of the circPs, circRNAs, and circRNA-SPs of the present invention can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids. Examples of dipeptides that the polynucleotide sequences can encode or include, but are not limited to, carnosine and anserine.

Generally, the length of the ORF encoding the polypeptide of interest of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides). As used herein, the ORF may be referred to as a "coding region" or "region encoding" or simply the ORF.

In some embodiments, the circPs, circSPs, circRNAs, and circRNA-SPs includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

In one embodiment, the circPs, circSPs, circRNAs, and circRNA-SPs of the present invention may comprise at least one flanking region. The flanking regions may range independently from 15-2000 nucleotides in length (e.g., greater than 30, 40, 45, 50, 55, 60, 70, 80, 90, 100, 120, 140, 160, 180, 200, 250, 300, 350, 400, 450, 500, 600, 700, 800, 900, 1000, 1100, 1200, 1300, 1400, 1500, 1600, 1700, 1800 and 1900 nucleotides or at least 30, 40, 45, 50, 55, 60, 70, 80, 90, 100, 120, 140, 160, 180, 200, 250, 300, 350, 400, 450, 500, 600, 700, 800, 900, 1000, 1100, 1200, 1300, 1400, 1500, 1600, 1700, 1800 and 1900 nucleotides).

In another embodiment, the circPs, circSPs, circRNAs, and circRNA-SPs of the present invention may comprise a tailing sequence. The tailing sequence may range from 1 to 500 nucleotides in length (e.g., at least 30, 40, 50, 60, 70, 80, 90, 120, 140, 160, 180, 200, 250, 300, 350, 400, 450, or 500 nucleotides). Where the tailing region is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

In one embodiment, the circPs, circSPs, circRNAs, and circRNA-SPs may comprise a first and/or second operational region. The first and/or second operational regions may range from 3 to 40, e.g., 5-30, 10-20, 15, or at least 4, or 30 or fewer nucleotides in length and may comprise, in addition to a Start and/or Stop codon, one or more signal and/or restriction sequences.

In some embodiments, the circular polynucleotides of the invention have a sequence comprising Formula II:

[A$_n$]-L$^1$-[B$_o$]  Formula II

wherein each A and B independently includes any nucleoside (e.g., a nucleotide);

n and o are, independently 10 to 10,000, e.g., 10 to 1000 or 10 to 2000; and

L$^1$ has the structure of Formula III:

Formula III

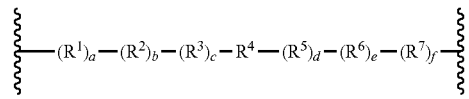

wherein a, b, c, d, e, and f are each, independently, 0 or 1;

each of R$^1$, R$^3$, R$^5$, and R$^7$, is, independently, selected from optionally substituted C$_1$-C$_6$ alkylene, optionally substituted C$_1$-C$_6$ heteroalkylene, O, S, and NR$^8$;

R$^2$ and R$^6$ are each, independently, selected from carbonyl, thiocarbonyl, sulfonyl, or phosphoryl;

R$^4$ is optionally substituted C$_1$-C$_{10}$ alkylene, optionally substituted C$_2$-C$_{10}$ alkenylene, optionally substituted C$_2$-C$_{10}$ alkynylene, optionally substituted C$_2$-C$_9$ heterocyclylene, optionally substituted C$_6$-C$_{12}$ arylene, optionally substituted C$_2$-C$_{100}$ polyethylene glycolene, or optionally substituted C$_1$-C$_{10}$ heteroalkylene, or a bond linking (R$^1$)$_a$—(R$^2$)$_b$—(R$^3$)$_c$ to (R$^5$)$_d$—(R$^6$)$_e$—(R$^7$)$_f$, wherein if a, b, c, d, e, and f are 0, R$^4$ is not a bond; and R$^8$ is hydrogen, optionally substituted C$_1$-C$_4$ alkyl, optionally substituted C$_2$-C$_4$ alkenyl, optionally substituted C$_2$-C$_4$ alkynyl, optionally substituted C$_2$-C$_6$ heterocyclyl, optionally substituted C$_6$-C$_{12}$ aryl, or optionally substituted C$_1$-C$_7$ heteroalkyl;

wherein L$^1$ is attached to [A$_n$] and [B$_o$] at the sugar of one of the nucleosides (e.g., at the 3' position of a sugar of a nucleoside of [A$_n$] and the 5' position of a sugar of a nucleoside of [B$_o$] or at the 5' position of a sugar of a nucleoside of [A$_n$] and the 3' position of a sugar of a nucleoside of [B$_o$]).

In other embodiments, the circular polynucleotides of the invention have a sequence comprising Formula II:

[A$_n$]-L$^1$-[B$_o$]  Formula II

wherein each A and B independently includes any nucleoside (e.g., a nucleotide);

n and o are, independently 10 to 10,000, e.g., 10 to 1000 or 10 to 2000; and

L$^1$ is a bond or has the structure of Formula III:

Formula III

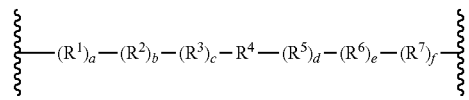

wherein a, b, c, d, e, and f are each, independently, 0 or 1;

each of $R^1$, $R^3$, $R^5$, and $R^7$, is, independently, selected from optionally substituted $C_1$-$C_6$ alkylene, optionally substituted $C_1$-$C_6$ heteroalkylene, O, S, and $NR^8$;

$R^2$ and $R^6$ are each, independently, selected from carbonyl, thiocarbonyl, sulfonyl, or phosphoryl;

$R^4$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_9$ heterocyclylene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^1)_a$—$(R^2)_b$—$(R^3)_c$ to $(R^5)_d$—$(R^6)_e$—$(R^7)_f$; and $R^8$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl;

wherein $L^1$ is attached to $[A_n]$ and $[B_o]$ at the sugar of one of the nucleosides (e.g., at the 3' position of a sugar of a nucleoside of $[A_n]$ and the 5' position of a sugar of a nucleoside of $[B_o]$ or at the 5' position of a sugar of a nucleoside of $[A_n]$ and the 3' position of a sugar of a nucleoside of $[B_o]$);

wherein at least one of $[A_n]$ or $[B_o]$ comprises the structure of Formula IV or Formula XVII:

Formula IV

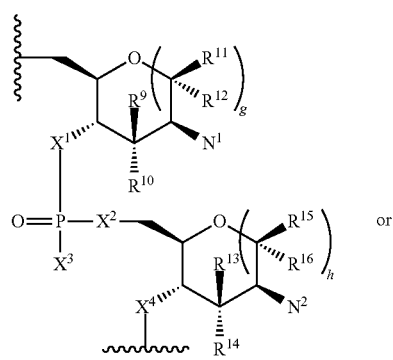

or

Formula XVIII

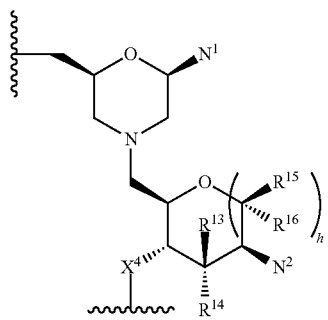

wherein each of $N^1$ and $N^2$ is independently a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, O, NH, or S; and each $X^2$ is independently O, NH, or S; and each $X^3$ is OH or SH, or a salt thereof;

wherein, for Formula IV, at least one of $X^1$, $X^2$, or $X^4$ is NH or S.

For example, in some embodiments, the circular polynucleotides of the invention include the structure:

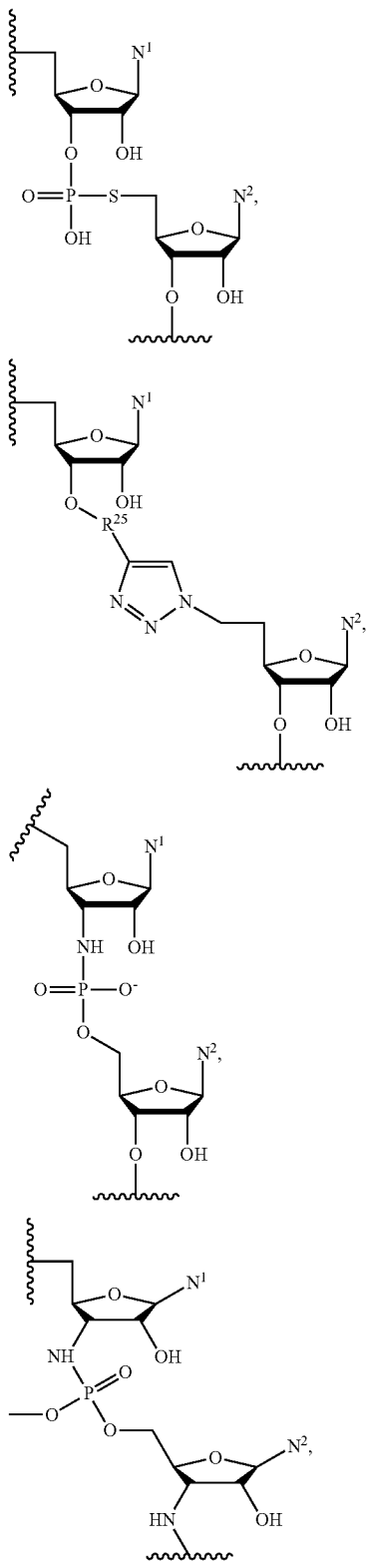

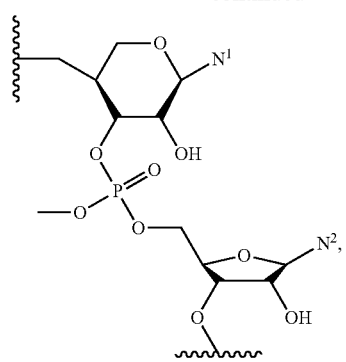
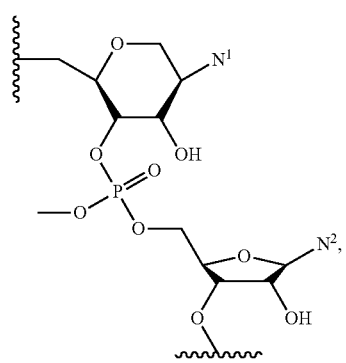
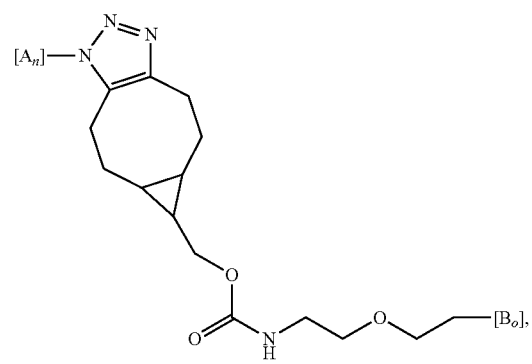
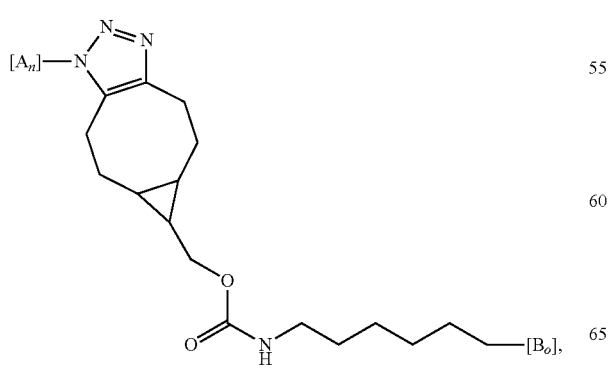
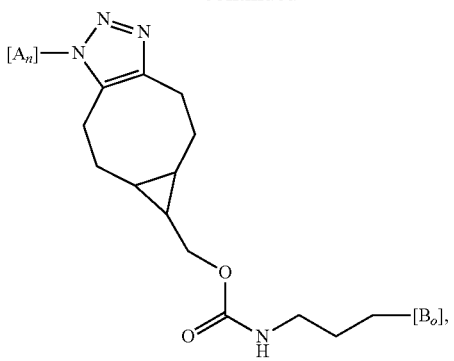
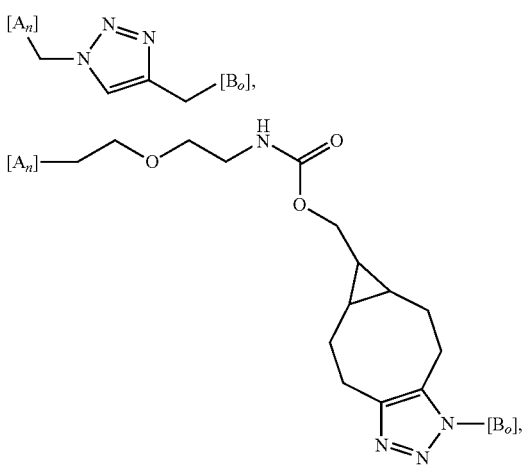
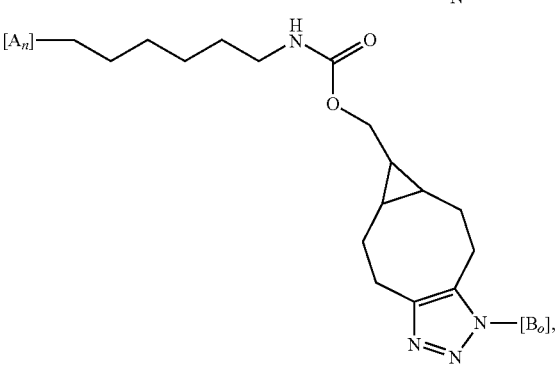
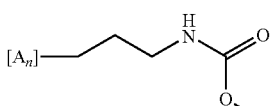
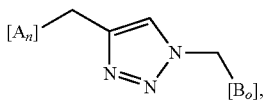

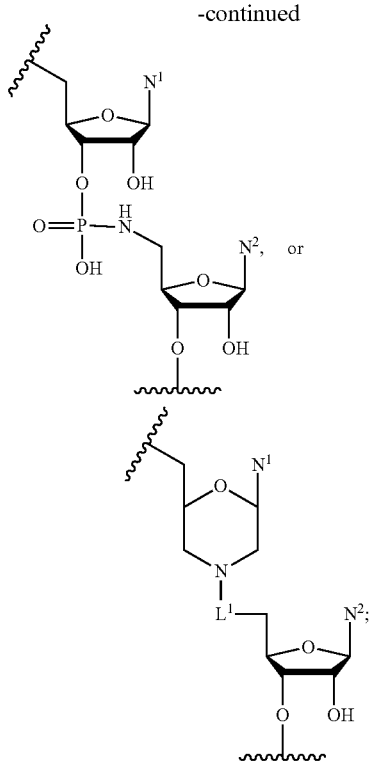

wherein $R^{25}$ is absent, optionally substituted $C_1$-$C_6$ alkylene, or optionally substituted $C_1$-$C_6$ heteroalkylene.

In some embodiments, the presence of a hydroxyl at the 2' position of the sugar allows for increased ribosomal recognition.

In certain embodiments, of the circular polynucleotides of the invention one of the coding region, the 5' UTR, the 3' UTR, the 5' cap structure, or the poly-A tail comprises $[A_n]$-$L^1$-$[B_o]$.

In other embodiments, of the circular polynucleotides of the invention one of the coding region, the 5' UTR, the 3' UTR, the 5' cap structure, or the poly-A tail comprises $[A_n]$ and another of the coding region, the 5' UTR, the 3' UTR, the 5' cap structure, or the poly-A tail comprises $[B_o]$. For example, in some embodiments, the poly A tail comprises one of $[A_n]$ or $[B_o]$ and the 3' UTR comprises the other. In other embodiments, the 5' cap structure comprises one of $[A_n]$ or $[B_o]$ and the 5' UTR comprises the other.

In some embodiments, the 5' UTR includes at least one Kozak sequence.

Conjugates and Combinations circPs, circRNAs, and circRNA-SPs of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug. In one embodiment, the circPs, circRNAs, and circRNA-SPs may be conjugated to other polynucleotides in order to further enhance protein production.

Conjugation may result in increased stability and/or half life and may be particularly useful in targeting the circPs, circSPs, circRNAs, and circRNA-SPs to specific sites in the cell, tissue or organism.

According to the present invention, the circPs, circSPs, circRNAs, and circRNA-SPs may be administered with one or more of RNAi agents, siRNAs, shRNAs, miRNAs, miRNA binding sites, antisense RNAs, ribozymes, catalytic DNA, tRNA, RNAs that induce triple helix formation, aptamers or vectors, and the like.

In one embodiment, the circPs, circRNAs, and circRNA-SPs may encode one or more of RNAi agents, siRNAs, shRNAs, miRNAs, miRNA binding sites, antisense RNAs, ribozymes, catalytic DNA, tRNA, RNAs that induce triple helix formation, aptamers or vectors, and the like.

In another embodiment, the circPs, circRNAs, and circRNA-SPs may comprise one or more of RNAi agents, siRNAs, shRNAs, miRNAs, miRNA binding sites, antisense RNAs, ribozymes, catalytic DNA, tRNA, RNAs that induce triple helix formation, aptamers or vectors, and the like.

Bifunctional Circular Polynucleotides

In one embodiment, the circP, circSP, circRNAs or circRNA-SPs of the invention are bifunctional. As the name implies, bifunctional circPs, bifunctional circSP, bifunctional circRNAs or bifunctional circRNA-SPs are those having or capable of at least two functions. These molecules may also by convention be referred to as multi-functional.

The multiple functionalities of bifunctional circPs, bifunctional circRNAs or bifunctional circRNA-SPs may be encoded by the RNA (the function may not manifest until the encoded product is translated) or the multiple functionality may be a property of the circP, circSP, circRNAs or circRNA-SPs itself. It may be structural or chemical. Bifunctional circP, circSP, circRNAs or circRNA-SPs may comprise a function that is covalently or electrostatically associated with the circP, circSP, circRNAs or circRNA-SPs. Further, the two functions may be provided in the context of a complex of a circP, circSP, circRNAs or circRNA-SPs and another molecule.

In one embodiment, the bifunctional circP, bifunctional circSP, bifunctional circRNAs or bifunctional circRNA-SPs may comprise at least one modification.

Bifunctional circP, bifunctional circRNAs or bifunctional circRNA-SPs may encode peptides which are anti-proliferative. These peptides may be linear, cyclic, constrained or random coil. They may function as aptamers, signaling molecules, ligands or mimics or mimetics thereof. Anti-proliferative peptides may, as translated, be from 3 to 50 amino acids in length. They may be 5-40, 10-30, or approximately 15 amino acids long. They may be single chain, multichain or branched and may form complexes, aggregates or any multi-unit structure once translated.

Noncoding Regions

As described herein, provided are circPs, circSPs, circRNAs or circRNA-SPs which may have regions which are partially or substantially not translatable, e.g., having a noncoding region. Such noncoding regions may located in any region of the circPs, circSPs, circRNAs or circRNA-SPs including, but not limited to, the first region of linked nucleosides, the sensor region, the spacer and/or the flanking regions. The noncoding regions may located in more than one region of the circP, circSP, circRNA or circRNA-SP.

Such molecules are generally not translated, but for circPs, circSP, circRNAs or circRNA-SPs they can exert an effect on protein production by one or more of binding to and sequestering one or more translational machinery components such as a ribosomal protein or a transfer RNA (tRNA), thereby effectively reducing protein expression in the cell or modulating one or more pathways or cascades in a cell which in turn alters protein levels. The circPs, circSPs, circRNAs or circRNA-SPs may contain or encode one or more long noncoding RNA (lncRNA, or lincRNA), a small nucleolar RNA (sno-RNA), micro RNA (miRNA), small interfering RNA (siRNA) or Piwi-interacting RNA (piRNA) and/or a portion thereof.

Polypeptides of Interest

According to the present invention, the circP, circRNA or circRNA-SP may be designed to encode one or more polypeptides of interest or fragments thereof. A polypeptide of interest may include, but is not limited to, whole polypeptides, a plurality of polypeptides or fragments of polypeptides, which independently may be encoded by one or more nucleic acids, a plurality of nucleic acids, fragments of nucleic acids or variants of any of the aforementioned. As used herein, the term "polypeptides of interest" refer to any polypeptide which is selected to be encoded in the primary construct of the present invention. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to polypeptide sequences means the corresponding sequence of other species having substantial identity to a second sequence of a second species.

"Analogs" is meant to include polypeptide variants which differ by one or more amino acid alterations, e.g., substitutions, additions or deletions of amino acid residues that still maintain one or more of the properties of the parent or starting polypeptide.

The present invention contemplates several types of compositions which are polypeptide based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As such, circP, circRNA or circRNA-SP encoding polypeptides containing substitutions, insertions and/or additions, deletions and covalent modifications with respect to reference sequences, in particular the polypeptide sequences disclosed herein, are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

"Features" when referring to polypeptides are defined as distinct amino acid sequence-based components of a molecule. Features of the polypeptides encoded by the circP, circRNA or circRNA-SP of the present invention include surface manifestations, local conformational shape, folds, loops, half-loops, domains, half-domains, sites, termini or any combination thereof.

As used herein when referring to polypeptides the term "surface manifestation" refers to a polypeptide based component of a protein appearing on an outermost surface.

As used herein when referring to polypeptides the term "local conformational shape" means a polypeptide based structural manifestation of a protein which is located within a definable space of the protein.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to polypeptides the term "loop" refers to a structural feature of a polypeptide which may serve to reverse the direction of the backbone of a peptide or polypeptide. Where the loop is found in a polypeptide and only alters the direction of the backbone, it may comprise four or more amino acid residues. Oliva et al. have identified at least 5 classes of protein loops (J. Mol Biol 266 (4): 814-830; 1997). Loops may be open or closed. Closed loops or "cyclic" loops may comprise 2, 3, 4, 5, 6, 7, 8, 9, 10 or more amino acids between the bridging moieties. Such bridging moieties may comprise a cysteine-cysteine bridge (Cys-Cys) typical in polypeptides having disulfide bridges or alternatively bridging moieties may be non-protein based such as the dibromozylyl agents used herein.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the term "half-domain" means a portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini" or "terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a desired component of a polypeptide to be encoded by the circular primary construct, circP, circRNA or circRNA-SP of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of experimentation. As used herein a "consensus" sequence is a single sequence which represents a collective population of sequences allowing for variability at one or more sites.

As recognized by those skilled in the art, protein fragments, functional protein domains, and homologous proteins are also considered to be within the scope of polypeptides of interest of this invention. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a polypeptide to be utilized in accordance with the invention includes 2, 3, 4, 5, 6, 7, 8, 9, 10, or more mutations as shown in any of the sequences provided or referenced herein.

Encoded Polypeptides

The circP, circRNA or circRNA-SP of the present invention may be designed to encode polypeptides of interest such as, but not limited to, any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery.

In one embodiment circP, circRNA or circRNA-SP may encode variant polypeptides which have a certain identity with a reference polypeptide sequence. As used herein, a "reference polypeptide sequence" refers to a starting polypeptide sequence. Reference sequences may be wild type sequences or any sequence to which reference is made in the design of another sequence. A "reference polypeptide sequence" may, e.g., be any one of the sequences disclosed in International Publication Nos. WO2013151666, WO2013151667, WO2013151668, WO2013151663, WO2013151669, WO2013151670, WO2013151664, WO2013151665, WO2013151671, WO2013151672, WO2013151736; the contents of each of which is herein incorporated by reference in its entirety.

The term "identity" as known in the art, refers to a relationship between the sequences of two or more peptides, as determined by comparing the sequences. In the art, identity also means the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988); each of which is herein incorporated by reference in its entirety.

In some embodiments, the polypeptide variant may have the same or a similar activity as the reference polypeptide. Alternatively, the variant may have an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402). Other tools are described herein, specifically in the definition of "Identity."

Default parameters in the BLAST algorithm include, for example, an expect threshold of 10, Word size of 28, Match/Mismatch Scores 1, -2, Gap costs Linear. Any filter can be applied as well as a selection for species specific repeats, e.g., *Homo sapiens*.

Biologics

The circP, circRNA or circRNA-SP disclosed herein, may encode one or more biologics. As used herein, a "biologic" is a polypeptide-based molecule produced by the methods provided herein and which may be used to treat, cure, mitigate, prevent, or diagnose a serious or life-threatening disease or medical condition. Biologics are described in co-pending International Publication No. WO2015034925, the contents which are herein incorporated by reference in its entirety, such as in paragraphs [000101] and [000102].

Antibodies

The circP, circRNA or circRNA-SP disclosed herein, may encode one or more antibodies or fragments thereof. The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments. Antibodies are described in co-pending International Publication No. WO2015034925, the contents which are herein incorporated by reference in its entirety, such as in paragraphs [000103]-[000109].

Vaccines

The circP, circRNA or circRNA-SP disclosed herein, may encode one or more vaccines. As used herein, a "vaccine" is a biological preparation that improves immunity to a particular disease or infectious agent. According to the present invention, one or more vaccines currently being marketed or in development may be encoded by the circP, circRNA or circRNA-SP of the present invention. While not wishing to be bound by theory, it is believed that incorporation into the circP, circRNA or circRNA-SP of the invention will result in improved therapeutic efficacy due at least in part to the specificity, purity and selectivity of the construct designs.

Vaccines encoded in the circP, circRNA or circRNA-SP of the invention may be utilized to treat conditions or diseases in many therapeutic areas such as, but not limited to, cardiovascular, CNS, dermatology, endocrinology, oncology, immunology, respiratory, and anti-infective.

Therapeutic Proteins or Peptides

The circP, circRNA or circRNA-SP disclosed herein, may encode one or more validated or "in testing" therapeutic proteins or peptides.

According to the present invention, one or more therapeutic proteins or peptides currently being marketed or in development may be encoded by the circP, circRNA or circRNA-SP of the present invention. While not wishing to be bound by theory, it is believed that incorporation into the circP, circRNA or circRNA-SP of the invention will result in improved therapeutic efficacy due at least in part to the specificity, purity and selectivity of the construct designs.

Therapeutic proteins and peptides encoded in the circP, circRNA or circRNA-SP of the invention may be utilized to treat conditions or diseases in many therapeutic areas such as, but not limited to, blood, cardiovascular, CNS, poisoning (including antivenoms), dermatology, endocrinology, genetic, genitourinary, gastrointestinal, musculoskeletal, oncology, and immunology, respiratory, sensory and anti-infective.

Cell-Penetrating Polypeptides

The circP, circRNA or circRNA-SP disclosed herein, may encode one or more cell-penetrating polypeptides. As used herein, "cell-penetrating polypeptide" or CPP refers to a polypeptide which may facilitate the cellular uptake of molecules. A cell-penetrating polypeptide of the present invention may contain one or more detectable labels. The polypeptides may be partially labeled or completely labeled throughout. The circP, circRNA or circRNA-SP may encode the detectable label completely, partially or not at all. The cell-penetrating peptide may also include a signal sequence. As used herein, a "signal sequence" refers to a sequence of amino acid residues bound at the amino terminus of a nascent protein during protein translation. The signal sequence may be used to signal the secretion of the cell-penetrating polypeptide.

In one embodiment, the circP, circRNA or circRNA-SP may also encode a fusion protein. The fusion protein may be created by operably linking a charged protein to a therapeutic protein. As used herein, "operably linked" refers to the therapeutic protein and the charged protein being connected in such a way to permit the expression of the complex when introduced into the cell. As used herein, "charged protein" refers to a protein that carries a positive, negative or overall neutral electrical charge. Preferably, the therapeutic protein may be covalently linked to the charged protein in the formation of the fusion protein. The ratio of surface charge to total or surface amino acids may be approximately 0.1, 0.2, 0.3, 0.4, 0.5, 0.6, 0.7, 0.8 or 0.9.

The cell-penetrating polypeptide encoded by the circP, circRNA or circRNA-SP may form a complex after being translated. The complex may comprise a charged protein linked, e.g. covalently linked, to the cell-penetrating polypeptide. "Therapeutic protein" refers to a protein that, when administered to a cell has a therapeutic, diagnostic, and/or prophylactic effect and/or elicits a desired biological and/or pharmacological effect.

In one embodiment, the cell-penetrating polypeptide may comprise a first domain and a second domain. The first domain may comprise a supercharged polypeptide. The second domain may comprise a protein-binding partner. As used herein, "protein-binding partner" includes, but is not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the circP, circRNA or circRNA-SP may be introduced. The cell-penetrating polypeptide may also be capable of penetrating the first cell.

In a further embodiment, the cell-penetrating polypeptide is capable of penetrating a second cell. The second cell may be from the same area as the first cell, or it may be from a different area. The area may include, but is not limited to, tissues and organs. The second cell may also be proximal or distal to the first cell.

In one embodiment, the circP, circRNA or circRNA-SP may encode a cell-penetrating polypeptide which may comprise a protein-binding partner. The protein binding partner may include, but is not limited to, an antibody, a supercharged antibody or a functional fragment. The circP, circRNA or circRNA-SP may be introduced into the cell where a cell-penetrating polypeptide comprising the protein-binding partner is introduced.

Secreted Proteins

Human and other eukaryotic cells are subdivided by membranes into many functionally distinct compartments. Each membrane-bounded compartment, or organelle, contains different proteins essential for the function of the organelle. The cell uses "sorting signals," which are amino acid motifs located within the protein, to target proteins to particular cellular organelles.

One type of sorting signal, called a signal sequence, a signal peptide, or a leader sequence, directs a class of proteins to an organelle called the endoplasmic reticulum (ER).

Proteins targeted to the ER by a signal sequence can be released into the extracellular space as a secreted protein. Similarly, proteins residing on the cell membrane can also be secreted into the extracellular space by proteolytic cleavage of a "linker" holding the protein to the membrane. While not wishing to be bound by theory, the molecules of the present invention may be used to exploit the cellular trafficking described above. As such, in some embodiments of the invention, circP, circRNA or circRNA-SP are provided to express a secreted protein. The secreted proteins may be selected from those described herein or those in US Patent Publication, 20100255574, the contents of which are incorporated herein by reference in their entirety.

In one embodiment, these may be used in the manufacture of large quantities of valuable human gene products.

Plasma Membrane Proteins

In some embodiments of the invention, circPs, circRNAs or circRNA-SPs are provided to express a protein of the plasma membrane.

Cytoplasmic or Cytoskeletal Proteins

In some embodiments of the invention, circPs, circRNAs or circRNA-SPs are provided to express a cytoplasmic or cytoskeletal protein.

Intracellular Membrane Bound Proteins

In some embodiments of the invention, circPs, circRNAs or circRNA-SPs are provided to express an intracellular membrane bound protein.

Nuclear Proteins

In some embodiments of the invention, circPs, circRNAs or circRNA-SPs are provided to express a nuclear protein.

Proteins Associated with Human Disease

In some embodiments of the invention, circPs, circRNAs or circRNA-SPs are provided to express a protein associated with human disease.

Miscellaneous Proteins

In some embodiments of the invention, circPs, circRNAs or circRNA-SPs are provided to express a protein with a presently unknown therapeutic function.

Targeting Moieties

In some embodiments of the invention, circPs, circRNAs or circRNA-SPs are provided to express a targeting moiety. These include a protein-binding partner or a receptor on the surface of the cell, which functions to target the cell to a specific tissue space or to interact with a specific moiety, either in vivo or in vitro. Suitable protein-binding partners include, but are not limited to, antibodies and functional fragments thereof, scaffold proteins, or peptides. Additionally, circRNAs can be employed to direct the synthesis and extracellular localization of lipids, carbohydrates, or other biological moieties or biomolecules.

Polypeptide Libraries

In one embodiment, circPs, circRNAs or circRNA-SPs may be used to produce polypeptide libraries. These libraries may arise from the production of a population of circPs, circRNAs or circRNA-SPs, each containing various structural or chemical modification designs. In this embodiment, a population of circPs, circRNAs or circRNA-SPs may comprise a plurality of encoded polypeptides, including but not limited to, an antibody or antibody fragment, protein binding partner, scaffold protein, and other polypeptides taught herein or known in the art. In a preferred embodiment, the circPs, circRNAs or circRNA-SPs may be suitable for direct introduction into a target cell or culture which in turn may synthesize the encoded polypeptides.

In certain embodiments, multiple variants of a protein, each with different amino acid modification(s), may be produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including, but not limited to, substitutions, deletions of one or more residues, and insertion of one or more residues).

Anti-Microbial and Anti-Viral Polypeptides

The circPs, circRNAs or circRNA-SPs of the present invention may be designed to encode on or more antimicrobial peptides (AMP) or antiviral peptides (AVP). AMPs and AVPs have been isolated and described from a wide range of animals such as, but not limited to, microorganisms, invertebrates, plants, amphibians, birds, fish, and mammals (Wang et al., *Nucleic Acids Res.* 2009; 37 (Database issue): D933-7). Anti-microbial and anti-viral polypeptides are described in International Publication No. WO2013151666, the contents of which are herein incorporated by reference. As a non-limiting example, anti-microbial polypeptides are described in paragraphs [000189]-[000199] of International Publication No. WO2013151666, the contents of which are herein incorporated by reference. As another non-limiting example, anti-viral polypeptides are described in paragraphs [000189]-[000195] and [000200] of International Publication No. WO2013151666, the contents of which are herein incorporated by reference.

Cytotoxic Nucleosides

In one embodiment, the circPs, circSPs, circRNAs or circRNA-SPs of the present invention may incorporate one or more cytotoxic nucleosides. Cytotoxic nucleosides are described in co-pending International Publication No. WO2015034925, the contents which are herein incorporated by reference in its entirety, such as in paragraphs [000135]-[000139].

Flanking Regions: Untranslated Regions (UTRs)

In one embodiment, the circPs, circSPs, circRNAs or circRNA-SPs comprise at least one flanking region which may include at least one untranslated region (UTR).

Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the circPs, circSPs, circRNAs or circRNA-SPs of the present invention to enhance the stability of the molecule. The specific features can also be incorporated to ensure controlled down-regulation of the transcript in case they are misdirected to undesired organs sites.

5' UTR and Translation Initiation

Natural 5'UTRs bear features which play roles in for translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

In one embodiment, the 5'UTRs described herein for use in the present invention contain at least one Kozak sequence.

In another embodiment, the 5'UTRs described herein for use in the present invention contain at least one Kozak sequence.

By engineering the features typically found in abundantly expressed genes of specific target organs, one can enhance the stability the circPs, circSPs, circRNAs or circRNA-SPs and protein production of circPs, circRNAs or circRNA-SPs of the invention. For example, introduction of 5' UTR of liver-expressed nucleic acid, such as albumin, serum amyloid A, Apolipoprotein A/B/E, transferrin, alpha fetoprotein, erythropoietin, or Factor VIII, could be used to enhance expression of a polynucleotide molecule, such as a circPs, circSPs, circRNAs or circRNA-SPs, in hepatic cell lines or liver. Likewise, use of 5' UTR from other tissue-specific nucleic acids to improve expression in that tissue is possible for muscle (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences may be incorporated into the 5' (or 3' UTR) UTRs. For example, introns or portions of introns sequences may be incorporated into the flanking regions of the circPs, circSPs, circRNAs or circRNA-SPs of the invention. Incorporation of intronic sequences may increase protein production of the circPs, circRNAs or circRNA-SPs of the invention.

3' UTR and the AU Rich Elements

3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif c-Jun and Myogenin are two well-studied examples of this class.

For linear nucleic acids, most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of the circPs, circSPs, circRNAs or circRNA-SPs of the invention. When engineering specific circPs, circSPs, circRNAs or circRNA-SPs, one or more copies of an ARE can be introduced to make the circPs, circSPs, circRNAs or circRNA-SPs of the invention less stable and for circPs, circRNAs or circRNA-SPs the copies of an ARE can curtail translation and decrease production of the resultant protein. Likewise, AREs can be identified and removed or mutated to increase the intracellular stability and thus increase translation and production of the resultant protein.

Transfection experiments can be conducted in relevant cell lines, using circPs, circSPs, circRNAs or circRNA-SPs of the invention and protein levels can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Translation Enhancer Elements (TEEs)

In one embodiment, the flanking regions of the circPs, circSPs, circRNAs or circRNA-SPs may include at least one translational enhancer polynucleotide, translation enhancer element, translational enhancer elements (collectively referred to as "TEE"s). As a non-limiting example, the TEE may be located between the transcription promoter and the start codon. The circPs, circSPs, circRNAs or circRNA-SPs with at least one TEE in the region may also include a cap structure. Further, at least one TEE may be located in the flanking regions of the circPs, circSPs, circRNAs or circRNA-SPs and undergo cap-dependent or cap-independent translation.

The term "translational enhancer element" or "translation enhancer element" (herein collectively referred to as "TEE") refers to sequences that increase the amount of polypeptide or protein produced from a polynucleotide.

In one embodiment, the flanking regions of the circPs, circSPs, circRNAs or circRNA-SPs may include at least one TEE as described in International Patent Publication No. WO2014081507, the contents of which is herein incorporated by reference in its entirety. Non-limiting examples of TEEs which may be incorporated into the flanking regions of the circPs, circSPs, circRNAs or circRNA-SPs are described in paragraphs [00116]-[00140] of International Patent Publication No. WO2014081507, the contents of which is herein incorporated by reference in its entirety.

Incorporating microRNA Binding Sites microRNAs (or miRNA) are 19-25 nucleotide long non-coding RNAs that bind to the 3'UTR of nucleic acid molecules and down-regulate gene expression either by reducing nucleic acid molecule stability or by inhibiting translation. The circPs, circSPs, circRNAs or circRNA-SPs of the invention may comprise one or more microRNA target sequences, microRNA sequences, or microRNA seeds. Such sequences may correspond to any known microRNA such as those taught in US Publication US2005/0261218 and US Publication US2005/0059005, the contents of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105; each of which is herein incorporated by reference in their entirety. The bases of the microRNA seed have complete complementarity with the target sequence. By engineering microRNA target sequences into the circPs, circSPs, circRNAs or circRNA-SPs of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; each of which is herein incorporated by reference in its entirety).

For example, if the circPs, circSPs, circRNAs or circRNA-SPs is not intended to be delivered to the liver but ends up there, then miR-122, a microRNA abundant in liver, can inhibit the expression of the gene of interest if one or multiple target sites of miR-122 are engineered into the 3' UTR of the circPs, circSPs, circRNAs or circRNA-SPs. Introduction of one or multiple binding sites for different microRNA can be engineered to further decrease the longevity, stability, and protein translation of a circRNA.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the circPs, circSPs, circRNAs or circRNA-SPs of the present invention, microRNA binding sites can be engineered out of (i.e. removed from) sequences in which they naturally occur in order to increase protein expression in specific tissues. For example, miR-122 binding sites may be removed to improve protein expression in the liver. Regulation of expression in multiple tissues can be accomplished through introduction or removal or one or several microRNA binding sites.

Examples of tissues where microRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126). MicroRNA can also regulate complex biological processes such as angiogenesis (miR-132) (Anand and Cheresh Curr Opin Hematol 2011 18:171-176; herein incorporated by reference in its entirety). In the circPs, circSPs, circRNAs or circRNA-SPs of the present invention, binding sites for microRNAs that are involved in such processes may be removed or introduced, in order to tailor the expression of the circPs, circSPs, circRNAs or circRNA-SPs expression to biologically relevant cell types or to the context of relevant biological processes. A listing of MicroRNA, miR sequences and miR binding sites is listed in Table 9 of U.S. Provisional Application No. 61/753,661 filed Jan. 17, 2013, in Table 9 of U.S. Provisional Application No. 61/754,159 filed Jan. 18, 2013, and in Table 7 of U.S. Provisional Application No. 61/758,921 filed Jan. 31, 2013, each of which are herein incorporated by reference in their entireties.

In one embodiment, the circPs, circSPs, circRNAs or circRNA-SPs of the present invention may comprise disease specific miR binding sites. Translation of the circPs, circRNAs or circRNA-SPs or sponge activity of the circSPs is not initiated unless the cell where the circPs, circSPs, circRNAs or circRNA-SPs are contained is experiencing conditions to be activated by the miR binding site. As a non-limiting example, a circPs, circRNAs or circRNA-SPs comprising at least one miR binding site may be administered to a cell, tissue or organism. The circPs, circRNAs or circRNA-SPs is not translated until the cell where the circPs, circRNAs or circRNA-SPs is located experiences certain conditions in order to unlock the construct and thus initiate translation.

Lastly, through an understanding of the expression patterns of microRNA in different cell types, circPs, circSPs, circRNAs or circRNA-SPs can be engineered for more targeted expression in specific cell types or only under specific biological conditions. Through introduction of tissue-specific microRNA binding sites, circPs, circSPs, circRNAs or circRNA-SPs could be designed that would be optimal for protein expression in a tissue or in the context of a biological condition. Examples of use of microRNA to drive tissue or disease-specific gene expression are listed (Getner and Naldini, Tissue Antigens. 2012, 80:393-403; herein incorporated by reference in its entirety). In addition, microRNA seed sites can be incorporated into mRNA to decrease expression in certain cells which results in a biological improvement. An example of this is incorporation of miR-142 sites into a UGT1A1-expressing lentiviral vector. The presence of miR-142 seed sites reduced expression in hematopoietic cells, and as a consequence reduced expression in antigen-presentating cells, leading to the absence of an immune response against the virally expressed UGT1A1 (Schmitt et al., Gastroenterology 2010; 139:999-1007; Gonzalez-Asequinolaza et al. Gastroenterology 2010, 139:726-729; both herein incorporated by reference in its entirety). Incorporation of miR-142 sites into circRNA could not only reduce expression of the encoded protein in hematopoietic cells, but could also reduce or abolish immune responses to the circPs, circRNAs or circRNA-SPs-encoded protein. Incorporation of miR-142 seed sites (one or multiple) into circPs, circSPs, circRNAs or circRNA-SPs would be important in the case of treatment of patients with complete protein deficiencies (UGT1A1 type I, LDLR-deficient patients, CRIM-negative Pompe patients, etc.).

Transfection experiments can be conducted in relevant cell lines, using engineered circPs, circSPs, circRNAs or circRNA-SPs and protein levels can be assayed at various time points post-transfection. For example, cells can be transfected with different microRNA binding site-engineering circPs, circSPs, circRNAs or circRNA-SPs and by using an ELISA kit to the relevant protein and assaying protein produced at 6 hour, 12 hour, 24 hour, 48 hour, 72 hour and 7 days post-transfection. In vivo experiments can also be conducted using microRNA-binding site-engineered molecules to examine changes in tissue-specific expression of formulated circPs, circSPs, circRNAs or circRNA-SPs.

Viral Sequences

Additional viral sequences such as, but not limited to, the translation enhancer sequence of the barley yellow dwarf virus (BYDV-PAV), the Jaagsiekte sheep retrovirus (JSRV) and/or the Enzootic nasal tumor virus (See e.g., International Pub. No. WO2012129648; herein incorporated by reference in its entirety) can be engineered and inserted in the 3' UTR of the circPs, circSPs, circRNAs or circRNA-SPs of the invention and can stimulate the translation of the construct in vitro and in vivo. Transfection experiments can be conducted in relevant cell lines at and protein production can be assayed by ELISA at 12 hr, 24 hr, 48 hr, 72 hr and day 7 post-transfection.

IRES Sequences

Further, provided are circPs, circSPs, circRNAs or circRNA-SPs which may contain an internal ribosome entry site (IRES). First identified as a feature Picorna virus RNA, IRES plays an important role in initiating protein synthesis in absence of the 5' cap structure. An IRES may act as the sole ribosome binding site, or may serve as one of multiple ribosome binding sites of polynucleotides. CircPs, circRNAs or circRNA-SPs containing more than one functional ribosome binding site may encode several peptides or polypeptides that are translated independently by the ribosomes ("multicistronic nucleic acid molecules"). When circPs, circSPs, circRNAs or circRNA-SPs are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Poly-A Tails

During RNA processing, a long chain of adenine nucleotides (poly-A tail) may be added to a polynucleotide such as circPs, circSPs, circRNAs or circRNA-SPs molecules in order to increase stability Immediately after transcription, the 3' end of the transcript may be cleaved to free a 3' hydroxyl. Then poly-A polymerase adds a chain of adenine nucleotides to the polynucleotide. The process, called polyadenylation, adds a poly-A tail that can be between, for example, approximately 100 and 250 residues long.

It has been discovered that unique poly-A tail lengths may provide certain advantages to the circPs, circSPs, circRNAs or circRNA-SPs of the present invention.

Generally, the length of a poly-A tail of the present invention is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the circPs, circSPs, circRNAs or circRNA-SPs includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail is designed relative to the length of the overall circPs, circSPs, circRNAs or circRNA-SPs. This design may be based on the length of the coding region, the length of a particular feature or region (such as the first or flanking regions), or based on the length of the ultimate product expressed from the circPs, circRNAs or circRNA-SPs.

In this context the poly-A tail may be 10, 20, 30, 40, 50, 60, 70, 80, 90, or 100% greater in length than the circPs, circSPs, circRNAs or circRNA-SPs or feature thereof. The poly-A tail may also be designed as a fraction of circPs, circSPs, circRNAs or circRNA-SPs to which it belongs. In this context, the poly-A tail may be 10, 20, 30, 40, 50, 60, 70, 80, or 90% or more of the total length of the construct or the total length of the construct minus the poly-A tail. Further, engineered binding sites and conjugation of circPs, circSPs, circRNAs or circRNA-SPs for Poly-A binding protein may enhance expression.

In one embodiment, the circPs, circSPs, circRNAs or circRNA-SPs of the present invention are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail. The resultant circPs, circSPs, circRNAs or circRNA-SPs construct is assayed for stability, protein production and/or other parameters including half-life at various time points. It has been discovered that the polyA-G quartet results in protein production equivalent to at least 75% of that seen using a poly-A tail of 120 nucleotides alone (SEQ ID NO: 49).

Start Codons

In one embodiment, the circPs, circRNAs or circRNA-SPs of the present invention comprise at least one start codon (ATG/AUG). The circPs, circRNAs or circRNA-SPs of the present invention may include more than 1 start codon such as, but not limited to, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 50, at least 60 or more than 60 start codons. Translation of the circPs, circRNAs or circRNA-SPs of the present invention may initiate on the first start codon or may initiate downstream of the start codon.

In one embodiment, translation of the circPs, circRNAs or circRNA-SPs of the present invention may initiate on a codon which is not the start codon AUG. Translation of the circPs, circRNAs or circRNA-SPs may initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety). As a non-limiting example, the translation of a circP, circRNA or circRNA-SP begins on the alternative start codon ACG. As another non-limiting example, circP, circRNA or circRNA-SP translation begins on the alternative start codon CTG/CUG. As yet another non-limiting example, the translation of a circP, circRNA or circRNA-SP begins on the alternative start codon GTG/GUG.

Nucleotides flanking a codon that initiates translation such as, but not limited to, a start codon or an alternative start codon, are known to affect the translation efficiency, the length and/or the structure of the circP, circRNA or circRNA-SP. (See e.g., Matsuda and Mauro PLoS ONE, 2010 5:11; the contents of which are herein incorporated by reference in its entirety). Masking any of the nucleotides flanking a codon that initiates translation may be used to alter the position of translation initiation, translation efficiency, length and/or structure of a circP, circRNA or circRNA-SP.

In one embodiment, a masking agent may be used near the start codon or alternative start codon in order to mask or hide the codon to reduce the probability of translation initiation at the masked start codon or alternative start codon. Non-limiting examples of masking agents include antisense locked nucleic acids (LNA) oligonucleotides and exon-junction complexes (EJCs) (See e.g., Matsuda and Mauro describing masking agents LNA oligonucleotides and EJCs (PLoS ONE, 2010 5:11); the contents of which are herein incorporated by reference in its entirety).

In another embodiment, a masking agent may be used to mask a start codon of a circP, circRNA or circRNA-SP in order to increase the likelihood that translation will initiate on an alternative start codon.

In one embodiment, a masking agent may be used to mask a first start codon or alternative start codon in order to increase the chance that translation will initiate on a start codon or alternative start codon downstream to the masked start codon or alternative start codon.

In one embodiment, a start codon or alternative start codon may be located within a perfect complement for a miR binding site. The perfect complement of a miR binding site may help control the translation, length and/or structure of the circP, circRNA or circRNA-SP similar to a masking agent. As a non-limiting example, the start codon or alternative start codon may be located in the middle of a perfect complement for a miR-122 binding site. The start codon or alternative start codon may be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a circP, circRNA or circRNA-SP may be removed from the circP, circRNA or circRNA-SP sequence in order to have the translation of the circP, circRNA or circRNA-SP begin on a codon which is not the start codon. Translation of the circP, circRNA or circRNA-SP may begin on the codon following the removed start codon or on a downstream start codon or an alternative start codon. In a non-limiting example, the start codon ATG/AUG is removed as the first 3 nucleotides of the circP, circRNA or circRNA-SP sequence in order to have translation initiate on a downstream start codon or alternative start codon. The circP, circRNA or circRNA-SP sequence where the start codon was removed may further comprise at least one masking agent for the downstream start codon and/or alternative start codons in order to control or attempt to control the initiation of translation, the length of the circP, circRNA or circRNA-SP and/or the structure of the circP, circRNA or circRNA-SP.

Quantification

In one embodiment, the circPs, circSPs, circRNAs or circRNA-SPs of the present invention may be quantified in exosomes derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

In the quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a circPs, circSPs, circRNAs or circRNA-SPs may be an expression level, presence, absence, truncation or alteration of the administered construct. It is advantageous to correlate the level with one or more clinical phenotypes or with an assay for a human disease biomarker. The assay may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of circPs, circSPs, circRNAs or circRNA-SPs remaining or delivered. This is possible because the circPs, circSPs, circRNAs or circRNA-SPs of the present invention differ from the endogenous forms due to the structural or chemical modifications.

II. Design and Synthesis of Circular Polynucleotides

The circPs, circSPs, circRNAs and circRNA-SPs for use in accordance with the invention may be prepared according to any available technique including, but not limited to chemical synthesis and enzymatic synthesis. In some embodiments, a linear primary construct or linear mRNA may be cyclized, or concatemerized to create a circPs, circSPs, circRNAs and circRNA-SPs of the present invention. The mechanism of cyclization or concatemerization may occur through methods such as, but not limited to, chemical, enzymatic, or ribozyme catalyzed methods. The newly formed 5'-/3'-linkage may be an intramolecular linkage or an intermolecular linkage.

In one embodiment, a linear primary construct or linear mRNA may be cyclized, or concatemerized using the chemical method to form a circPs, circSPs, circRNAs and circRNA-SPs. In the chemical method, the 5'-end and the 3'-end of the nucleic acid (e.g., linear primary construct or linear mRNA) contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a linear RNA molecule will undergo a nucleophilic attack on the 5'-NHS-ester moiety forming a new 5'-/3'-amide bond.

In one embodiment, a DNA or RNA ligase may be used to enzymatically link a 5'-phosphorylated nucleic acid molecule (e.g., a linear primary construct or linear mRNA) to the 3'-hydroxyl group of a nucleic acid forming a new phosphorodiester linkage. In an example reaction, 1 µg of a nucleic acid molecule is incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction.

In one embodiment, a DNA or RNA ligase may be used in the synthesis of the circular polynucleotides. As a non-limiting example, the ligase may be a circ ligase or circular ligase.

In another embodiment, protein ligation may be used to enzymatically link a first protein associated with the 5' end of the linear primary construct or linear mRNA with a second protein associated with the 3' end of a the linear primary construct or linear mRNA. In one aspect, the first and second protein may be the same protein. In another embodiment, the first and second proteins are different. As a non-limiting example, one or both proteins may be a RNA binding fusion enzyme. In another non-limiting example, one or both proteins may be PUF1 protein which may be derived from *Plasmodium falciparum*. As yet another non-limiting example, one or both proteins may fused with other enzymes in order to cyclize or concatermerize the linear primary constructs or linear mRNA.

In one embodiment, protein ligation may be used to enzymatically link a first fusion enzyme associated with the 5' end of the linear primary construct or linear mRNA with a second fusion enzyme associated with the 3' end of a the linear primary construct or linear mRNA.

In one embodiment, either the 5'- or 3'-end of the cDNA template can encode a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In one embodiment, a linear primary construct or linear mRNA may be cyclized or concatermerized by using at least one non-nucleic acid moiety. In one aspect, the at least one non-nucleic acid moiety may react with regions or features near the 5' terminus and/or near the 3' terminus of the linear primary construct or linear mRNA in order to cyclize or concatermerize the linear primary construct or linear mRNA. In another aspect, the at least one non-nucleic acid moiety may be located in or linked to or near the 5' terminus and/or the 3' terminus of the linear primary construct or linear mRNA. The non-nucleic acid moieties contemplated in the present invention may be homologous or heterologous. As a non-limiting example, the non-nucleic acid moiety may be a linkage such as a hydrophobic linkage, ionic linkage, a biodegradable linkage and/or a cleavable linkage. As another non-limiting example, the non-nucleic acid moiety is a ligation moiety. As yet another non-limiting example, the non-nucleic acid moiety may be an oligonucleotide or a peptide moiety such as an apatamer.

In one embodiment, a linear primary construct or linear mRNA may be cyclized or concatermized due to a non-nucleic acid moiety that causes an attraction between atoms, molecules surfaces at, near or linked to the 5' and 3' ends of the linear primary construct or linear mRNA. As a non-limiting example, a linear primary construct or linear mRNA may be cyclized or concatermized by intermolecular forces or intramolecular forces. Non-limiting examples of intermolecular forces include dipole-dipole forces, dipole-induced dipole forces, induced dipole-induced dipole forces, Van der Waals forces, and London dispersion forces. Non-limiting examples of intramolecular forces include covalent bonds, metallic bonds, ionic bonds, resonant bonds, agnostic bonds, dipolar bonds, conjugation, hyperconjugation and antibonding.

In one embodiment, the linear primary construct or linear mRNA may comprise a ribozyme RNA sequence near the 5' terminus and near the 3' terminus. The ribozyme RNA sequence may covalently link to a peptide when the sequence is exposed to the remainder of the ribozyme. In one aspect, the peptides covalently linked to the ribozyme RNA sequence near the 5' terminus and the 3' terminus may associate with each other causing the linear primary construct or linear mRNA to cyclize or concatemerize. In another aspect, the peptides covalently linked to the ribozyme RNA near the 5' terminus and the 3' terminus may cause the linear primary construct or linear mRNA to cyclize or concatemerize after being subjected to ligation using various methods known in the art such as, but not limited to, protein ligation. Non-limiting examples of ribozymes for use in the linear primary constructs or linear RNA of the present invention or a non-exhaustive listing of methods to incorporate and/or covalently link peptides are described in US patent application No. US20030082768, the contents of which is here in incorporated by reference in its entirety.

Various methods of synthesizing circPs are also described in the art (see, e.g., U.S. Pat. Nos. 6,210,931, 5,773,244, 5,766,903, 5,712,128, 5,426,180, US Publication No. US20100137407, International Publication No. WO1992001813 and International Publication No. WO2010084371; the contents of each of which are herein incorporated by reference in their entirety).

In some embodiment, the process of design and synthesis of the circPs, circSPs, circRNAs or circRNA-SPs of the invention generally includes the steps of gene construction, linear mRNA production (either with or without modifications) and purification, and cyclization of the linear mRNA. In the enzymatic synthesis method, a target polynucleotide sequence encoding the polypeptide of interest is first selected for incorporation into a vector which will be amplified to produce a cDNA template. Optionally, the target polynucleotide sequence and/or any flanking sequences may be codon optimized. The cDNA template is then used to produce mRNA through in vitro transcription (IVT). After production, the mRNA may undergo purification and the cyclization processes. The steps of producing a linear polynucleotide encoding a polypeptide of interest, which then may undergo a cyclization process, are provided in more detail below.

For example, polynucleotides of the invention having a sequence comprising Formula I:

$$[A_n]\text{-}L^1\text{-}[B_o], \quad \quad \text{Formula I}$$

may be synthesized by reacting a compound having the structure of Formula XVI:

$$[A_n]\text{-}(R^1)_a\text{—}(R^2)_b\text{—}(R^3)_c\text{—}N_3 \quad \quad \text{Formula XVI}$$

with a compound having the structure of Formula XVII:

$$R^{27}\text{—}(R^5)_d\text{—}(R^6)_e\text{—}(R^7)_f\text{—}[B_o] \quad \quad \text{Formula XVII}$$

wherein each A and B is independently include any nucleoside (e.g., a nucleotide);

n and o are, independently 10 to 10,000, e.g., 10 to 1000 or 10 to 2000; and

L¹ has the structure of Formula III:

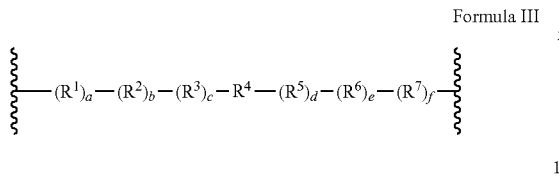
Formula III wherein a, b, c, d, e, and f are each, independently, 0 or 1;

R¹, R³, R⁵, and R⁷ each, independently, is selected from optionally substituted $C_1$-$C_6$ alkylene, optionally substituted $C_1$-$C_6$ heteroalkylene, O, S, and $NR^8$;

$R^2$ and $R^6$ are each, independently, selected from carbonyl, thiocarbonyl, sulfonyl, or phosphoryl;

$R^4$ is an optionally substituted triazolene; and $R^8$ is hydrogen, optionally substituted $C_1$-$C_4$ alkyl, optionally substituted $C_3$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_2$ heteroalkyl; and $R^{27}$ is an optionally substituted $C_2$-$C_3$ alkynyl or an optionally substituted $C_8$-$C_{12}$ cycloalkynyl, wherein L¹ is attached to [$A_n$] and [$B_o$] at the sugar of one of the nucleosides.

Circular polynucleotides of the invention including the structure of Formula XIa, XIb, XIIa, or XIIb:

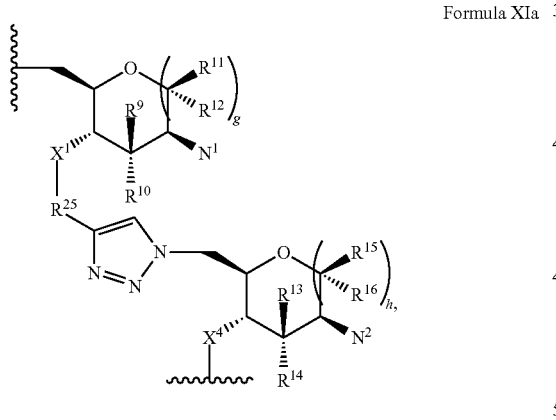
Formula XIa

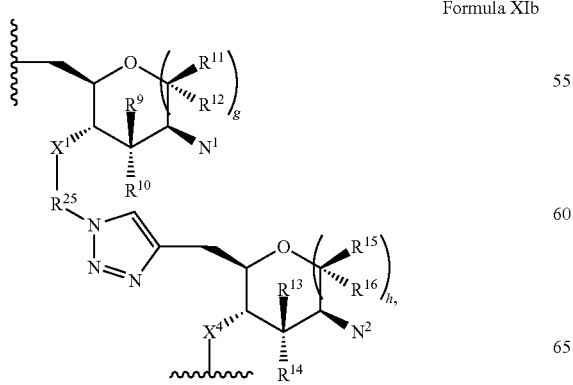
Formula XIb

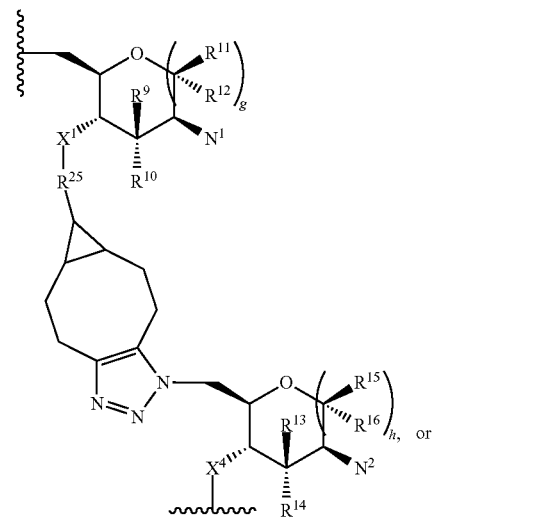
Formula XIIa

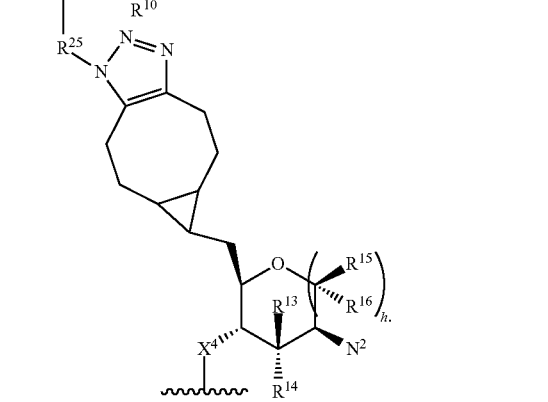
Formula XIIb may be synthesized by reacting (e.g., under [3+2] cycloaddition conditions in the presence or absence of a copper source) a compound having the structure of Formula XIIIa, XIIIb, XIVa, or XIVb:

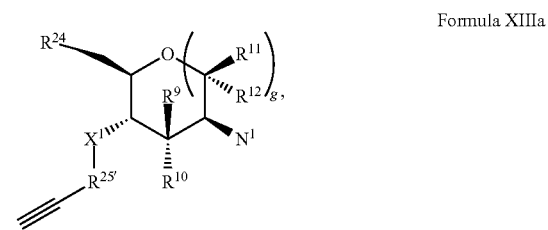
Formula XIIIa

-continued

Formula XIIIb

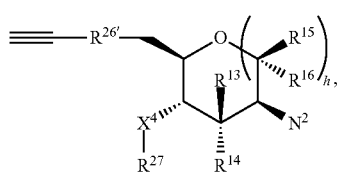

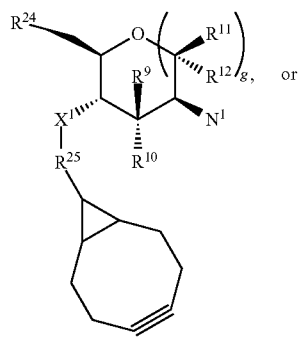

Formula XIVa

Formula XIVb

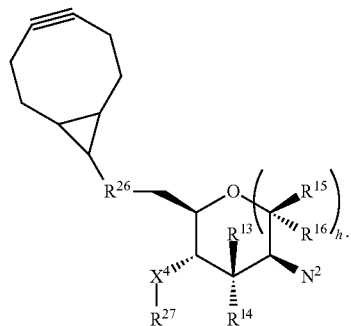

with a compound having the structure of Formula XVa or XVb:

Formula XVa

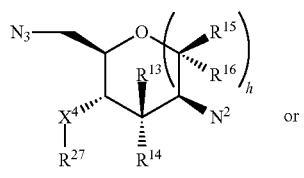

or

Formula XVb

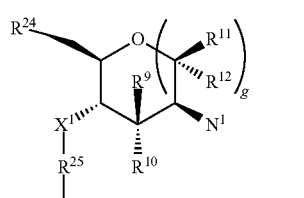

wherein each of $N^1$ and $N^2$ is independently a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, O, NH, or S; and each of $R^{24}$ and $R^{27}$ is, independently, a region of linked nucleosides; and each of $R^{25}$, $R^{25'}$, $R^{26}$ and $R^{26'}$ is, independently, optionally substituted $C_1$-$C_6$ alkylene or optionally substituted $C_1$-$C_6$ heteroalkylene or $R^{25'}$ or $R^{26'}$ and the alkynyl group together form optionally substituted cycloalkynyl.

For example, the circular polynucleotides of the invention may be synthesized as shown below:

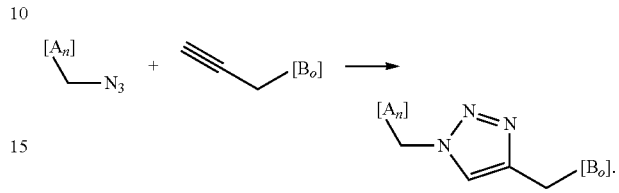

In some embodiments, the 5' cap structure or poly-A tail may be attached to a linear polynucleotide with this method and the linear polynucleotide may be circularized by the methods described herein.

Figure 10:
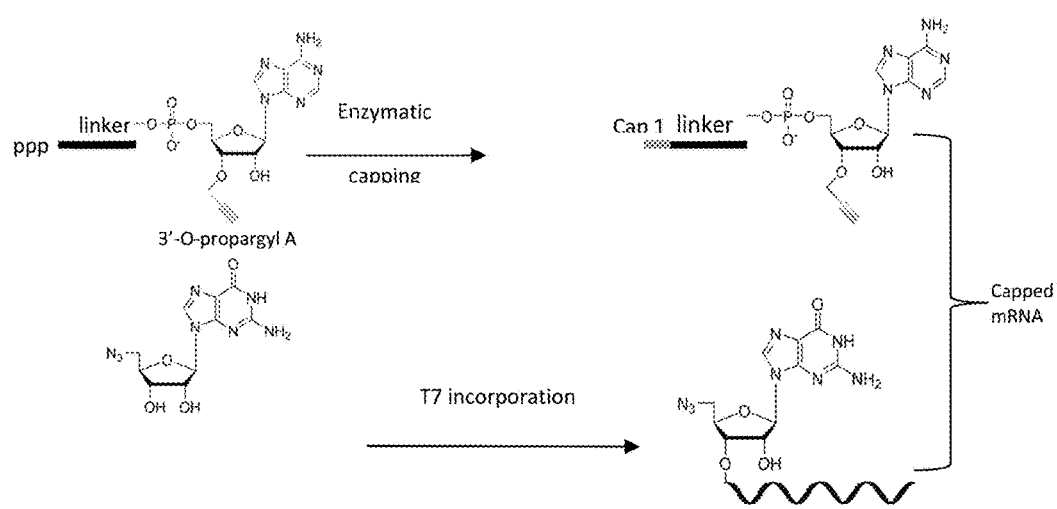
FIG. 10 is an image showing a method of attaching a 5' cap structure to a polynucleotide of the invention.

A 5' cap structure may be attached to a polynucleotide of the invention as shown in FIG. 10.

The polynucleotide may be circularized after the 5' cap structure is attached.

Figure 11:
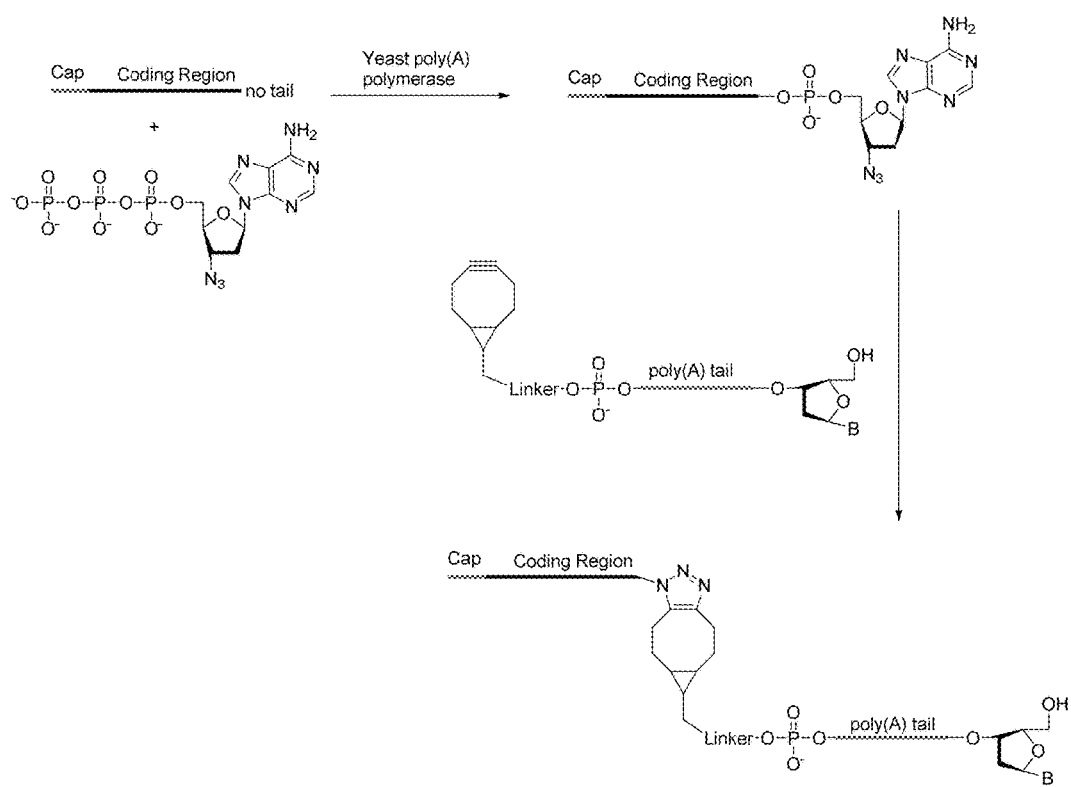
FIG. 11 is an image showing a method of attaching a poly-A tail to a polynucleotide of the invention.
Figure 12:
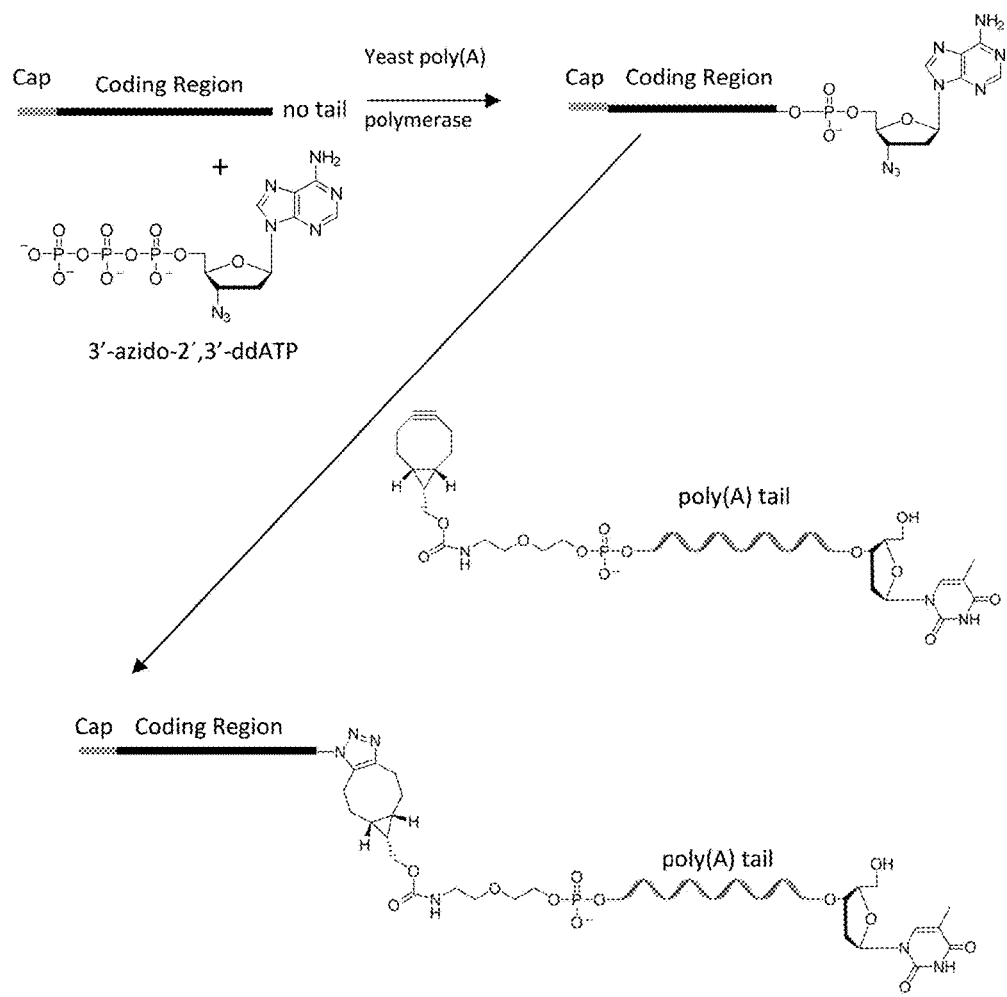
FIG. 12 is an image showing a method of attaching a poly-A tail to a polynucleotide of the invention.

A poly-A tail may be attached to a polynucleotide of the invention as shown in FIG. 11 and FIG. 12.

The polynucleotide may be circularized after the poly-A tail is attached.

Polynucleotides which may be circularized may be made using various methods.

For example, polynucleotides of the invention may comprise the structure of Formula Va or Vb:

Formula Va

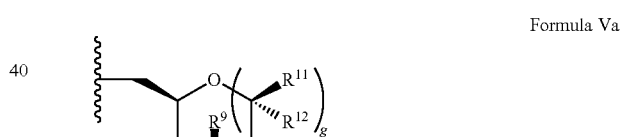

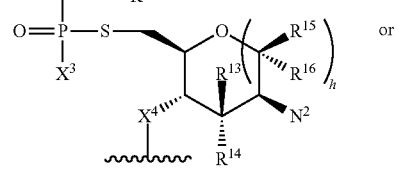

or

Formula Vb

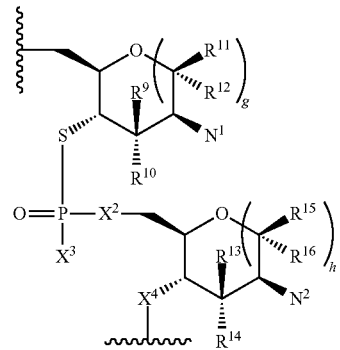

The circular polynucleotides may comprise a structure made by a method which includes reacting (e.g., under alkylating conditions) a compound having the structure of Formula VIa or VIb:

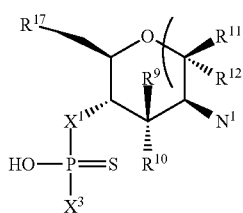

Formula VIa or

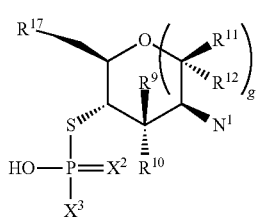

Formula VIb with a compound having the structure of Formula VII:

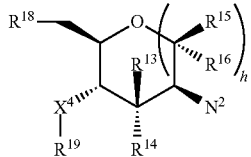

Formula VII wherein each of $N^1$ and $N^2$ is, independently, a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, O, NH, or S;

each $X^2$ is independently O or S; and each $X^3$ is independently OH or SH, or a salt thereof;

each of $R^{17}$ and $R^{19}$ is, independently, a region of linked nucleosides; and $R^{18}$ is a halogen.

Circular polynucleotides of the invention may include the structure of Formula VIIIa or VIIIb:

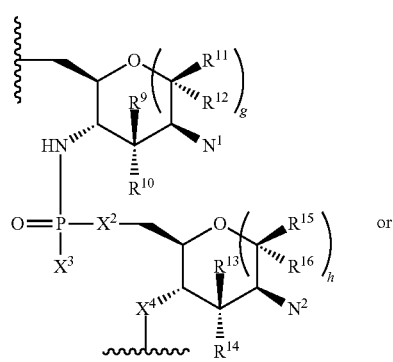

Formula VIIIa or

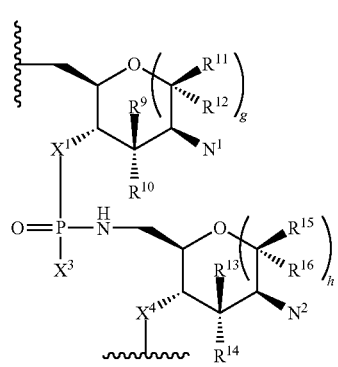

Formula VIIIb

This method includes reacting (e.g., under Staudinger reaction conditions) a compound having the structure of Formula IXa or IXb:

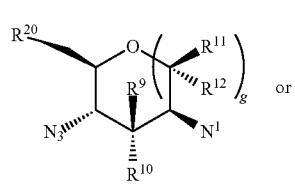

Formula IXa or

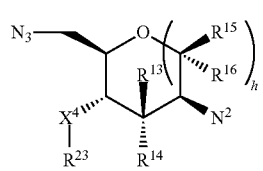

Formula IXb with a compound having the structure of Formula Xa or Xb:

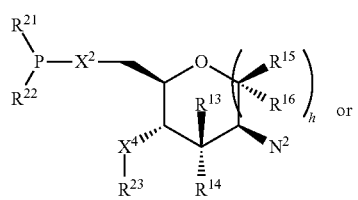

Formula Xa or

-continued

Formula Xb

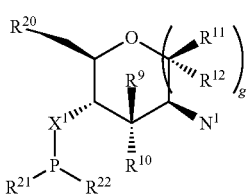

wherein each of $N^1$ and $N^2$ is, independently, a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^4$ is, independently, O, NH, or S; and each $X^1$ and $X^2$ is independently O or S;

each $X^3$ is independently OH, SH, or a salt thereof;

each of $R^{20}$ and $R^{23}$ is, independently, a region of linked nucleosides; and each of $R^{21}$ and $R^{22}$ is, independently, optionally substituted $C_1$-$C_6$ alkoxy.

Circular polynucleotides of the invention including the structure of Formula XIa, XIb, XIIa, or XIIa:

Formula XIa

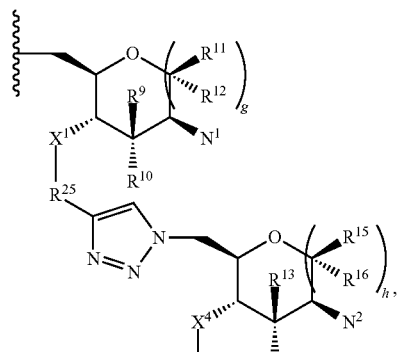

Formula XIb

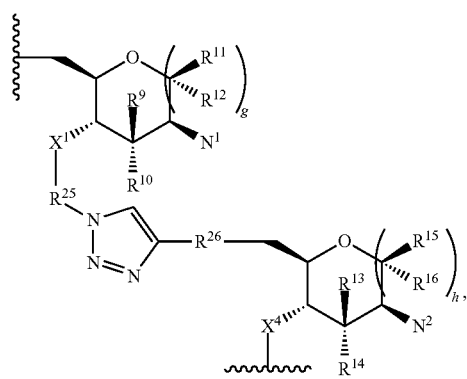

Formula XIIa

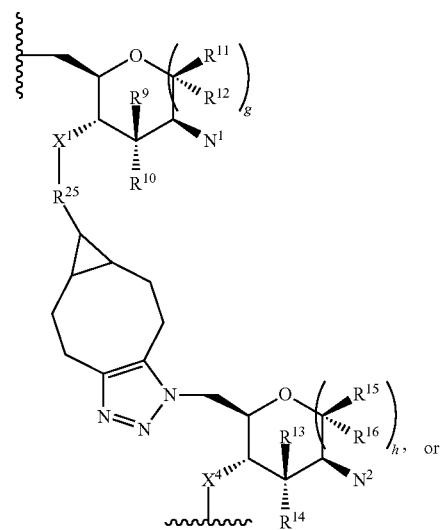

Formula XIIb

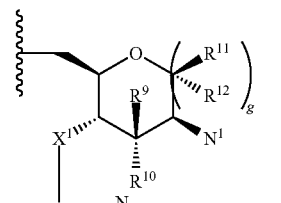

This method includes reacting (e.g., under [3+2] cycloaddition conditions in the presence or absence of a copper source) a compound having the structure of Formula XIIIa, XIIIb, XIVa, or XIVb:

Formula XIIIa

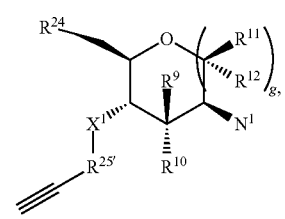

-continued

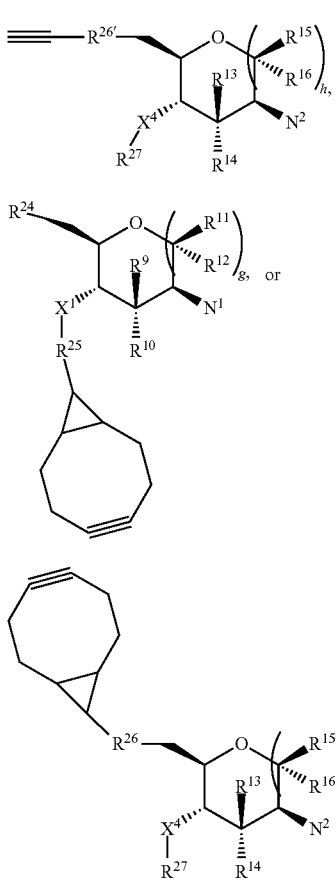

with a compound having the structure of Formula XVa or XVb:

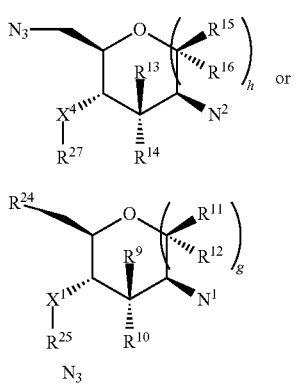

wherein each of $N^1$ and $N^2$ is, independently, a nucleobase;
each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;
each of g and h is, independently, 0 or 1;
each $X^1$ and $X^4$ is, independently, absent, O, NH, or S or a salt thereof;

each of $R^{24}$ and $R^{27}$ is, independently, a region of linked nucleosides; and
each of $R^{25}$, $R^{25'}$, $R^{26}$ and $R^{26'}$ is independently absent or optionally substituted $C_1$-$C_6$ alkylene or optionally substituted $C_1$-$C_6$ heteroalkylene or $R^{25}$ and the alkynyl group together form optionally substituted cycloalkynylene.

Circular polynucleotides of the invention may be synthesized as shown below:

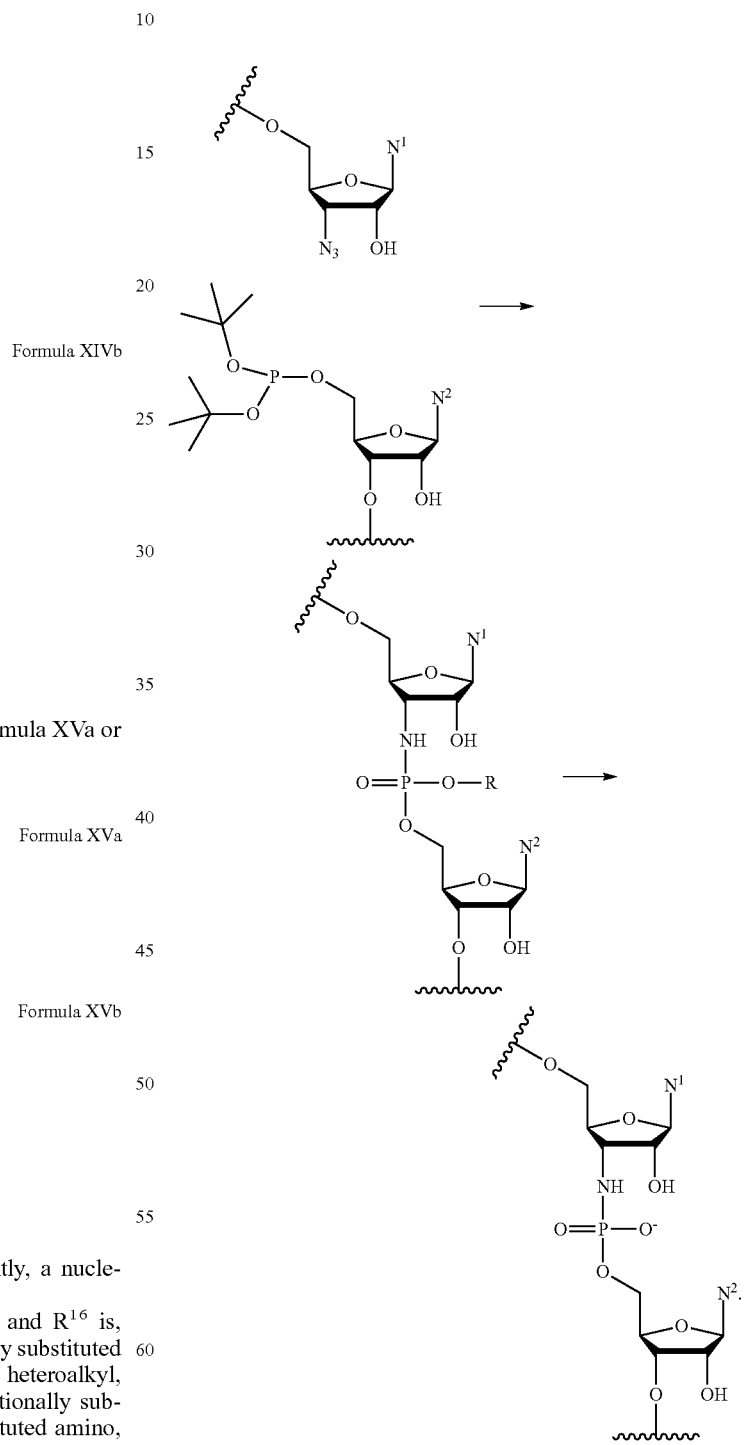

Other methods for the synthesis of the circular polynucleotides of the invention are shown below:

a)
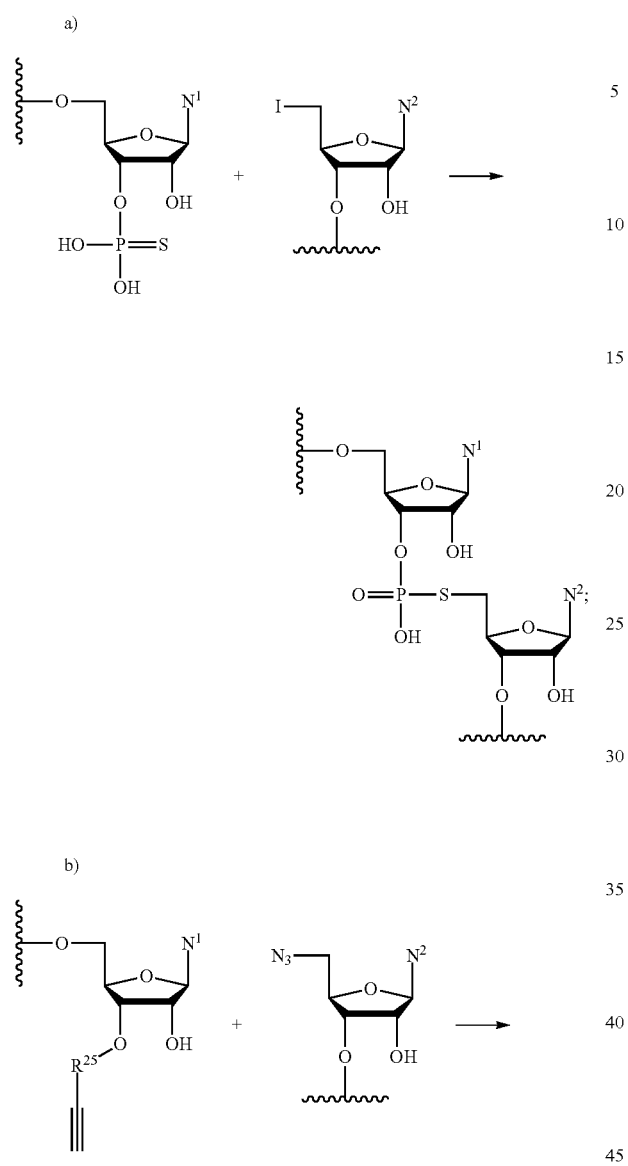
b)
c)
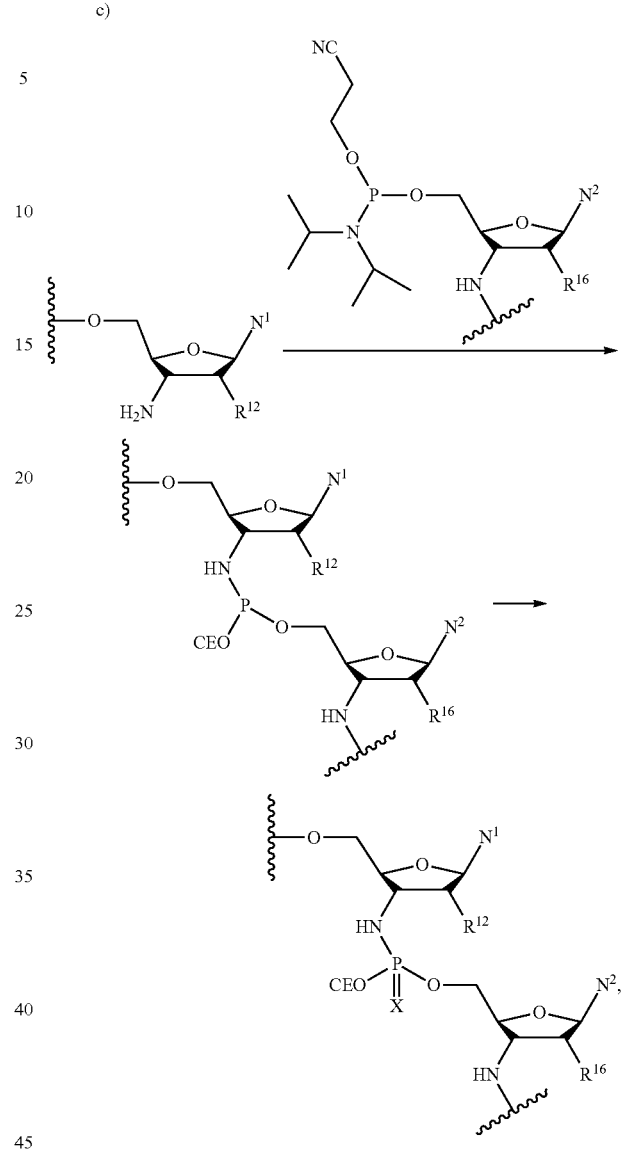
where CEO is 2-cyanoethoxy, and X is O or S.
Other methods for the synthesis of the circular polynucleotides of the invention are shown below:
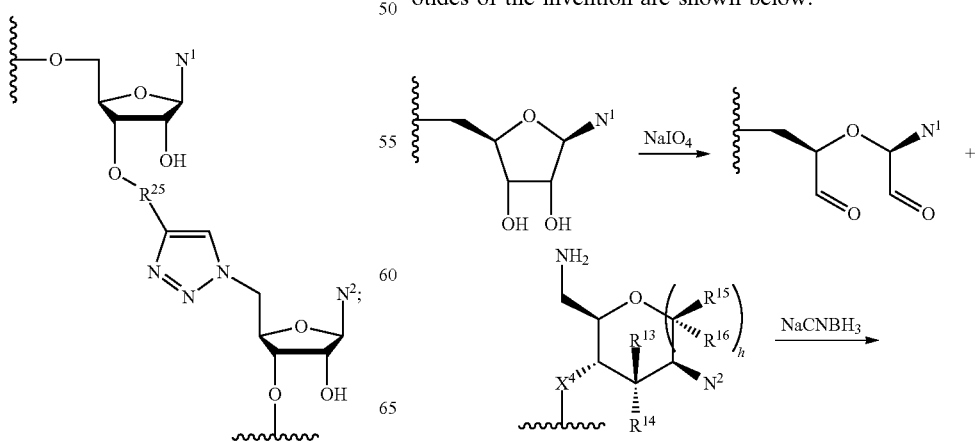

-continued

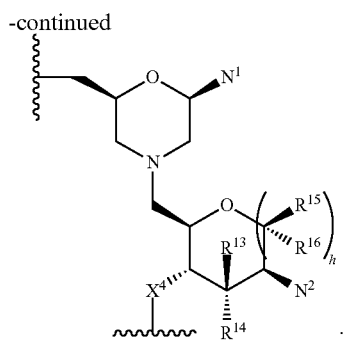

It will be understood that the reactive group shown at the 3' (or 4' position, when g or h is 1) and at the 5' (or 6' position, when g or h is 1) can be reversed. For example, the halogen, azido, or alkynyl group may be attached to the 5' position (or 6' position, when g or h is 1), and the thiophosphate, (thio)phosphoryl, or azido group may be attached to the 3' position (or 4' position, when g or h is 1).

Gene Construction for Circular Polynucleotides

The step of gene construction may include, but is not limited to gene synthesis, vector amplification, plasmid purification, plasmid linearization and clean-up, and cDNA template synthesis and clean-up.

Gene Synthesis

In one embodiment, the circular primary construct will be a circP, circRNA or a circRNA-SP and may include a coding region for a polypeptide of interest. For the circular primary construct, a polypeptide of interest, target, is selected for production, and a circular primary construct is designed. Within the circular primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

In another embodiment, the circular primary construct will be a circSP and does not include a coding region for a polypeptide of interest. Within the circular primary construct there is a first region of linked nucleosides that includes at least one sensor region. The first region of linked nucleosides may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45 or at least 50 sensor regions.

Further, the nucleotide sequence of the first region may be codon optimized. Codon optimization methods are known in the art and may be useful in efforts to achieve one or more of several goals. These goals include to match codon frequencies in target and host organisms to ensure proper folding, bias GC content to increase stability or reduce secondary structures, minimize tandem repeat codons or base runs that may impair gene construction or expression, customize transcriptional and translational control regions, insert or remove protein trafficking sequences, remove/add post translation modification sites in encoded protein (e.g. glycosylation sites), add, remove or shuffle protein domains, insert or delete restriction sites, modify ribosome binding sites and degradation sites, to adjust translational rates to allow the various domains of the protein to fold properly, or to reduce or eliminate problem secondary structures within the circP, circSP, circRNA or circRNA-SP. Codon optimization tools, algorithms and services are known in the art, non-limiting examples include services from GeneArt (Life Technologies), DNA2.0 (Menlo Park Calif.) and/or proprietary methods. In one embodiment, the ORF sequence, the flanking regions and/or the sensor regions are optimized using optimization algorithms. Codon options for each amino acid are given in Table 1.

TABLE 1

| Codon Options | | |
|---|---|---|
| Amino Acid | Single Letter Code | Codon Options |
| Isoleucine | I | ATT, ATC, ATA, AUU, AUC, AUA |
| Leucine | L | CTT, CTC, CTA, CTG, TTA, TTG, CUU, CUC, CUA, CUG, UUA, UUG |
| Valine | V | GTT, GTC, GTA, GTG, GUU, GUC, GUA, GUG |
| Phenylalanine | F | TTT, TTC, UUU, UUC |
| Methionine | M | ATG, AUG |
| Cysteine | C | TGT, TGC, UGU, UGC |
| Alanine | A | GCT, GCC, GCA, GCG, GCU |
| Glycine | G | GGT, GGC, GGA, GGG, GGU |
| Proline | P | CCT, CCC, CCA, CCG, CCU |
| Threonine | T | ACT, ACC, ACA, ACG, ACU |
| Serine | S | TCT, TCC, TCA, TCG, AGT, AGC, UCU, UCC, UCA, UCG, AGU |
| Tyrosine | Y | TAT, TAC, UAU, UAC |
| Tryptophan | W | TGG, UGG |
| Glutamine | Q | CAA, CAG |
| Asparagine | N | AAT, AAC, AAU |
| Histidine | H | CAT, CAC, CAU |
| Glutamic acid | E | GAA, GAG |
| Aspartic acid | D | GAT, GAC, GAU |
| Lysine | K | AAA, AAG |
| Arginine | R | CGT, CGC, CGA, CGG, AGA, AGG, CGU |
| Selenocysteine | Sec | UGA in mRNA in presence of Selenocystein insertion element (SECIS) |
| Stop codons | Stop | TAA, TAG, TGA, UAA, UAG, UGA |

Features, which may be considered beneficial in some embodiments of the present invention, may be encoded by the circular primary construct and may flank the first region of linked nucleosides as a flanking region. The flanking regions may be incorporated into the circular primary construct before and/or after optimization of any of the regions, or portions thereof, of the circular primary construct. It is not required that a circular primary construct contain both a 5' and 3' flanking region. Examples of such features include, but are not limited to, untranslated regions (UTRs), Kozak sequences, an IRES sequence or fragment thereof, an oligo (dT) sequence, and detectable tags and may include multiple cloning sites which may have XbaI recognition.

In some embodiments, a 5' UTR and/or a 3' UTR may be provided as flanking regions. Multiple 5' or 3' UTRs may be included in the flanking regions and may be the same or of different sequences. Any portion of the flanking regions, including none, may be codon optimized and any may independently contain one or more different structural or chemical modifications, before and/or after codon optimization. Combinations of features may be included in the flanking regions and may be contained within other features. For example, the first region of linked nucleosides may be flanked by a 5' UTR which may contain a strong Kozak translational initiation signal and/or a 3' UTR which may include an oligo(dT) sequence for templated addition of a poly-A tail. The 5'UTR may comprise a first polynucleotide fragment and a second polynucleotide fragment from the same and/or different polypeptide of interest such as the 5'UTRs described in US Patent Application Publication No. 20100293625, herein incorporated by reference in its entirety.

Tables 2 and 3 provide a listing of exemplary UTRs which may be utilized in the circular primary construct of the present invention as flanking regions. Shown in Table 2 is a listing of a 5'-untranslated region of the invention. Variants of 5' UTRs may be utilized wherein one or more nucleotides are added or removed to the termini, including A, T, U, C or G.

TABLE 2

5'-Untranslated Regions

| 5' UTR Identifier | Name/Description | SEQ ID NO. |
|---|---|---|
| 5UTR-001 | Upstream UTR | 1 |
| 5UTR-002 | Upstream UTR | 2 |
| 5UTR-003 | Upstream UTR | 3 |
| 5UTR-004 | Upstream UTR | 4 |

Shown in Table 3 is a representative listing of 3'-untranslated regions of the invention. Variants of 3' UTRs may be utilized wherein one or more nucleotides are added or removed to the termini, including A, T, U, C or G.

TABLE 3

3'-Untranslated Regions

| 3' UTR Identifier | Name/Description | SEQ ID NO. |
|---|---|---|
| 3UTR-001 | Creatine Kinase | 5 |
| 3UTR-002 | Myoglobin | 6 |
| 3UTR-003 | α-actin | 7 |
| 3UTR-004 | Albumin | 8 |
| 3UTR-005 | α-globin | 9 |
| 3UTR-006 | G-CSF | 10 |
| 3UTR-007 | Col1a2; collagen, type I, alpha 2 | 11 |
| 3UTR-008 | Col6a2; collagen, type VI, alpha 2 | 12 |
| 3UTR-009 | RPN1; ribophorin I | 13 |
| 3UTR-010 | LRP1; low density lipoprotein receptor-related protein 1 | 14 |
| 3UTR-011 | Nnt1; cardiotrophin-like cytokine factor 1 | 15 |
| 3UTR-012 | Col6a1; collagen, type VI, alpha 1 | 16 |
| 3UTR-013 | Calr; calreticulin | 17 |
| 3UTR-014 | Col1a1; collagen, type I, alpha 1 | 18 |
| 3UTR-015 | Plod1; procollagen-lysine, 2-oxoglutarate 5-dioxygenase 1 | 19 |
| 3UTR-016 | Nucb1; nucleobindin 1 | 20 |
| 3UTR-017 | α-globin | 21 |

It should be understood that those listed in the previous tables are examples and that any UTR from any gene may be incorporated into the respective flanking regions of the circular primary construct. As a non-limiting example, the UTR or a fragment thereof which may be incorporated is a UTR listed in US Provisional Application Nos. U.S. 61/775,509 and U.S. 61/829,372, or in International Patent Application No. PCT/US2014/021522; the contents of each of which are herein incorporated by reference in its entirety. Furthermore, multiple wild-type UTRs of any known gene may be utilized. It is also within the scope of the present invention to provide artificial UTRs which are not variants of wild type genes. These UTRs or portions thereof may be placed in the same orientation as in the transcript from which they were selected or may be altered in orientation or location. Hence a 5' or 3' UTR may be inverted, shortened, lengthened, made chimeric with one or more other 5' UTRs or 3' UTRs. As used herein, the term "altered" as it relates to a UTR sequence, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In one embodiment, a double, triple or quadruple UTR such as a 5' or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present invention to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In one embodiment, flanking regions are selected from a family of transcripts whose proteins share a common function, structure, feature of property. For example, polypeptides of interest may belong to a family of proteins which are expressed in a particular cell, tissue or at some time during development. The UTRs from any of these genes may be swapped for any other UTR of the same or different family of proteins to create a new chimeric primary transcript. As used herein, a "family of proteins" is used in the broadest sense to refer to a group of two or more polypeptides of interest which share at least one function, structure, feature, localization, origin, or expression pattern.

After optimization (if desired), the circular primary construct components may be reconstituted and transformed into a vector such as, but not limited to, plasmids, viruses, cosmids, and artificial chromosomes. For example, the optimized construct may be reconstituted and transformed into chemically competent *E. coli*, yeast, *neurospora*, maize, *drosophila*, etc. where high copy plasmid-like or chromosome structures occur by methods described herein.

The untranslated region may also include translation enhancer elements (TEE). As a non-limiting example, the TEE may include those described in US Application No. 20090226470, herein incorporated by reference in its entirety, and those known in the art.

Stop Codons

In one embodiment, the circular primary constructs of the present invention may include at least two stop codons prior to a flanking region such as, but not limited to a flanking region comprising a 3' untranslated region (UTR). The stop codon may be selected from TGA, TAA and TAG (or UGA, UAA and UAG). In one embodiment, the circular primary constructs of the present invention include the stop codon TGA or UGA and one additional stop codon. In a further embodiment the addition stop codon may be TAA or UAA. In another embodiment, the circular primary constructs of the present invention include three stop codons.

Gene Construction for Circular Polynucleotides from Linear Polynucleotides

In one embodiment, a linear primary construct is made using the methods described in International Publication Nos. WO2013151666, WO2013151667, WO2013151668, WO2013151663, WO2013151669, WO2013151670, WO2013151664, WO2013151665, WO2013151671, WO2013151672, WO2013151736, the contents of each of which are herein incorporated by reference in their entireties.

The linear primary construct is then placed in a vector and then is amplified and the plasmid isolated and purified using methods known in the art such as, but not limited to, a maxi prep using the Invitrogen PURELINK™ HiPure Maxiprep Kit (Carlsbad, Calif.). The plasmid may then be linearized using methods known in the art such as, but not limited to, the use of restriction enzymes and buffers. The linearization reaction may be purified using methods including, for example Invitrogen's PURELINK™ PCR Micro Kit (Carlsbad, Calif.), and HPLC based purification methods such as, but not limited to, strong anion exchange HPLC, weak anion exchange HPLC, reverse phase HPLC (RP-HPLC), and hydrophobic interaction HPLC (HIC-HPLC) and Invitrogen's standard PURELINK™ PCR Kit (Carlsbad, Calif.). The purification method may be modified depending on the size of the linearization reaction which was conducted. The linearized plasmid is then used to generate cDNA for in vitro transcription (IVT) reactions. The cDNA may then by cyclized using methods known in the art and/or described herein.

cDNA Template Synthesis

A cDNA template may be synthesized by having a linearized plasmid undergo polymerase chain reaction (PCR). Table 4 of International Patent Publication No. WO2013151666, the contents of which are herein incorporated by reference in its entirety, is a listing of primers and probes that may be usefully in the PCR reactions of the present invention. It should be understood that the listing is not exhaustive and that primer-probe design for any amplification is within the skill of those in the art. Probes may also contain chemically modified bases to increase base-pairing fidelity to the target molecule and base-pairing strength. Such modifications may include 5-methyl-Cytidine, 2, 6-diamino-purine, 2'-fluoro, phosphoro-thioate, or locked nucleic acids.

In one embodiment, the cDNA may be submitted for sequencing analysis before undergoing cyclization and/or transcription.

mRNA Production

The process of linear mRNA production may include, but is not limited to, in vitro transcription, cDNA template removal and RNA clean-up, and mRNA capping and/or tailing reactions.

In Vitro Transcription

The cDNA produced in the previous step may be transcribed using an in vitro transcription (IVT) system. The system typically comprises a transcription buffer, nucleotide triphosphates (NTPs), an RNase inhibitor and a polymerase. The NTPs may be manufactured in house, may be selected from a supplier, or may be synthesized as described herein. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

cDNA Template Removal and Clean-Up

The cDNA template may be removed using methods known in the art such as, but not limited to, treatment with Deoxyribonuclease I (DNase I). RNA clean-up may also include a purification method such as, but not limited to, AGENCOURT® CLEANSEQ® system from Beckman Coulter (Danvers, Mass.), RNAse III purification methods (See e.g., the methods described in International Publication No. WO2013102203, herein incorporated by reference in its entirety), HPLC based purification methods such as, but not limited to, strong anion exchange HPLC, weak anion exchange HPLC, reverse phase HPLC (RP-HPLC), and hydrophobic interaction HPLC (HIC-HPLC).

Circular Polynucleotide Production

The linear mRNA and/or linear primary construct described herein and/or known in the art may undergo a cyclization process. This process may be one of the methods described herein and/or one of the methods that are known in the art.

RNA Polymerases which May be Useful for Synthesis

Any number of RNA polymerases or variants may be used in the design of the circular primary constructs of the present invention.

RNA polymerases may be modified by inserting or deleting amino acids of the RNA polymerase sequence. As a non-limiting example, the RNA polymerase may be modified to exhibit an increased ability to incorporate a 2'-modified nucleotide triphosphate compared to an unmodified RNA polymerase (see International Publication WO2008078180 and U.S. Pat. No. 8,101,385; each of which are herein incorporated by reference in their entireties).

Variants may be obtained by evolving an RNA polymerase, optimizing the RNA polymerase amino acid and/or nucleic acid sequence and/or by using other methods known in the art. As a non-limiting example, T7 RNA polymerase variants may be evolved using the continuous directed evolution system set out by Esvelt et al. (Nature (2011) 472(7344):499-503; herein incorporated by reference in its entirety) where clones of T7 RNA polymerase may encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants may encode at least mutation as described in U.S. Pub. Nos. 20100120024 and 20070117112; herein incorporated by reference in their entireties. Variants of RNA polymerase may also include, but are not limited to, substitutional variants, conservative amino acid substitution, insertional variants, deletional variants and/or covalent derivatives.

In one embodiment, the circular primary construct may be designed to be recognized by the wild type or variant RNA polymerases. In doing so, the circular primary construct may be modified to contain sites or regions of sequence changes from the wild type or parent circular or linear primary construct.

Polynucleotide or nucleic acid synthesis reactions may be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. Coli, Bacillus* DNA polymerase I, *Thermus aquaticus* (Taq) DNA polymerases, and the T7 RNA and DNA polymerases, is among the best studied of these families. Another large family is DNA polymerase a (pol a) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., *PNAS*, Vol. 91, 5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one embodiment, the RNA polymerase which may be used in the synthesis of the circular polynucleotides described herein is a Syn5 RNA polymerase (see Zhu et al. Nucleic Acids Research 2013, the contents of which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one embodiment, a Syn5 RNA polymerase may be used in the synthesis of the circular polynucleotides described herein. As a non-limiting example, a Syn5 RNA polymerase may be used in the synthesis of the circular polynucleotide requiring a precise 3'-termini.

In one embodiment, a Syn5 promoter may be used in the synthesis of the circular polynucleotides. As a non-limiting example, the Syn5 promoter may be 5'-ATTGGGCACCCG-TAAGGG-3' (SEQ ID NO: 22) as described by Zhu et al. (Nucleic Acids Research 2013, the contents of which is herein incorporated by reference in its entirety).

In one embodiment, a Syn5 RNA polymerase may be used in the synthesis of circular polynucleotides comprising at least one chemical modification described herein and/or known in the art. (see e.g., the incorporation of pseudo-UTP and 5Me-CTP described in Zhu et al. Nucleic Acids Research 2013, the contents of which is herein incorporated by reference in its entirety).

In one embodiment, the circular polynucleotides described herein may be synthesized using a Syn5 RNA polymerase which has been purified using modified and improved purification procedure described by Zhu et al. (Nucleic Acids Research 2013, the contents of which is herein incorporated by reference in its entirety).

In one embodiment, the circular polynucleotides described herein may be synthesized using T7 RNA polymerase variants with improved affinity for 2' modified nucleotides, as described in International Patent Publication WO2014067551, the contents of which is herein incorporated by reference in its entirety.

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods may be applied in the manufacture of the circular polynucleotides of the invention. In one embodiment, the circular primary construct may be designed to include at least one substitution and/or insertion upstream of an RNA polymerase binding or recognition site, downstream of the RNA polymerase binding or recognition site, upstream of the TATA box sequence, downstream of the TATA box sequence of the circular primary construct but upstream of the coding region of the circular primary construct, within the 5'UTR, before the 5'UTR and/or after the 5'UTR.

In one embodiment, the 5'UTR of the circular primary construct may be replaced by the insertion of at least one region and/or string of nucleotides of the same base. The region and/or string of nucleotides may include, but is not limited to, at least 3, at least 4, at least 5, at least 6, at least 7 or at least 8 nucleotides and the nucleotides may be natural and/or unnatural. As a non-limiting example, the group of nucleotides may include 5-8 adenine, cytosine, thymine, a string of any of the other nucleotides disclosed herein and/or combinations thereof.

In one embodiment, the 5'UTR of the circular primary construct may be replaced by the insertion of at least two regions and/or strings of nucleotides of two different bases such as, but not limited to, adenine, cytosine, thymine, any of the other nucleotides disclosed herein and/or combinations thereof. For example, the 5'UTR may be replaced by inserting 5-8 adenine bases followed by the insertion of 5-8 cytosine bases. In another example, the 5'UTR may be replaced by inserting 5-8 cytosine bases followed by the insertion of 5-8 adenine bases.

In one embodiment, the circular primary construct may include at least one substitution and/or insertion downstream of the transcription start site which may be recognized by an RNA polymerase. As a non-limiting example, at least one substitution and/or insertion may occur downstream the transcription start site by substituting at least one nucleic acid in the region just downstream of the transcription start site (such as, but not limited to, +1 to +6). Changes to region of nucleotides just downstream of the transcription start site may affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleic acid may cause a silent mutation of the nucleic acid sequence or may cause a mutation in the amino acid sequence.

In one embodiment, the circular primary construct may include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In one embodiment, the circular primary construct may include the substitution of at least 1, at least 2, at least 3, at least 4, at least 5 or at least 6 guanine bases in the region just downstream of the transcription start site. As a non-limiting example, if the nucleotides in the region are GGGAGA the guanine bases may be substituted by at least 1, at least 2, at least 3 or at least 4 adenine nucleotides. In another non-limiting example, if the nucleotides in the region are GGGAGA the guanine bases may be substituted by at least 1, at least 2, at least 3 or at least 4 cytosine bases. In another non-limiting example, if the nucleotides in the region are GGGAGA the guanine bases may be substituted by at least 1, at least 2, at least 3 or at least 4 thymine, and/or any of the nucleotides described herein.

In one embodiment, the circular primary construct may include at least one substitution and/or insertion upstream of the start codon. For the purpose of clarity, one of skill in the art would appreciate that the start codon is the first codon of the protein coding region whereas the transcription start site is the site where transcription begins. The circular primary construct may include, but is not limited to, at least 1, at least 2, at least 3, at least 4, at least 5, at least 6, at least 7 or at least 8 substitutions and/or insertions of nucleotide bases. The nucleotide bases may be inserted or substituted at 1, at least 1, at least 2, at least 3, at least 4 or at least 5 locations upstream of the start codon. The nucleotides inserted and/or substituted may be the same base (e.g., all A or all C or all T or all G), two different bases (e.g., A and C, A and T, or C and T), three different bases (e.g., A, C and T or A, C and T) or at least four different bases. As a non-limiting example, the guanine base upstream of the coding region in the circular primary construct may be substituted with adenine, cytosine, thymine, or any of the nucleotides described herein. In another non-limiting example the substitution of guanine bases in the cyclic circular primary construct may be designed so as to leave one guanine base in the region downstream of the transcription start site and before the start codon (see Esvelt et al. Nature (2011) 472(7344):499-503; herein incorporated by reference in its entirety). As a non-limiting example, at least 5 nucleotides may be inserted at 1 location downstream of the transcription start site but upstream of the start codon and the at least 5 nucleotides may be the same base type.

Capping and/or Tailing Reactions

The circular primary construct, circPs circSP, circRNA and circRNA-SP may also undergo capping and/or tailing reactions. A capping reaction may be performed by methods known in the art to add a 5' cap to the 5' end of the circular primary construct, circP, circSP, circRNA or circRNA-SP. Methods for capping include, but are not limited to, using a Vaccinia Capping enzyme (New England Biolabs, Ipswich, Mass.).

A poly-A tailing reaction may be performed by methods known in the art, such as, but not limited to, 2' O-methyltransferase and by methods as described herein. If the circular primary construct, circP, circSP, circRNA or circRNA-SP does not include a poly-T, it may be beneficial to perform the poly-A-tailing reaction before the circular primary construct, circP, circSP, circRNA or circRNA-SP is cleaned.

Purification

Circular primary construct, circP, circSP, circRNA or circRNA-SP purification may include, but is not limited to, clean-up, quality assurance and quality control. Circular primary construct, circP, circSP, circRNA or circRNA-SP clean-up may be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark), RNAse III treatment (see e.g., International Publication No. WO2013102203, herein incorporated by reference in its entirety) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a circular polynucleotide such as a "purified circP," "purified circSP," "purified circRNA," "purified circRNA-SP" or "purified circular primary construct" refers to one that is separated from at least one contaminant. As used herein, a "contaminant" is any substance which makes another unfit, impure or inferior. Thus, a purified circular polynucleotide (e.g., circP, circSP, circRNA or circRNA-SP) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In another embodiment, the circular primary construct, circP, circSP, circRNA or circRNA-SP may be sequenced by methods including, but not limited to reverse-transcriptase-PCR.

In one embodiment, the circular primary construct, circP, circRNA or circRNA-SP may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified circP, circRNA or circRNA-SP may be analyzed in order to determine if the polynucleotide in the circP, circRNA or circRNA-SP may be of proper size, check that no degradation of the circP, circSP, circRNA or circRNA-SP has occurred. Degradation of the circP, circSP, circRNA or circRNA-SP may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Signal Sequences

The circular primary construct, circP, circSP, circRNA or circRNA-SP may also include and/or encode additional features which facilitate trafficking of the polypeptides to therapeutically relevant sites. One such feature which aids in protein trafficking is the signal sequence. As used herein, a "signal sequence" or "signal peptide" is a polynucleotide or polypeptide, respectively, which is from about 9 to 200 nucleotides (3-60 amino acids) in length which is incorporated at the 5' (or N-terminus) of the coding region or polypeptide encoded, respectively. In circPs, circRNAs and circRNA-SPs, the addition of these sequences result in trafficking of the encoded polypeptide to the endoplasmic reticulum through one or more secretory pathways. Some signal peptides are cleaved from the protein by signal peptidase after the proteins are transported.

In one embodiment the circular primary construct, circP, circSP, circRNA or circRNA-SP may comprise a protein signal sequence such as, but not limited to, any of the nucleic acid sequences (SEQ ID NO: 32-93) in Table 5 of International Patent Publication No. WO2013151666, the contents of which are herein incorporated by reference in its entirety. These sequences may be included at the beginning of the first region of linked nucleosides, in the middle or at the terminus or alternatively into a flanking region. Further, any of the circular primary construct, circP, circSP, circRNA or circRNA-SP of the present invention may also comprise one or more of the nucleic acid sequences in Table 5 of International Patent Publication No. WO2013151666, the contents of which are herein incorporated by reference in its entirety. These may be in the first region linked nucleosides or either flanking region.

In one embodiment the circular primary construct, circP, circSP, circRNA or circRNA-SP may encode a protein signal sequence such as, but not limited to, any of the protein sequences (SEQ ID NO: 94-155) in Table 5 of International Patent Publication No. WO2013151666, the contents of which are herein incorporated by reference in its entirety. These sequences may be included at the beginning of the first region of linked nucleosides, in the middle or at the terminus or alternatively into a flanking region. Further, any of the circular primary construct, circP, circSP, circRNA or circRNA-SP of the present invention may also comprise one or more of the nucleic acid sequences in encoding the protein sequences listed in Table 5 of International Patent Publication No. WO2013151666, the contents of which are herein incorporated by reference in its entirety. These may be in the first region linked nucleosides or either flanking region. Additional signal sequences which may be utilized in the present invention include those taught in, for example, databases such as those found at http://www.signalpeptide.de/ or http://proline.bic.nus.edu.sg/spdb/. Those described in U.S. Pat. Nos. 8,124,379; 7,413,875 and 7,385,034 are also within the scope of the invention and the contents of each are incorporated herein by reference in their entirety.

Target Selection

According to the present invention, the circP, circRNA or circRNA-SP comprise at least a first region of linked nucleosides encoding at least one polypeptide of interest. Non limiting examples of polypeptides of interest or "Targets" of the present invention are listed in Table 6 of International Publication Nos. WO2013151666, WO2013151668, WO2013151663, WO2013151669, WO2013151670, WO2013151664, WO2013151665, WO2013151736; Tables 6 and 7 International Publication No. WO2013151672; Tables 6, 178 and 179 of International Publication No. WO2013151671; Tables 6, 185 and 186 of International Publication No WO2013151667; the contents of each of which are herein incorporated by reference in their entireties.

Protein Cleavage Signals and Sites

In one embodiment, the polypeptides encoded by the circP, circRNA or circRNA-SP of the present invention may include at least one protein cleavage signal containing at least one protein cleavage site. The protein cleavage site may be located at the N-terminus, the C-terminus, at any space between the N- and the C-termini such as, but not limited to, half-way between the N- and C-termini, between the N-terminus and the half way point, between the half way point and the C-terminus, and combinations thereof.

The polypeptides encoded by the circP, circRNA or circRNA-SP of the present invention may include, but is not limited to, a proprotein convertase (or prohormone convertase), thrombin or Factor Xa protein cleavage signal. Proprotein convertases are a family of nine proteinases, comprising seven basic amino acid-specific subtilisin-like serine proteinases related to yeast kexin, known as prohormone convertase 1/3 (PC1/3), PC2, furin, PC4, PC5/6, paired basic amino-acid cleaving enzyme 4 (PACE4) and PC7, and two other subtilases that cleave at non-basic residues, called subtilisin kexin isozyme 1 (SKI-1) and proprotein convertase subtilisin kexin 9 (PCSK9). Non-limiting examples of protein cleavage signal amino acid sequences are listed in Table 7 of International Publication No. WO2013151666, the contents of which are herein incorporated by reference in its entirety. In one embodiment, the circular primary construct, circP, circSP, circRNA or circRNA-SP of the present invention may be engineered such that the circular primary construct, circP, circSP, circRNA or circRNA-SP contains at least one encoded protein cleavage signal. The encoded protein cleavage signal may be located before the start codon, after the start codon, before the coding region, within the coding region such as, but not limited to, half way in the coding region, between the start codon and the half way point, between the half way point and the stop codon, after the coding region, before the stop codon, between two stop codons, after the stop codon and combinations thereof.

In one embodiment, the circular primary construct, circP, circSP, circRNA or circRNA-SP of the present invention may include at least one encoded protein cleavage signal containing at least one protein cleavage site. The encoded protein cleavage signal may include, but is not limited to, a proprotein convertase (or prohormone convertase), thrombin and/or Factor Xa protein cleavage signal. One of skill in the art may use Table 1 above or other known methods to determine the appropriate encoded protein cleavage signal to include in the circular primary constructs, circP, circSP, circRNA or circRNA-SP of the present invention. For example, starting with the signal of Table 7 of International Publication No. WO2013151666 and considering the codons of Table 1 one can design a signal for the circular primary construct which can produce a protein signal in the resulting polypeptide.

In one embodiment, the polypeptides encoded by the circP, circRNA or circRNA-SP of the present invention may include at least one protein cleavage signal and/or site.

As a non-limiting example, U.S. Pat. No. 7,374,930 and U.S. Pub. No. 20090227660, herein incorporated by reference in their entireties, use a furin cleavage site to cleave the N-terminal methionine of GLP-1 in the expression product from the Golgi apparatus of the cells. In one embodiment, the polypeptides encoded by the circular primary construct, circP, circRNA or circRNA-SP of the present invention include at least one protein cleavage signal and/or site with the proviso that the polypeptide is not GLP-1.

In one embodiment, the circular primary construct, circP, circRNA or circRNA-SP of the present invention includes at least one encoded protein cleavage signal and/or site.

In one embodiment, the circular primary construct, circP, circRNA or circRNA-SP of the present invention includes at least one encoded protein cleavage signal and/or site with the proviso that the circular primary construct, circP, circRNA or circRNA-SP does not encode GLP-1.

In one embodiment, the circular primary construct, circP, circRNA or circRNA-SP of the present invention may include more than one coding region. Where multiple coding regions are present in the circular primary construct, circP, circRNA or circRNA-SP of the present invention, the multiple coding regions may be separated by encoded protein cleavage sites. As a non-limiting example, the circular primary construct, circSP, circRNA or circRNA-SP may be signed in an ordered pattern. On such pattern follows AXBY form where A and B are coding regions which may be the same or different coding regions and/or may encode the same or different polypeptides, and X and Y are encoded protein cleavage signals which may encode the same or different protein cleavage signals. A second such pattern follows the form AXYBZ where A and B are coding regions which may be the same or different coding regions and/or may encode the same or different polypeptides, and X, Y and Z are encoded protein cleavage signals which may encode the same or different protein cleavage signals. A third pattern follows the form ABXCY where A, B and C are coding regions which may be the same or different coding regions and/or may encode the same or different polypeptides, and X and Y are encoded protein cleavage signals which may encode the same or different protein cleavage signals.

In one embodiment, the circP, circSP, circRNA or circRNA-SP can also contain sequences that encode protein cleavage sites so that the circular primary construct, circP, circSP, circRNA or circRNA-SP can be released from a carrier region or a fusion partner by treatment with a specific protease for said protein cleavage site.

In one embodiment, the circP, circSP, circRNA or circRNA-SP of the present invention may include a sequence encoding the 2A peptide. In one embodiment, the sequence encoding the 2A peptide may be used to separate the coding region of two or more polypeptides of interest. In another embodiment, this sequence may be used to separate a coding sequence and a sensor region. In yet another embodiment, the sequence encoding the 2A peptide may be used to separate two sensor regions. As a non-limiting example, the sequence encoding the 2A peptide may be between region A and region B (A-2Apep-B). The presence of the 2A peptide would result in the cleavage of one long protein into protein A, protein B and the 2A peptide. Protein A and protein B may be the same or different polypeptides of interest. In another embodiment, the 2A peptide may be used in the circP, circRNA or circRNA-SP of the present invention to produce two, three, four, five, six, seven, eight, nine, ten or more proteins.

Incorporating Post Transcriptional Control Modulators

In one embodiment, the circP, circRNA or circRNA-SP of the present invention may include at least one post transcriptional control modulator. These post transcriptional control modulators may be, but are not limited to, small molecules, compounds and regulatory sequences. As a non-limiting example, post transcriptional control may be achieved using small molecules identified by PTC Therapeutics Inc. (South Plainfield, N.J.) using their GEMS™ (Gene Expression Modulation by Small-Molecules) screening technology.

In one embodiment, the circP, circRNA or circRNA-SP of the present invention may include at least one post transcriptional control modulator as described in International Patent Publication No. WO2013151666, the contents of which are herein incorporated by reference in its entirety. Non-limiting examples of post transcriptional control modulators are described in paragraphs [000299]-[000304] of International Patent Publication No. WO2013151666, the contents of which are herein incorporated by reference in its entirety.

Cyclization of Linear Polynucleotides

Linear polynucleotides and/or linear primary constructs maybe cyclized to generate the circP, circSP, circRNA or circRNA-SP of the present invention including but not limited to, 3 different routes such as 1) chemical, 2) enzymatic, and 3) ribozyme catalyzed. Non-limiting examples of these routes are outlined below. The newly formed 5'-/3'-linkage may be intramolecular or intermolecular.

As a non-limiting example, the linear polynucleotides and linear primary constructs which may be circularized may be selected from those described in; International Publication Nos. WO2013151666, WO2013151667, WO2013151668, WO2013151663, WO2013151669, WO2013151670, WO2013151664, WO2013151665, WO2013151671, WO2013151672, WO2013151736, the contents of each of which are herein incorporated by reference in their entireties.

In the first route, the 5'-end and the 3'-end of the nucleic acid contain the chemically reactive group or groups that, when close together, form a new covalent linkage between the 5'-end and the 3'-end of the molecule. The 5'-end may contain, but is not limited to, an NHS-ester reactive group and the 3'-end may contain, but is not limited to, a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond resulting in a circRNA.

In the second route, T4 RNA ligase may be used to enzymatically link a 5'-phosphorylated nucleic acid molecule to the 3'-hydroxyl group of a nucleic acid forming a new phosphorodiester linkage. In a non-limiting example reaction, 1 µg of a nucleic acid molecule is incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction. The reaction would create a circP, circSP, circRNA or circRNA-SP.

In the third route, either the 5'- or 3'-end of the cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0° C. and 37° C.

Figure 13:
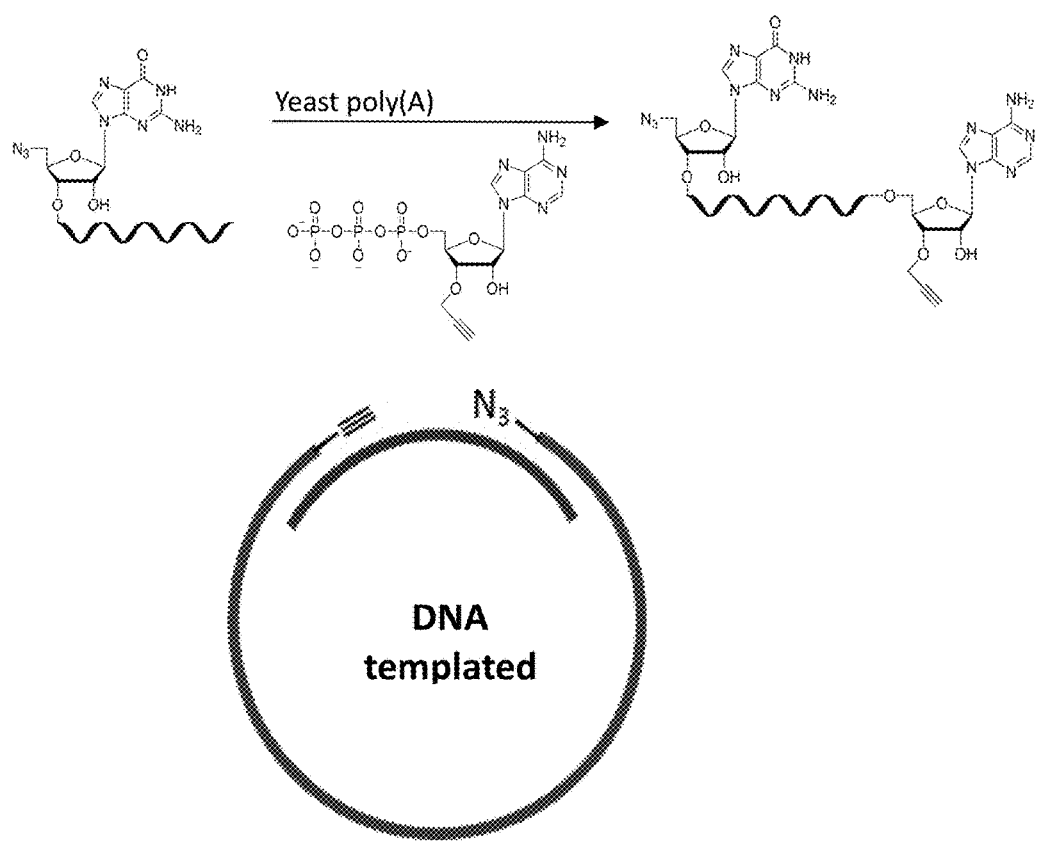
FIG. 13 is an image showing a method of preparing circular polynucleotides of the invention.

The circular polynucleotides of the invention may be synthesized as shown in FIG. 13.

Alternatively, the alkynyl and azido groups may be replaced with other reactive groups as described herein, e.g., halogen and thiophosphate or azido and (thio) phosphoryl.

III. Modifications

Herein, in a circular polynucleotide (such as a circP, circSP, circRNA or circRNA-SP), the terms "modification" or, as appropriate, "modified" refer to modification with respect to A, G, T, U or C ribonucleotides. Generally, herein, these terms are not intended to refer to the ribonucleotide modifications in naturally occurring 5'-terminal mRNA cap moieties. In a polypeptide, the term "modification" refers to a modification as compared to the canonical set of 20 amino acids.

The modifications may be various distinct modifications. In some embodiments, the coding region, the flanking regions and/or the terminal regions may contain one, two, or more (optionally different) nucleoside or nucleotide modifications. In some embodiments, a modified circP, circSP, circRNA or circRNA-SP introduced to a cell may exhibit reduced degradation in the cell, as compared to an unmodified circP, circSP, circRNA or circRNA-SP.

Modifications which are useful in the present invention include, but are not limited to those in Table 4. Noted in the table are the symbol of the modification, the nucleobase type and whether the modification is naturally occurring or not.

TABLE 4

Modifications

| Name | Symbol | Base | Naturally Occurring |
|---|---|---|---|
| 2-methylthio-N6-(cis-hydroxyisopentenyl)adenosine | ms2i6A | A | YES |
| 2-methylthio-N6-methyladenosine | ms2m6A | A | YES |
| 2-methylthio-N6-threonyl carbamoyladenosine | ms2t6A | A | YES |
| N6-glycinylcarbamoyladenosine | g6A | A | YES |
| N6-isopentenyladenosine | i6A | A | YES |
| N6-methyladenosine | m6A | A | YES |
| N6-threonylcarbamoyladenosine | t6A | A | YES |
| 1,2'-O-dimethyladenosine | m1Am | A | YES |
| 1-methyladenosine | m1A | A | YES |
| 2'-O-methyladenosine | Am | A | YES |
| 2'-O-ribosyladenosine (phosphate) | Ar(p) | A | YES |
| 2-methyladenosine | m2A | A | YES |
| 2-methylthio-N6 isopentenyladenosine | ms2i6A | A | YES |
| 2-methylthio-N6-hydroxynorvalyl carbamoyladenosine | ms2hn6A | A | YES |
| 2'-O-methyladenosine | m6A | A | YES |
| 2'-O-ribosyladenosine (phosphate) | Ar(p) | A | YES |
| isopentenyladenosine | Iga | A | YES |
| N6-(cis-hydroxyisopentenyl)adenosine | io6A | A | YES |
| N6,2'-O-dimethyladenosine | m6Am | A | YES |
| N$^6$,2'-O-dimethyladenosine | m$^6$Am | A | YES |
| N6,N6,2'-O-trimethyladenosine | m62Am | A | YES |
| N6,N6-dimethyladenosine | m62A | A | YES |
| N6-acetyladenosine | ac6A | A | YES |
| N6-hydroxynorvalylcarbamoyladenosine | hn6A | A | YES |
| N6-methyl-N6-threonylcarbamoyladenosine | m6t6A | A | YES |
| 2-methyladenosine | m$^2$A | A | YES |
| 2-methylthio-N$^6$-isopentenyladenosine | ms$^2$i$^6$A | A | YES |
| 7-deaza-adenosine | — | A | NO |
| N1-methyl-adenosine | — | A | NO |
| N6,N6 (dimethyl)adenine | — | A | NO |
| N6-cis-hydroxy-isopentenyl-adenosine | — | A | NO |
| α-thio-adenosine | — | A | NO |
| 2 (amino)adenine | — | A | NO |
| 2 (aminopropyl)adenine | — | A | NO |
| 2 (methylthio) N6 (isopentenyl)adenine | — | A | NO |
| 2-(alkyl)adenine | — | A | NO |
| 2-(aminoalkyl)adenine | — | A | NO |
| 2-(aminopropyl)adenine | — | A | NO |
| 2-(halo)adenine | — | A | NO |
| 2-(halo)adenine | — | A | NO |
| 2-(propyl)adenine | — | A | NO |
| 2'-Amino-2'-deoxy-ATP | — | A | NO |
| 2'-Azido-2'-deoxy-ATP | — | A | NO |
| 2'-Deoxy-2'-a-aminoadenosine TP | — | A | NO |
| 2'-Deoxy-2'-a-azidoadenosine TP | — | A | NO |
| 6 (alkyl)adenine | — | A | NO |
| 6 (methyl)adenine | — | A | NO |
| 6-(alkyl)adenine | — | A | NO |
| 6-(methyl)adenine | — | A | NO |
| 7 (deaza)adenine | — | A | NO |
| 8 (alkenyl)adenine | — | A | NO |
| 8 (alkynyl)adenine | — | A | NO |
| 8 (amino)adenine | — | A | NO |
| 8 (thioalkyl)adenine | — | A | NO |
| 8-(alkenyl)adenine | — | A | NO |
| 8-(alkyl)adenine | — | A | NO |
| 8-(alkynyl)adenine | — | A | NO |
| 8-(amino)adenine | — | A | NO |
| 8-(halo)adenine | — | A | NO |
| 8-(hydroxyl)adenine | — | A | NO |
| 8-(thioalkyl)adenine | — | A | NO |
| 8-(thiol)adenine | — | A | NO |
| 8-azido-adenosine | — | A | NO |
| aza adenine | — | A | NO |
| deaza adenine | — | A | NO |
| N6 (methyl)adenine | — | A | NO |
| N6-(isopentyl)adenine | — | A | NO |

TABLE 4-continued

Modifications

| Name | Symbol | Base | Naturally Occurring |
|---|---|---|---|
| 7-deaza-8-aza-adenosine | — | A | NO |
| 7-methyladenine | — | A | NO |
| 1-Deazaadenosine TP | — | A | NO |
| 2'Fluoro-N6-Bz-deoxyadenosine TP | — | A | NO |
| 2'-OMe-2-Amino-ATP | — | A | NO |
| 2'O-methyl-N6-Bz-deoxyadenosine TP | — | A | NO |
| 2'-a-Ethynyladenosine TP | — | A | NO |
| 2-aminoadenine | — | A | NO |
| 2-Aminoadenosine TP | — | A | NO |
| 2-Amino-ATP | — | A | NO |
| 2'-a-Trifluoromethyladenosine TP | — | A | NO |
| 2-Azidoadenosine TP | — | A | NO |
| 2'-b-Ethynyladenosine TP | — | A | NO |
| 2-Bromoadenosine TP | — | A | NO |
| 2'-b-Trifluoromethyladenosine TP | — | A | NO |
| 2-Chloroadenosine TP | — | A | NO |
| 2'-Deoxy-2',2'-difluoroadenosine TP | — | A | NO |
| 2'-Deoxy-2'-a-mercaptoadenosine TP | — | A | NO |
| 2'-Deoxy-2'-a-thiomethoxyadenosine TP | — | A | NO |
| 2'-Deoxy-2'-b-aminoadenosine TP | — | A | NO |
| 2'-Deoxy-2'-azidoadenosine TP | — | A | NO |
| 2'-Deoxy-2'-b-bromoadenosine TP | — | A | NO |
| 2'-Deoxy-2'-b-chloroadenosine TP | — | A | NO |
| 2'-Deoxy-2'-b-fluoroadenosine TP | — | A | NO |
| 2'-Deoxy-2'-b-iodoadenosine TP | — | A | NO |
| 2'-Deoxy-2'-b-mercaptoadenosine TP | — | A | NO |
| 2'-Deoxy-2'-b-thiomethoxyadenosine TP | — | A | NO |
| 2-Fluoroadenosine TP | — | A | NO |
| 2-Iodoadenosine TP | — | A | NO |
| 2-Mercaptoadenosine TP | — | A | NO |
| 2-methoxy-adenine | — | A | NO |
| 2-methylthio-adenine | — | A | NO |
| 2-Trifluoromethyladenosine TP | — | A | NO |
| 3-Deaza-3-bromoadenosine TP | — | A | NO |
| 3-Deaza-3-chloroadenosine TP | — | A | NO |
| 3-Deaza-3-fluoroadenosine TP | — | A | NO |
| 3-Deaza-3-iodoadenosine TP | — | A | NO |
| 3-Deazaadenosine TP | — | A | NO |
| 4'-Azidoadenosine TP | — | A | NO |
| 4'-Carbocyclic adenosine TP | — | A | NO |
| 4'-Ethynyladenosine TP | — | A | NO |
| 5'-Homo-adenosine TP | — | A | NO |
| 8-Aza-ATP | — | A | NO |
| 8-bromo-adenosine TP | — | A | NO |
| 8-Trifluoromethyladenosine TP | — | A | NO |
| 9-Deazaadenosine TP | — | A | NO |
| 2-aminopurine | — | A/G | NO |
| 7-deaza-2,6-diaminopurine | — | A/G | NO |
| 7-deaza-8-aza-2,6-diaminopurine | — | A/G | NO |
| 7-deaza-8-aza-2-aminopurine | — | A/G | NO |
| 2,6-diaminopurine | — | A/G | NO |
| 7-deaza-8-aza-adenine, 7-deaza-2-aminopurine | — | A/G | NO |
| 2-thiocytidine | s2C | C | YES |
| 3-methylcytidine | m3C | C | YES |
| 5-formylcytidine | f5C | C | YES |
| 5-hydroxymethylcytidine | hm5C | C | YES |
| 5-methylcytidine | m5C | C | YES |
| N4-acetylcytidine | ac4C | C | YES |
| 2'-O-methylcytidine | Cm | C | YES |
| 5,2'-O-dimethylcytidine | m5Cm | C | YES |
| 5-formyl-2'-O-methylcytidine | f5Cm | C | YES |
| lysidine | k2C | C | YES |
| N4,2'-O-dimethylcytidine | m4Cm | C | YES |
| N4-acetyl-2'-O-methylcytidine | ac4Cm | C | YES |
| N4-methylcytidine | m4C | C | YES |
| N4,N4-Dimethyl-2'-OMe-Cytidine TP | — | C | YES |
| 4-methylcytidine | — | C | NO |
| 5-aza-cytidine | — | C | NO |
| Pseudo-iso-cytidine | — | C | NO |
| pyrrolo-cytidine | — | C | NO |
| α-thio-cytidine | — | C | NO |
| 2-(thio)cytosine | — | C | NO |
| 2'-Amino-2'-deoxy-CTP | — | C | NO |
| 2'-Azido-2'-deoxy-CTP | — | C | NO |
| 2'-Deoxy-2'-a-aminocytidine TP | — | C | NO |

TABLE 4-continued

Modifications

| Name | Symbol | Base | Naturally Occurring |
|---|---|---|---|
| 2'-Deoxy-2'-a-azidocytidine TP | — | C | NO |
| 3 (deaza) 5 (aza)cytosine | — | C | NO |
| 3 (methyl)cytosine | — | C | NO |
| 3-(alkyl)cytosine | — | C | NO |
| 3-(deaza) 5 (aza)cytosine | — | C | NO |
| 3-(methyl)cytidine | — | C | NO |
| 4,2'-O-dimethylcytidine | — | C | NO |
| 5 (halo)cytosine | — | C | NO |
| 5 (methyl)cytosine | — | C | NO |
| 5 (propynyl)cytosine | — | C | NO |
| 5 (trifluoromethyl)cytosine | — | C | NO |
| 5-(alkyl)cytosine | — | C | NO |
| 5-(alkynyl)cytosine | — | C | NO |
| 5-(halo)cytosine | — | C | NO |
| 5-(propynyl)cytosine | — | C | NO |
| 5-(trifluoromethyl)cytosine | — | C | NO |
| 5-bromo-cytidine | — | C | NO |
| 5-iodo-cytidine | — | C | NO |
| 5-propynyl cytosine | — | C | NO |
| 6-(azo)cytosine | — | C | NO |
| 6-aza-cytidine | — | C | NO |
| aza cytosine | — | C | NO |
| deaza cytosine | — | C | NO |
| N4 (acetyl)cytosine | — | C | NO |
| 1-methyl-1-deaza-pseudoisocytidine | — | C | NO |
| 1-methyl-pseudoisocytidine | — | C | NO |
| 2-methoxy-5-methyl-cytidine | — | C | NO |
| 2-methoxy-cytidine | — | C | NO |
| 2-thio-5-methyl-cytidine | — | C | NO |
| 4-methoxy-1-methyl-pseudoisocytidine | — | C | NO |
| 4-methoxy-pseudoisocytidine | — | C | NO |
| 4-thio-1-methyl-1-deaza-pseudoisocytidine | — | C | NO |
| 4-thio-1-methyl-pseudoisocytidine | — | C | NO |
| 4-thio-pseudoisocytidine | — | C | NO |
| 5-aza-zebularine | — | C | NO |
| 5-methyl-zebularine | — | C | NO |
| pyrrolo-pseudoisocytidine | — | C | NO |
| zebularine | — | C | NO |
| (E)-5-(2-Bromo-vinyl)cytidine TP | — | C | NO |
| 2,2'-anhydro-cytidine TP hydrochloride | — | C | NO |
| 2'Fluor-N4-Bz-cytidine TP | — | C | NO |
| 2'Fluoro-N4-Acetyl-cytidine TP | — | C | NO |
| 2'-O-Methyl-N4-Acetyl-cytidine TP | — | C | NO |
| 2'O-methyl-N4-Bz-cytidine TP | — | C | NO |
| 2'-a-Ethynylcytidine TP | — | C | NO |
| 2'-a-Trifluoromethylcytidine TP | — | C | NO |
| 2'-b-Ethynylcytidine TP | — | C | NO |
| 2'-b-Trifluoromethylcytidine TP | — | C | NO |
| 2'-Deoxy-2',2'-difluorocytidine TP | — | C | NO |
| 2'-Deoxy-2'-a-mercaptocytidine TP | — | C | NO |
| 2'-Deoxy-2'-a-thiomethoxycytidine TP | — | C | NO |
| 2'-Deoxy-2'-b-aminocytidine TP | — | C | NO |
| 2'-Deoxy-2'-b-azidocytidine TP | — | C | NO |
| 2'-Deoxy-2'-b-bromocytidine TP | — | C | NO |
| 2'-Deoxy-2'-b-chlorocytidine TP | — | C | NO |
| 2'-Deoxy-2'-b-fluorocytidine TP | — | C | NO |
| 2'-Deoxy-2'-b-iodocytidine TP | — | C | NO |
| 2'-Deoxy-2'-b-mercaptocytidine TP | — | C | NO |
| 2'-Deoxy-2'-b-thiomethoxycytidine TP | — | C | NO |
| 2'-O-Methyl-5-(1-propynyl)cytidine TP | — | C | NO |
| 3'-Ethynylcytidine TP | — | C | NO |
| 4'-Azidocytidine TP | — | C | NO |
| 4'-Carbocyclic cytidine TP | — | C | NO |
| 4'-Ethynylcytidine TP | — | C | NO |
| 5-(1-Propynyl)ara-cytidine TP | — | C | NO |
| 5-(2-Chloro-phenyl)-2-thiocytidine TP | — | C | NO |
| 5-(4-Amino-phenyl)-2-thiocytidine TP | — | C | NO |
| 5-Aminoallyl-CTP | — | C | NO |
| 5-Cyanocytidine TP | — | C | NO |
| 5-Ethynylara-cytidine TP | — | C | NO |
| 5-Ethynylcytidine TP | — | C | NO |
| 5'-Homo-cytidine TP | — | C | NO |
| 5-Methoxycytidine TP | — | C | NO |
| 5-Trifluoromethyl-Cytidine TP | — | C | NO |
| N4-Amino-cytidine TP | — | C | NO |

TABLE 4-continued

Modifications

| Name | Symbol | Base | Naturally Occurring |
|---|---|---|---|
| N4-Benzoyl-cytidine TP | — | C | NO |
| pseudoisocytidine | — | C | NO |
| 7-methylguanosine | m7G | G | YES |
| N2,2'-O-dimethylguanosine | m2Gm | G | YES |
| N2-methylguanosine | m2G | G | YES |
| wyosine | imG | G | YES |
| 1,2'-O-dimethylguanosine | m1Gm | G | YES |
| 1-methylguanosine | m1G | G | YES |
| 2'-O-methylguanosine | Gm | G | YES |
| 2'-O-ribosylguanosine (phosphate) | Gr(p) | G | YES |
| 2'-O-methylguanosine | Gm | G | YES |
| 2'-O-ribosylguanosine (phosphate) | Gr(p) | G | YES |
| 7-aminomethyl-7-deazaguanosine | preQ1 | G | YES |
| 7-cyano-7-deazaguanosine | preQ0 | G | YES |
| archaeosine | G+ | G | YES |
| methylwyosine | mimG | G | YES |
| N2,7-dimethylguanosine | m2,7G | G | YES |
| N2,N2,2'-O-trimethylguanosine | m22Gm | G | YES |
| N2,N2,7-trimethylguanosine | m2,2,7G | G | YES |
| N2,N2-dimethylguanosine | m22G | G | YES |
| $N^2,7,2'$-O-trimethylguanosine | $m^{2,7}Gm$ | G | YES |
| 6-thio-guanosine | — | G | NO |
| 7-deaza-guanosine | — | G | NO |
| 8-oxo-guanosine | — | G | NO |
| N1-methyl-guanosine | — | G | NO |
| α-thio-guanosine | — | G | NO |
| 2 (propyl)guanine | — | G | NO |
| 2-(alkyl)guanine | — | G | NO |
| 2'-Amino-2'-deoxy-GTP | — | G | NO |
| 2'-Azido-2'-deoxy-GTP | — | G | NO |
| 2'-Deoxy-2'-a-aminoguanosine TP | — | G | NO |
| 2'-Deoxy-2'-a-azidoguanosine TP | — | G | NO |
| 6 (methyl)guanine | — | G | NO |
| 6-(alkyl)guanine | — | G | NO |
| 6-(methyl)guanine | — | G | NO |
| 6-methyl-guanosine | — | G | NO |
| 7 (alkyl)guanine | — | G | NO |
| 7 (deaza)guanine | — | G | NO |
| 7 (methyl)guanine | — | G | NO |
| 7-(alkyl)guanine | — | G | NO |
| 7-(deaza)guanine | — | G | NO |
| 7-(methyl)guanine | — | G | NO |
| 8 (alkyl)guanine | — | G | NO |
| 8 (alkynyl)guanine | — | G | NO |
| 8 (halo)guanine | — | G | NO |
| 8 (thioalkyl)guanine | — | G | NO |
| 8-(alkenyl)guanine | — | G | NO |
| 8-(alkyl)guanine | — | G | NO |
| 8-(alkynyl)guanine | — | G | NO |
| 8-(amino)guanine | — | G | NO |
| 8-(halo)guanine | — | G | NO |
| 8-(hydroxyl)guanine | — | G | NO |
| 8-(thioalkyl)guanine | — | G | NO |
| 8-(thiol)guanine | — | G | NO |
| aza guanine | — | G | NO |
| deaza guanine | — | G | NO |
| N-(methyl)guanine | — | G | NO |
| 1-methyl-6-thio-guanosine | — | G | NO |
| 6-methoxy-guanosine | — | G | NO |
| 6-thio-7-deaza-8-aza-guanosine | — | G | NO |
| 6-thio-7-deaza-guanosine | — | G | NO |
| 6-thio-7-methyl-guanosine | — | G | NO |
| 7-deaza-8-aza-guanosine | — | G | NO |
| 7-methyl-8-oxo-guanosine | — | G | NO |
| N2,N2-dimethyl-6-thio-guanosine | — | G | NO |
| N2-methyl-6-thio-guanosine | — | G | NO |
| 1-Me-GTP | — | G | NO |
| 2'Fluoro-N2-isobutyl-guanosine TP | — | G | NO |
| 2'O-methyl-N2-isobutyl-guanosine TP | — | G | NO |
| 2'-a-Ethynylguanosine TP | — | G | NO |
| 2'-a-Trifluoromethylguanosine TP | — | G | NO |
| 2'-b-Ethynylguanosine TP | — | G | NO |
| 2'-b-Trifluoromethylguanosine TP | — | G | NO |
| 2'-Deoxy-2',2'-difluoroguanosine TP | — | G | NO |
| 2'-Deoxy-2'-a-mercaptoguanosine TP | — | G | NO |

TABLE 4-continued

Modifications

| Name | Symbol | Base | Naturally Occurring |
|---|---|---|---|
| 2'-Deoxy-2'-a-thiomethoxyguanosine TP | — | G | NO |
| 2'-Deoxy-2'-b-aminoguanosine TP | — | G | NO |
| 2'-Deoxy-2'-b-azidoguanosine TP | — | G | NO |
| 2'-Deoxy-2'-b-bromoguanosine TP | — | G | NO |
| 2'-Deoxy-2'-b-chloroguanosine TP | — | G | NO |
| 2'-Deoxy-2'-b-fluoroguanosine TP | — | G | NO |
| 2'-Deoxy-2'-b-iodoguanosine TP | — | G | NO |
| 2'-Deoxy-2'-b-mercaptoguanosine TP | — | G | NO |
| 2'-Deoxy-2'-b-thiomethoxyguanosine TP | — | G | NO |
| 4'-Azidoguanosine TP | — | G | NO |
| 4'-Carbocyclic guanosine TP | — | G | NO |
| 4'-Ethynylguanosine TP | — | G | NO |
| 5'-Homo-guanosine TP | — | G | NO |
| 8-bromo-guanosine TP | — | G | NO |
| 9-Deazaguanosine TP | — | G | NO |
| N2-isobutyl-guanosine TP | — | G | NO |
| 1-methylinosine | m1I | I | YES |
| inosine | I | I | YES |
| 1,2'-O-dimethylinosine | m1Im | I | YES |
| 2'-O-methylinosine | Im | I | YES |
| 7-methylinosine | | I | NO |
| 2'-O-methylinosine | Im | I | YES |
| epoxyqueuosine | oQ | Q | YES |
| galactosyl-queuosine | galQ | Q | YES |
| mannosylqueuosine | manQ | Q | YES |
| queuosine | Q | Q | YES |
| allyamino-thymidine | — | T | NO |
| aza thymidine | — | T | NO |
| deaza thymidine | — | T | NO |
| deoxy-thymidine | — | T | NO |
| 2'-O-methyluridine | — | U | YES |
| 2-thiouridine | s2U | U | YES |
| 3-methyluridine | m3U | U | YES |
| 5-carboxymethyluridine | cm5U | U | YES |
| 5-hydroxyuridine | ho5U | U | YES |
| 5-methyluridine | m5U | U | YES |
| 5-taurinomethyl-2-thiouridine | τm5s2U | U | YES |
| 5-taurinomethyluridine | τm5U | U | YES |
| dihydrouridine | D | U | YES |
| pseudouridine | Ψ | U | YES |
| (3-(3-amino-3-carboxypropyl)uridine | acp3U | U | YES |
| 1-methyl-3-(3-amino-5-carboxypropyl)pseudouridine | m1acp3Ψ | U | YES |
| 1-methylpseduouridine | m1Ψ | U | YES |
| 2'-O-methyluridine | Um | U | YES |
| 2'-O-methylpseudouridine | Ψm | U | YES |
| 2-thio-2'-O-methyluridine | s2Um | U | YES |
| 3-(3-amino-3-carboxypropyl)uridine | acp3U | U | YES |
| 3,2'-O-dimethyluridine | m3Um | U | YES |
| 3-Methyl-pseudo-Uridine TP | — | U | YES |
| 4-thiouridine | s4U | U | YES |
| 5-(carboxyhydroxymethyl)uridine | chm5U | U | YES |
| 5-(carboxyhydroxymethyl)uridine methyl ester | mchm5U | U | YES |
| 5,2'-O-dimethyluridine | m5Um | U | YES |
| 5,6-dihydro-uridine | — | U | YES |
| 5-aminomethyl-2-thiouridine | nm5s2U | U | YES |
| 5-carbamoylmethyl-2'-O-methyluridine | ncm5Um | U | YES |
| 5-carbamoylmethyluridine | ncm5U | U | YES |
| 5-carboxyhydroxymethyluridine | — | U | YES |
| 5-carboxyhydroxymethyluridine methyl ester | — | U | YES |
| 5-carboxymethylaminomethyl-2'-O-methyluridine | cmnm5Um | U | YES |
| 5-carboxymethylaminomethyl-2-thiouridine | cmnm5s2U | U | YES |
| 5-carboxymethylaminomethyluridine | cmnm5U | U | YES |
| 5-Carbamoylmethyluridine TP | — | U | YES |
| 5-methoxycarbonylmethyl-2'-O-methyluridine | mcm5Um | U | YES |
| 5-methoxycarbonylmethyl-2-thiouridine | mcm5s2U | U | YES |
| 5-methoxycarbonylmethyluridine | mcm5U | U | YES |
| 5-methoxyuridine | mo5U | U | YES |
| 5-methyl-2-thiouridine | m5s2U | U | YES |
| 5-methylaminomethyl-2-selenouridine | mnm5se2U | U | YES |
| 5-methylaminomethyl-2-thiouridine | mnm5s2U | U | YES |
| 5-methylaminomethyluridine | mnm5U | U | YES |
| 5-Methyldihydrouridine | — | U | YES |
| 5-Oxyacetic acid-Uridine TP | — | U | YES |

TABLE 4-continued

Modifications

| Name | Symbol | Base | Naturally Occurring |
|---|---|---|---|
| 5-Oxyacetic acid-methyl ester-Uridine TP | — | U | YES |
| N1-methyl-pseudo-uridine | — | U | YES |
| uridine 5-oxyacetic acid | cmo5U | U | YES |
| uridine 5-oxyacetic acid methyl ester | mcmo5U | U | YES |
| 3-(3-Amino-3-carboxypropyl)-Uridine TP | — | U | YES |
| 5-(iso-Pentenylaminomethyl)-2-thiouridine TP | — | U | YES |
| 5-(iso-Pentenylaminomethyl)-2'-O-methyluridine TP | — | U | YES |
| 5-(iso-Pentenylaminomethyl)uridine TP | — | U | YES |
| 5-propynyl uracil | — | U | NO |
| α-thio-uridine | — | U | NO |
| 1 (aminoalkylamino-carbonylethylenyl)-2(thio)-pseudouracil | — | U | NO |
| 1 (aminoalkylaminocarbonylethylenyl)-2,4-(dithio)pseudouracil | — | U | NO |
| 1 (aminoalkylaminocarbonylethylenyl)-4 (thio)pseudouracil | — | U | NO |
| 1 (aminoalkylaminocarbonylethylenyl)-pseudouracil | — | U | NO |
| 1 (aminocarbonylethylenyl)-2(thio)-pseudouracil | — | U | NO |
| 1 (aminocarbonylethylenyl)-2,4-(dithio)pseudouracil | — | U | NO |
| 1 (aminocarbonylethylenyl)-4 (thio)pseudouracil | — | U | NO |
| 1 (aminocarbonylethylenyl)-pseudouracil | — | U | NO |
| 1 substituted 2(thio)-pseudouracil | — | U | NO |
| 1 substituted 2,4-(dithio)pseudouracil | — | U | NO |
| 1 substituted 4 (thio)pseudouracil | — | U | NO |
| 1 substituted pseudouracil | — | U | NO |
| 1-(aminoalkylamino-carbonylethylenyl)-2-(thio)-pseudouracil | — | U | NO |
| 1-Methyl-3-(3-amino-3-carboxypropyl) pseudouridine TP | — | U | NO |
| 1-Methyl-3-(3-amino-3-carboxypropyl)pseudo-UTP | — | U | NO |
| 1-Methyl-pseudo-UTP | — | U | NO |
| 2 (thio)pseudouracil | — | U | NO |
| 2' deoxy uridine | — | U | NO |
| 2' fluorouridine | — | U | NO |
| 2-(thio)uracil | — | U | NO |
| 2,4-(dithio)psuedouracil | — | U | NO |
| 2' methyl, 2'amino, 2'azido, 2'fluro-guanosine | — | U | NO |
| 2'-Amino-2'-deoxy-UTP | — | U | NO |
| 2'-Azido-2'-deoxy-UTP | — | U | NO |
| 2'-Azido-deoxyuridine TP | — | U | NO |
| 2'-O-methylpseudouridine | — | U | NO |
| 2' deoxy uridine | 2' dU | U | NO |
| 2' fluorouridine | — | U | NO |
| 2'-Deoxy-2'-a-aminouridine TP | — | U | NO |
| 2'-Deoxy-2'-a-azidouridine TP | — | U | NO |
| 2-methylpseudouridine | m3Ψ | U | NO |
| 3 (3 amino-3 carboxypropyl)uracil | — | U | NO |
| 4 (thio)pseudouracil | — | U | NO |
| 4-thiouracil | — | U | NO |
| 5 (1,3-diazole-1-alkyl)uracil | — | U | NO |
| 5 (2-aminopropyl)uracil | — | U | NO |
| 5 (aminoalkyl)uracil | — | U | NO |
| 5 (dimethylaminoalkyl)uracil | — | U | NO |
| 5 (guanidiniumalkyl)uracil | — | U | NO |
| 5 (methoxycarbonylmethyl)-2-(thio)uracil | — | U | NO |
| 5 (methoxycarbonyl-methyl)uracil | — | U | NO |
| 5 (methyl) 2 (thio)uracil | — | U | NO |
| 5 (methyl) 2,4 (dithio)uracil | — | U | NO |
| 5 (methyl) 4 (thio)uracil | — | U | NO |
| 5 (methylaminomethyl)-2 (thio)uracil | — | U | NO |
| 5 (methylaminomethyl)-2,4 (dithio)uracil | — | U | NO |
| 5 (methylaminomethyl)-4 (thio)uracil | — | U | NO |
| 5 (propynyl)uracil | — | U | NO |
| 5 (trifluoromethyl)uracil | — | U | NO |
| 5-(2-aminopropyl)uracil | — | U | NO |
| 5-(alkyl)-2-(thio)pseudouracil | — | U | NO |
| 5-(alkyl)-2,4 (dithio)pseudouracil | — | U | NO |
| 5-(alkyl)-4 (thio)pseudouracil | — | U | NO |

TABLE 4-continued

| Modifications | | | |
|---|---|---|---|
| Name | Symbol | Base | Naturally Occurring |
| 5-(alkyl)pseudouracil | — | U | NO |
| 5-(alkyl)uracil | — | U | NO |
| 5-(alkynyl)uracil | — | U | NO |
| 5-(allylamino)uracil | — | U | NO |
| 5-(cyanoalkyl)uracil | — | U | NO |
| 5-(dialkylaminoalkyl)uracil | — | U | NO |
| 5-(dimethylaminoalkyl)uracil | — | U | NO |
| 5-(guanidiniumalkyl)uracil | — | U | NO |
| 5-(halo)uracil | — | U | NO |
| 5-(1,3-diazole-1-alkyl)uracil | — | U | NO |
| 5-(methoxy)uracil | — | U | NO |
| 5-(methoxycarbonylmethyl)-2-(thio)uracil | — | U | NO |
| 5-(methoxycarbonyl-methyl)uracil | — | U | NO |
| 5-(methyl) 2(thio)uracil | — | U | NO |
| 5-(methyl) 2,4 (dithio)uracil | — | U | NO |
| 5-(methyl) 4 (thio)uracil | — | U | NO |
| 5-(methyl)-2-(thio)pseudouracil | — | U | NO |
| 5-(methyl)-2,4 (dithio)pseudouracil | — | U | NO |
| 5-(methyl)-4 (thio)pseudouracil | — | U | NO |
| 5-(methyl)pseudouracil | — | U | NO |
| 5-(methylaminomethyl)-2 (thio)uracil | — | U | NO |
| 5-(methylaminomethyl)-2,4(dithio)uracil | — | U | NO |
| 5-(methylaminomethyl)-4-(thio)uracil | — | U | NO |
| 5-(propynyl)uracil | — | U | NO |
| 5-(trifluoromethyl)uracil | — | U | NO |
| 5-aminoallyl-uridine | — | U | NO |
| 5-bromo-uridine | — | U | NO |
| 5-iodo-uridine | — | U | NO |
| 5-uracil | — | U | NO |
| 6-(azo)uracil | — | U | NO |
| 6-aza-uridine | — | U | NO |
| allyamino-uracil | — | U | NO |
| aza uracil | — | U | NO |
| deaza uracil | — | U | NO |
| N3 (methyl)uracil | — | U | NO |
| P seudo-UTP-1-2-ethanoic acid | — | U | NO |
| pseudouracil | — | U | NO |
| 4-Thio-pseudo-UTP | — | U | NO |
| 1-carboxymethyl-pseudouridine | — | U | NO |
| 1-methyl-1-deaza-pseudouridine | — | U | NO |
| 1-propynyl-uridine | — | U | NO |
| 1-taurinomethyl-1-methyl-uridine | — | U | NO |
| 1-taurinomethyl-4-thio-uridine | — | U | NO |
| 1-taurinomethyl-pseudouridine | — | U | NO |
| 2-methoxy-4-thio-pseudouridine | — | U | NO |
| 2-thio-1-methyl-1-deaza-pseudouridine | — | U | NO |
| 2-thio-1-methyl-pseudouridine | — | U | NO |
| 2-thio-5-aza-uridine | — | U | NO |
| 2-thio-dihydropseudouridine | — | U | NO |
| 2-thio-dihydrouridine | — | U | NO |
| 2-thio-pseudouridine | — | U | NO |
| 4-methoxy-2-thio-pseudouridine | — | U | NO |
| 4-methoxy-pseudouridine | — | U | NO |
| 4-thio-1-methyl-pseudouridine | — | U | NO |
| 4-thio-pseudouridine | — | U | NO |
| 5-aza-uridine | — | U | NO |
| dihydropseudouridine | — | U | NO |
| (±)1-(2-Hydroxypropyl)pseudouridine TP | — | U | NO |
| (2R)-1-(2-Hydroxypropyl)pseudouridine TP | — | U | NO |
| (2S)-1-(2-Hydroxypropyl)pseudouridine TP | — | U | NO |
| (E)-5-(2-Bromo-vinyl)ara-uridine TP | — | U | NO |
| (E)-5-(2-Bromo-vinyl)uridine TP | — | U | NO |
| (Z)-5-(2-Bromo-vinyl)ara-uridine TP | — | U | NO |
| (Z)-5-(2-Bromo-vinyl)uridine TP | — | U | NO |
| 1-(2,2,2-Trifluoroethyl)-pseudo-UTP | — | U | NO |
| 1-(2,2,3,3,3-Pentafluoropropyl)pseudouridine TP | — | U | NO |
| 1-(2,2-Diethoxyethyl)pseudouridine TP | — | U | NO |
| 1-(2,4,6-Trimethylbenzyl)pseudouridine TP | — | U | NO |
| 1-(2,4,6-Trimethyl-benzyl)pseudo-UTP | — | U | NO |
| 1-(2,4,6-Trimethyl-phenyl)pseudo-UTP | — | U | NO |
| 1-(2-Amino-2-carboxyethyl)pseudo-UTP | — | U | NO |
| 1-(2-Amino-ethyl)pseudo-UTP | — | U | NO |
| 1-(2-Hydroxyethyl)pseudouridine TP | — | U | NO |
| 1-(2-Methoxyethyl)pseudouridine TP | — | U | NO |

TABLE 4-continued

Modifications

| Name | Symbol | Base | Naturally Occurring |
|---|---|---|---|
| 1-(3,4-Bis-trifluoromethoxybenzyl)pseudouridine TP | — | U | NO |
| 1-(3,4-Dimethoxybenzyl)pseudouridine TP | — | U | NO |
| 1-(3-Amino-3-carboxypropyl)pseudo-UTP | — | U | NO |
| 1-(3-Amino-propyl)pseudo-UTP | — | U | NO |
| 1-(3-Cyclopropyl-prop-2-ynyl)pseudouridine TP | — | U | NO |
| 1-(4-Amino-4-carboxybutyl)pseudo-UTP | — | U | NO |
| 1-(4-Amino-benzyl)pseudo-UTP | — | U | NO |
| 1-(4-Amino-butyl)pseudo-UTP | — | U | NO |
| 1-(4-Amino-phenyl)pseudo-UTP | — | U | NO |
| 1-(4-Azidobenzyl)pseudouridine TP | — | U | NO |
| 1-(4-Bromobenzyl)pseudouridine TP | — | U | NO |
| 1-(4-Chlorobenzyl)pseudouridine TP | — | U | NO |
| 1-(4-Fluorobenzyl)pseudouridine TP | — | U | NO |
| 1-(4-Iodobenzyl)pseudouridine TP | — | U | NO |
| 1-(4-Methanesulfonylbenzyl)pseudouridine TP | — | U | NO |
| 1-(4-Methoxybenzyl)pseudouridine TP | — | U | NO |
| 1-(4-Methoxy-phenyl)pseudo-UTP | — | U | NO |
| 1-(4-Methylbenzyl)pseudouridine TP | — | U | NO |
| 1-(4-Nitrobenzyl)pseudouridine TP | — | U | NO |
| 1(4-Nitro-phenyl)pseudo-UTP | — | U | NO |
| 1-(4-Thiomethoxybenzyl)pseudouridine TP | — | U | NO |
| 1-(4-Trifluoromethoxybenzyl)pseudouridine TP | — | U | NO |
| 1-(4-Trifluoromethylbenzyl)pseudouridine TP | — | U | NO |
| 1-(5-Amino-pentyl)pseudo-UTP | — | U | NO |
| 1-(6-Amino-hexyl)pseudo-UTP | — | U | NO |
| 1,6-Dimethyl-pseudo-UTP | — | U | NO |
| 1-[3-(2-{2-[2-(2-Aminoethoxy)-ethoxy]-ethoxy}-ethoxy)-propionyl]pseudouridine TP | — | U | NO |
| 1-{3-[2-(2-Aminoethoxy)-ethoxy]-propionyl}pseudouridine TP | — | U | NO |
| 1-Acetylpseudouridine TP | — | U | NO |
| 1-Alkyl-6-(1-propynyl)-pseudo-UTP | — | U | NO |
| 1-Alkyl-6-(2-propynyl)-pseudo-UTP | — | U | NO |
| 1-Alkyl-6-allyl-pseudo-UTP | — | U | NO |
| 1-Alkyl-6-ethynyl-pseudo-UTP | — | U | NO |
| 1-Alkyl-6-homoallyl-pseudo-UTP | — | U | NO |
| 1-Alkyl-6-vinyl-pseudo-UTP | — | U | NO |
| 1-Allylpseudouridine TP | — | U | NO |
| 1-Aminomethyl-pseudo-UTP | — | U | NO |
| 1-Benzoylpseudouridine TP | — | U | NO |
| 1-Benzyloxymethylpseudouridine TP | — | U | NO |
| 1-Benzyl-pseudo-UTP | — | U | NO |
| 1-Biotinyl-PEG2-pseudouridine TP | — | U | NO |
| 1-Biotinylpseudouridine TP | — | U | NO |
| 1-Butyl-pseudo-UTP | — | U | NO |
| 1-Cyanomethylpseudouridine TP | — | U | NO |
| 1-Cyclobutylmethyl-pseudo-UTP | — | U | NO |
| 1-Cyclobutyl-pseudo-UTP | — | U | NO |
| 1-Cycloheptylmethyl-pseudo-UTP | — | U | NO |
| 1-Cycloheptyl-pseudo-UTP | — | U | NO |
| 1-Cyclohexylmethyl-pseudo-UTP | — | U | NO |
| 1-Cyclohexyl-pseudo-UTP | — | U | NO |
| 1-Cyclooctylmethyl-pseudo-UTP | — | U | NO |
| 1-Cyclooctyl-pseudo-UTP | — | U | NO |
| 1-Cyclopentylmethyl-pseudo-UTP | — | U | NO |
| 1-Cyclopentyl-pseudo-UTP | — | U | NO |
| 1-Cyclopropylmethyl-pseudo-UTP | — | U | NO |
| 1-Cyclopropyl-pseudo-UTP | — | U | NO |
| 1-Ethyl-pseudo-UTP | — | U | NO |
| 1-Hexyl-pseudo-UTP | — | U | NO |
| 1-Homoallylpseudouridine TP | — | U | NO |
| 1-Hydroxymethylpseudouridine TP | — | U | NO |
| 1-iso-propyl-pseudo-UTP | — | U | NO |
| 1-Me-2-thio-pseudo-UTP | — | U | NO |
| 1-Me-4-thio-pseudo-UTP | — | U | NO |
| 1-Me-alpha-thio-pseudo-UTP | — | U | NO |
| 1-Methanesulfonylmethylpseudouridine TP | — | U | NO |
| 1-Methoxymethylpseudouridine TP | — | U | NO |
| 1-Methyl-6-(2,2,2-Trifluoroethyl)pseudo-UTP | — | U | NO |
| 1-Methyl-6-(4-morpholino)-pseudo-UTP | — | U | NO |
| 1-Methyl-6-(4-thiomorpholino)-pseudo-UTP | — | U | NO |
| 1-Methyl-6-(substituted phenyl)pseudo-UTP | — | U | NO |

TABLE 4-continued

Modifications

| Name | Symbol | Base | Naturally Occurring |
|---|---|---|---|
| 1-Methyl-6-amino-pseudo-UTP | — | U | NO |
| 1-Methyl-6-azido-pseudo-UTP | — | U | NO |
| 1-Methyl-6-bromo-pseudo-UTP | — | U | NO |
| 1-Methyl-6-butyl-pseudo-UTP | — | U | NO |
| 1-Methyl-6-chloro-pseudo-UTP | — | U | NO |
| 1-Methyl-6-cyano-pseudo-UTP | — | U | NO |
| 1-Methyl-6-dimethylamino-pseudo-UTP | — | U | NO |
| 1-Methyl-6-ethoxy-pseudo-UTP | — | U | NO |
| 1-Methyl-6-ethylcarboxylate-pseudo-UTP | — | U | NO |
| 1-Methyl-6-ethyl-pseudo-UTP | — | U | NO |
| 1-Methyl-6-fluoro-pseudo-UTP | — | U | NO |
| 1-Methyl-6-formyl-pseudo-UTP | — | U | NO |
| 1-Methyl-6-hydroxyamino-pseudo-UTP | — | U | NO |
| 1-Methyl-6-hydroxy-pseudo-UTP | — | U | NO |
| 1-Methyl-6-iodo-pseudo-UTP | — | U | NO |
| 1-Methyl-6-iso-propyl-pseudo-UTP | — | U | NO |
| 1-Methyl-6-methoxy-pseudo-UTP | — | U | NO |
| 1-Methyl-6-methylamino-pseudo-UTP | — | U | NO |
| 1-Methyl-6-phenyl-pseudo-UTP | — | U | NO |
| 1-Methyl-6-propyl-pseudo-UTP | — | U | NO |
| 1-Methyl-6-tert-butyl-pseudo-UTP | — | U | NO |
| 1-Methyl-6-trifluoromethoxy-pseudo-UTP | — | U | NO |
| 1-Methyl-6-trifluoromethyl-pseudo-UTP | — | U | NO |
| 1-Morpholinomethylpseudouridine TP | — | U | NO |
| 1-Pentyl-pseudo-UTP | — | U | NO |
| 1-Phenyl-pseudo-UTP | — | U | NO |
| 1-Pivaloylpseudouridine TP | — | U | NO |
| 1-Propargylpseudouridine TP | — | U | NO |
| 1-Propyl-pseudo-UTP | — | U | NO |
| 1-propynyl-pseudouridine | — | U | NO |
| 1-p-tolyl-pseudo-UTP | — | U | NO |
| 1-tert-Butyl-pseudo-UTP | — | U | NO |
| 1-Thiomethoxymethylpseudouridine TP | — | U | NO |
| 1-Thiomorpholinomethylpseudouridine TP | — | U | NO |
| 1-Trifluoroacetylpseudouridine TP | — | U | NO |
| 1-Trifluoromethyl-pseudo-UTP | — | U | NO |
| 1-Vinylpseudouridine TP | — | U | NO |
| 2,2'-anhydro-uridine TP | — | U | NO |
| 2'-bromo-deoxyuridine TP | — | U | NO |
| 2'-F-5-Methyl-2'-deoxy-UTP | — | U | NO |
| 2'-OMe-5-Me-UTP | — | U | NO |
| 2'-OMe-pseudo-UTP | — | U | NO |
| 2'-a-Ethynyluridine TP | — | U | NO |
| 2'-a-Trifluoromethyluridine TP | — | U | NO |
| 2'-b-Ethynyluridine TP | — | U | NO |
| 2'-b-Trifluoromethyluridine TP | — | U | NO |
| 2'-Deoxy-2',2'-difluorouridine TP | — | U | NO |
| 2'-Deoxy-2'-a-mercaptouridine TP | — | U | NO |
| 2'-Deoxy-2'-a-thiomethoxyuridine TP | — | U | NO |
| 2'-Deoxy-2'-b-aminouridine TP | — | U | NO |
| 2'-Deoxy-2'-b-azidouridine TP | — | U | NO |
| 2'-Deoxy-2'-b-bromouridine TP | — | U | NO |
| 2'-Deoxy-2'-b-chlorouridine TP | — | U | NO |
| 2'-Deoxy-2'-b-fluorouridine TP | — | U | NO |
| 2'-Deoxy-2'-b-iodouridine TP | — | U | NO |
| 2'-Deoxy-2'-b-mercaptouridine TP | — | U | NO |
| 2'-Deoxy-2'-b-thiomethoxyuridine TP | — | U | NO |
| 2-methoxy-4-thio-uridine | — | U | NO |
| 2-methoxyuridine | — | U | NO |
| 2'-O-Methyl-5-(1-propynyl)uridine TP | — | U | NO |
| 3-Alkyl-pseudo-UTP | — | U | NO |
| 4'-Azidouridine TP | — | U | NO |
| 4'-Carbocyclic uridine TP | — | U | NO |
| 4'-Ethynyluridine TP | — | U | NO |
| 5-(1-Propynyl)ara-uridine TP | — | U | NO |
| 5-(2-Furanyl)uridine TP | — | U | NO |
| 5-Cyanouridine TP | — | U | NO |
| 5-Dimethylaminouridine TP | — | U | NO |
| 5'-Homo-uridine TP | — | U | NO |
| 5-iodo-2'-fluoro-deoxyuridine TP | — | U | NO |
| 5-Phenylethynyluridine TP | — | U | NO |
| 5-Trideuteromethyl-6-deuterouridine TP | — | U | NO |
| 5-Trifluoromethyl-Uridine TP | — | U | NO |
| 5-Vinylarauridine TP | — | U | NO |
| 6-(2,2,2-Trifluoroethyl)-pseudo-UTP | — | U | NO |

TABLE 4-continued

Modifications

| Name | Symbol | Base | Naturally Occurring |
|---|---|---|---|
| 6-(4-Morpholino)-pseudo-UTP | — | U | NO |
| 6-(4-Thiomorpholino)-pseudo-UTP | — | U | NO |
| 6-(Substituted-Phenyl)-pseudo-UTP | — | U | NO |
| 6-Amino-pseudo-UTP | — | U | NO |
| 6-Azido-pseudo-UTP | — | U | NO |
| 6-Bromo-pseudo-UTP | — | U | NO |
| 6-Butyl-pseudo-UTP | — | U | NO |
| 6-Chloro-pseudo-UTP | — | U | NO |
| 6-Cyano-pseudo-UTP | — | U | NO |
| 6-Dimethylamino-pseudo-UTP | — | U | NO |
| 6-Ethoxy-pseudo-UTP | — | U | NO |
| 6-Ethylcarboxylate-pseudo-UTP | — | U | NO |
| 6-Ethyl-pseudo-UTP | — | U | NO |
| 6-Fluoro-pseudo-UTP | — | U | NO |
| 6-Formyl-pseudo-UTP | — | U | NO |
| 6-Hydroxyamino-pseudo-UTP | — | U | NO |
| 6-Hydroxy-pseudo-UTP | — | U | NO |
| 6-Iodo-pseudo-UTP | — | U | NO |
| 6-iso-Propyl-pseudo-UTP | — | U | NO |
| 6-Methoxy-pseudo-UTP | — | U | NO |
| 6-Methylamino-pseudo-UTP | — | U | NO |
| 6-Methyl-pseudo-UTP | — | U | NO |
| 6-Phenyl-pseudo-UTP | — | U | NO |
| 6-Propyl-pseudo-UTP | — | U | NO |
| 6-tert-Butyl-pseudo-UTP | — | U | NO |
| 6-Trifluoromethoxy-pseudo-UTP | — | U | NO |
| 6-Trifluoromethyl-pseudo-UTP | — | U | NO |
| Alpha-thio-pseudo-UTP | — | U | NO |
| Pseudouridine 1-(4-methylbenzenesulfonic acid) TP | — | U | NO |
| Pseudouridine 1-(4-methylbenzoic acid) TP | — | U | NO |
| Pseudouridine TP 1-[3-(2-ethoxy)]propionic acid | — | U | NO |
| Pseudouridine TP 1-[3-{2-(2-[2-(2-ethoxy)-ethoxy]-ethoxy)-ethoxy}]propionic acid | — | U | NO |
| Pseudouridine TP 1-[3-{2-(2-[2-{2(2-ethoxy)-ethoxy}-ethoxy)-ethoxy}]propionic acid | — | U | NO |
| Pseudouridine TP 1-[3-{2-(2-[2-ethoxy]-ethoxy)-ethoxy}]propionic acid | — | U | NO |
| Pseudouridine TP 1-[3-{2-(2-ethoxy)-ethoxy}] propionic acid | — | U | NO |
| Pseudouridine TP 1-methylphosphonic acid | — | U | NO |
| Pseudouridine TP 1-methylphosphonic acid diethyl ester | — | U | NO |
| Pseudo-UTP-N1-3-propionic acid | — | U | NO |
| Pseudo-UTP-N1-4-butanoic acid | — | U | NO |
| Pseudo-UTP-N1-5-pentanoic acid | — | U | NO |
| Pseudo-UTP-N1-6-hexanoic acid | — | U | NO |
| Pseudo-UTP-N1-7-heptanoic acid | — | U | NO |
| Pseudo-UTP-N1-methyl-p-benzoic acid | — | U | NO |
| Pseudo-UTP-N1-p-benzoic acid | — | U | NO |
| wybutosine | yW | W | YES |
| hydroxywybutosine | OHyW | W | YES |
| isowyosine | imG2 | W | YES |
| peroxywybutosine | o2yW | W | YES |
| undermodified hydroxywybutosine | OHyW* | W | YES |
| 4-demethylwyosine | imG-14 | W | YES |

Other modifications which may be useful in the circP, circSP, circRNA or circRNA-SP of the present invention are listed in Table 5.

TABLE 5

Additional Modification types

| Name | Type |
|---|---|
| 2,6-(diamino)purine | Other |
| 1-(aza)-2-(thio)-3-(aza)-phenoxazin-1-yl | Other |
| 1,3-(diaza)-2-(oxo)-phenthiazin-1-yl | Other |
| 1,3-(diaza)-2-(oxo)-phenoxazin-1-yl | Other |
| 1,3,5-(triaza)-2,6-(dioxa)-naphthalene | Other |
| 2 (amino)purine | Other |
| 2,4,5-(trimethyl)phenyl | Other |
| 2' methyl, 2'amino, 2'azido, 2'fluro-cytidine | Other |
| 2' methyl, 2'amino, 2'azido, 2'fluro-adenine | Other |
| 2'methyl, 2'amino, 2'azido, 2'fluro-uridine | Other |

TABLE 5-continued

Additional Modification types

| Name | Type |
|---|---|
| 2'-amino-2'-deoxyribose | Other |
| 2-amino-6-Chloro-purine | Other |
| 2-aza-inosinyl | Other |
| 2'-azido-2'-deoxyribose | Other |
| 2'fluoro-2'-deoxyribose | Other |
| 2'-fluoro-modified bases | Other |
| 2'-O-methyl-ribose | Other |
| 2-oxo-7-aminopyridopyrimidin-3-yl | Other |
| 2-oxo-pyridopyrimidine-3-yl | Other |
| 2-pyridinone | Other |
| 3 nitropyrrole | Other |
| 3-(methyl)-7-(propynyl)isocarbostyrilyl | Other |
| 3-(methyl)isocarbostyrilyl | Other |
| 4-(fluoro)-6-(methyl)benzimidazole | Other |
| 4-(methyl)benzimidazole | Other |
| 4-(methyl)indolyl | Other |
| 4,6-(dimethyl)indolyl | Other |
| 5 nitroindole | Other |
| 5 substituted pyrimidines | Other |
| 5-(methyl)isocarbostyrilyl | Other |
| 5-nitroindole | Other |
| 6-(aza)pyrimidine | Other |
| 6-(azo)thymine | Other |
| 6-(methyl)-7-(aza)indolyl | Other |
| 6-chloro-purine | Other |
| 6-phenyl-pyrrolo-pyrimidin-2-on-3-yl | Other |
| 7-(aminoalkylhydroxy)-1-(aza)-2-(thio)-3-(aza)-phenthiazin-1-yl | Other |
| 7-(aminoalkylhydroxy)-1-(aza)-2-(thio)-3-(aza)-phenoxazin-1-yl | Other |
| 7-(aminoalkylhydroxy)-1,3-(diaza)-2-(oxo)-phenoxazin-1-yl | Other |
| 7-(aminoalkylhydroxy)-1,3-(diaza)-2-(oxo)-phenthiazin-1-yl | Other |
| 7-(aminoalkylhydroxy)-1,3-(diaza)-2-(oxo)-phenoxazin-1-yl | Other |
| 7-(aza)indolyl | Other |
| 7-(guanidiniumalkylhydroxy)-1-(aza)-2-(thio)-3-(aza)-phenoxazinl-yl | Other |
| 7-(guanidiniumalkylhydroxy)-1-(aza)-2-(thio)-3-(aza)-phenthiazin-1-yl | Other |
| 7-(guanidiniumalkylhydroxy)-1-(aza)-2-(thio)-3-(aza)-phenoxazin-1-yl | Other |
| 7-(guanidiniumalkylhydroxy)-1,3-(diaza)-2-(oxo)-phenoxazin-1-yl | Other |
| 7-(guanidiniumalkyl-hydroxy)-1,3-(diaza)-2-(oxo)-phenthiazin-1-yl | Other |
| 7-(guanidiniumalkylhydroxy)-1,3-(diaza)-2-(oxo)-phenoxazin-1-yl | Other |
| 7-(propynyl)isocarbostyrilyl | Other |
| 7-(propynyl)isocarbostyrilyl, propynyl-7-(aza)indolyl | Other |
| 7-deaza-inosinyl | Other |
| 7-substituted 1-(aza)-2-(thio)-3-(aza)-phenoxazin-1-yl | Other |
| 7-substituted 1,3-(diaza)-2-(oxo)-phenoxazin-1-yl | Other |
| 9-(methyl)-imidizopyridinyl | Other |
| aminoindolyl | Other |
| anthracenyl | Other |
| bis-ortho-(aminoalkylhydroxy)-6-phenyl-pyrrolo-pyrimidin-2-on-3-yl | Other |
| bis-ortho-substituted-6-phenyl-pyrrolo-pyrimidin-2-on-3-yl | Other |
| difluorotolyl | Other |
| hypoxanthine | Other |
| imidizopyridinyl | Other |
| inosinyl | Other |
| isocarbostyrilyl | Other |
| isoguanisine | Other |
| N2-substituted purines | Other |
| N6-methyl-2-amino-purine | Other |
| N6-substituted purines | Other |
| N-alkylated derivative | Other |
| napthalenyl | Other |
| nitrobenzimidazolyl | Other |
| nitroimidazolyl | Other |
| nitroindazolyl | Other |
| nitropyrazolyl | Other |
| nubularine | Other |
| O6-substituted purines | Other |
| O-alkylated derivative | Other |
| ortho-(aminoalkylhydroxy)-6-phenyl-pyrrolo-pyrimidin-2-on-3-yl | Other |
| ortho-substituted-6-phenyl-pyrrolo-pyrimidin-2-on-3-yl | Other |
| Oxoformycin TP | Other |
| para-(aminoalkylhydroxy)-6-phenyl-pyrrolo-pyrimidin-2-on-3-yl | Other |
| para-substituted-6-phenyl-pyrrolo-pyrimidin-2-on-3-yl | Other |
| pentacenyl | Other |
| phenanthracenyl | Other |
| phenyl | Other |
| propynyl-7-(aza)indolyl | Other |
| pyrenyl | Other |
| pyridopyrimidin-3-yl | Other |
| pyridopyrimidin-3-yl, 2-oxo-7-amino-pyridopyrimidin-3-yl | Other |
| pyrrolo-pyrimidin-2-on-3-yl | Other |
| pyrrolopyrimidinyl | Other |
| pyrrolopyrizinyl | Other |
| stilbenzyl | Other |
| substituted 1,2,4-triazoles | Other |
| tetracenyl | Other |
| tubercidine | Other |
| xanthine | Other |
| Xanthosine-5'-TP | Other |
| 2-thio-zebularine | Other |
| 5-aza-2-thio-zebularine | Other |
| 7-deaza-2-amino-purine | Other |
| pyridin-4-one ribonucleoside | Other |
| 2-Amino-riboside-TP | Other |
| Formycin A TP | Other |
| Formycin B TP | Other |
| Pyrrolosine TP | Other |
| 2'-OH-ara-adenosine TP | Other |
| 2'-OH-ara-cytidine TP | Other |
| 2'-OH-ara-uridine TP | Other |
| 2'-OH-ara-guanosine TP | Other |
| 5-(2-carbomethoxyvinyl)uridine TP | Other |
| N6-(19-Amino-pentaoxanonadecyl)adenosine TP | Other |

The circP, circSP, circRNA or circRNA-SP can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

As described herein, in some embodiments, the circP, circSP, circRNA or circRNA-SP of the invention do not substantially induce an innate immune response of a cell into which the circP, circSP, circRNA or circRNA-SP is introduced. Features of an induced innate immune response include 1) increased expression of pro-inflammatory cytokines, 2) activation of intracellular PRRs (RIG-I, MDA5, etc., and/or 3) termination or reduction in protein translation. In other embodiments, an immune response is induced.

In certain embodiments, it may desirable to intracellularly degrade a modified circP, circSP, circRNA or circRNA-SP introduced into the cell. For example, degradation of a circP, circRNA or circRNA-SP molecule may be preferable if precise timing of protein production is desired. Thus, in some embodiments, the invention provides a modified circP, circRNA or circRNA-SP containing a degradation domain, which is capable of being acted on in a directed manner within a cell.

Circular Polynucleotide Architecture

The circular polynucleotides of the present invention are distinguished from wild type polynucleotides in their functional and/or structural design features which came be used in nucleic acid-based therapeutics.

FIG. 1 shows a representative circular primary construct 100 of the present invention. As used herein, the term "circular primary construct" refers to a circular polynucleotide transcript which may act substantially similar to and have properties of a RNA molecule. If the circular primary construct encodes one or more polypeptides of interest (e.g., a circRNA or circRNA-SP) then the polynucleotide transcript retains sufficient structural and/or chemical features to allow the polypeptide of interest encoded therein to be translated. Circular primary constructs may be polynucleotides of the invention. When structurally or chemically modified, the circular primary construct may be referred to as a modified circP, circSP, circRNA or circRNA-SP.

Returning to FIG. 1, the circular primary construct 100 here contains a first region of linked nucleotides 102 that is flanked by a first flanking region 104 and a second flaking region 106. As used herein, the "first region" may be referred to as a "coding region," a "non-coding region" or "region encoding" or simply the "first region." In one embodiment, this first region may comprise nucleotides such as, but not limited to, nucleotides encoding the polypeptide of interest and/or nucleotides encodes or comprises a sensor region. The polypeptide of interest may comprise at its 5' terminus one or more signal peptide sequences encoded by a signal sequence region 103. The first flanking region 104 may comprise a region of linked nucleosides or portion thereof which may act similarly to an untranslated region (UTR) in an mRNA and/or DNA sequence. The first flanking region may also comprise a region of polarity 108. The region of polarity 108 may include an IRES sequence or portion thereof. As a non-limiting example, when linearized this region may be split to have a first portion be on the 5' terminus of the first region 102 and second portion be on the 3' terminus of the first region 102. The second flanking region 106 may comprise a tailing sequence region 110 and may comprise a region of linked nucleotides or portion thereof 112 which may act similarly to a UTR in an mRNA and/or DNA. The second flanking region 106 may comprise an IRES sequence or portion thereof. As a non-limiting example, an IRES sequence may be split into a first portion and a second portion, where the first portion may be located in the first region 102 and the second portion may be located in the second flanking region 106.

Bridging the 5' terminus of the first region 102 and the first flanking region 104 is a first operational region 105. In one embodiment, this operational region may comprise a start codon. The operational region may alternatively comprise any translation initiation sequence or signal including a start codon.

Bridging the 3' terminus of the first region 102 and the second flanking region 106 is a second operational region 107. Traditionally this operational region comprises a stop codon. The operational region may alternatively comprise any translation initiation sequence or signal including a stop codon. According to the present invention, multiple serial stop codons may also be used. In one embodiment, the operation region of the present invention may comprise two stop codons. The first stop codon may be "TGA" or "UGA" and the second stop codon may be selected from the group consisting of "TAA," "TGA," "TAG," "UAA," "UGA" or "UAG."

Figure 2:
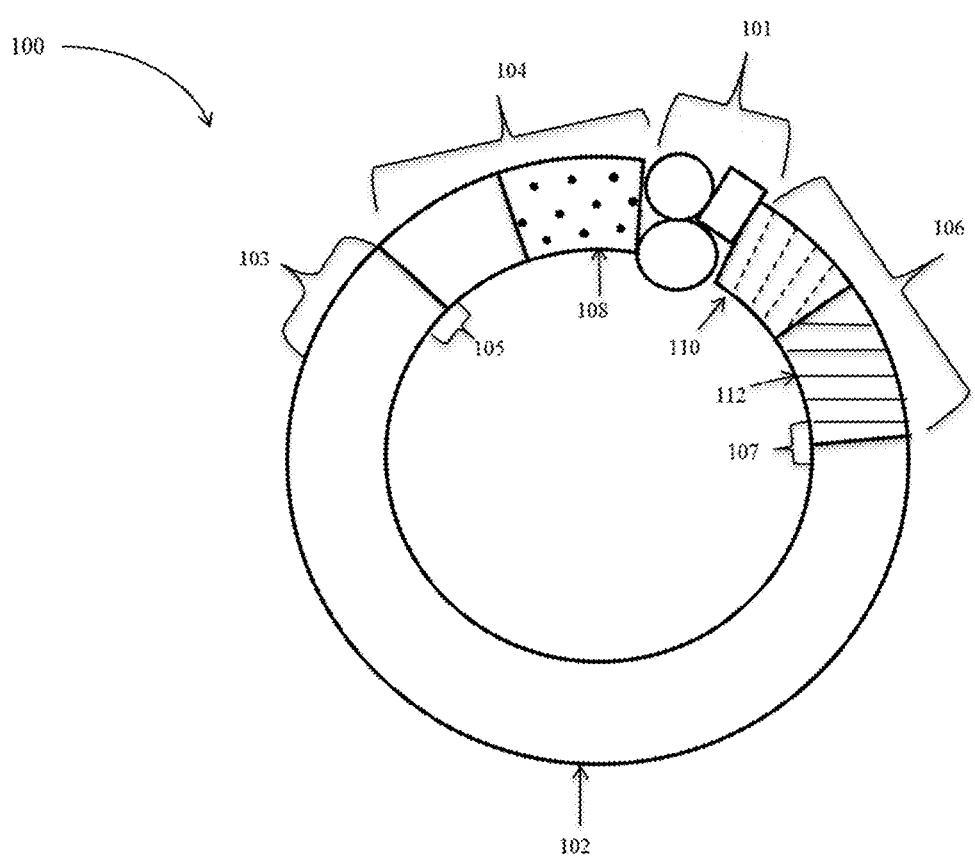
FIG. 2 is a schematic of a circular primary construct of the present invention.

Turning to FIG. 2, at least one non-nucleic acid moiety 101 may be used to prepare a circular polynucleotide 100 where the non-nucleic acid moiety 101 is used to bring the first flanking region 104 near the second flanking region 106. Non-limiting examples of non-nucleic acid moieties which may be used in the present invention are described herein. The circular polynucleotides 100 may comprise more than one non-nucleic acid moiety wherein the additional non-nucleic acid moieties may be heterologous or homologous to the first non-nucleic acid moiety.

Figure 3:
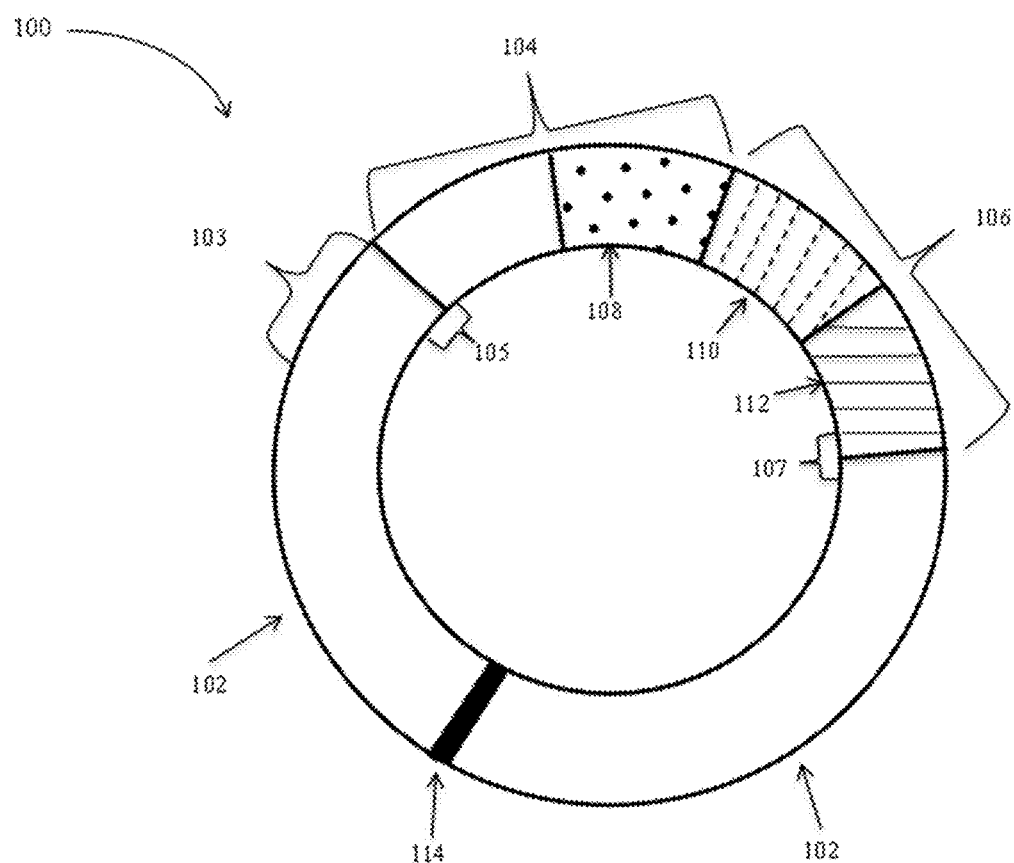
FIG. 3 is a schematic of a circular primary construct of the present invention comprising at least one spacer region.

Turning to FIG. 3, the first region of linked nucleosides 102 may comprise a spacer region 114. This spacer region 114 may be used to separate the first region of linked nucleosides 102 so that the circular primary construct can include more than one open reading frame, non-coding region or an open reading frame and a non-coding region.

Figure 4:
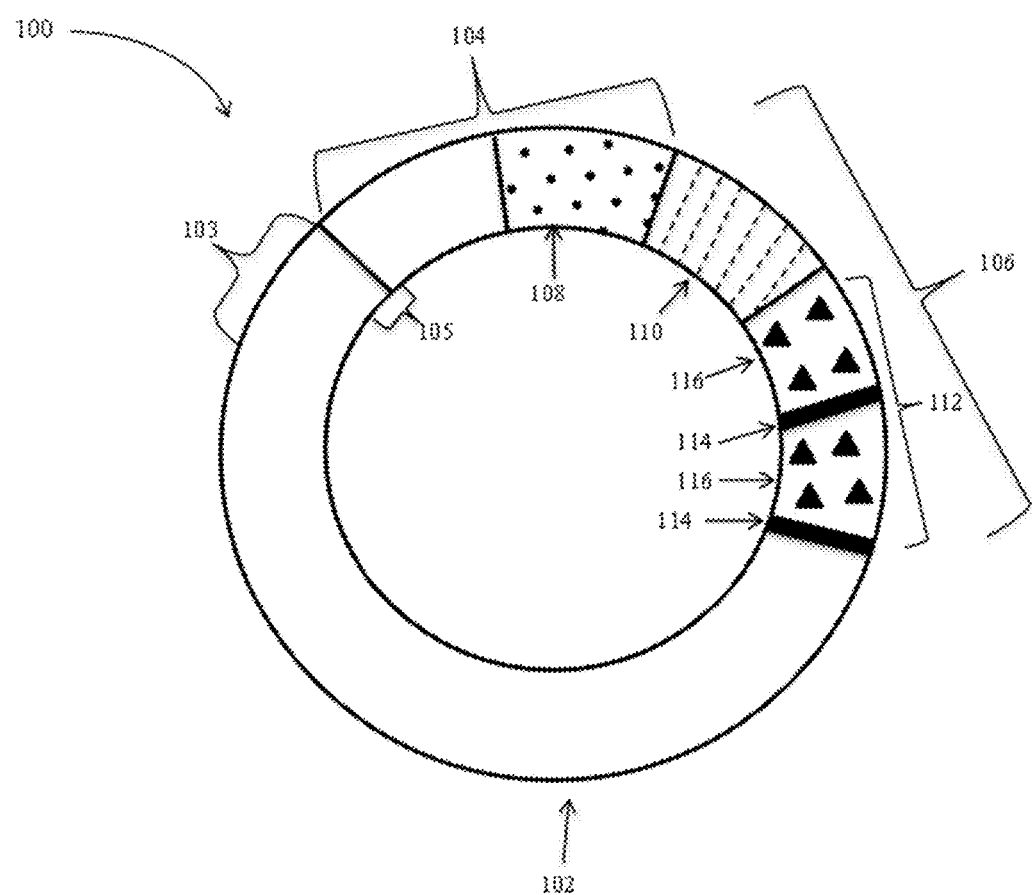
FIG. 4 is a schematic of a circular primary construct of the present invention comprising at least one sensor region.

Turning to FIG. 4, the second flanking region 106 may comprise one or more sensor regions 116 in the 3'UTR 112. These sensor sequences as discussed herein operate as pseudo-receptors (or binding sites) for ligands of the local microenvironment of the circular primary construct or circular polynucleotide. For example, microRNA binding sites or miRNA seeds may be used as sensors such that they function as pseudoreceptors for any microRNAs present in the environment of the circular polynucleotide. As shown in FIG. 4, the one or more sensor regions 116 may be separated by a spacer region 114.

Figure 5:
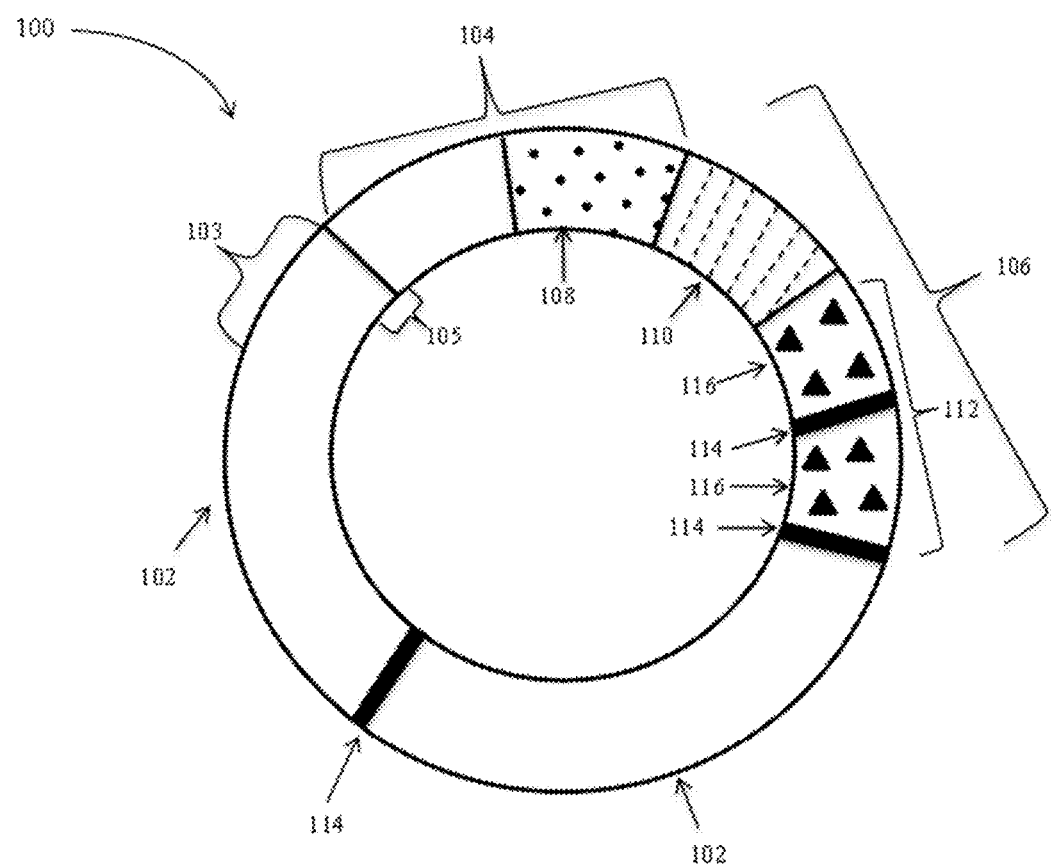
FIG. 5 is a schematic of a circular primary construct of the present invention comprising at least one sensor region and a spacer region.

As shown in FIG. 5, a circular primary construct 100, which includes one or more sensor regions 116, may also include a spacer region 114 in the first region of linked nucleosides 102. As discussed above for FIG. 3, this spacer region 114 may be used to separate the first region of linked nucleosides 102 so that the circular primary construct can include more than one open reading frame and/or more than one non-coding region.

Figure 6:
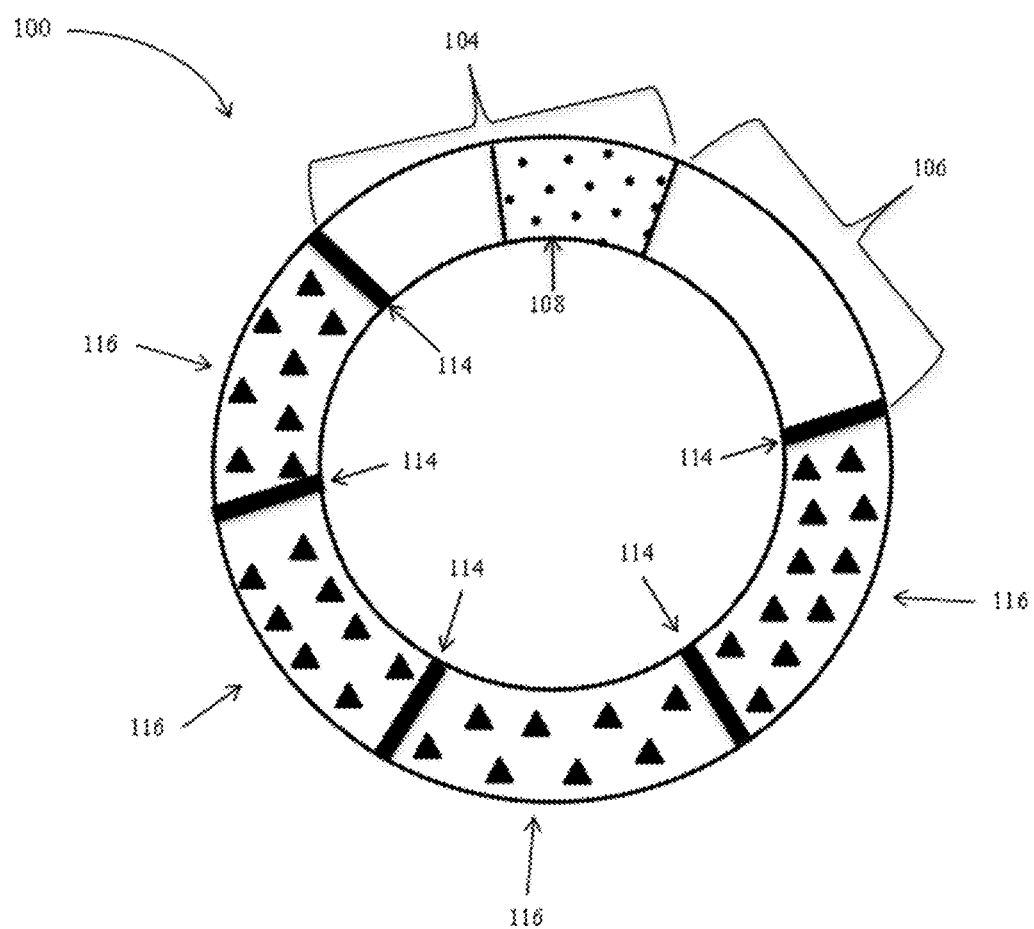
FIG. 6 is a schematic of a non-coding circular primary construct of the present invention.

Turning to FIG. 6, a circular primary construct 100 may be a non-coding construct known as a circSP comprising at least one non-coding region such as, but not limited to, a sensor region 116. Each of the sensor regions 116 may include, but are not limited to, a miR sequence, a miR seed, a miR binding site and/or a miR sequence without the seed.

Figure 7:
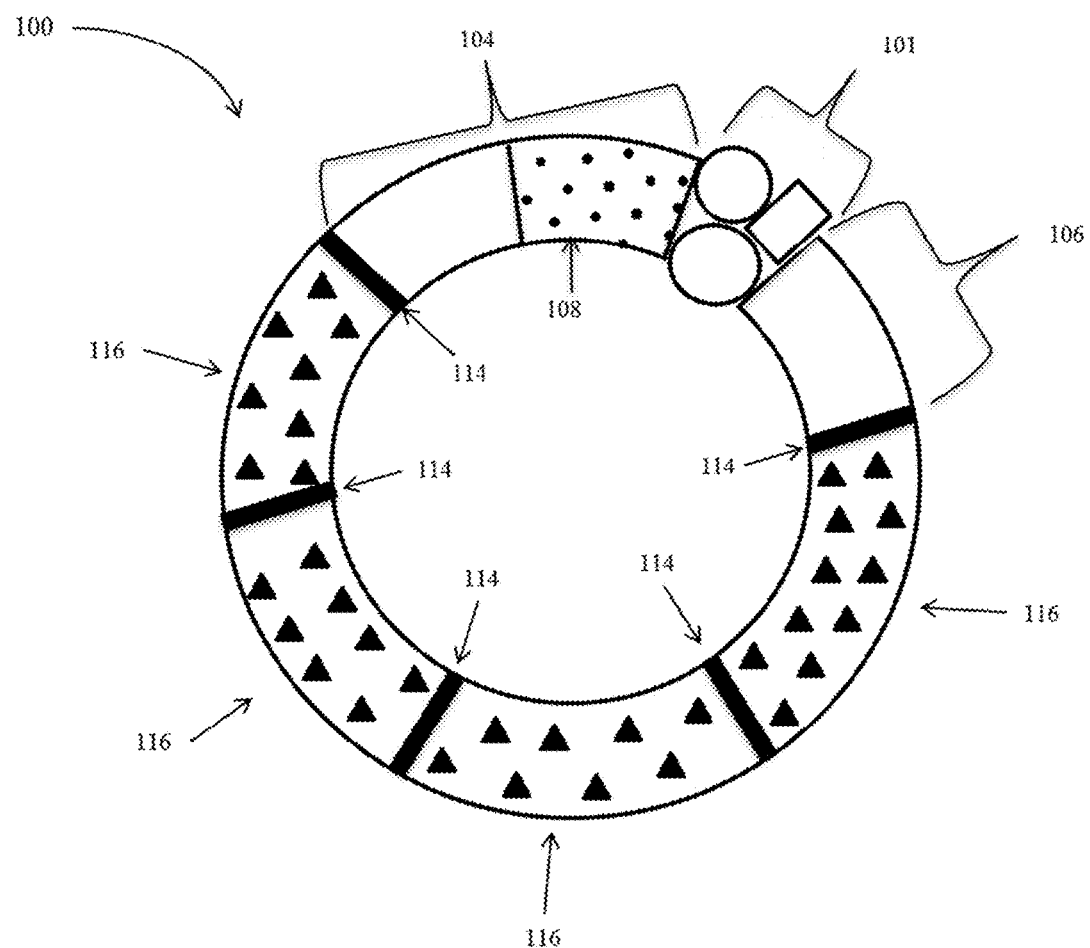
FIG. 7 is a schematic of a non-coding circular primary construct of the present invention.

Turning to FIG. 7, at least one non-nucleic acid moiety 101 may be used to prepare a circular polynucleotide 100 which is a non-coding construct. The circular polynucleotides 100 which is a non-coding construct may comprise more than one non-nucleic acid moiety wherein the additional non-nucleic acid moieties may be heterologous or homologous to the first non-nucleic acid moiety.

Figure 8:
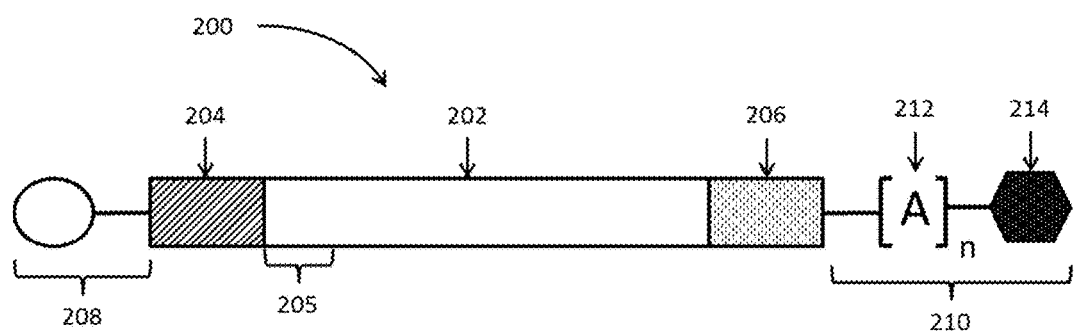
FIG. 8 is a schematic of a linear primary construct which may be circularized.

Turning to FIG. 8, a linear primary construct 200 may be circularized using any of the methods described herein, in order to prepare a circular polynucleotide 100. Returning to FIG. 8, the linear primary construct 200 contains a first region of linked nucleotides 202 that is flanked by a first flanking region 204 and a second flaking region 206. As used herein, the "first region" may be referred to as a "coding region" or "region encoding" or simply the "first region." This first region may include, but is not limited to, the encoded polypeptide of interest. In one aspect, the first region 202 may include, but is not limited to, the open reading frame encoding at least one polypeptide of interest. The open reading frame may be codon optimized in whole or in part. The flanking region 204 may comprise a region of linked nucleotides comprising one or more complete or incomplete 5' UTRs sequences which may be completely codon optimized or partially codon optimized. The flanking region 204 may include at least one nucleic acid sequence including, but not limited to, miR sequences, TERZAK™ sequences and translation control sequences. The flanking region 204 may also comprise a 5' terminal cap 208. The 5' terminal capping region 208 may include cap, such as, but not limited to, a naturally occurring cap, a synthetic cap or an optimized cap. Non-limiting examples of optimized caps include the caps taught by Rhoads in U.S. Pat. No. 7,074,596 and International Patent Publication No. WO2008157668, WO2009149253 and WO2013103659, the contents of each of which are herein incorporated by reference in its entirety. The second flanking region 206 may comprise a region of linked nucleotides comprising one or more complete or incomplete 3' UTRs. The second flanking region 206 may be completely codon optimized or partially codon optimized. The flanking region 206 may include at least one nucleic acid sequence including, but not limited to, miR sequences and translation control sequences. After the second flanking region 206 the primary construct 200 may comprise a 3' tailing sequence 210. The 3' tailing sequence 210 may include a synthetic tailing region 212 and/or a chain terminating nucleoside 214. Non-liming examples of a synthetic tailing region include a polyA sequence, a polyC sequence, and a polyA-G quartet. Non-limiting examples of chain terminating nucleosides include 2'-O methyl, F and locked nucleic acids (LNA).

Bridging the 5' terminus of the first region 202 and the first flanking region 204 is a first operational region 216. Traditionally this operational region comprises a Start codon. The operational region may alternatively comprise any translation initiation sequence or signal including a Start codon.

Bridging the 3' terminus of the first region 202 and the second flanking region 206 is a second operational region 218. Traditionally this operational region comprises a Stop codon. The operational region may alternatively comprise any translation initiation sequence or signal including a Stop codon. According to the present invention, multiple serial stop codons may also be used.

Generally, the shortest length of the first region of the circular primary construct of the present invention, when it encodes a polypeptide of interest such as a circP, circRNA or circRNA-SP, can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids. Non-limiting examples of dipeptides that the circular polynucleotide sequences can encode or include, but are not limited to, carnosine and anserine.

Generally, the length of the first region of linked nucleosides of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides). As used herein, the "first region" may be referred to as a "coding region," "non-coding region," "region encoding" or simply the "first region."

In some embodiments, the circP, circSP, circRNA or circRNA-SP includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

According to the present invention, the flanking regions may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

According to the present invention, the tailing sequence may range from absent to 500 nucleotides in length (e.g., at least 60, 70, 80, 90, 120, 140, 160, 180, 200, 250, 300, 350, 400, 450, or 500 nucleotides). Where the tailing region is a polyA tail, the length may be determined in units of or as a function of polyA binding protein binding. In this embodiment, the polyA tail is long enough to bind at least 4 monomers of polyA binding protein. PolyA binding protein monomers bind to stretches of approximately 38 nucleotides. As such, it has been observed that polyA tails of about 80 nucleotides and 160 nucleotides are functional.

According to the present invention, the capping region may comprise a single cap or a series of nucleotides forming the cap. In this embodiment the capping region may be from 1 to 10, e.g. 2-9, 3-8, 4-7, 1-5, 5-10, or at least 2, or 10 or fewer nucleotides in length. In some embodiments, the cap is absent.

According to the present invention, the first and second operational regions may range from 3 to 40, e.g., 5-30, 10-20, 15, or at least 4, or 30 or fewer nucleotides in length and may comprise, in addition to a start and/or stop codon, one or more signal and/or restriction sequences.

In one embodiment, the circular primary construct, circP, circSP, circRNA or circRNA-SP do not comprise Kozak sequences.

In another embodiment, the circular primary construct, circP, circSP, circRNA or circRNA-SP comprise at least one Kozak sequence.

In another aspect, the present disclosure provides circP, circSP, circRNA or circRNA-SP comprising a nucleoside or nucleotide that can disrupt the binding of a major groove interacting, e.g. binding, partner with the polynucleotide (e.g., where the modified nucleotide has decreased binding affinity to major groove interacting partner, as compared to an unmodified nucleotide).

The circP, circSP, circRNA or circRNA-SP can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors, etc.). In some embodiments, the circP, circSP, circRNA or circRNA-SP may include one or more messenger RNAs (mRNAs) and one or more modified nucleoside or nucleotides (e.g., modified circRNA molecules).

Modified circRNA Molecules

The present invention includes the building blocks, e.g., modified nucleotides, of modified circular polynucleotides molecules. For example, these building blocks can be useful for preparing modified circP, modified circSP, modified circRNA or modified circRNA-SP of the invention. Such building blocks are taught in co-pending International Application WO2013052523 filed Oct. 3, 2012, the contents of which are incorporated herein by reference in their entirety.

Modifications on the Nucleobase

The present disclosure provides for modified nucleosides and nucleotides. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. In some embodiments, the nucleosides and nucleotides described herein are generally chemically modified on the major groove face. Exemplary non-limiting modifications include an amino group, a thiol group, an alkyl group, a halo group, or any described herein. The modified nucleotides may by synthesized by any useful method, as described herein (e.g., chemically, enzymatically, or recombinantly to include one or more modified or non-natural nucleosides).

The modified nucleosides and nucleotides can include a modified nucleobase. Examples of nucleobases found in RNA include, but are not limited to, adenine, guanine, cytosine, and uracil. Examples of nucleobase found in DNA include, but are not limited to, adenine, guanine, cytosine, and thymine. These nucleobases can be modified or wholly replaced to provide circRNA molecules having enhanced properties. For example, the nucleosides and nucleotides described herein can be chemically modified. In some embodiments, chemical modifications can include an amino group, a thiol group, an alkyl group, or a halo group.

Modifications on the Internucleoside Linkage

The modified nucleotides, which may be incorporated into a circP, circSP, circRNA or circRNA-SP molecule, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked circRNA molecules are expected to also reduce the innate immune response through weaker binding/activation of cellular innate immune molecules.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present invention, including internucleoside linkages which do not contain a phosphorous atom, are described herein below.

Combinations of Modified Sugars, Nucleobases, and Internucleoside Linkages

The circP, circSP, circRNA or circRNA-SP of the invention can include a combination of modifications to the sugar, the nucleobase, and/or the internucleoside linkage. These combinations can include any one or more modifications described herein or in International Application WO2013052523 filed Oct. 3, 2012, the contents of which are incorporated herein by reference in their entirety.

Synthesis of Circular Polynucleotides

The circP, circSP, circRNA or circRNA-SP for use in accordance with the invention may be prepared according to any useful technique, as described herein. The modified nucleosides and nucleotides used in the synthesis of circP, circSP, circRNA or circRNA-SP disclosed herein can be prepared from readily available starting materials using the following general methods and procedures. Where typical or preferred process conditions (e.g., reaction temperatures, times, mole ratios of reactants, solvents, pressures, etc.) are provided, a skilled artisan would be able to optimize and develop additional process conditions. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of circP, circSP, circRNA or circRNA-SP of the present invention can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of modified nucleosides and nucleotides (e.g., modified circP, circSP, circRNA or circRNA-SP) can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Modified nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The circP, circSP, circRNA or circRNA-SP of the invention may or may not be uniformly modified along the entire length of the molecule. For example, one or more or all types of nucleotide (e.g., purine or pyrimidine, or any one or more or all of A, G, U, C) may or may not be uniformly modified in a polynucleotide of the invention, or in a given predetermined sequence region thereof (e.g. one or more of the sequence regions represented in FIG. 1). In some embodiments, all nucleotides X in a circP, circSP, circRNA or circRNA-SP of the invention (or in a given sequence region thereof) are modified, wherein X may any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in the circP, circSP, circRNA or circRNA-SP. One of ordinary skill in the art will appreciate that the nucleotide analogs or other modification(s) may be located at any position(s) of a circP, circSP, circRNA or circRNA-SP such that the function of circP, circSP, circRNA or circRNA-SP is not substantially decreased. A modification may also be a non-coding region modification. The circP, circSP, circRNA or circRNA-SP may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the circP, circSP, circRNA or circRNA-SP includes a modified pyrimidine (e.g., a modified uracil/uridine/U or modified cytosine/cytidine/C). In some embodiments, the uracil or uridine (generally: U) in the circP, circSP, circRNA or circRNA-SP molecule may be replaced with from about 1% to about 100% of a modified uracil or modified uridine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified uracil or modified uridine). The modified uracil or uridine can be replaced by a compound having a single unique structure or by a plurality of compounds having different structures (e.g., 2, 3, 4 or more unique structures, as described herein). In some embodiments, the cytosine or cytidine (generally: C) in the circP, circSP, circRNA or circRNA-SP molecule may be replaced with from about 1% to about 100% of a modified cytosine or modified cytidine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified cytosine or modified cytidine). The modified cytosine or cytidine can be replaced by a compound having a single unique structure or by a plurality of compounds having different structures (e.g., 2, 3, 4 or more unique structures, as described herein).

Combinations of Nucleotides

Further examples of modified nucleotides and modified nucleotide combinations are provided in International Application WO2013052523 filed Oct. 3, 2012 the contents of which are incorporated herein by reference in their entirety.

In some embodiments, at least 25% of the cytosines are replaced (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines are replaced, and at least 25% of the uracils are replaced (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

Combinations of Modified Sugars, Nucleobases, and Internucleoside Linkages

The circP chimeric polynucleotides of the invention can include a combination of modifications to the sugar, the nucleobase, and/or the internucleoside linkage. These combinations can include any one or more modifications described herein.

Examples of modified nucleotides and modified nucleotide combinations are provided below in Table 6 and Table 7. These combinations of modified nucleotides can be used to form the chimeric polynucleotides of the invention. Unless otherwise noted, the modified nucleotides may be completely substituted for the natural nucleotides of the chimeric polynucleotides of the invention. As a non-limiting example, the natural nucleotide uridine may be substituted with a modified nucleoside described herein. In another non-limiting example, the natural nucleotide uridine may be partially substituted (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein. Any combination of base/sugar or linker may be incorporated into the chimeric polynucleotides of the invention and such modifications are taught in International Publication No. WO2013052523; International Application No. WO2014093924; International Publication No. WO2015051173; the contents of each of which are incorporated herein by reference in its entirety.

TABLE 6

Combinations

| Modified Nucleotide | Modified Nucleotide Combination |
|---|---|
| α-thio-cytidine | α-thio-cytidine/5-iodo-uridine |
| | α-thio-cytidine/N1-methyl-pseudouridine |
| | α-thio-cytidine/α-thio-uridine |
| | α-thio-cytidine/5-methyl-uridine |
| | α-thio-cytidine/pseudo-uridine |
| | about 50% of the cytosines are α-thio-cytidine |
| pseudoisocytidine | pseudoisocytidine/5-iodo-uridine |
| | pseudoisocytidine/N1-methyl-pseudouridine |
| | pseudoisocytidine/α-thio-uridine |
| | pseudoisocytidine/5-methyl-uridine |
| | pseudoisocytidine/pseudouridine |
| | about 25% of cytosines are pseudoisocytidine |
| | pseudoisocytidine/about 50% of uridines are N1-methyl-pseudouridine and about 50% of uridines are pseudouridine |
| | pseudoisocytidine/about 25% of uridines are N1-methyl-pseudouridine and about 25% of uridines are pseudouridine |
| pyrrolo-cytidine | pyrrolo-cytidine/5-iodo-uridine |
| | pyrrolo-cytidine/N1-methyl-pseudouridine |
| | pyrrolo-cytidine/α-thio-uridine |
| | pyrrolo-cytidine/5-methyl-uridine |
| | pyrrolo-cytidine/pseudouridine |
| | about 50% of the cytosines are pyrrolo-cytidine |
| 5-methyl-cytidine | 5-methyl-cytidine/5-iodo-uridine |
| | 5-methyl-cytidine/N1-methyl-pseudouridine |
| | 5-methyl-cytidine/α-thio-uridine |

TABLE 6-continued

Combinations

| Modified Nucleotide | Modified Nucleotide Combination |
|---|---|
| | 5-methyl-cytidine/5-methyl-uridine |
| | 5-methyl-cytidine/pseudouridine |
| | about 25% of cytosines are 5-methyl-cytidine |
| | about 50% of cytosines are 5-methyl-cytidine |
| | 5-methyl-cytidine/5-methoxy-uridine |
| | 5-methyl-cytidine/5-bromo-uridine |
| | 5-methyl-cytidine/2-thio-uridine |
| | 5-methyl-cytidine/about 50% of uridines are 2-thio-uridine |
| | about 50% of uridines are 5-methyl-cytidine/about 50% of uridines are 2-thio-uridine |
| N4-acetyl-cytidine | N4-acetyl-cytidine/5-iodo-uridine |
| | N4-acetyl-cytidine/N1-methyl-pseudouridine |
| | N4-acetyl-cytidine/α-thio-uridine |
| | N4-acetyl-cytidine/5-methyl-uridine |
| | N4-acetyl-cytidine/pseudouridine |
| | about 50% of cytosines are N4-acetyl-cytidine |
| | about 25% of cytosines are N4-acetyl-cytidine |
| | N4-acetyl-cytidine/5-methoxy-uridine |
| | N4-acetyl-cytidine/5-bromo-uridine |
| | N4-acetyl-cytidine/2-thio-uridine |
| | about 50% of cytosines are N4-acetyl-cytidine/about 50% of uridines are 2-thio-uridine |

TABLE 7

Combinations 1-(2,2,2-Trifluoroethyl)pseudo-UTP
1-Ethyl-pseudo-UTP
1-Methyl-pseudo-U-alpha-thio-TP
1-methyl-pseudouridine TP, ATP, GTP, CTP
1-methyl-pseudo-UTP/5-methyl-CTP/ATP/GTP
1-methyl-pseudo-UTP/CTP/ATP/GTP
1-Propyl-pseudo-UTP
25% 5-Aminoallyl-CTP + 75% CTP/25% 5-Methoxy-UTP + 75% UTP
25% 5-Aminoallyl-CTP + 75% CTP/75% 5-Methoxy-UTP + 25% UTP
25% 5-Bromo-CTP + 75% CTP/25% 5-Methoxy-UTP + 75% UTP
25% 5-Bromo-CTP + 75% CTP/75% 5-Methoxy-UTP + 25% UTP
25% 5-Bromo-CTP + 75% CTP/1-Methyl-pseudo-UTP
25% 5-Carboxy-CTP + 75% CTP/25% 5-Methoxy-UTP + 75% UTP
25% 5-Carboxy-CTP + 75% CTP/75% 5-Methoxy-UTP + 25% UTP
25% 5-Ethyl-CTP + 75% CTP/25% 5-Methoxy-UTP + 75% UTP
25% 5-Ethyl-CTP + 75% CTP/75% 5-Methoxy-UTP + 25% UTP
25% 5-Ethynyl-CTP + 75% CTP/25% 5-Methoxy-UTP + 75% UTP
25% 5-Ethynyl-CTP + 75% CTP/75% 5-Methoxy-UTP + 25% UTP
25% 5-Fluoro-CTP + 75% CTP/25% 5-Methoxy-UTP + 75% UTP
25% 5-Fluoro-CTP + 75% CTP/75% 5-Methoxy-UTP + 25% UTP
25% 5-Formyl-CTP + 75% CTP/25% 5-Methoxy-UTP + 75% UTP
25% 5-Formyl-CTP + 75% CTP/75% 5-Methoxy-UTP + 25% UTP
25% 5-Hydroxymethyl-CTP + 75% CTP/25% 5-Methoxy-UTP + 75% UTP
25% 5-Hydroxymethyl-CTP + 75% CTP/75% 5-Methoxy-UTP + 25% UTP
25% 5-Iodo-CTP + 75% CTP/25% 5-Methoxy-UTP + 75% UTP
25% 5-Iodo-CTP + 75% CTP/75% 5-Methoxy-UTP + 25% UTP
25% 5-Methoxy-CTP + 75% CTP/25% 5-Methoxy-UTP + 75% UTP
25% 5-Methoxy-CTP + 75% CTP/75% 5-Methoxy-UTP + 25% UTP
25% 5-Methyl-CTP + 75% CTP/25% 5-Methoxy-UTP + 75% 1-Methyl-pseudo-UTP
25% 5-Methyl-CTP + 75% CTP/25% 5-Methoxy-UTP + 75% UTP
25% 5-Methyl-CTP + 75% CTP/50% 5-Methoxy-UTP + 50% 1-Methyl-pseudo-UTP
25% 5-Methyl-CTP + 75% CTP/50% 5-Methoxy-UTP + 50% UTP
25% 5-Methyl-CTP + 75% CTP/5-Methoxy-UTP
25% 5-Methyl-CTP + 75% CTP/75% 5-Methoxy-UTP + 25% 1-Methyl-pseudo-UTP
25% 5-Methyl-CTP + 75% CTP/75% 5-Methoxy-UTP + 25% UTP
25% 5-Phenyl-CTP + 75% CTP/25% 5-Methoxy-UTP + 75% UTP
25% 5-Phenyl-CTP + 75% CTP/75% 5-Methoxy-UTP + 25% UTP
25% 5-Trifluoromethyl-CTP + 75% CTP/25% 5-Methoxy-UTP + 75% UTP

TABLE 7-continued

Combinations

25% 5-Trifluoromethyl-CTP + 75% CTP/75% 5-Methoxy-UTP + 25% UTP
25% 5-Trifluoromethyl-CTP + 75% CTP/1-Methyl-pseudo-UTP
25% N4-Ac-CTP + 75% CTP/25% 5-Methoxy-UTP + 75% UTP
25% N4-Ac-CTP + 75% CTP/75% 5-Methoxy-UTP + 25% UTP
25% N4-Bz-CTP + 75% CTP/25% 5-Methoxy-UTP + 75% UTP
25% N4-Bz-CTP + 75% CTP/75% 5-Methoxy-UTP + 25% UTP
25% N4-Methyl-CTP + 75% CTP/25% 5-Methoxy-UTP + 75% UTP
25% N4-Methyl-CTP + 75% CTP/75% 5-Methoxy-UTP + 25% UTP
25% Pseudo-iso-CTP + 75% CTP/25% 5-Methoxy-UTP + 75% UTP
25% Pseudo-iso-CTP + 75% CTP/75% 5-Methoxy-UTP + 25% UTP
25% 5-Bromo-CTP/75% CTP/Pseudo-UTP
25% 5-methoxy-UTP/25% 5-methyl-CTP/ATP/GTP
25% 5-methoxy-UTP/5-methyl-CTP/ATP/GTP
25% 5-methoxy-UTP/75% 5-methyl-CTP/ATP/GTP
25% 5-methoxy-UTP/CTP/ATP/GTP
25% 5-metoxy-UTP/50% 5-methyl-CTP/ATP/GTP
2-Amino-ATP
2-Thio-CTP
2-thio-pseudouridine TP, ATP, GTP, CTP
2-Thio-pseudo-UTP
2-Thio-UTP
3-Methyl-CTP
3-Methyl-pseudo-UTP
4-Thio-UTP
50% 5-Bromo-CTP + 50% CTP/1-Methyl-pseudo-UTP
50% 5-Hydroxymethyl-CTP + 50% CTP/1-Methyl-pseudo-UTP
50% 5-methoxy-UTP/5-methyl-CTP/ATP/GTP
50% 5-Methyl-CTP + 50% CTP/25% 5-Methoxy-UTP + 75% 1-Methyl-pseudo-UTP
50% 5-Methyl-CTP + 50% CTP/25% 5-Methoxy-UTP + 75% UTP
50% 5-Methyl-CTP + 50% CTP/50% 5-Methoxy-UTP + 50% 1-Methyl-pseudo-UTP
50% 5-Methyl-CTP + 50% CTP/50% 5-Methoxy-UTP + 50% UTP
50% 5-Methyl-CTP + 50% CTP/5-Methoxy-UTP
50% 5-Methyl-CTP + 50% CTP/75% 5-Methoxy-UTP + 25% 1-Methyl-pseudo-UTP
50% 5-Methyl-CTP + 50% CTP/75% 5-Methoxy-UTP + 25% UTP
50% 5-Trifluoromethyl-CTP + 50% CTP/1-Methyl-pseudo-UTP
50% 5-Bromo-CTP/50% CTP/Pseudo-UTP
50% 5-methoxy-UTP/25% 5-methyl-CTP/ATP/GTP
50% 5-methoxy-UTP/50% 5-methyl-CTP/ATP/GTP
50% 5-methoxy-UTP/75% 5-methyl-CTP/ATP/GTP
50% 5-methoxy-UTP/CTP/ATP/GTP
5-Aminoallyl-CTP
5-Aminoallyl-CTP/5-Methoxy-UTP
5-Aminoallyl-UTP
5-Bromo-CTP
5-Bromo-CTP/5-Methoxy-UTP
5-Bromo-CTP/1-Methyl-pseudo-UTP
5-Bromo-CTP/Pseudo-UTP
5-bromocytidine TP, ATP, GTP, UTP
5-Bromo-UTP
5-Carboxy-CTP/5-Methoxy-UTP
5-Ethyl-CTP/5-Methoxy-UTP
5-Ethynyl-CTP/5-Methoxy-UTP
5-Fluoro-CTP/5-Methoxy-UTP
5-Formyl-CTP/5-Methoxy-UTP
5-Hydroxy-methyl-CTP/5-Methoxy-UTP
5-Hydroxymethyl-CTP
5-Hydroxymethyl-CTP/1-Methyl-pseudo-UTP
5-Hydroxymethyl-CTP/5-Methoxy-UTP
5-hydroxymethyl-cytidine TP, ATP, GTP, UTP
5-Iodo-CTP/5-Methoxy-UTP
5-Me-CTP/5-Methoxy-UTP
5-Methoxy carbonyl methyl-UTP
5-Methoxy-CTP/5-Methoxy-UTP
5-methoxy-uridine TP, ATP, GTP, UTP
5-methoxy-UTP
5-Methoxy-UTP
5-Methoxy-UTP/N6-Isopentenyl-ATP
5-methoxy-UTP/25% 5-methyl-CTP/ATP/GTP
5-methoxy-UTP/5-methyl-CTP/ATP/GTP
5-methoxy-UTP/75% 5-methyl-CTP/ATP/GTP
5-methoxy-UTP/CTP/ATP/GTP
5-Methyl-2-thio-UTP
5-Methylaminomethyl-UTP
5-Methyl-CTP/5-Methoxy-UTP
5-Methyl-CTP/5-Methoxy-UTP(cap 0)
5-Methyl-CTP/5-Methoxy-UTP(No cap)
5-Methyl-CTP/25% 5-Methoxy-UTP + 75% 1-Methyl-pseudo-UTP
5-Methyl-CTP/25% 5-Methoxy-UTP + 75% UTP
5-Methyl-CTP/50% 5-Methoxy-UTP + 50% 1-Methyl-pseudo-UTP
5-Methyl-CTP/50% 5-Methoxy-UTP + 50% UTP
5-Methyl-CTP/5-Methoxy-UTP/N6-Me-ATP
5-Methyl-CTP/75% 5-Methoxy-UTP + 25% 1-Methyl-pseudo-UTP
5-Methyl-CTP/75% 5-Methoxy-UTP + 25% UTP
5-Phenyl-CTP/5-Methoxy-UTP
5-Trifluoro-methyl-CTP/5-Methoxy-UTP
5-Trifluoromethyl-CTP
5-Trifluoromethyl-CTP/5-Methoxy-UTP
5-Trifluoromethyl-CTP/1-Methyl-pseudo-UTP
5-Trifluoromethyl-CTP/Pseudo-UTP
5-Trifluoromethyl-UTP
5-trifluromethylcytidine TP, ATP, GTP, UTP
75% 5-Aminoallyl-CTP + 25% CTP/25% 5-Methoxy-UTP + 75% UTP
75% 5-Aminoallyl-CTP + 25% CTP/75% 5-Methoxy-UTP + 25% UTP
75% 5-Bromo-CTP + 25% CTP/25% 5-Methoxy-UTP + 75% UTP
75% 5-Bromo-CTP + 25% CTP/75% 5-Methoxy-UTP + 25% UTP
75% 5-Carboxy-CTP + 25% CTP/25% 5-Methoxy-UTP + 75% UTP
75% 5-Carboxy-CTP + 25% CTP/75% 5-Methoxy-UTP + 25% UTP
75% 5-Ethyl-CTP + 25% CTP/25% 5-Methoxy-UTP + 75% UTP
75% 5-Ethyl-CTP + 25% CTP/75% 5-Methoxy-UTP + 25% UTP
75% 5-Ethynyl-CTP + 25% CTP/25% 5-Methoxy-UTP + 75% UTP
75% 5-Ethynyl-CTP + 25% CTP/75% 5-Methoxy-UTP + 25% UTP
75% 5-Fluoro-CTP + 25% CTP/25% 5-Methoxy-UTP + 75% UTP
75% 5-Fluoro-CTP + 25% CTP/75% 5-Methoxy-UTP + 25% UTP
75% 5-Formyl-CTP + 25% CTP/25% 5-Methoxy-UTP + 75% UTP
75% 5-Formyl-CTP + 25% CTP/75% 5-Methoxy-UTP + 25% UTP
75% 5-Hydroxymethyl-CTP + 25% CTP/25% 5-Methoxy-UTP + 75% UTP
75% 5-Hydroxymethyl-CTP + 25% CTP/75% 5-Methoxy-UTP + 25% UTP
75% 5-Iodo-CTP + 25% CTP/25% 5-Methoxy-UTP + 75% UTP
75% 5-Iodo-CTP + 25% CTP/75% 5-Methoxy-UTP + 25% UTP
75% 5-Methoxy-CTP + 25% CTP/25% 5-Methoxy-UTP + 75% UTP
75% 5-Methoxy-CTP + 25% CTP/75% 5-Methoxy-UTP + 25% UTP
75% 5-methoxy-UTP/5-methyl-CTP/ATP/GTP
75% 5-Methyl-CTP + 25% CTP/25% 5-Methoxy-UTP + 75% 1-Methyl-pseudo-UTP
75% 5-Methyl-CTP + 25% CTP/25% 5-Methoxy-UTP + 75% UTP
75% 5-Methyl-CTP + 25% CTP/50% 5-Methoxy-UTP + 50% 1-Methyl-pseudo-UTP
75% 5-Methyl-CTP + 25% CTP/50% 5-Methoxy-UTP + 50% UTP
75% 5-Methyl-CTP + 25% CTP/5-Methoxy-UTP
75% 5-Methyl-CTP + 25% CTP/75% 5-Methoxy-UTP + 25% 1-Methyl-pseudo-UTP
75% 5-Methyl-CTP + 25% CTP/75% 5-Methoxy-UTP + 25% UTP
75% 5-Phenyl-CTP + 25% CTP/25% 5-Methoxy-UTP + 75% UTP
75% 5-Phenyl-CTP + 25% CTP/75% 5-Methoxy-UTP + 25% UTP
75% 5-Trifluoromethyl-CTP + 25% CTP/25% 5-Methoxy-UTP + 75% UTP
75% 5-Trifluoromethyl-CTP + 25% CTP/75% 5-Methoxy-UTP + 25% UTP
75% 5-Trifluoromethyl-CTP + 25% CTP/1-Methyl-pseudo-UTP
75% N4-Ac-CTP + 25% CTP/25% 5-Methoxy-UTP + 75% UTP
75% N4-Ac-CTP + 25% CTP/75% 5-Methoxy-UTP + 25% UTP
75% N4-Bz-CTP + 25% CTP/25% 5-Methoxy-UTP + 75% UTP
75% N4-Bz-CTP + 25% CTP/75% 5-Methoxy-UTP + 25% UTP
75% N4-Methyl-CTP + 25% CTP/25% 5-Methoxy-UTP + 75% UTP
75% N4-Methyl-CTP + 25% CTP/75% 5-Methoxy-UTP + 25% UTP
75% Pseudo-iso-CTP + 25% CTP/25% 5-Methoxy-UTP + 75% UTP
75% Pseudo-iso-CTP + 25% CTP/75% 5-Methoxy-UTP + 25% UTP
75% 5-Bromo-CTP/25% CTP/1-Methyl-pseudo-UTP
75% 5-Bromo-CTP/25% CTP/Pseudo-UTP
75% 5-methoxy-UTP/25% 5-methyl-CTP/ATP/GTP
75% 5-methoxy-UTP/50% 5-methyl-CTP/ATP/GTP
75% 5-methoxy-UTP/75% 5-methyl-CTP/ATP/GTP
75% 5-methoxy-UTP/CTP/ATP/GTP
8-Aza-ATP
Alpha-thio-CTP
CTP/25% 5-Methoxy-UTP + 75% 1-Methyl-pseudo-UTP
CTP/25% 5-Methoxy-UTP + 75% UTP
CTP/50% 5-Methoxy-UTP + 50% 1-Methyl-pseudo-UTP
CTP/50% 5-Methoxy-UTP + 50% UTP
CTP/5-Methoxy-UTP TABLE 7-continued Combinations CTP/5-Methoxy-UTP (cap 0)
CTP/5-Methoxy-UTP(No cap)
CTP/75% 5-Methoxy-UTP + 25% 1-Methyl-pseudo-UTP
CTP/75% 5-Methoxy-UTP + 25% UTP
CTP/UTP(No cap)
N1-Me-GTP
N4-Ac-CTP
N4Ac-CTP/1-Methyl-pseudo-UTP
N4Ac-CTP/5-Methoxy-UTP
N4-acetyl-cytidine TP, ATP, GTP, UTP
N4-Bz-CTP/5-Methoxy-UTP
N4-methyl CTP
N4-Methyl-CTP/5-Methoxy-UTP
Pseudo-iso-CTP/5-Methoxy-UTP
PseudoU-alpha-thio-TP
pseudouridine TP, ATP, GTP, CTP
pseudo-UTP/5-methyl-CTP/ATP/GTP
UTP-5-oxyacetic acid Me ester
Xanthosine According to the invention, polynucleotides of the invention may be synthesized to comprise the combinations or single modifications of Table 7.

Where a single modification is listed, the listed nucleoside or nucleotide represent 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

IV. Pharmaceutical Compositions

Formulation, Administration, Delivery and Dosing

The present invention provides circP, circSP, circRNA or circRNA-SP compositions and complexes in combination with one or more pharmaceutically acceptable excipients. Pharmaceutical compositions may optionally comprise one or more additional active substances, e.g. therapeutically and/or prophylactically active substances. Pharmaceutical compositions of the present invention may be sterile and/or pyrogen-free. General considerations in the formulation and/or manufacture of pharmaceutical agents may be found, for example, in Remington: The Science and Practice of Pharmacy 21$^{st}$ ed., Lippincott Williams & Wilkins, 2005 (incorporated herein by reference).

In some embodiments, compositions are administered to humans, human patients or subjects. For the purposes of the present disclosure, the phrase "active ingredient" generally refers to circP, circSP, circRNA or circRNA-SP to be delivered as described herein.

In one embodiment, the compositions described herein include at least one of circP, circSP, circRNA or circRNA-SP.

In one embodiment, the compositions described herein may include at least one circSP and/or at least one circRNA. In another embodiment, the compositions described herein may include at least one circSP and/or at least one circRNA-SP. In yet another embodiment, the compositions described herein may include at least one circRNA and/or at least one circRNA-SP.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Formulations

The circP, circSP, circRNA or circRNA-SP of the invention can be formulated using one or more excipients to: (1) increase stability; (2) increase cell transfection; (3) permit the sustained or delayed release (e.g., from a depot formulation of the circP, circSP, circRNA or circRNA-SP); (4) alter the biodistribution (e.g., target the circP, circSP, circRNA or circRNA-SP to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with circP, circSP, circRNA or circRNA-SP (e.g., for transplantation into a subject), hyaluronidase, nanoparticle mimics and combinations thereof. Accordingly, the formulations of the invention can include one or more excipients, each in an amount that together increases the stability of the circP, circSP, circRNA or circRNA-SP, increases cell transfection by the circP, circSP, circRNA or circRNA-SP, increases the expression of circP, circRNA or circRNA-SP encoded protein, and/or alters the release profile of the circP, circRNA or circRNA- SP encoded proteins. Further, the circP, circSP, circRNA or circRNA-SP of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient.

In some embodiments, the formulations described herein may contain at least one circP, circSP, circRNA or circRNA-SP. As a non-limiting example, the formulations may contain 1, 2, 3, 4 or 5 circP, circSP, circRNA or circRNA-SP. In one embodiment the formulation may contain circP, circRNA or circRNA-SP encoding proteins selected from categories such as, but not limited to, human proteins, veterinary proteins, bacterial proteins, biological proteins, antibodies, immunogenic proteins, therapeutic peptides and proteins, secreted proteins, plasma membrane proteins, cytoplasmic and cytoskeletal proteins, intracellular membrane bound proteins, nuclear proteins, proteins associated with human disease and/or proteins associated with non-human diseases. In one embodiment, the formulation contains at least three circP, circRNA or circRNA-SP encoding proteins. In one embodiment, the formulation contains at least five circP, circRNA or circRNA-SP encoding proteins.

As another non-limiting example, the formulations may contain 1, 2, 3, 4 or 5 circP or circSP which are considered circular polynucleotide sponges. As used herein, "circular polynucleotide sponges," "sponges" "circRNA-SP" or "circSP" means a competitive inhibitors which can include at least one miR binding site to a microRNA of interest. The circSP can include at least one miR binding site, at least two miR binding sites, at least three miR binding sites, at least four miR binding sites, at least five miR binding sites, at least, six miR binding sites, at least seven miR binding sites, at least eight miR binding sites, at least nine miR binding sites, at least ten miR binding sites, at least 15 miR binding sites, at least 20 miR binding sites, at least 25 miR binding sites, at least 30 miR binding sites, at least 35 miR binding sites, at least 40 miR binding sites, at least 45 miR binding sites, at least 50 miR binding sites, at least 55 miR binding sites, at least 60 miR binding sites, at least 65 miR binding sites, at least 70 miR binding sites, at least 75 miR binding sites, at least 80 miR binding sites, at least 85 miR binding sites, at least 90 miR binding sites, at least 100 miR binding sites, at least 150 miR binding sites, or at least 200 miR binding sites. In one embodiment, the formulation contains at least three circSP sponges. In one embodiment, the formulation contains at least five circSP sponges.

In one embodiment a circSP may comprise at least 1 miR-122 sequence, at least 2 mir-122 sequences, at least 3 mir-122 sequences, at least 4 mir-122 sequences, at least 5 mir-122 sequences, at least 6 mir-122 sequences, at least 7 mir-122 sequences, at least 8 mir-122 sequences, at least 9 mir-122 sequences, at least 10 miR-122 sequences, at least 15 miR-122 sequences, at least 20 miR miR-122 sequences, at least 25 miR miR-122 sequences, at least 30 miR miR-122 sequences, at least 35 miR-122 sequences, at least 40 miR-122 sequences, at least 45 miR-122 sequences, at least 50 miR-122 sequences, at least 55 miR-122 sequences, at least 60 miR-122 sequences, at least 65 miR-122 sequences, at least 70 miR-122 sequences, at least 75 miR-122 sequences, at least 80 miR-122 sequences, at least 85 miR-122 sequences, at least 90 miR-122 sequences, at least 100 miR-122 sequences, at least 150 miR-122 sequences, or at least 200 miR-122 sequences. The miR-122 sequences in the circSP may be a miR binding site, a miR seed sequence, a miR binding site sequence without the seed or a combination thereof.

In one embodiment, a circSP may comprise at least one miR binding site and at least one spacer. The spacer may be 1 mer, 2 mer, 3 mer, 4 mer, 5 mer, 6 mer, 7 mer, 8 mer, 9 mer, 10 mer, 11, mer, 12 mer, 13 mer, 14 mer, 15 mer, 16 mer, 17 mer, 18 mer, 19 mer, 20 mer, 21 mer, 22 mer, 23 mer, 24 mer, 25 mer, 30 mer, 35 mer, 40 mer, 50 mer, or greater than 50 mer in length.

In one embodiment, a circSP does not comprise a start or stop codon and does not comprise an untranslated region. As a non-limiting example, the circSP comprises at least 50 miR-122 binding sites with a 20 mer spacer between each of the miR-122 binding sites. As a non-limiting example, the circSP with the 50 miR-122 binding sites and a 20 mer spacer between each miR-122 binding site may be transfected in vitro into primary hepatocyte cells and the free miR-122 may be measured using the methods known in the art and described herein. Further, the circSP may comprise at least one modified nucleoside. As another non-limiting example, the circSP with the 50 miR-122 binding sites and a 20 mer spacer between each miR-122 binding site may be formulated in a lipid nanoparticle at various doses and administered to mice using the mouse HCV model. Further, the circSP may comprise at least one modified nucleoside.

In one embodiment, the degradation of circSP may be controlled by using protein motifs to obscure ENDO nuclease motifs. As a non-limiting example, a circSP may be stabilized to degradation using binding protein motifs to obscure ENDO nuclease motifs. The stabilized circSP may be de-stabilized by administering siRNA or another circSP which can target the binding protein. As another non-limiting example, a circSP may be stabilized to degradation by using the binding protein motif PUF1 to obscure ENDO nuclease motifs.

In another embodiment, the formulation may include at least one circSP and at least one circP encoding a polypeptide of interest (e.g., circRNA or circRNA-SP).

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid nanoparticle may be increased and/or decreased. The change in particle size may be able to help counter biological reaction such as, but not limited to, inflammation or may increase the biological effect of the circP, circSP, circRNA or circRNA-SP delivered to mammals.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention.

Lipidoids

The synthesis of lipidoids has been extensively described and formulations containing these compounds are particularly suited for delivery of circP, circSP, circRNA or circRNA-SP (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure describes their formulation and use in delivering circP, circSP, circRNA or circRNA-SP.

Complexes, micelles, liposomes or particles can be prepared containing these lipidoids and therefore, can result in an effective delivery of the circP, circSP, circRNA or circRNA-SP, as judged by the production of an encoded protein, following the injection of a lipidoid formulation via localized and/or systemic routes of administration. Lipidoid complexes of circP, circSP, circRNA or circRNA-SP can be administered by various means including, but not limited to, intravenous, intramuscular, or subcutaneous routes.

In vivo delivery of nucleic acids may be affected by many parameters, including, but not limited to, the formulation composition, nature of particle PEGylation, degree of loading, oligonucleotide to lipid ratio, and biophysical parameters such as, but not limited to, particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010); herein incorporated by reference in its entirety), C12-200 (including derivatives and variants), and MD1, can be tested for in vivo activity.

The lipidoid referred to herein as "98N12-5" is disclosed by Akinc et al., Mol Ther. 2009 17:872-879 and is incorporated by reference in its entirety.

The lipidoid referred to herein as "C12-200" is disclosed by Love et al., Proc Natl Acad Sci USA. 2010 107:1864-1869 and Liu and Huang, Molecular Therapy. 2010 669-670; both of which are herein incorporated by reference in their entirety. The lipidoid formulations can include particles comprising either 3 or 4 or more components in addition to circP, circSP, circRNA or circRNA-SP. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In one embodiment, a circP, circSP, circRNA or circRNA-SP formulated with a lipidoid for systemic intravenous administration can target the liver. For example, a final optimized intravenous formulation using circP, circSP, circRNA or circRNA-SP, and comprising a lipid molar composition of 42% 98N12-5, 48% cholesterol, and 10% PEG-lipid with a final weight ratio of about 7.5 to 1 total lipid to circRNA, and a C14 alkyl chain length on the PEG lipid, with a mean particle size of roughly 50-60 nm, can result in the distribution of the formulation to be greater than 90% to the liver. (See, Akinc et al., Mol Ther. 2009 17:872-879; herein incorporated by reference in its entirety). In another example, an intravenous formulation using a C12-200 (see U.S. provisional application 61/175,770 and published international application WO2010129709, each of which is herein incorporated by reference in their entirety) lipidoid may have a molar ratio of 50/10/38.5/1.5 of C12-200/disteroylphosphatidyl choline/cholesterol/PEG-DMG, with a weight ratio of 7 to 1 total lipid to circP, circSP, circRNA or circRNA-SP, and a mean particle size of 80 nm may be effective to deliver circP, circSP, circRNA or circRNA-SP to hepatocytes (see, Love et al., Proc Natl Acad Sci USA. 2010 107:1864-1869 herein incorporated by reference in its entirety). In another embodiment, an MD1 lipidoid-containing formulation may be used to effectively deliver circP, circSP, circRNA or circRNA-SP to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879 herein incorporated by reference in its entirety), use of a lipidoid-formulated circP, circSP, circRNA or circRNA-SP to deliver the formulation to other cells types including, but not limited to, endothelial cells, myeloid cells, and muscle cells may not be similarly size-limited.

Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; 8$^{th}$ International Judah Folkman Conference, Cambridge, Mass. Oct. 8-9, 2010; each of which is herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of the circP, circSP, circRNA or circRNA-SP for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and %1.5 PEG-DMG (see Leuschner et al., Nat Biotechnol 2011 29:1005-1010; herein incorporated by reference in its entirety). The use of lipidoid formulations for the localized delivery of nucleic acids to cells (such as, but not limited to, adipose cells and muscle cells) via either subcutaneous or intramuscular delivery, may not require all of the formulation components desired for systemic delivery, and as such may comprise only the lipidoid and the circP, circSP, circRNA or circRNA-SP.

Combinations of different lipidoids may be used to improve the efficacy of circRNA directed protein production as the lipidoids may be able to increase cell transfection by the circP, circRNA, circRNA-SP; and/or increase the translation of encoded protein (see Whitehead et al., Mol. Ther. 2011, 19:1688-1694, herein incorporated by reference in its entirety).

Liposomes, Lipoplexes, and Lipid Nanoparticles

The circP, circSP, circRNA or circRNA-SP of the invention can be formulated using one or more liposomes, lipoplexes, or lipid nanoparticles. In one embodiment, pharmaceutical compositions of circP, circSP, circRNA or circRNA-SP include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations may be composed of 3 to 4 lipid components in addition to the circP, circSP, circRNA or circRNA-SP. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In a preferred embodiment, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In one embodiment, pharmaceutical compositions may include liposomes which may be formed to deliver circP, circSP, circRNA or circRNA-SP which may encode at least one immunogen or another polypeptide of interest. The circP, circSP, circRNA or circRNA-SP may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In another embodiment, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are herein incorporated by reference in its entirety.

In another embodiment, the circP, circSP, circRNA or circRNA-SP which may encode an immunogen may be formulated in a cationic oil-in-water emulsion where the emulsion particle comprises an oil core and a cationic lipid which can interact with the circP, circSP, circRNA or circRNA-SP anchoring the molecule to the emulsion particle (see International Pub. No. WO2012006380; herein incorporated by reference in its entirety).

In one embodiment, the circPs, circSPs, circRNAs or circRNA-SPs may be formulated in a water-in-oil emulsion comprising a continuous hydrophobic phase in which the hydrophilic phase is dispersed. As a non-limiting example, the emulsion may be made by the methods described in International Publication No. WO201087791, herein incorporated by reference in its entirety.

In another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; the contents of each of which is herein incorporated by reference in their entirety). In another embodiment, the circP, circSP, circRNA or circRNA-SP encoding an immunogen may be formulated in a lipid vesicle which may have crosslinks between functionalized lipid bilayers (see U.S. Pub. No. 20120177724, the contents of which are herein incorporated by reference in its entirety).

In one embodiment, the circP, circSP, circRNA or circRNA-SP may be formulated in a liposome as described in International Patent Publication No. WO2013086526, herein incorporated by reference in its entirety. The circPs, circSPs, circRNAs or circRNA-SPs may be encapsulated in a liposome using reverse pH gradients and/or optimized internal buffer compositions as described in International Patent Publication No. WO2013086526, herein incorporated by reference in its entirety.

In one embodiment, the cationic lipid may be a low molecular weight cationic lipid such as those described in US Patent Application No. 20130090372, the contents of which are herein incorporated by reference in its entirety.

In one embodiment, the circP, circSP, circRNA or circRNA-SP may be formulated in a lipid vesicle which may have crosslinks between functionalized lipid bilayers.

In one embodiment, the circP, circSP, circRNA or circRNA-SP may be formulated in a liposome comprising a cationic lipid. The liposome may have a molar ratio of nitrogen atoms in the cationic lipid to the phosphates in the RNA (N:P ratio) of between 1:1 and 20:1 as described in International Publication No. WO2013006825, herein incorporated by reference in its entirety. In another embodiment, the liposome may have an N:P ratio of greater than 20:1 or less than 1:1.

In one embodiment, the circP, circSP, circRNA or circRNA-SP may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the circP, circSP, circRNA or circRNA-SP may be formulated in a lipid-polycation complex which may further include a neutral lipid such as, but not limited to, cholesterol or dioleoyl phosphatidylethanolamine (DOPE).

In one embodiment, the circPs, circSPs, circRNAs or circRNA-SPs may be formulated in an aminoalcohol lipidoid. Aminoalcohol lipidoids which may be used in the present invention may be prepared by the methods described in U.S. Pat. No. 8,450,298, the contents of which is herein incorporated by reference in its entirety.

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol)), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the circP, circSP, circRNA or circRNA-SP may be formulated in a lipid nanoparticle such as those described in International Publication No. WO2012170930, herein incorporated by reference in its entirety.

In one embodiment, the formulation comprising the circP, circSP, circRNA or circRNA-SP is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-01 (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

In one embodiment, the cationic lipid may be selected from, but not limited to, a cationic lipid described in paragraph [000370] in co-pending International Publication No. WO2015034925, the contents of which is herein incorporated by reference in its entirety.

In one embodiment, the lipid may be a cleavable lipid such as those described in International Publication No. WO2012170889, herein incorporated by reference in its entirety.

In another embodiment, the lipid may be a cationic lipid such as, but not limited to, Formula (I) of U.S. Patent Application No. US20130064894, the contents of which are herein incorporated by reference in its entirety.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354; the contents of each of which are herein incorporated by reference in their entirety.

In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In one embodiment, the LNP formulations of the circP, circSP, circRNA or circRNA-SP may contain PEG-c-DOMG at 3% lipid molar ratio. In another embodiment, the LNP formulations circP, circSP, circRNA or circRNA-SP may contain PEG-c-DOMG at 1.5% lipid molar ratio.

In one embodiment, the pharmaceutical compositions of the circP, circSP, circRNA or circRNA-SP may include at least one of the PEGylated lipids described in International Publication No. WO2012099755, herein incorporated by reference.

In one embodiment, the LNP formulation may contain PEG-DMG 2000 (1,2-dimyristoyl-sn-glycero-3-phophoethanolamine-N-[methoxy(polyethylene glycol)-2000]). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety).

In one embodiment, the LNP formulation may be formulated by the methods described in International Publication Nos. WO2011127255 or WO2008103276, the contents of each of which is herein incorporated by reference in their entirety. As a non-limiting example, the circPs, circSPs, circRNAs or circRNA-SPs described herein may be encapsulated in LNP formulations as described in WO2011127255 and/or WO2008103276; each of which is herein incorporated by reference in their entirety.

In one embodiment, the circP, circSP, circRNA or circRNA-SP described herein may be formulated in a nanoparticle to be delivered by a parenteral route as described in U.S. Pub. No. US20120207845; the contents of which are herein incorporated by reference in its entirety.

In one embodiment, the circPs, circSPs, circRNAs or circRNA-SPs may be formulated in a lipid nanoparticle made by the methods described in US Patent Publication No US20130156845 or International Publication No. WO2013093648 or WO2012024526, each of which is herein incorporated by reference in its entirety.

The lipid nanoparticles described herein may be made in a sterile environment by the system and/or methods described in US Patent Publication No. US20130164400, herein incorporated by reference in its entirety.

In one embodiment, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the circPs, circSPs, circRNAs or circRNA-SPs described herein and/or are known in the art.

In one embodiment, the LNP formulation may be formulated by the methods described in International Publication Nos. WO2011127255 or WO2008103276, the contents of each of which are herein incorporated by reference in their entirety. As a non-limiting example, circP, circSP, circRNA or circRNA-SP described herein may be encapsulated in LNP formulations as described in WO2011127255 and/or WO2008103276; the contents of each of which are herein incorporated by reference in their entirety.

In one embodiment, LNP formulations described herein may comprise a polycationic composition. As a non-limiting example, the polycationic composition may be selected from formula 1-60 of US Patent Publication No. US20050222064; the content of which is herein incorporated by reference in its entirety. In another embodiment, the LNP formulations comprising a polycationic composition may be used for the delivery of the circP, circSP, circRNA or circRNA-SP described herein in vivo and/or in vitro.

In one embodiment, the LNP formulations described herein may additionally comprise a permeability enhancer molecule. Non-limiting permeability enhancer molecules are described in US Patent Publication No.

US20050222064; the content of which is herein incorporated by reference in its entirety.

In one embodiment, the pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In one embodiment, the circP, circSP, circRNA or circRNA-SP may be formulated in a lyophilized gel-phase liposomal composition as described in US Publication No. US2012060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Application No. WO2013033438 or US Patent Publication No. US20130196948, the contents of each of which are herein incorporated by reference in its entirety. As a non-limiting example, the phosphate conjugates may include a compound of any one of the formulas described in International Application No. WO2013033438, herein incorporated by reference in its entirety.

The nanoparticle formulation may comprise a polymer conjugate. The polymer conjugate may be a water soluble conjugate. The polymer conjugate may have a structure as described in U.S. Patent Application No. 20130059360, the contents of which are herein incorporated by reference in its entirety. In one aspect, polymer conjugates with the circP, circSP, circRNA or circRNA-SP of the present invention may be made using the methods and/or segmented polymeric reagents described in U.S. Patent Application No. 20130072709, herein incorporated by reference in its entirety. In another aspect, the polymer conjugate may have pendant side groups comprising ring moieties such as, but not limited to, the polymer conjugates described in US Patent Publication No. US20130196948, the contents of which are herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al (Science 2013 339, 971-975), herein incorporated by reference in its entirety). As shown by Rodriguez et al. the self-peptides delayed macrophage-mediated clearance of nanoparticles which enhanced delivery of the nanoparticles. In another aspect, the conjugate may be the membrane protein CD47 (e.g., see Rodriguez et al. Science 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In one embodiment, the circP, circSP, circRNA or circRNA-SP of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In another aspect the nanoparticle may comprise PEG and a conjugate of CD47 or a derivative thereof. In yet another aspect, the nanoparticle may comprise both the "self" peptide described above and the membrane protein CD47.

In another aspect, a "self" peptide and/or CD47 protein may be conjugated to a virus-like particle or pseudovirion, as described herein for delivery of the circP, circSP, circRNA or circRNA-SP of the present invention.

In another embodiment, pharmaceutical compositions comprising the circP, circSP, circRNA or circRNA-SP of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443, the contents of which are herein incorporated by reference in its entirety.

The nanoparticle formulations may be a carbohydrate nanoparticle comprising a carbohydrate carrier and circP, circSP, circRNA or circRNA-SP. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Nanoparticle formulations of the present invention may be coated with a surfactant or polymer in order to improve the delivery of the particle. In one embodiment, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, circP, circSP, circRNA or circRNA-SP within the central nervous system. As a non-limiting example nanoparticles comprising a hydrophilic coating and methods of making such nanoparticles are described in US Patent Publication No. US20130183244, the contents of which are herein incorporated by reference in its entirety.

In one embodiment, the lipid nanoparticles of the present invention may be hydrophilic polymer particles. Non-limiting examples of hydrophilic polymer particles and methods of making hydrophilic polymer particles are described in US Patent Publication No. US20130210991, the contents of which are herein incorporated by reference in its entirety.

In another embodiment, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the internal ester linkage may be located on either side of the saturated carbon such as the reLNPs described in paragraph [000398] of co-pending International Publication No. WO2015034925, the contents of which are herein incorporated by reference in its entirety.

In one embodiment, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, circP, circSP, circRNA or circRNA-SP described herein. In one embodiment, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosla tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670, or International Patent Publication No. WO2013110028, the contents of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in its entirety. The polymeric material may additionally be irradiated. As a non-limiting example, the polymeric material may be gamma irradiated (See e.g., International App. No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth) acrylate) (PMMA), poly(ethyl(meth)acrylate), poly(butyl (meth)acrylate), poly(isobutyl(meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., US Publication 20120121718 and US Publication 20100003337 and U.S. Pat. No. 8,263,665; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in its entirety). A non-limiting scalable method to produce nanoparticles which can penetrate human mucus is described by Xu et al. (See e.g., J Control Release 2013, 170(2):279-86; the contents of which are herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, circP, circSP, circRNA or circRNA-SP, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., US Publication 20100215580 and US Publication 20080166414 and US20130164343; the contents of each of are is herein incorporated by reference in their entirety).

The mucus penetrating lipid nanoparticles may comprise at least one circRNA described herein. The circP, circSP, circRNA or circRNA-SP may be encapsulated in the lipid nanoparticle and/or disposed on the surface of the particle. The circP, circSP, circRNA or circRNA-SP may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In another embodiment, the mucus penetrating lipid nanoparticles may be a hypotonic formulation comprising a mucosal penetration enhancing coating. The formulation may be hypotonice for the epithelium to which it is being delivered. Non-limiting examples of hypotonic formulations may be found in International Patent Publication No. WO2013110028, the contents of which are herein incorporated by reference in its entirety.

In one embodiment, in order to enhance the delivery through the mucosal barrier the formulation may comprise or be a hypotonic solution. Hypotonic solutions were found to increase the rate at which mucoinert particles such as, but not limited to, mucus-penetrating particles, were able to reach the vaginal epithelial surface (See e.g., Ensign et al. Biomaterials 2013 34(28):6922-9; the contents of which is herein incorporated by reference in its entirety).

In one embodiment, the circP, circSP, circRNA or circRNA-SP is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; all of which are incorporated herein by reference in its entirety).

In one embodiment, the circP, circSP, circRNA or circRNA-SP is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety). As a non-limiting example, the SLN may be the SLN described in International Patent Publication No. WO2013105101, the contents of which are herein incorporated by reference in its entirety. As another non-limiting example, the SLN may be made by the methods or processes described in International Patent Publication No. WO2013105101, the contents of which are herein incorporated by reference in its entirety.

Liposomes, lipoplexes, or lipid nanoparticles may be used to improve the efficacy of circP, circSP, circRNA or circRNA-SP directed protein production as these formulations may be able to increase cell transfection by the circP, circSP, circRNA or circRNA-SP; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles may also be used to increase the stability of the circP, circSP, circRNA or circRNA-SP.

In one embodiment, the circP, circSP, circRNA or circRNA-SP of the present invention can be formulated for controlled release and/or targeted delivery. As used herein, "controlled release" refers to a pharmaceutical composition or compound release profile that conforms to a particular pattern of release to effect a therapeutic outcome. In one embodiment, the circP, circSP, circRNA or circRNA-SP may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In one embodiment, the controlled release formulation may include, but is not limited to, tri-block co-polymers. As a non-limiting example, the formulation may include two different types of tri-block co-polymers (International Pub. No. WO2012131104 and WO2012131106; each of which is herein incorporated by reference in its entirety).

In another embodiment, the circP, circSP, circRNA or circRNA-SP may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In one embodiment, the circP, circSP, circRNA or circRNA-SP formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradable polyesters include, but are not limited to, poly (serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the controlled release and/or targeted delivery formulation comprising at least one circP, circSP, circRNA or circRNA-SP may comprise at least one PEG and/or PEG related polymer derivatives as described in U.S. Pat. No. 8,404,222, herein incorporated by reference in its entirety.

In another embodiment, the controlled release delivery formulation comprising at least one circP, circSP, circRNA or circRNA-SP may be the controlled release polymer system described in US20130130348, herein incorporated by reference in its entirety.

In one embodiment, the circP, circSP, circRNA or circRNA-SP of the present invention may be encapsulated in a therapeutic nanoparticle. Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, herein incorporated by reference in its entirety.

In one embodiment, the therapeutic nanoparticle may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the circP, circSP, circRNA or circRNA-SP of the present invention (see International Pub No. 2010075072 and US Pub No. US20100216804, US20110217377 and US20120201859, each of which is herein incorporated by reference in their entirety). In another non-limiting example, the sustained release formulation may comprise agents which permit persistent bioavailability such as, but not limited to, crystals, macromolecular gels and/or particulate suspensions (see US Patent Publication No US20130150295, the contents of which is herein incorporated by reference in its entirety).

In one embodiment, the therapeutic nanoparticles may be formulated to be target specific. As a non-limiting example, the therapeutic nanoparticles may include a corticosteroid (see International Pub. No. WO2011084518; herein incorporated by reference in its entirety). In one embodiment, the therapeutic nanoparticles may be formulated to be cancer specific. As a non-limiting example, the therapeutic nanoparticles may be formulated in nanoparticles described in International Pub No. WO2008121949, WO2010005726, WO2010005725, WO2011084521 and US Pub No.

US20100069426, US20120004293 and US20100104655, each of which is herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof. In another embodiment, the diblock copolymer may comprise the diblock copolymers described in European Patent Publication No. the contents of which are herein incorporated by reference in its entirety. In yet another embodiment, the diblock copolymer may be a high-X diblock copolymer such as those described in International Patent Publication No. WO2013120052, the contents of which are herein incorporated by reference in its entirety.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in its entirety). In yet another non-limiting example, the therapeutic nanoparticle is a stealth nanoparticle or a target-specific stealth nanoparticle as described in US Patent Publication No. US20130172406, the contents of which are herein incorporated by reference in its entirety.

In one embodiment, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety). The circP, circSP, circRNA or circRNA-SP of the present invention may be formulated in lipid nanoparticles comprising the PEG-PLGA-PEG block copolymer.

In one embodiment, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In one embodiment, the block copolymers described herein may be included in a polyion complex comprising a non-polymeric micelle and the block copolymer. (See e.g., U.S. Pub. No. 20120076836; herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or US Patent Publication No US20130121954, the contents of which are herein incorporated by reference in its entirety. In one aspect, the poly(vinyl ester) polymers may be conjugated to the circP, circSP, circRNA or circRNA-SP described herein. In another aspect, the poly(vinyl ester) polymer which may be used in the present invention may be those described in, herein incorporated by reference in its entirety.

In one embodiment, the therapeutic nanoparticle may comprise at least one diblock copolymer. The diblock copolymer may be, but it not limited to, a poly(lactic) acid-poly (ethylene)glycol copolymer (see e.g., International Patent Publication No. WO2013044219; herein incorporated by reference in its entirety). As a non-limiting example, the therapeutic nanoparticle may be used to treat cancer (see International publication No. WO2013044219; herein incorporated by reference in its entirety).

In one embodiment, the therapeutic nanoparticles may comprise at least one cationic polymer described herein and/or known in the art.

In one embodiment, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; herein incorporated by reference in its entirety) and combinations thereof.

In another embodiment, the nanoparticles described herein may comprise an amine cationic lipid such as those described in International Patent Application No. WO2013059496, the contents of which are herein incorporated by reference in its entirety. In one aspect the cationic lipids may have an amino-amine or an amino-amide moiety.

In one embodiment, the therapeutic nanoparticles may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; herein incorporated by reference in its entirety).

In one embodiment, the therapeutic nanoparticle may be formulated in an aqueous solution which may be used to target cancer (see International Pub No. WO2011084513 and US Pub No. US20110294717, each of which is herein incorporated by reference in their entirety).

In one embodiment, the therapeutic nanoparticle comprising at least one circP, circSP, circRNA or circRNA-SP may be formulated using the methods described by Podobinski et al in U.S. Pat. No. 8,404,799, the contents of which are herein incorporated by reference in its entirety.

In one embodiment, the circP, circSP, circRNA or circRNA-SP may be encapsulated in, linked to and/or associated with synthetic nanocarriers. Synthetic nanocarriers include, but are not limited to, those described in paragraphs [000440]-[000449] of copending International Publication No. WO2015034925, the contents of which are herein incorporated by reference in its entirety.

In one embodiment, the circP, circSP, circRNA and/or circRNA-SP may be encapsulated in, linked to and/or associated with zwitterionic lipids. Non-limiting examples of zwitterionic lipids and methods of using zwitterionic lipids are described in US Patent Publication No. US20130216607, the contents of which are herein incorporated by reference in its entirety. In one aspect, the zwitterionic lipids may be used in the liposomes and lipid nanoparticles described herein.

In one embodiment, the circP, circSP, circRNA and/or circRNA-SP may be formulated in colloid nanocarriers as described in US Patent Publication No. US20130197100, the contents of which are herein incorporated by reference in its entirety.

In one embodiment, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, circP, circSP, circRNA and/or circRNA-SP may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 45 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, less than 975 um.

In another embodiment, circP, circSP, circRNA and/or circRNA-SP may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigital micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51; each of which is herein incorporated by reference in its entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In one embodiment, the circP, circSP, circRNA and/or circRNA-SP of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In one embodiment, the circP, circSP, circRNA and/or circRNA-SP of the present invention may be formulated in lipid nanoparticles created using microfluidic technology (see Whitesides, George M. The Origins and the Future of Microfluidics. Nature, 2006 442: 368-373; and Abraham et al. Chaotic Mixer for Microchannels. Science, 2002 295: 647-651; each of which is herein incorporated by reference in its entirety). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647-651; which is herein incorporated by reference in its entirety).

In one embodiment, the circP, circSP, circRNA and/or circRNA-SP of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In one embodiment, the circP, circSP, circRNA and/or circRNA-SP of the invention may be formulated for delivery using the drug encapsulating microspheres described in International Patent Publication No. WO2013063468 or U.S. Pat. No. 8,440,614, each of which is herein incorporated by reference in its entirety. The microspheres may comprise a compound of the formula (I), (II), (III), (IV), (V) or (VI) as described in International patent application No. WO2013063468, the contents of which are herein incorporated by reference in its entirety. In another aspect, the amino acid, peptide, polypeptide, lipids (APPL) are useful in delivering the circP, circSP, circRNA and/or circRNA-SP of the invention to cells (see International Patent Publication No. WO2013063468, herein incorporated by reference in its entirety).

In one embodiment, the circP, circSP, circRNA and/or circRNA-SP of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles may have a diameter from about 10 to 500 nm.

In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle may be a limit size lipid nanoparticle described in International Patent Publication No. WO2013059922, the contents of which are herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle may comprise a polyethylene glycol-lipid such as, but not limited to, DLPE-PEG, DMPE-PEG, DPPC-PEG and DSPE-PEG.

In one embodiment, the circP, circSP, circRNA and/or circRNA-SP may be delivered, localized and/or concentrated in a specific location using the delivery methods described in International Patent Publication No. WO2013063530, the contents of which are herein incorporated by reference in its entirety. As a non-limiting example, a subject may be administered an empty polymeric particle prior to, simultaneously with or after delivering the circP, circSP, circRNA and/or circRNA-SP to the subject. The empty polymeric particle undergoes a change in volume once in contact with the subject and becomes lodged, embedded, immobilized or entrapped at a specific location in the subject.

In one embodiment, the circP, circSP, circRNA and/or circRNA-SP may be formulated in an active substance release system (See e.g., US Patent Publication No. US20130102545, herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., circP, circSP, circRNA and/or circRNA-SP described herein), where the therapeutically active substance is released by the cleavage of the substrate molecule by the catalytically active nucleic acid.

In one embodiment, the circP, circSP, circRNA and/or circRNA-SP may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, herein incorporated by reference in its entirety. As another non-limiting example, the nanoparticle described in International Patent Publication No. WO2013052167, herein incorporated by reference in its entirety, may be used to deliver the circP, circSP, circRNA and/or circRNA-SP described herein.

In one embodiment, the circP, circSP, circRNA and/or circRNA-SP may be formulated in porous nanoparticlesupported lipid bilayers (protocells). Protocells are described in International Patent Publication No. WO2013056132, the contents of which are herein incorporated by reference in its entirety.

In one embodiment, the circP, circSP, circRNA and/or circRNA-SP described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in its entirety. As another non-limiting example, the polymer nanoparticle for oral, parenteral and topical formulations may be made by the methods described in European Patent No. EP2073848B1, the contents of which are herein incorporated by reference in its entirety.

In another embodiment, the circP, circSP, circRNA and/or circRNA-SP described herein may be formulated in nanoparticles used in imaging. The nanoparticles may be liposome nanoparticles such as those described in US Patent Publication No US20130129636, herein incorporated by reference in its entirety. As a non-limiting example, the liposome may comprise gadolinium(III)2-{4,7-bis-carboxymethyl-10-[(N,N-distearylamidomethyl-N'-amidomethyl]-1,4,7,10-tetra-azacyclododec-1-yl}-acetic acid and a neutral, fully saturated phospholipid component (see e.g., US Patent Publication No US20130129636, the contents of which is herein incorporated by reference in its entirety).

In one embodiment, the nanoparticles which may be used in the present invention are formed by the methods described in U.S. Patent Application No. US20130130348, the contents of which are herein incorporated by reference in its entirety.

The nanoparticles of the present invention may further include nutrients such as, but not limited to, those which deficiencies can lead to health hazards from anemia to neural tube defects (see e.g., the nanoparticles described in International Patent Publication No WO2013072929, the contents of which is herein incorporated by reference in its entirety). As a non-limiting example, the nutrient may be iron in the form of ferrous, ferric salts or elemental iron, iodine, folic acid, vitamins or micronutrients.

In one embodiment, the circP, circSP, circRNA and/or circRNA-SP of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the circP, circSP, circRNA and/or circRNA-SP of the present invention to the pulmonary system (see e.g., U.S. Pat. No. 8,440,231, the contents of which is herein incorporated by reference in its entirety).

The circP, circSP, circRNA and/or circRNA-SP of the present invention may be formulated in polyanhydride nanoparticles such as, but not limited to, those described in U.S. Pat. No. 8,449,916, the contents of which are herein incorporated by reference in its entirety.

The nanoparticles and microparticles of the present invention may be geometrically engineered to modulate macrophage and/or the immune response. In one aspect, the geometrically engineered particles may have varied shapes, sizes and/or surface charges in order to incorporated the circP, circSP, circRNA and/or circRNA-SP of the present invention for targeted delivery such as, but not limited to, pulmonary delivery (see e.g., International Publication No WO2013082111, the contents of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No WO2013082111, the contents of which are herein incorporated by reference in its entirety.

In one embodiment, the nanoparticles of the present invention may be water soluble nanoparticles such as, but not limited to, those described in International Publication No. WO2013090601, the contents of which are herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In one embodiment the nanoparticles of the present invention may be developed by the methods described in US Patent Publication No. US20130172406, the contents of which are herein incorporated by reference in its entirety.

In one embodiment, the nanoparticles of the present invention are stealth nanoparticles or target-specific stealth nanoparticles such as, but not limited to, those described in US Patent Publication No. US20130172406; the contents of which are herein incorporated by reference in its entirety. The nanoparticles of the present invention may be made by the methods described in US Patent Publication No. US20130172406, the contents of which are herein incorporated by reference in its entirety.

In another embodiment, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In one embodiment, the nanoparticle may be a nanoparticle-nucleic acid hybrid structure having a high density nucleic acid layer. As a non-limiting example, the nanoparticle-nucleic acid hybrid structure may made by the methods described in US Patent Publication No. US20130171646, the contents of which are herein incorporated by reference in its entirety. The nanoparticle may comprise a nucleic acid such as, but not limited to, circP, circSP, circRNA and/or circRNA-SP described herein and/or known in the art.

At least one of the nanoparticles of the present invention may be embedded in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in its entirety.

Polymers, Biodegradable Nanoparticles, and Core-Shell Nanoparticles

The circP, circSP, circRNA or circRNA-SP of the invention can be formulated using natural and/or synthetic polymers. Non-limiting examples of polymers which may be used for delivery include, but are not limited to, DYNAMIC POLYCONJUGATE® (Arrowhead Research Corp., Pasadena, Calif.) formulations from MIRUS® Bio (Madison, Wis.) and Roche Madison (Madison, Wis.), PHASERX™ polymer formulations such as, without limitation, SMARTT POLYMER TECHNOLOGY™ (PHASERX®, Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly(lactic-co-glycolic acid) (PLGA) polymers. RONDEL™ (RNAi/Oligonucleotide Nanoparticle Delivery) polymers (Arrowhead Research Corporation, Pasadena, Calif.) and pH responsive co-block polymers such as, but not limited to, PHASERX® (Seattle, Wash.).

A non-limiting example of chitosan formulation includes a core of positively charged chitosan and an outer portion of negatively charged substrate (U.S. Pub. No. 20120258176; herein incorporated by reference in its entirety). Chitosan includes, but is not limited to N-trimethyl chitosan, mono-N-carboxymethyl chitosan (MCC), N-palmitoyl chitosan (NPCS), EDTA-chitosan, low molecular weight chitosan, chitosan derivatives, or combinations thereof.

In one embodiment, the polymers used in the present invention have undergone processing to reduce and/or inhibit the attachment of unwanted substances such as, but not limited to, bacteria, to the surface of the polymer. The polymer may be processed by methods known and/or described in the art and/or described in International Pub. No. WO2012150467, herein incorporated by reference in its entirety.

A non-limiting example of PLGA formulations include, but are not limited to, PLGA injectable depots (e.g., ELIGARD® which is formed by dissolving PLGA in 66% N-methyl-2-pyrrolidone (NMP) and the remainder being aqueous solvent and leuprolide. Once injected, the PLGA and leuprolide peptide precipitates into the subcutaneous space).

Many of these polymer approaches have demonstrated efficacy in delivering oligonucleotides in vivo into the cell cytoplasm (reviewed in deFougerolles *Hum Gene Ther.* 2008 19:125-132; herein incorporated by reference in its entirety). Two polymer approaches that have yielded robust in vivo delivery of nucleic acids, in this case with small interfering RNA (siRNA), are dynamic polyconjugates and cyclodextrin-based nanoparticles (see e.g., US Patent Publication No. US20130156721, herein incorporated by reference in its entirety). The first of these delivery approaches uses dynamic polyconjugates and has been shown in vivo in mice to effectively deliver siRNA and silence endogenous target mRNA in hepatocytes (Rozema et al., Proc Natl Acad Sci USA. 2007 104:12982-12887; herein incorporated by reference in its entirety). This particular approach is a multicomponent polymer system whose key features include a membrane-active polymer to which nucleic acid, in this case siRNA, is covalently coupled via a disulfide bond and where both PEG (for charge masking) and N-acetylgalactosamine (for hepatocyte targeting) groups are linked via pH-sensitive bonds (Rozema et al., Proc Natl Acad Sci USA. 2007 104:12982-12887; herein incorporated by reference in its entirety). On binding to the hepatocyte and entry into the endosome, the polymer complex disassembles in the low-pH environment, with the polymer exposing its positive charge, leading to endosomal escape and cytoplasmic release of the siRNA from the polymer. Through replacement of the N-acetylgalactosamine group with a mannose group, it was shown one could alter targeting from asialoglycoprotein receptor-expressing hepatocytes to sinusoidal endothelium and Kupffer cells. Another polymer approach involves using transferrin-targeted cyclodextrin-containing polycation nanoparticles. These nanoparticles have demonstrated targeted silencing of the EWS-FLI1 gene product in transferrin receptor-expressing Ewing's sarcoma tumor cells (Hu-Lieskovan et al., Cancer Res. 2005 65: 8984-8992; herein incorporated by reference in its entirety) and siRNA formulated in these nanoparticles was well tolerated in non-human primates (Heidel et al., Proc Natl Acad Sci USA 2007 104:5715-21; herein incorporated by reference in its entirety). Both of these delivery strategies incorporate rational approaches using both targeted delivery and endosomal escape mechanisms.

The polymer formulation can permit the sustained or delayed release of circP, circSP, circRNA or circRNA-SP (e.g., following intramuscular or subcutaneous injection). The altered release profile for the circP, circSP, circRNA or circRNA-SP can result in, for example, translation of an encoded protein over an extended period of time. The polymer formulation may also be used to increase the stability of the circP, circSP, circRNA or circRNA-SP. Biodegradable polymers have been previously used to protect nucleic acids other than circRNA from degradation and been shown to result in sustained release of payloads in vivo (Rozema et al., Proc Natl Acad Sci USA. 2007 104:12982-12887; Sullivan et al., Expert Opin Drug Deliv. 2010 7:1433-1446; Convertine et al., Biomacromolecules. 2010 Oct. 1; Chu et al., Acc Chem Res. 2012 Jan. 13; Manganiello et al., Biomaterials. 2012 33:2301-2309; Benoit et al., Biomacromolecules. 2011 12:2708-2714; Singha et al., Nucleic Acid Ther. 2011 2:133-147; deFougerolles Hum Gene Ther. 2008 19:125-132; Schaffert and Wagner, Gene Ther. 2008 16:1131-1138; Chaturvedi et al., Expert Opin Drug Deliv. 2011 8:1455-1468; Davis, Mol Pharm. 2009 6:659-668; Davis, Nature 2010 464:1067-1070; each of which is herein incorporated by reference in its entirety).

In one embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

As a non-limiting example circP, circSP, circRNA or circRNA-SP may be formulated in PLGA microspheres by preparing the PLGA microspheres with tunable release rates (e.g., days and weeks) and encapsulating the circP, circSP, circRNA or circRNA-SP in the PLGA microspheres while maintaining the integrity of the circP, circSP, circRNA or circRNA-SP during the encapsulation process. EVAc are non-biodegradable, biocompatible polymers which are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C. PEG-based surgical sealants comprise two synthetic PEG components mixed in a delivery device which can be prepared in one minute, seals in 3 minutes and is reabsorbed within 30 days. GELSITE® and natural polymers are capable of in-situ gelation at the site of administration. They have been shown to interact with protein and peptide therapeutic candidates through ionic interaction to provide a stabilizing effect.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; each of which is herein incorporated by reference in its entirety).

The circP, circSP, circRNA or circRNA-SP of the invention may be formulated with or in a polymeric compound. The polymer may include at least one polymer such as, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, a biodegradable polymer, elastic biodegradable polymer, biodegradable block copolymer, biodegradable random copolymer, biodegradable polyester copolymer, biodegradable polyester block copolymer, biodegradable polyester block random copolymer, multiblock copolymers, linear biodegradable copolymer, poly[α-(4-aminobutyl)-L-glycolic acid] (PAGA), biodegradable cross-linked cationic multiblock copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), acrylic polymers, amine-containing polymers, dextran polymers, dextran polymer derivatives or combinations thereof.

As a non-limiting example, the circP, circSP, circRNA or circRNA-SP of the invention may be formulated with the polymeric compound of PEG grafted with PLL as described in U.S. Pat. No. 6,177,274; herein incorporated by reference in its entirety. The formulation may be used for transfecting cells in vitro or for in vivo delivery of the circP, circSP, circRNA or circRNA-SP. In another example, the circP, circSP, circRNA or circRNA-SP may be suspended in a solution or medium with a cationic polymer, in a dry pharmaceutical composition or in a solution that is capable of being dried as described in U.S. Pub. Nos. 20090042829 and 20090042825; each of which are herein incorporated by reference in their entireties.

As another non-limiting example the circP, circSP, circRNA or circRNA-SP of the invention may be formulated with a PLGA-PEG block copolymer (see US Pub. No. US20120004293 and U.S. Pat. No. 8,236,330, herein incorporated by reference in their entireties) or PLGA-PEG-PLGA block copolymers (See U.S. Pat. No. 6,004,573, herein incorporated by reference in its entirety). As a non-limiting example, the circP, circSP, circRNA or circRNA-SP of the invention may be formulated with a diblock copolymer of PEG and PLA or PEG and PLGA (see U.S. Pat. No. 8,246,968, herein incorporated by reference in its entirety).

A polyamine derivative may be used to deliver nucleic acids or to treat and/or prevent a disease or to be included in an implantable or injectable device (U.S. Pub. No. 20100260817 (now U.S. Pat. No. 8,460,696) the contents of each of which is herein incorporated by reference in its entirety). As a non-limiting example, a pharmaceutical composition may include the modified nucleic acids and circP, circSP, circRNA or circRNA-SP and the polyamine derivative described in U.S. Pub. No. 20100260817 (now U.S. Pat. No. 8,460,696; the contents of which are incorporated herein by reference in its entirety. As a non-limiting example the circP, circSP, circRNA or circRNA-SP of the present invention may be delivered using a polyaminde polymer such as, but not limited to, a polymer comprising a 1,3-dipolar addition polymer prepared by combining a carbohydrate diazide monomer with a dilkyne unite comprising oligoamines (U.S. Pat. No. 8,236,280; herein incorporated by reference in its entirety).

The circP, circSP, circRNA or circRNA-SP of the invention may be formulated with at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the circP, circSP, circRNA or circRNA-SP of the present invention may be formulated with at least one polymer and/or derivatives thereof described in International Publication Nos. WO2011115862, WO2012082574 and WO2012068187 and U.S. Pub. No. 20120283427, each of which are herein incorporated by reference in their entireties. In another embodiment, the circP, circSP, circRNA or circRNA-SP of the present invention may be formulated with a polymer of formula Z as described in WO2011115862, herein incorporated by reference in its entirety. In yet another embodiment, the circP, circSP, circRNA or circRNA-SP may be formulated with a polymer of formula Z, Z' or Z" as described in International Pub. Nos. WO2012082574 or WO2012068187 and U.S. Pub. No. 2012028342, each of which are herein incorporated by reference in their entireties. The polymers formulated with the circP, circSP, circRNA or circRNA-SP of the present invention may be synthesized by the methods described in International Pub. Nos. WO2012082574 or WO2012068187, each of which are herein incorporated by reference in their entireties.

The circP, circSP, circRNA or circRNA-SP of the invention may be formulated with at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

Formulations of the circP, circSP, circRNA or circRNA-SP of the invention may include at least one amine-containing polymer such as, but not limited to polylysine, polyethylene imine, poly(amidoamine) dendrimers, poly(amine-co-esters) or combinations thereof. As a non-limiting example, the poly(amine-co-esters) may be the polymers described in and/or made by the methods described in International Publication No WO2013082529, the contents of which are herein incorporated by reference in its entirety.

For example, the circP, circSP, circRNA or circRNA-SP of the invention may be formulated in a pharmaceutical compound including a poly(alkylene imine), a biodegradable cationic lipopolymer, a biodegradable block copolymer, a biodegradable polymer, or a biodegradable random copolymer, a biodegradable polyester block copolymer, a biodegradable polyester polymer, a biodegradable polyester random copolymer, a linear biodegradable copolymer, PAGA, a biodegradable cross-linked cationic multi-block copolymer or combinations thereof. The biodegradable cationic lipopolymer may be made by methods known in the art and/or described in U.S. Pat. No. 6,696,038, U.S. App. Nos. 20030073619 and 20040142474 each of which is herein incorporated by reference in their entireties. The poly(alkylene imine) may be made using methods known in the art and/or as described in U.S. Pub. No. 20100004315, herein incorporated by reference in its entirety. The biodegradable polymer, biodegradable block copolymer, the biodegradable random copolymer, biodegradable polyester block copolymer, biodegradable polyester polymer, or biodegradable polyester random copolymer may be made using methods known in the art and/or as described in U.S. Pat. Nos. 6,517,869 and 6,267,987, the contents of which are each incorporated herein by reference in their entirety. The linear biodegradable copolymer may be made using methods known in the art and/or as described in U.S. Pat. No. 6,652,886. The PAGA polymer may be made using methods known in the art and/or as described in U.S. Pat. No. 6,217,912 herein incorporated by reference in its entirety. The PAGA polymer may be copolymerized to form a copolymer or block copolymer with polymers such as but not limited to, poly-L-lysine, polyargine, polyornithine, histones, avidin, protamines, polylactides and poly(lactide-co-glycolides). The biodegradable cross-linked cationic multi-block copolymers may be made my methods known in the art and/or as described in U.S. Pat. Nos. 8,057,821, 8,444, 992 or U.S. Pub. No. 2012009145 each of which are herein incorporated by reference in their entireties. For example, the multi-block copolymers may be synthesized using linear polyethyleneimine (LPEI) blocks which have distinct patterns as compared to branched polyethyleneimines. Further, the composition or pharmaceutical composition may be made by the methods known in the art, described herein, or as described in U.S. Pub. No. 20100004315 or U.S. Pat. Nos. 6,267,987 and 6,217,912 each of which are herein incorporated by reference in their entireties.

The circP, circSP, circRNA or circRNA-SP of the invention may be formulated with at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

The circP, circSP, circRNA or circRNA-SP of the invention may be formulated with at least one crosslinkable polyester. Crosslinkable polyesters include those known in the art and described in US Pub. No. 20120269761, herein incorporated by reference in its entirety.

The circP, circSP, circRNA or circRNA-SP of the invention may be formulated in or with at least one cyclodextrin polymer. Cyclodextrin polymers and methods of making cyclodextrin polymers include those known in the art and described in US Pub. No. 20130184453, the contents of which are herein incorporated by reference in its entirety.

In one embodiment, the circP, circSP, circRNA or circRNA-SP of the invention may be formulated in or with at least one crosslinked cation-binding polymers. Crosslinked cation-binding polymers and methods of making crosslinked cation-binding polymers include those known in the art and described in International Patent Publication No. WO2013106072, WO2013106073 and WO2013106086, the contents of each of which are herein incorporated by reference in its entirety.

In one embodiment, the circP, circSP, circRNA or circRNA-SP of the invention may be formulated in or with at least one branched polymer. Branched polymers and methods of making branched polymers include those known in the art and described in International Patent Publication No. WO2013113071, the contents of each of which are herein incorporated by reference in its entirety.

In one embodiment, the circP, circSP, circRNA or circRNA-SP of the invention may be formulated in or with at least PEGylated albumin polymer. PEGylated albumin polymer and methods of making PEGylated albumin polymer include those known in the art and described in US Patent Publication No. US20130231287, the contents of each of which are herein incorporated by reference in its entirety.

In one embodiment, the polymers described herein may be conjugated to a lipid-terminating PEG. As a non-limiting example, PLGA may be conjugated to a lipid-terminating PEG forming PLGA-DSPE-PEG. As another non-limiting example, PEG conjugates for use with the present invention are described in International Publication No. WO2008103276, herein incorporated by reference in its entirety. The polymers may be conjugated using a ligand conjugate such as, but not limited to, the conjugates described in U.S. Pat. No. 8,273,363, herein incorporated by reference in its entirety.

In one embodiment, the circP, circSP, circRNA or circRNA-SP disclosed herein may be mixed with the PEGs or the sodium phosphate/sodium carbonate solution prior to administration. In another embodiment, a circP, circRNA or circRNA-SP encoding a protein of interest may be mixed with the PEGs and also mixed with the sodium phosphate/sodium carbonate solution. In yet another embodiment, circP, circRNA or circRNA-SP encoding a protein of interest may be mixed with the PEGs and a circP, circRNA or circRNA-SP encoding a second protein of interest may be mixed with the sodium phosphate/sodium carbonate solution.

In one embodiment, the circP, circSP, circRNA or circRNA-SP described herein may be conjugated with another compound. Non-limiting examples of conjugates are described in U.S. Pat. Nos. 7,964,578 and 7,833,992, each of which are herein incorporated by reference in their entireties. In another embodiment, circP, circSP, circRNA or circRNA-SP of the present invention may be conjugated with conjugates of formula 1-122 as described in U.S. Pat. Nos. 7,964,578 and 7,833,992, each of which are herein incorporated by reference in their entireties. The circP, circSP, circRNA or circRNA-SP described herein may be conjugated with a metal such as, but not limited to, gold. (See e.g., Giljohann et al. Journ. Amer. Chem. Soc. 2009 131(6): 2072-2073; herein incorporated by reference in its entirety). In another embodiment, the circP, circSP, circRNA or circRNA-SP described herein may be conjugated and/or encapsulated in gold-nanoparticles. (International Pub. No. WO201216269 and U.S. Pub. No. 20120302940 and US20130177523; the contents of each of which is herein incorporated by reference in its entirety).

As described in U.S. Pub. No. 20100004313, herein incorporated by reference in its entirety, a gene delivery composition may include a nucleotide sequence and a poloxamer. For example, the circP, circSP, circRNA or circRNA-SP of the present invention may be used in a gene delivery composition with the poloxamer described in U.S. Pub. No. 20100004313.

In one embodiment, the polymer formulation of the present invention may be stabilized by contacting the polymer formulation, which may include a cationic carrier, with a cationic lipopolymer which may be covalently linked to cholesterol and polyethylene glycol groups. The polymer formulation may be contacted with a cationic lipopolymer using the methods described in U.S. Pub. No. 20090042829 herein incorporated by reference in its entirety. The cationic carrier may include, but is not limited to, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethyl-amino)ethyl methacrylate, poly(lysine), poly(histidine), poly(arginine), cationized gelatin, dendrimers, chitosan, 1,2-Dioleoyl-3-Trimethylammonium-Propane(DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N',N'-Dimethylaminoethane)-carbamoyl]Cholesterol Hydrochloride (DC-Cholesterol HCl) diheptadecylamidoglycyl spermidine (DOGS), N,N-distearyl-N,N-dimethyl-ammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride DODAC) and combinations thereof. As a non-limiting example, the circP, circSP, circRNA or circRNA-SP may be formulated with a cationic lipopolymer such as those described in U.S. Patent Application No. 20130065942, herein incorporated by reference in its entirety.

The circP, circSP, circRNA or circRNA-SP of the invention may be formulated in a polyplex of one or more polymers (See e.g., U.S. Pat. No. 8,501,478, U.S. Pub. No. 20120237565 and 20120270927 and 20130149783 and International Patent Pub. No. WO2013090861; the contents of each of which is herein incorporated by reference in its entirety). As a non-limiting example, the polyplex may be formed using the novel alpha-aminoamidine polymers described in International Publication No. WO2013090861, the contents of which are herein incorporated by reference in its entirety. As another non-limiting example, the polyplex may be formed using the click polymers described in U.S. Pat. No. 8,501,478, the contents of which is herein incorporated by reference in its entirety.

In one embodiment, the polyplex comprises two or more cationic polymers. The cationic polymer may comprise a poly(ethylene imine) (PEI) such as linear PEI. In another embodiment, the polyplex comprises p(TETA/CBA) its PEGylated analog p(TETA/CBA)-g-PEG2k and mixtures thereof (see e.g., US Patent Publication No. US20130149783, the contents of which are herein incorporated by reference in its entirety.

The circP, circSP, circRNA or circRNA-SP of the invention can also be formulated as a nanoparticle using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so to delivery of the circP, circSP, circRNA or circRNA-SP may be enhanced (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in its entirety). As a non-limiting example, the nanoparticle may comprise a plurality of polymers such as, but not limited to hydrophilic-hydrophobic polymers (e.g., PEG-PLGA), hydrophobic polymers (e.g., PEG) and/or hydrophilic polymers (International Pub. No. WO20120225129; the contents of which are herein incorporated by reference in its entirety).

As another non-limiting example the nanoparticle comprising hydrophilic polymers for the circP, circSP, circRNA-SP and/or circRNA may be those described in or made by the methods described in International Patent Publication No. WO2013119936, the contents of which are herein incorporated by reference in its entirety.

In one embodiment, the biodegradable polymers which may be used in the present invention are poly(ether-anhydride) block copolymers. As a non-limiting example, the biodegradable polymers used herein may be a block copolymer as described in International Patent Publication No WO2006063249, herein incorporated by reference in its entirety, or made by the methods described in International Patent Publication No WO2006063249, herein incorporated by reference in its entirety.

In another embodiment, the biodegradable polymers which may be used in the present invention are alkyl and cycloalkyl terminated biodegradable lipids. As a non-limiting example, the alkyl and cycloalkyl terminated biodegradable lipids may be those described in International Publication No. WO2013086322 and/or made by the methods described in International Publication No. WO2013086322; the contents of which are herein incorporated by reference in its entirety.

In yet another embodiment, the biodegradable polymers which may be used in the present invention are cationic lipids having one or more biodegradable group located in a lipid moiety. As a non-limiting example, the biodegradable lipids may be those described in US Patent Publication No. US20130195920, the contents of which are herein incorporated by reference in its entirety.

Biodegradable calcium phosphate nanoparticles in combination with lipids and/or polymers have been shown to deliver circP, circSP, circRNA or circRNA-SP in vivo. In one embodiment, a lipid coated calcium phosphate nanoparticle, which may also contain a targeting ligand such as anisamide, may be used to deliver the circP, circSP, circRNA or circRNA-SP of the present invention. For example, to effectively deliver siRNA in a mouse metastatic lung model a lipid coated calcium phosphate nanoparticle was used (Li et al., J Contr Rel. 2010 142: 416-421; Li et al., J Contr Rel. 2012 158:108-114; Yang et al., Mol Ther. 2012 20:609-615; herein incorporated by reference in its entirety). This delivery system combines both a targeted nanoparticle and a component to enhance the endosomal escape, calcium phosphate, in order to improve delivery of the siRNA.

In one embodiment, calcium phosphate with a PEG-polyanion block copolymer may be used to deliver circP, circSP, circRNA or circRNA-SP (Kazikawa et al., J Contr Rel. 2004 97:345-356; Kazikawa et al., J Contr Rel. 2006 111:368-370; the contents of which are herein incorporated by reference in its entirety).

In one embodiment, a PEG-charge-conversional polymer (Pitella et al., Biomaterials. 2011 32:3106-3114; the contents of which are herein incorporated by reference in its entirety) may be used to form a nanoparticle to deliver the circP, circSP, circRNA or circRNA-SP of the present invention. The PEG-charge-conversional polymer may improve upon the PEG-polyanion block copolymers by being cleaved into a polycation at acidic pH, thus enhancing endosomal escape.

In one embodiment, a polymer used in the present invention may be a pentablock polymer such as, but not limited to, the pentablock polymers described in International Patent Publication No. WO2013055331, herein incorporated by reference in its entirety. As a non-limiting example, the pentablock polymer comprises PGA-PCL-PEG-PCL-PGA, wherein PEG is polyethylene glycol, PCL is poly(E-caprolactone), PGA is poly(glycolic acid), and PLA is poly(lactic acid). As another non-limiting example, the pentablock polymer comprises PEG-PCL-PLA-PCL-PEG, wherein PEG is polyethylene glycol, PCL is poly(E-caprolactone), PGA is poly(glycolic acid), and PLA is poly(lactic acid).

In one embodiment, a polymer which may be used in the present invention comprises at least one diepoxide and at least one aminoglycoside (See e.g., International Patent Publication No. WO2013055971, the contents of which are herein incorporated by reference in its entirety). The diepoxide may be selected from, but is not limited to, 1,4 butanediol diglycidyl ether (1,4 B), 1,4-cyclohexanedimethanol diglycidyl ether (1,4 C), 4-vinylcyclohexene diepoxide (4VCD), ethyleneglycol diglycidyl ether (EDGE), glycerol diglycidyl ether (GDE), neopentylglycol diglycidyl ether (NPDGE), poly(ethyleneglycol) diglycidyl ether (PEGDE), poly(propyleneglycol) diglycidyl ether (PPGDE) and resorcinol diglycidyl ether (RDE). The aminoglycoside may be selected from, but is not limited to, streptomycin, neomycin, framycetin, paromomycin, ribostamycin, kanamycin, amikacin, arbekacin, bekanamycin, dibekacin, tobramycin, spectinomycin, hygromycin, gentamicin, netilmicin, sisomicin, isepamicin, verdamicin, astromicin, and apramycin. As a non-limiting example, the polymers may be made by the methods described in International Patent Publication No. WO2013055971, the contents of which are herein incorporated by reference in its entirety. As another non-limiting example, compositions comprising any of the polymers comprising at least one least one diepoxide and at least one aminoglycoside may be made by the methods described in International Patent Publication No. WO2013055971, the contents of which are herein incorporated by reference in its entirety.

In one embodiment, a polymer which may be used in the present invention may be a cross-linked polymer. As a non-limiting example, the cross-linked polymers may be used to form a particle as described in U.S. Pat. No. 8,414,927, the contents of which are herein incorporated by reference in its entirety. As another non-limiting example, the cross-linked polymer may be obtained by the methods described in US Patent Publication No. US20130172600, the contents of which are herein incorporated by reference in its entirety.

In another embodiment, a polymer which may be used in the present invention may be a cross-linked polymer such as those described in U.S. Pat. No. 8,461,132, the contents of which are herein incorporated by reference in its entirety. As a non-limiting example, the cross-linked polymer may be used in a therapeutic composition for the treatment of a body tissue. The therapeutic composition may be administered to damaged tissue using various methods known in the art and/or described herein such as injection or catheterization.

In one embodiment, a polymer which may be used in the present invention may be a di-alphatic substituted pegylated lipid such as, but not limited to, those described in International Patent Publication No. WO2013049328, the contents of which are herein incorporated by reference in its entirety.

In one embodiment, a block copolymer is PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety) may be used in the present invention. The present invention may be formulated with PEG-PLGA-PEG for administration such as, but not limited to, intramuscular and subcutaneous administration.

In another embodiment, the PEG-PLGA-PEG block copolymer is used in the present invention to develop a biodegradable sustained release system. In one aspect, the circP, circSP, circRNA and/or circRNA-SP of the present invention are mixed with the block copolymer prior to administration. In another aspect, the circP, circSP, circRNA and/or circRNA-SP of the present invention are co-administered with the block copolymer.

In one embodiment, the polymer used in the present invention may be a multi-functional polymer derivative such as, but not limited to, a multi-functional N-maleimidyl polymer derivatives as described in U.S. Pat. No. 8,454,946, the contents of which are herein incorporated by reference in its entirety.

The use of core-shell nanoparticles has additionally focused on a high-throughput approach to synthesize cationic cross-linked nanogel cores and various shells (Siegwart et al., Proc Natl Acad Sci USA. 2011 108:12996-13001; the contents of which are herein incorporated by reference in its entirety). The complexation, delivery, and internalization of the polymeric nanoparticles can be precisely controlled by altering the chemical composition in both the core and shell components of the nanoparticle. For example, the core-shell nanoparticles may efficiently deliver siRNA to mouse hepatocytes after they covalently attach cholesterol to the nanoparticle.

In one embodiment, a hollow lipid core comprising a middle PLGA layer and an outer neutral lipid layer containing PEG may be used to delivery of the circP, circSP, circRNA or circRNA-SP of the present invention. As a non-limiting example, in mice bearing a luciferase-expressing tumor, it was determined that the lipid-polymer-lipid hybrid nanoparticle significantly suppressed luciferase expression, as compared to a conventional lipoplex (Shi et al, Angew Chem Int Ed. 2011 50:7027-7031; herein incorporated by reference in its entirety).

In one embodiment, the lipid nanoparticles may comprise a core of the circP, circSP, circRNA or circRNA-SP disclosed herein and a polymer shell. The polymer shell may be any of the polymers described herein and are known in the art. In an additional embodiment, the polymer shell may be used to protect the circP, circSP, circRNA or circRNA-SP in the core.

Core-shell nanoparticles for use with the circP, circSP, circRNA or circRNA-SP of the present invention are described and may be formed by the methods described in U.S. Pat. No. 8,313,777 or International Patent Publication No. WO2013124867, the contents of which are herein incorporated by reference in their entirety.

In one embodiment, the core-shell nanoparticles may comprise a core of the circP, circSP, circRNA or circRNA-SP disclosed herein and a polymer shell. The polymer shell may be any of the polymers described herein and are known in the art. In an additional embodiment, the polymer shell may be used to protect the circP, circSP, circRNA or circRNA-SP in the core.

In one embodiment, the polymer used with the formulations described herein may be a modified polymer (such as, but not limited to, a modified polyacetal) as described in International Publication No. WO2011120053, the contents of which are herein incorporated by reference in its entirety.

In one embodiment, the formulation may be a polymeric carrier cargo complex comprising a polymeric carrier and at least one nucleic acid molecule. Non-limiting examples of polymeric carrier cargo complexes are described in International Patent Publications Nos. WO2013113326, WO2013113501, WO2013113325, WO2013113502 and WO2013113736 and European Patent Publication No. EP2623121, the contents of each of which are herein incorporated by reference in their entireties. In one aspect the polymeric carrier cargo complexes may comprise a negatively charged nucleic acid molecule such as, but not limited to, those described in International Patent Publication Nos. WO2013113325 and WO2013113502, the contents of each of which are herein incorporated by reference in its entirety.

In one embodiment, a pharmaceutical composition may comprise circP, circSP, circRNA and/or circRNA-SP of the invention and a polymeric carrier cargo complex. The circP, circRNA and/or circRNA-SP may encode a protein of interest such as, but not limited to, an antigen from a pathogen associated with infectious disease, an antigen associated with allergy or allergic disease, an antigen associated with autoimmune disease or an antigen associated with cancer or tumor disease (See e.g., the antigens described in International Patent Publications Nos. WO2013113326, WO2013113501, WO2013113325, WO2013113502 and WO2013113736 and European Patent Publication No. EP2623121, the contents of each of which are herein incorporated by reference in their entireties).

As a non-limiting example, the core-shell nanoparticle may be used to treat an eye disease or disorder (See e.g. US Publication No. 20120321719, the contents of which are herein incorporated by reference in its entirety).

In one embodiment, the polymer used with the formulations described herein may be a modified polymer (such as, but not limited to, a modified polyacetal) as described in International Publication No. WO2011120053, herein incorporated by reference in its entirety.

Peptides and Proteins

The circP, circSP, circRNA or circRNA-SP of the invention can be formulated with peptides and/or proteins in order to increase transfection of cells by the circP, circSP, circRNA or circRNA-SP. Peptides and/or proteins which may be used in the present invention are described in paragraphs [000540]-[000543] of co-pending International Publication No. WO2015034925, the contents of which is herein incorporated by reference in its entirety.

Cells

The circP, circSP, circRNA or circRNA-SP of the invention can be transfected ex vivo into cells, which are subsequently transplanted into a subject. As non-limiting examples, the pharmaceutical compositions may include red blood cells to deliver circP, circSP, circRNA or circRNA-SP to liver and myeloid cells, virosomes to deliver circP, circSP, circRNA or circRNA-SP in virus-like particles (VLPs), and electroporated cells such as, but not limited to, those described in paragraphs [000544]-[000546] of co-pending International Publication No. WO2015034925, the contents of which is herein incorporated by reference in its entirety.

Introduction into Cells

A variety of methods are known in the art and suitable for introduction of nucleic acid into a cell, including viral and non-viral mediated techniques. Examples of introduction methods which may be used in the present invention are described in paragraphs [000547]-[000549] of co-pending International Publication No. WO2015034925, the contents of which is herein incorporated by reference in its entirety.

Micro-Organ

The circP, circSP, circRNA or circRNA-SP may be contained in a micro-organ which can then express an encoded polypeptide of interest in a long-lasting therapeutic formulation. Micro-organs which may be used in the present invention are described in paragraphs [000550]-[000554] of co-pending International Publication No. WO2015034925, the contents of which is herein incorporated by reference in its entirety.

Hyaluronidase

The intramuscular or subcutaneous localized injection of circP, circSP, circRNA or circRNA-SP of the invention can include hyaluronidase, which catalyzes the hydrolysis of hyaluronan. By catalyzing the hydrolysis of hyaluronan, a constituent of the interstitial barrier, hyaluronidase lowers the viscosity of hyaluronan, thereby increasing tissue permeability (Frost, Expert Opin. Drug Deliv. (2007) 4:427-440; herein incorporated by reference in its entirety). It is useful to speed their dispersion and systemic distribution of encoded proteins produced by transfected cells. Alternatively, the hyaluronidase can be used to increase the number of cells exposed to a circP, circSP, circRNA or circRNA-SP of the invention administered intramuscularly or subcutaneously.

Nanoparticle Mimics

The circP, circSP, circRNA or circRNA-SP of the invention may be encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example the circP, circSP, circRNA or circRNA-SP of the invention may be encapsulated in a non-viron particle which can mimic the delivery function of a virus (see International Pub. No. WO2012006376 and US Patent Publication No. US20130171241 and US20130195968, the contents of which are herein incorporated by reference in its entirety).

Nanotubes

The circP, circSP, circRNA or circRNA-SP of the invention can be attached or otherwise bound to at least one nanotube such as, but not limited to, rosette nanotubes, rosette nanotubes having twin bases with a linker, carbon nanotubes and/or single-walled carbon nanotubes. Nanotubes which may be used in the present invention are described in paragraphs [000556]-[000560] of co-pending International Publication No. WO2015034925, the contents of which is herein incorporated by reference in its entirety.

Conjugates

The circP, circSP, circRNA or circRNA-SP of the invention include conjugates, such as a circP, circSP, circRNA or circRNA-SP covalently linked to a carrier or targeting group, or including two encoding regions that together produce a fusion protein (e.g., bearing a targeting group and therapeutic protein or peptide).

The conjugates of the invention include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Representative U.S. patents that teach the preparation of polynucleotide conjugates, particularly to RNA, include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference in their entireties.

In one embodiment, the conjugate of the present invention may function as a carrier for the circP, circSP, circRNA or circRNA-SP of the present invention. The conjugate may comprise a cationic polymer such as, but not limited to, polyamine, polylysine, polyalkylenimine, and polyethylenimine which may be grafted to with poly(ethylene glycol). As a non-limiting example, the conjugate may be similar to the polymeric conjugate and the method of synthesizing the polymeric conjugate described in U.S. Pat. No. 6,586,524 herein incorporated by reference in its entirety.

A non-limiting example of a method for conjugation to a substrate is described in US Patent Publication No. US20130211249, the contents of which are herein incorporated by reference in its entirety. The method may be used to make a conjugated polymeric particle comprising a circP, circSP, circRNA and/or circRNA-SP.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, aptamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

As a non-limiting example, the targeting group may be a glutathione receptor (GR)-binding conjugate for targeted delivery across the blood-central nervous system barrier (See e.g., US Patent Publication No. US2013021661012, the contents of which are herein incorporated by reference in its entirety.

In one embodiment, the conjugate of the present invention may be a synergistic biomolecule-polymer conjugate. The synergistic biomolecule-polymer conjugate may be long-acting continuous-release system to provide a greater therapeutic efficacy. The synergistic biomolecule-polymer conjugate may be those described in US Patent Publication No. US20130195799, the contents of which are herein incorporated by reference in its entirety.

In another embodiment, the conjugate which may be used in the present invention may be an aptamer conjugate. Non-limiting examples of apatamer conjugates are described in International Patent Publication No. WO2012040524, the contents of which are herein incorporated by reference in its entirety. The aptamer conjugates may be used to provide targeted delivery of formulations comprising circP, circSP, circRNA-SP and circRNA.

In one embodiment, the conjugate which may be used in the present invention may be an amine containing polymer conjugate. Non-limiting examples of amine containing polymer conjugate are described in U.S. Pat. No. 8,507,653, the contents of which are herein incorporated by reference in its entirety. The factor IX moiety polymer conjugate may comprise releasable linkages to release the circP, circSP, circRNA-SP and circRNA upon and/or after delivery to a subject.

In some embodiments, the formulation may include polypeptide conjugates linked through a modified amino acid. In a non-limiting example, the conjugates may comprise the compound of claim 1 and dependent claims of International Patent Publication No. WO2014074218, the contents of which is incorporated herein by reference in its entirety.

In one embodiment, pharmaceutical compositions of the present invention may include chemical modifications such as, but not limited to, modifications similar to locked nucleic acids.

Representative U.S. patents that teach the preparation of locked nucleic acid (LNA) such as those from Santaris, include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include circP, circSP, circRNA or circRNA-SP with phosphorothioate backbones and oligonucleosides with other modified backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P(O)$_2$—O—$CH_2$—] of the above-referenced U.S. Pat. No. 5,489,677, and the amide backbones of the above-referenced U.S. Pat. No. 5,602,240. In some embodiments, the circP, circSP, circRNA or circRNA-SP featured herein have morpholino backbone structures of the above-referenced U.S. Pat. No. 5,034,506.

Modifications at the 2' position may also aid in delivery. Preferably, modifications at the 2' position are not located in a polypeptide-coding sequence, i.e., not in a translatable region. Modifications at the 2' position may be located in a 5'UTR, a 3'UTR and/or a tailing region. Modifications at the 2' position can include one of the following at the 2' position: H (i.e., 2'-deoxy); F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$).$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$]$_2$, where n and m are from 1 to about 10. In other embodiments, the circP, circSP, circRNA or circRNA-SP include one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties, or a group for improving the pharmacodynamic properties, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH$_2$)$_2$ON (CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_3$)$_2$, also described in examples herein below. Other modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions, particularly the 3' position of the sugar on the 3' terminal nucleotide or in 2'-5' linked dsRNAs and the 5' position of 5' terminal nucleotide. Polynucleotides of the invention may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920; the contents of each of which is herein incorporated by reference in their entirety.

In still other embodiments, the circP, circSP, circRNA or circRNA-SP is covalently conjugated to a cell penetrating polypeptide. The cell-penetrating peptide may also include a signal sequence. The conjugates of the invention can be designed to have increased stability; increased cell transfection; and/or altered the biodistribution (e.g., targeted to specific tissues or cell types).

In one embodiment, the circP, circSP, circRNA or circRNA-SP may be conjugated to an agent to enhance delivery. As a non-limiting example, the agent may be a monomer or polymer such as a targeting monomer or a polymer having targeting blocks as described in International Publication No. WO2011062965, herein incorporated by reference in its entirety. In another non-limiting example, the agent may be a transport agent covalently coupled to the circP, circSP, circRNA or circRNA-SP of the present invention (See e.g., U.S. Pat. Nos. 6,835,393 and 7,374,778, each of which is herein incorporated by reference in its entirety). In yet another non-limiting example, the agent may be a membrane barrier transport enhancing agent such as those described in U.S. Pat. Nos. 7,737,108 and 8,003,129, each of which is herein incorporated by reference in its entirety.

In another embodiment, the circP, circSP, circRNA or circRNA-SP may be conjugated to SMARTT POLYMER TECHNOLOGY® (PHASERX®, Inc. Seattle, Wash.).

In another aspect, the conjugate may be a peptide that selectively directs the nanoparticle to neurons in a tissue or organism. As a non-limiting example, the peptide used may be, but is not limited to, the peptides described in US Patent Publication No US20130129627, herein incorporated by reference in its entirety.

In yet another aspect, the conjugate may be a peptide that can assist in crossing the blood-brain barrier.

In one embodiment, the formulations may include small molecule conjugates according to the formula of claim 1 and dependent claims of US Patent Publication No. 20140135381, the contents of which is herein incorporated by reference in its entirety.

In one embodiment, the formulation may contain one or more polymeric compounds according to the formula of claim 1 and dependent claims of US Patent Publication No. 20140135380, the contents of which is herein incorporated by reference in its entirety, covalently attached to the polynucleotides of the invention.

Self-Assembled Nanoparticles

Self-assembled nanoparticles including nucleic acid self-assembled nanoparticles, and polymer-based self-assembled nanoparticles, which may be used in the present invention are described in paragraphs [000586]-[000594] co-pending International Publication No. WO2015034925, the contents of which is herein incorporated by reference in its entirety.

Self-Assembled Macromolecules

The circP, circSP, circRNA and/or circRNA-SP may be formulated in amphiphilic macromolecules (AMs) for delivery. AMs comprise biocompatible amphiphilic polymers which have an alkylated sugar backbone covalently linked to poly(ethylene glycol). In aqueous solution, the AMs self-assemble to form micelles. Non-limiting examples of methods of forming AMs and AMs are described in US Patent Publication No. US20130217753, the contents of which are herein incorporated by reference in its entirety.

Inorganic Nanoparticles

The circP, circSP, circRNA or circRNA-SP of the present invention may be formulated in inorganic nanoparticles (U.S. Pat. No. 8,257,745, herein incorporated by reference in its entirety). The inorganic nanoparticles may include, but are not limited to, clay substances that are water swellable. As a non-limiting example, the inorganic nanoparticle may include synthetic smectite clays which are made from simple silicates (See e.g., U.S. Pat. Nos. 5,585,108 and 8,257,745 each of which are herein incorporated by reference in their entirety).

In one embodiment, the inorganic nanoparticles may comprise a core of the modified nucleic acids disclosed herein and a polymer shell. The polymer shell may be any of the polymers described herein and are known in the art. In an additional embodiment, the polymer shell may be used to protect the modified nucleic acids in the core.

Semi-Conductive and Metallic Nanoparticles

The circP, circSP, circRNA or circRNA-SP of the present invention may be formulated in water-dispersible nanoparticle comprising a semiconductive or metallic material (U.S. Pub. No. 20120228565; herein incorporated by reference in its entirety) or formed in a magnetic nanoparticle (U.S. Pub. No. 20120265001 and 20120283503; each of which is herein incorporated by reference in its entirety). The water-dispersible nanoparticles may be hydrophobic nanoparticles or hydrophilic nanoparticles.

In one embodiment, the semi-conductive and/or metallic nanoparticles may comprise a core of the circP, circSP, circRNA or circRNA-SP disclosed herein and a polymer shell. The polymer shell may be any of the polymers described herein and are known in the art. In an additional embodiment, the polymer shell may be used to protect the circP, circSP, circRNA or circRNA-SP in the core.

Surgical Sealants: Gels and Hydrogels

In one embodiment, the circP, circSP, circRNA or circRNA-SP disclosed herein may be encapsulated into any hydrogel known in the art which may form a gel when injected into a subject. Hydrogels are a network of polymer chains that are hydrophilic, and are sometimes found as a colloidal gel in which water is the dispersion medium. Hydrogels are highly absorbent (they can contain over 99% water) natural or synthetic polymers. Hydrogels also possess a degree of flexibility very similar to natural tissue, due to their significant water content. The hydrogel described herein may be used to encapsulate lipid nanoparticles which are biocompatible, biodegradable and/or porous. A hydrogel can be made in situ from solution injection or implanted. Gels and hydrogels which may be used in the present invention are described in paragraphs [000600]-[000639] of co-pending International Publication No. WO2015034925, the contents of which is herein incorporated by reference in its entirety Suspension Formulations In some embodiments, suspension formulations are provided comprising circP, circSP, circRNA-SP and/or circRNA, water immiscible oil depots, surfactants and/or co-surfactants and/or co-solvents. Combinations of oils and surfactants may enable suspension formulation with circP, circSP, circRNA and/or circRNA-SP. Delivery of circP, circSP, circRNA-SP and/or circRNA in a water immiscible depot may be used to improve bioavailability through sustained release of mRNA from the depot to the surrounding physiologic environment and prevent circP, circSP, circRNA and/or circRNA-SP degradation by nucleases. Suspension formulations which may be used in the present invention are described in paragraphs [000640]-[000646] of co-pending International Publication No. WO2015034925, the contents of which is herein incorporated by reference in its entirety.

Cations and Anions

Formulations of the circP, circSP, circRNA or circRNA-SP disclosed herein may include cations or anions. In one embodiment, the formulations include metal cations such as, but not limited to, $Zn^{2+}$, $Ca^{2+}$, $Cu^{2+}$, $Mg+$ and combinations thereof. As a non-limiting example, formulations may include polymers and a circP, circSP, circRNA or circRNA-SP complexed with a metal cation (See e.g., U.S. Pat. Nos. 6,265,389 and 6,555,525, each of which is herein incorporated by reference in its entirety).

In some embodiments, cationic nanoparticles comprising combinations of divalent and monovalent cations may be formulated with circP, circSP, circRNA-SP and/or circRNA. Such nanoparticles may form spontaneously in solution over a given period (e.g. hours, days, etc.). Such nanoparticles do not form in the presence of divalent cations alone or in the presence of monovalent cations alone. The delivery of circP, circSP, circRNA-SP and/or circRNA in cationic nanoparticles or in one or more depot comprising cationic nanoparticles may improve circP, circSP, circRNA-SP and/or circRNA bioavailability by acting as a long-acting depot and/or reducing the rate of degradation by nucleases.

Molded Nanoparticles and Microparticles

The circP, circSP, circRNA or circRNA-SP disclosed herein may be formulated in nanoparticles and/or microparticles. These nanoparticles and/or microparticles may be molded into any size shape and chemistry. As an example, the nanoparticles and/or microparticles may be made using the PRINT® technology by LIQUIDA TECHNOLOGIES® (Morrisville, N.C.) (See e.g., International Pub. No. WO2007024323; the contents of which are herein incorporated by reference in its entirety).

In one embodiment, the molded nanoparticles may comprise a core of the circP, circSP, circRNA or circRNA-SP disclosed herein and a polymer shell. The polymer shell may be any of the polymers described herein and are known in the art. In an additional embodiment, the polymer shell may be used to protect the circP, circSP, circRNA or circRNA-SP in the core.

In one embodiment, the circP, circSP, circRNA or circRNA-SP of the present invention may be formulated in microparticles. The microparticles may contain a core of the circP, circSP, circRNA or circRNA-SP and a cortex of a biocompatible and/or biodegradable polymer. As a non-limiting example, the microparticles which may be used with the present invention may be those described in U.S. Pat. No. 8,460,709, U.S. Patent Publication No. US20130129830 and International Patent Publication No WO2013075068, each of which is herein incorporated by reference in its entirety. As another non-limiting example, the microparticles may be designed to extend the release of the circP, circSP, circRNA or circRNA-SP of the present invention over a desired period of time (see e.g., extended release of a therapeutic protein in U.S. Patent Publication No. US20130129830, herein incorporated by reference in its entirety).

The microparticle for use with the present invention may have a diameter of at least 1 micron to at least 100 microns (e.g., at least 1 micron, at least 5 micron, at least 10 micron, at least 15 micron, at least 20 micron, at least 25 micron, at least 30 micron, at least 35 micron, at least 40 micron, at least 45 micron, at least 50 micron, at least 55 micron, at least 60 micron, at least 65 micron, at least 70 micron, at least 75 micron, at least 80 micron, at least 85 micron, at least 90 micron, at least 95 micron, at least 97 micron, at least 99 micron, and at least 100 micron).

NanoJackets and NanoLiposomes

The circP, circSP, circRNA or circRNA-SP disclosed herein may be formulated in NanoJackets and NanoLiposomes by Keystone Nano (State College, Pa.). NanoJackets are made of compounds that are naturally found in the body including calcium, phosphate and may also include a small amount of silicates. Nanojackets may range in size from 5 to 50 nm and may be used to deliver hydrophilic and hydrophobic compounds such as, but not limited to, circP, circSP, circRNA or circRNA-SP.

NanoLiposomes are made of lipids such as, but not limited to, lipids which naturally occur in the body. Nano-Liposomes may range in size from 60-80 nm and may be used to deliver hydrophilic and hydrophobic compounds such as, but not limited to, circP, circSP, circRNA or circRNA-SP. In one aspect, the circP, circSP, circRNA or circRNA-SP disclosed herein are formulated in a NanoLiposome such as, but not limited to, Ceramide NanoLiposomes.

Pseudovirions

In one embodiment, the circP, circSP, circRNA or circRNA-SP disclosed herein may be formulated in Pseudovirions (e.g., pseudo-virions). Pseudovirions which may be used in the present invention are described in paragraphs [000655]-[000660] of co-pending International Publication No. WO2015034925, the contents of which is herein incorporated by reference in its entirety.

Minicells

In one aspect, the circP, circSP, circRNA or circRNA-SP may be formulated in bacterial minicells. As a non-limiting example, bacterial minicells may be those described in International Publication No. WO2013088250 or US Patent Publication No. US20130177499, the contents of each of which are herein incorporated by reference in its entirety. The bacterial minicells comprising therapeutic agents such as circP, circSP, circRNA and/or circRNA-SP described herein may be used to deliver the therapeutic agents to brain tumors.

Semi-Solid Compositions

In one embodiment, the circP, circSP, circRNA or circRNA-SP may be formulated with a hydrophobic matrix to form a semi-solid composition. As a non-limiting example, the semi-solid composition or paste-like composition may be made by the methods described in International Patent Publication No WO201307604, herein incorporated by reference in its entirety. The semi-solid composition may be a sustained release formulation as described in International Patent Publication No WO201307604, herein incorporated by reference in its entirety.

In another embodiment, the semi-solid composition may further have a micro-porous membrane or a biodegradable polymer formed around the composition (see e.g., International Patent Publication No WO201307604, herein incorporated by reference in its entirety).

The semi-solid composition using the circP, circSP, circRNA or circRNA-SP of the present invention may have the characteristics of the semi-solid mixture as described in International Patent Publication No WO201307604, herein incorporated by reference in its entirety (e.g., a modulus of elasticity of at least $10^{-4}$ N·mm$^{-2}$, and/or a viscosity of at least 100 mPa·s).

Exosomes

In one embodiment, the circP, circSP, circRNA or circRNA-SP may be formulated in exosomes. The exosomes may be loaded with at least one circP, circSP, circRNA and/or circRNA-SP and delivered to cells, tissues and/or organisms. As a non-limiting example, the circP, circSP, circRNA or circRNA-SP may be loaded in the exosomes described in International Publication No. WO2013084000, herein incorporated by reference in its entirety.

Silk-Based Delivery

In one embodiment, the circP, circSP, circRNA or circRNA-SP may be formulated in a sustained release silk-based delivery system. The silk-based delivery system may be formed by contacting a silk fibroin solution with a therapeutic agent such as, but not limited to, the circP, circSP, circRNA or circRNA-SP described herein and/or known in the art. As a non-limiting example, the sustained release silk-based delivery system which may be used in the present invention and methods of making such system are described in US Patent Publication No. US20130177611, the contents of which are herein incorporated by reference in its entirety.

Microparticles

In one embodiment, formulations comprising circP, circSP, circRNA or circRNA-SP may comprise microparticles. The microparticles may comprise a polymer described herein and/or known in the art such as, but not limited to, poly(α-hydroxy acid), a polyhydroxy butyric acid, a polycaprolactone, a polyorthoester and a polyanhydride. The microparticle may have adsorbent surfaces to adsorb biologically active molecules such as circP, circSP, circRNA or circRNA-SP. As a non-limiting example microparticles for use with the present invention and methods of making microparticles are described in US Patent Publication No. US2013195923 and US20130195898 and U.S. Pat. Nos. 8,309,139 and 8,206,749, the contents of each of which are herein incorporated by reference in its entirety.

In another embodiment, the formulation may be a microemulsion comprising microparticles and circP, circSP, circRNA or circRNA-SP. As a non-limiting example, microemulsions comprising microparticles are described in US Patent Publication No. US2013195923 and US20130195898 and U.S. Pat. Nos. 8,309,139 and 8,206,749, the contents of each of which are herein incorporated by reference in its entirety.

Amino Acid Lipids

In one embodiment, the circP, circSP, circRNA or circRNA-SP may be formulated in amino acid lipids Amino acid lipids are lipophilic compounds comprising an amino acid residue and one or more lipophilic tails. Non-limiting examples of amino acid lipids and methods of making amino acid lipids are described in U.S. Pat. No. 8,501,824, the contents of which are herein incorporated by reference in its entirety.

In one embodiment, the amino acid lipids have a hydrophilic portion and a lipophilic portion. The hydrophilic portion may be an amino acid residue and a lipophilic portion may comprise at least one lipophilic tail.

In one embodiment, the amino acid lipid formulations may be used to deliver the circP, circSP, circRNA and/or circRNA-SP to a subject.

In another embodiment, the amino acid lipid formulations may deliver a circP, circSP, circRNA or circRNA-SP in releasable form which comprises an amino acid lipid that binds and releases the circP, circSP, circRNA or circRNA-SP. As a non-limiting example, the release of the circP, circSP, circRNA or circRNA-SP may be provided by an acid-labile linker such as, but not limited to, those described in U.S. Pat. Nos. 7,098,032, 6,897,196, 6,426,086, 7,138,382, 5,563,250, and 5,505,931, the contents of each of which are herein incorporated by reference in its entirety.

Microvesicles

In one embodiment, circP, circSP, circRNA or circRNA-SP may be formulated in microvesicles. Non-limiting examples of microvesicles include those described in US Patent Publication No. US20130209544, the contents of which are herein incorporated by reference in its entirety.

In one embodiment, the microvesicle is an ARRDC1-mediated microvesicles (ARMMs). Non-limiting examples of ARMMs and methods of making ARMMs are described in International Patent Publication No. WO2013119602, the contents of which are herein incorporated by reference in its entirety.

Interpolyelectrolyte Complexes

In one embodiment, the circP, circSP, circRNA or circRNA-SP may be formulated in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, the contents of which is herein incorporated by reference in its entirety.

Crystalline Polymeric Systems

In one embodiment, the circP, circSP, circRNA or circRNA-SP may be formulated in crystalline polymeric systems. Crystalline polymeric systems are polymers with crystalline moieties and/or terminal units comprising crystalline moieties. Non-limiting examples of polymers with crystalline moieties and/or terminal units comprising crystalline moieties termed "CYC polymers," crystalline polymer systems and methods of making such polymers and systems are described in U.S. Pat. No. 8,524,259, the contents of which are herein incorporated by reference in its entirety.

Excipients

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants, flavoring agents, stabilizers, antioxidants, osmolality adjusting agents, pH adjusting agents and the like, as suited to the particular dosage form desired. Various excipients for formulating pharmaceutical compositions and techniques for preparing the composition are known in the art (see *Remington: The Science and Practice of Pharmacy*, 21$^{st}$ Edition, A. R. Gennaro (Lippincott, Williams & Wilkins, Baltimore, Md., 2006; incorporated herein by reference in its entirety). The use of a conventional excipient medium may be contemplated within the scope of the present disclosure, except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions. The composition may also include excipients such as cocoa butter and suppository waxes, coloring agents, coating agents, sweetening, flavoring, and/or perfuming agents.

Exemplary diluents, granulating and/or dispersing agents, surface active agents and/or emulsifiers, binding agents, preservatives, buffers, lubricating agents, oils, additives, cocoa butter and suppository waxes, coloring agents, coating agents, sweetening, flavoring, and/or perfuming agents are described in co-pending International Patent Publication No. WO2015038892, the contents of which is incorporated by reference in its entirety, such as, but not limited to, in paragraphs [000828]-[000838].

Cryoprotectants for mRNA

In some embodiments, circP, circSP, circRNA or circRNA-SP formulations may comprise cyroprotectants. As used herein, there term "cryoprotectant" refers to one or more agent that when combined with a given substance, helps to reduce or eliminate damage to that substance that occurs upon freezing. In some embodiments, cryoprotectants are combined with circP, circSP, circRNA or circRNA-SP in order to stabilize them during freezing. Frozen storage of mRNA between −20° C. and −80° C. may be advantageous for long term (e.g. 36 months) stability of circP, circSP, circRNA or circRNA-SP. In some embodiments, cryoprotectants are included in circP, circSP, circRNA or circRNA-SP formulations to stabilize circP, circSP, circRNA or circRNA-SP through freeze/thaw cycles and under frozen storage conditions. Cryoprotectants of the present invention may include, but are not limited to sucrose, trehalose, lactose, glycerol, dextrose, raffinose and/or mannitol. Trehalose is listed by the Food and Drug Administration as being generally regarded as safe (GRAS) and is commonly used in commercial pharmaceutical formulations.

Bulking Agents

In some embodiments, circP, circSP, circRNA or circRNA-SP formulations may comprise bulking agents. As used herein, the term "bulking agent" refers to one or more agents included in formulations to impart a desired consistency to the formulation and/or stabilization of formulation components. In some embodiments, bulking agents are included in lyophilized circP, circSP, circRNA or circRNA-SP formulations to yield a "pharmaceutically elegant" cake, stabilizing the lyophilized circP, circSP, circRNA or circRNA-SP during long term (e.g. 36 month) storage. Bulking agents of the present invention may include, but are not limited to sucrose, trehalose, mannitol, glycine, lactose and/or raffinose. In some embodiments, combinations of cryoprotectants and bulking agents (for example, sucrose/glycine or trehalose/mannitol) may be included to both stabilize circP, circSP, circRNA or circRNA-SP during freezing and provide a bulking agent for lyophilization.

Non-limiting examples of formulations and methods for formulating the circP, circSP, circRNA or circRNA-SP of the present invention are also provided in International Publication No WO2013090648 filed Dec. 14, 2012, the contents of which are incorporated herein by reference in their entirety.

Inactive Ingredients

In some embodiments, circP, circSP, circRNA or circRNA-SP formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA). A non-exhaustive list of inactive ingredients and the routes of administration the inactive ingredients may be formulated in are described in Table 4 of co-pending International Application No. WO2014152211.

Delivery

The present disclosure encompasses the delivery of the circP, circSP, circRNA or circRNA-SP for any of therapeutic, pharmaceutical, diagnostic or imaging by any appropriate route taking into consideration likely advances in the sciences of drug delivery. Delivery may be naked or formulated.

Naked Delivery

The circP, circSP, circRNA or circRNA-SP of the present invention may be delivered to a cell naked. As used herein in, "naked" refers to delivering circP, circSP, circRNA or circRNA-SP free from agents which promote transfection. For example, the circP, circSP, circRNA or circRNA-SP delivered to the cell may contain no modifications. The naked circP, circSP, circRNA or circRNA-SP may be delivered to the cell using routes of administration known in the art and described herein.

Formulated Delivery

The circP, circSP, circRNA or circRNA-SP of the present invention may be formulated, using the methods described herein. The formulations may contain circP, circSP, circRNA or circRNA-SP which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated circP, circSP, circRNA or circRNA-SP may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like.

Administration

The circP, circSP, circRNA or circRNA-SP of the present invention may be administered by any route which results in a therapeutically effective outcome. These include, but are not limited to enteral (into the intestine), gastroenteral, epidural (into the dura mater), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity), intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions may be administered in a way which allows them cross the blood-brain barrier, vascular barrier, or other epithelial barrier.

In one embodiment, a formulation for a route of administration may include at least one inactive ingredient. Non-limiting examples of routes of administration and inactive ingredients which may be included in formulations for the specific route of administration is shown in Table 9 of co-pending International Publication No. WO2015038892, the contents of which is herein incorporated by reference in its entirety.

Non-limiting routes of administration for the circP, circSP, circRNA or circRNA-SP of the present invention are described below.

Parenteral and Injectable Administration

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

A pharmaceutical composition for parenteral administration may comprise at least one inactive ingredient. Any or none of the inactive ingredients used may have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulations may also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Rectal and Vaginal Administration

Rectal and vaginal administration and corresponding dosage forms are described in co-pending International Patent Publication No. WO2015038892, the contents of which is incorporated by reference in its entirety, such as, but not limited to, in paragraphs [000856]-[000859].

Oral Administration

Oral administration and corresponding dosage forms (e.g., liquid dosage forms) are described in co-pending International Patent Publication No. WO2015038892, the contents of which is incorporated by reference in its entirety, such as, but not limited to, in paragraphs [000860]-[000869].

Topical or Transdermal Administration

As described herein, compositions containing the circP, circSP, circRNA or circRNA-SP of the invention may be formulated for administration topically and/or transdermally. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compositions will depend on the route of nucleic acid delivery. Three routes are commonly considered to deliver circRNA to the skin: (i) topical application (e.g. for local/regional treatment and/or cosmetic applications); (ii) intradermal injection (e.g. for local/regional treatment and/or cosmetic applications); and (iii) systemic delivery (e.g. for treatment of dermatologic diseases that affect both cutaneous and extracutaneous regions). The circP, circSP, circRNA or circRNA-SP can be delivered to the skin by several different approaches known in the art. Most topical delivery approaches have been shown to work for delivery of DNA, such as but not limited to, topical application of non-cationic liposome-DNA complex, cationic liposome-DNA complex, particle-mediated (gene gun), puncture-mediated gene transfections, and viral delivery approaches. After delivery of the nucleic acid, gene products have been detected in a number of different skin cell types, including, but not limited to, basal keratinocytes, sebaceous gland cells, dermal fibroblasts and dermal macrophages.

Ointments, creams and gels for topical administration, can, for example, can be formulated with an aqueous or oily base with the addition of suitable thickening and/or gelling agent and/or solvents. Non limiting examples of such bases can thus, for example, include water and/or an oil such as liquid paraffin or a vegetable oil such as arachis oil or castor oil, or a solvent such as polyethylene glycol. Various thickening agents and gelling agents can be used depending on the nature of the base. Non-limiting examples of such agents include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

Lotions for topical administration may be formulated with an aqueous or oily base and will in general also contain one or more emulsifying agents, stabilizing agents, dispersing agents, suspending agents or thickening agents.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or the circP, circSP, circRNA or circRNA-SP described herein to allow a user to perform multiple treatments of a subject(s).

In one embodiment, the invention provides for the circP, circSP, circRNA or circRNA-SP compositions to be delivered in more than one injection.

In one embodiment, before topical and/or transdermal administration at least one area of tissue, such as skin, may be subjected to a device and/or solution which may increase permeability. In one embodiment, the tissue may be subjected to an abrasion device to increase the permeability of the skin (see U.S. Patent Publication No. 20080275468, herein incorporated by reference in its entirety). In another embodiment, the tissue may be subjected to an ultrasound enhancement device. An ultrasound enhancement device may include, but is not limited to, the devices described in U.S. Publication No. 20040236268 and U.S. Pat. Nos. 6,491,657 and 6,234,990; each of which are herein incorporated by reference in their entireties. Methods of enhancing the permeability of tissue are described in U.S. Publication Nos. 20040171980 and 20040236268 and U.S. Pat. No. 6,190,315; each of which are herein incorporated by reference in their entireties.

In one embodiment, a device may be used to increase permeability of tissue before delivering formulations of the circP, circSP, circRNA or circRNA-SP described herein. The permeability of skin may be measured by methods known in the art and/or described in U.S. Pat. No. 6,190,315, herein incorporated by reference in its entirety. As a non-limiting example, a modified mRNA formulation may be delivered by the drug delivery methods described in U.S. Pat. No. 6,190,315, herein incorporated by reference in its entirety.

In another non-limiting example tissue may be treated with a eutectic mixture of local anesthetics (EMLA) cream before, during and/or after the tissue may be subjected to a device which may increase permeability. Katz et al. (Anesth Analg (2004); 98:371-76; herein incorporated by reference in its entirety) showed that using the EMLA cream in combination with a low energy, an onset of superficial cutaneous analgesia was seen as fast as 5 minutes after a pretreatment with a low energy ultrasound.

In one embodiment, enhancers may be applied to the tissue before, during, and/or after the tissue has been treated to increase permeability. Enhancers include, but are not limited to, transport enhancers, physical enhancers, and cavitation enhancers. Non-limiting examples of enhancers are described in U.S. Pat. No. 6,190,315, herein incorporated by reference in its entirety.

In one embodiment, a device may be used to increase permeability of tissue before delivering formulations of the circP, circSP, circRNA or circRNA-SP described herein, which may further contain a substance that invokes an immune response. In another non-limiting example, a formulation containing a substance to invoke an immune response may be delivered by the methods described in U.S. Publication Nos. 20040171980 and 20040236268; each of which are herein incorporated by reference in their entireties.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required.

Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 0.1% to about 10% (w/w) active ingredient, although the concentration of active ingredient may be as high as the solubility limit of the active ingredient in the solvent. Formulations for topical administration may further comprise one or more of the additional ingredients described herein.

Topical, transdermal and transcutaneous administration and corresponding dosage forms are described in co-pending International Patent Publication No. WO2015038892, the contents of which is incorporated by reference in its entirety, such as, but not limited to, in paragraphs [000870]-[000888].

Depot Administration

As described herein, in some embodiments, the composition is formulated in depots for extended release. Generally, a specific organ or tissue (a "target tissue") is targeted for administration.

In some aspects of the invention, the circP, circSP, circRNA or circRNA-SP are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a ribonucleic acid and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a circRNA such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains circP, circSP, circRNA or circRNA-SP characterized in that a unit quantity of composition has been determined to produce the polypeptide of interest in a substantial percentage of cells contained within a predetermined volume of the target tissue.

In some embodiments, the composition includes a plurality of different circRNAs, where one or more than one of the circP, circSP, circRNA or circRNA-SP encodes a polypeptide of interest. Optionally, the composition also contains a cell penetration agent to assist in the intracellular delivery of the composition. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

In one embodiment, the invention provides for the circP, circSP, circRNA or circRNA-SP to be delivered in more than one injection or by split dose injections.

In one embodiment, the invention may be retained near target tissue using a small disposable drug reservoir, patch pump or osmotic pump. Non-limiting examples of patch pumps include those manufactured and/or sold by BD® (Franklin Lakes, N.J.), Insulet Corporation (Bedford, Mass.), SteadyMed Therapeutics (San Francisco, Calif.), Medtronic (Minneapolis, Minn.) (e.g., MiniMed), UniLife (York, Pa.), Valeritas (Bridgewater, N.J.), and SpringLeaf Therapeutics (Boston, Mass.). A non-limiting example of an osmotic pump include those manufactured by DURECT® (Cupertino, Calif.) (e.g., DUROS® and ALZET®).

Pulmonary Administration

A pharmaceutical composition may be prepared, packaged, and/or sold in a formulation suitable for pulmonary administration via the buccal cavity. Pulmonary administration and corresponding dosage forms are described in co-pending International Patent Publication No. WO2015038892, the contents of which is incorporated by reference in its entirety, such as, but not limited to, in paragraphs [000896]-[000901].

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose. Intranasal, nasal and buccal administration and corresponding dosage forms are described in co-pending International Patent Publication No. WO2015038892, the contents of which is incorporated by reference in its entirety, such as, but not limited to, in paragraphs [000902]-[000905].

Ophthalmic and Auricular (Otic) Administration

A pharmaceutical composition may be prepared, packaged, and/or sold in a formulation suitable for delivery to and/or around the eye and/or delivery to the ear (e.g., auricular (otic) administration). Non-limiting examples of route of administration for delivery to and/or around the eye include retrobulbar, conjunctival, intracorneal, intraocular, intravitreal, ophthalmic and subconjuctiva. Ophthalmic and auricular administration and corresponding dosage forms are described in co-pending International Patent Publication No. WO2015038892, the contents of which is incorporated by reference in its entirety, such as, but not limited to, in paragraphs [000906]-[000912].

Payload Administration: Detectable Agents and Therapeutic Agents

The circP, circSP, circRNA or circRNA-SP described herein can be used in a number of different scenarios in which delivery of a substance (the "payload") to a biological target is desired, for example delivery of detectable substances for detection of the target, or delivery of a therapeutic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

The circP, circSP, circRNA or circRNA-SP can be designed to include both a linker and a payload in any useful orientation. For example, a linker having two ends is used to attach one end to the payload and the other end to the nucleobase, such as at the C-7 or C-8 positions of the deaza-adenosine or deaza-guanosine or to the N-3 or C-5 positions of cytosine or uracil. The polynucleotide of the invention can include more than one payload (e.g., a label and a transcription inhibitor), as well as a cleavable linker. In one embodiment, the modified nucleotide is a modified 7-deaza-adenosine triphosphate, where one end of a cleavable linker is attached to the C7 position of 7-deaza-adenine, the other end of the linker is attached to an inhibitor (e.g., to the C5 position of the nucleobase on a cytidine), and a label (e.g., Cy5) is attached to the center of the linker (see, e.g., compound 1 of A*pCp C5 Parg Capless in FIG. 5 and columns 9 and 10 of U.S. Pat. No. 7,994,304, incorporated herein by reference). Upon incorporation of the modified 7-deaza-adenosine triphosphate to an encoding region, the resulting polynucleotide having a cleavable linker attached to a label and an inhibitor (e.g., a polymerase inhibitor). Upon cleavage of the linker (e.g., with reductive conditions to reduce a linker having a cleavable disulfide moiety), the label and inhibitor are released. Additional linkers and payloads (e.g., therapeutic agents, detectable labels, and cell penetrating payloads) are described herein and in International Publication No. WO2013151666, the contents of which are incorporated herein by reference in their entirety.

For example, the circP, circSP, circRNA or circRNA-SP described herein can be used in reprogramming induced pluripotent stem cells (iPS cells), which can directly track cells that are transfected compared to total cells in the cluster. In another example, a drug that may be attached to the circP, circSP, circRNA or circRNA-SP via a linker and may be fluorescently labeled can be used to track the drug in vivo, e.g. intracellularly. Other examples include, but are not limited to, the use of a circP, circSP, circRNA or circRNA-SP in reversible drug delivery into cells.

The circP, circSP, circRNA or circRNA-SP described herein can be used in intracellular targeting of a payload, e.g., detectable or therapeutic agent, to specific organelle. Exemplary intracellular targets can include, but are not limited to, the nuclear localization for advanced mRNA processing, or a nuclear localization sequence (NLS) linked to the circP, circSP, circRNA or circRNA-SP containing an inhibitor.

In addition, the circP, circSP, circRNA or circRNA-SP described herein can be used to deliver therapeutic agents to cells or tissues, e.g., in living animals. For example, the circP, circSP, circRNA or circRNA-SP described herein can be used to deliver highly polar chemotherapeutics agents to kill cancer cells. The circP, circSP, circRNA or circRNA-SP attached to the therapeutic agent through a linker can facilitate member permeation allowing the therapeutic agent to travel into a cell to reach an intracellular target.

In one example, the linker is attached at the 2'-position of the ribose ring and/or at the 3' and/or 5' position of the circP, circSP, circRNA or circRNA-SP (See e.g., International Pub. No. WO2012030683, herein incorporated by reference in its entirety). The linker may be any linker disclosed herein, known in the art and/or disclosed in International Pub. No. WO2012030683, herein incorporated by reference in its entirety.

In another example, the circP, circSP, circRNA or circRNA-SP can be attached to a viral inhibitory peptide (VIP) through a cleavable linker. The cleavable linker can release the VIP and dye into the cell. In another example, the circP, circSP, circRNA or circRNA-SP can be attached through the linker to an ADP-ribosylate, which is responsible for the actions of some bacterial toxins, such as cholera toxin, diphtheria toxin, and pertussis toxin. These toxin proteins are ADP-ribosyltransferases that modify target proteins in human cells. For example, cholera toxin ADP-ribosylates G proteins modifies human cells by causing massive fluid secretion from the lining of the small intestine, which results in life-threatening diarrhea.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, $^{3}$H or $^{99m}$Tc (e.g., as pertechnetate (technetate (VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2' disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine(1:1) (IR144); 5-chloro-2-[2-[3-[(5-chloro-3-ethyl-2(3H)-benzothiazolylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBACRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5

(Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

Combinations

The circP, circSP, circRNA or circRNA-SP may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, the circP, circSP, circRNA or circRNA-SP may be used in combination with a pharmaceutical agent for the treatment of cancer or to control hyperproliferative cells. In U.S. Pat. No. 7,964,571, herein incorporated by reference in its entirety, a combination therapy for the treatment of solid primary or metastasized tumor is described using a pharmaceutical composition including a DNA plasmid encoding for interleukin-12 with a lipopolymer and also administering at least one anticancer agent or chemotherapeutic. Further, the circP, circSP, circRNA or circRNA-SP of the present invention that encodes anti-proliferative molecules may be in a pharmaceutical composition with a lipopolymer (see e.g., U.S. Pub. No. 20110218231, herein incorporated by reference in its entirety, claiming a pharmaceutical composition comprising a DNA plasmid encoding an anti-proliferative molecule and a lipopolymer) which may be administered with at least one chemotherapeutic or anticancer agent. (See e.g., the "Combination" Section in U.S. Pat. No. 8,518,907 and International Patent Publication No. WO201218754; the contents of each of which are herein incorporated by reference in its entirety).

The circP, circSP, circRNA or circRNA-SP and pharmaceutical formulations thereof may be administered to a subject alone or used in combination with or include one or more other therapeutic agents, for example, anticancer agents. Thus, combinations of circP, circSP, circRNA or circRNA-SP with other anti-cancer or chemotherapeutic agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The circP, circSP, circRNA or circRNA-SP may also be useful in combination with any therapeutic agent used in the treatment of HCC, for example, but not limitation sorafenib. CircP, circSP, circRNA or circRNA-SP may be particularly useful when co-administered with radiation therapy.

In certain embodiments, the circP, circSP, circRNA or circRNA-SP may be useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of estrogen receptor modulators, androgen receptor modulators, retinoid receptor modulators, cytotoxic agents, a hypoxia activatable, proteasome inhibitors, microtubule inhibitors/microtubule-stabilising agents, topoisomerase inhibitors, inhibitors of mitotic kinesins, histone deacetylase inhibitors, inhibitors of kinases involved in mitotic progression, antiproliferative agents, monoclonal antibody targeted therapeutic agents, HMG-CoA reductase inhibitors, prenyl-protein transferase inhibitors, angiogenesis inhibitors, therapeutic agents that modulate or inhibit angiogenesis, agents that interfere with cell cycle checkpoints, agents that interfere with receptor tyrosine kinases (RTKs), inhibitors of cell proliferation and survival signaling pathway, apoptosis inducing agents, NSAIDs that are selective COX-2 inhibitors, inhibitors of COX-2, compounds that have been described as specific inhibitors of COX-2, angiogenesis inhibitors, tyrosine kinase inhibitors, compounds other than anti-cancer compounds, inhibitor of inherent multidrug resistance (MDR), anti-emetic agents to treat nausea or emesis, and neurokinin-1 receptor antagonists, are described in co-pending International Patent Publication No. WO2015038892, the contents of which is incorporated by reference in its entirety, such as, but not limited to, in pargraphs [000925]-[000957].

Another embodiment of the instant invention is the use of the circP, circSP, circRNA or circRNA-SP in combination with gene therapy for the treatment of cancer. For an overview of genetic strategies to treating cancer see Hall et al. (*Am J Hum Genet* 61:785-789 (1997)) and Kufe et al. (*Cancer Medicine*, 5th Ed, pp 876-889, BC Decker, Hamilton, 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), an uPA/uPAR antagonist ("Adenovirus-Mediated Delivery of an uPA/uPAR Antagonist Suppresses Angiogenesis-Dependent Tumor Growth and Dissemination in Mice," *Gene Therapy*, August 5(8):1105-13 (1998)), and interferon gamma (*J Immunol* 164:217-222 (2000)).

CircP, circSP, circRNA or circRNA-SP may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

CircP, circSP, circRNA or circRNA-SP may also be administered with an agent useful in the treatment of anemia. Such an anemia treatment agent is, for example, a continuous erythropoiesis receptor activator (such as epoetin alfa).

CircP, circSP, circRNA or circRNA-SP may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim and PEG-filgrastim.

CircP, circSP, circRNA or circRNA-SP may also be administered with an immunologic-enhancing drug, such as levamisole, isoprinosine and Zadaxin.

CircP, circSP, circRNA or circRNA-SP may also be useful for treating or preventing breast cancer in combination with aromatase inhibitors. Examples of aromatase inhibitors include but are not limited to: anastrozole, letrozole and exemestane.

CircP, circSP, circRNA or circRNA-SP may also be useful for treating or preventing cancer in combination with other nucleic acid therapeutics.

CircP, circSP, circRNA or circRNA-SP may also be administered in combination with γ-secretase inhibitors and/or inhibitors of NOTCH signaling. Such inhibitors include compounds described in co-pending International Patent Publication No. WO2015038892, the contents of which is incorporated by reference in its entirety, such as, but not limited to, in paragraph [000964].

CircP, circSP, circRNA or circRNA-SP may also be useful for treating or preventing cancer in combination with PARP inhibitors.

CircP, circSP, circRNA or circRNA-SP may also be useful for treating cancer in combination with the therapeutic agents described in co-pending International Patent Publication No. WO2015038892, the contents of which is incorporated by reference in its entirety, such as, but not limited to, in paragraph [000966].

The combinations referred to above can conveniently be presented for use in the form of a pharmaceutical formulation and thus pharmaceutical compositions comprising a combination as defined above together with a pharmaceutically acceptable diluent or carrier represent a further aspect of the invention.

The individual compounds of such combinations can be administered either sequentially or simultaneously in separate or combined pharmaceutical formulations. In one embodiment, the individual compounds will be administered simultaneously in a combined pharmaceutical formulation.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually. In one embodiment, the combinations, each or together may be administered according to the split dosing regimens described herein.

Dosing

The present invention provides methods comprising administering circP, circSP, circRNA or circRNA-SP and their encoded proteins or complexes in accordance with the invention to a subject in need thereof. Nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

According to the present invention, it has been discovered that administration of circP, circSP, circRNA or circRNA-SP in split-dose regimens produce higher levels of proteins in mammalian subjects. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the circP, circSP, circRNA or circRNA-SP of the present invention are administered to a subject in split doses. The circP, circSP, circRNA or circRNA-SP may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, and subcutaneous).

Liquid Dosage Forms

Liquid dosage forms for parenteral administration are described in co-pending International Patent Publication No. WO2015038892, the contents of which is incorporated by reference in its entirety, such as, but not limited to, in paragraph [0001037].

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of the circP, circSP, circRNA or circRNA-SP then depends upon its rate of dissolution which, in turn, may depend upon crystal size and crystalline form. Alternatively, delayed absorption of a parenterally administered circP, circSP, circRNA or circRNA-SP may be accomplished by dissolving or suspending the circP, circSP, circRNA or circRNA-SP in an oil vehicle. Injectable depot forms are made by forming microencapsule matrices of the circP, circSP, circRNA or circRNA-SP in biodegradable polymers such as polylactide-polyglycolide. Depending upon the ratio of the circP, circSP, circRNA or circRNA-SP to polymer and the nature of the particular polymer employed, the rate of circP, circSP, circRNA or circRNA-SP release can be controlled. Examples of other biodegradable polymers include, but are not limited to, poly(orthoesters) and poly(anhydrides). Depot injectable formulations may be prepared by entrapping the circP, circSP, circRNA or circRNA-SP in liposomes or microemulsions which are compatible with body tissues.

Pulmonary

Pulmonary and intranasal formulations for delivery and administration are described in co-pending International Patent Publication No. WO2013151666, the contents of which is incorporated by reference in its entirety, such as, but not limited to, in paragraphs [000766]-[000781].

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Multi-Dose and Repeat-Dose Administration

In some embodiments, compounds and/or compositions of the present invention may be administered in two or more doses (referred to herein as "multi-dose administration"). Such doses may comprise the same components or may comprise components not included in a previous dose. Such doses may comprise the same mass and/or volume of components or an altered mass and/or volume of components in comparison to a previous dose. In some embodiments, multi-dose administration may comprise repeat-dose administration. As used herein, the term "repeat-dose administration" refers to two or more doses administered consecutively or within a regimen of repeat doses comprising substantially the same components provided at substantially the same mass and/or volume. In some embodiments, subjects may display a repeat-dose response. As used herein, the term "repeat-dose response" refers to a response in a subject to a repeat-dose that differs from that of another dose administered within a repeat-dose administration regimen. In some embodiments, such a response may be the expression of a protein in response to a repeat-dose comprising mRNA. In such embodiments, protein expression may be elevated in comparison to another dose administered within a repeat-dose administration regimen or protein expression may be reduced in comparison to another dose administered within a repeat-dose administration regimen. Alteration of protein expression may be from about 1% to about 20%, from about 5% to about 50% from about 10% to about 60%, from about 25% to about 75%, from about 40% to about 100% and/or at least 100%. A reduction in expression of mRNA administered as part of a repeat-dose regimen, wherein the level of protein translated from the administered RNA is reduced by more than 40% in comparison to another dose within the repeat-dose regimen is referred to herein as "repeat-dose resistance."

Properties of the Pharmaceutical Compositions

The pharmaceutical compositions described herein can be characterized by one or more of the following properties:

Bioavailability

The circP, circSP, circRNA or circRNA-SP, when formulated into a composition with a delivery agent as described herein, can exhibit an increase in bioavailability as compared to a composition lacking a delivery agent as described herein. As used herein, the term "bioavailability" refers to the systemic availability of a given amount of circP, circSP, circRNA or circRNA-SP administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference in its entirety.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a first circP, circSP, circRNA or circRNA-SP, measured as AUC, $C_{max}$, or $C_{min}$ in a mammal is greater, when co-administered with a delivery agent as described herein, than when such co-administration does not take place. In some embodiments, the bioavailability of the circP, circSP, circRNA or circRNA-SP can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

In some embodiments, liquid formulations of circP, circSP, circRNA-SP or circRNA may have varying in vivo half-life, requiring modulation of doses to yield a therapeutic effect. To address this, in some embodiments of the present invention, circP, circSP, circRNA-SP or circRNA formulations may be designed to improve bioavailability and/or therapeutic effect during repeat administrations. Such formulations may enable sustained release of circP, circSP, circRNA-SP or circRNA and/or reduce circP, circSP, circRNA and/or circRNA-SP degradation rates by nucleases. In some embodiments, suspension formulations are provided comprising circP, circSP, circRNA-SP or circRNA, water immiscible oil depots, surfactants and/or co-surfactants and/or co-solvents. Combinations of oils and surfactants may enable suspension formulation with circP, circSP, circRNA-SP or circRNA. Delivery of circP, circSP, circRNA-SP or circRNA in a water immiscible depot may be used to improve bioavailability through sustained release of circP, circSP, circRNA and/or circRNA-SP from the depot to the surrounding physiologic environment and/or prevent circP, circSP, circRNA-SP or circRNA degradation by nucleases.

In some embodiments, cationic nanoparticles comprising combinations of divalent and monovalent cations may be formulated with circP, circSP, circRNA-SP or circRNA. Such nanoparticles may form spontaneously in solution over a given period (e.g. hours, days, etc.). Such nanoparticles do not form in the presence of divalent cations alone or in the presence of monovalent cations alone. The delivery of circP, circSP, circRNA-SP or circRNA in cationic nanoparticles or in one or more depot comprising cationic nanoparticles may improve circP, circSP, circRNA-SP or circRNA bioavailability by acting as a long-acting depot and/or reducing the rate of degradation by nucleases.

Therapeutic Window

The circP, circSP, circRNA or circRNA-SP, when formulated into a composition with a delivery agent as described herein, can exhibit an increase in the therapeutic window of the administered circP, circSP, circRNA or circRNA-SP composition as compared to the therapeutic window of the administered circP, circSP, circRNA or circRNA-SP composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the circP, circSP, circRNA or circRNA-SP when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

The circP, circSP, circRNA or circRNA-SP, when formulated into a composition with a delivery agent as described herein, can exhibit an improved volume of distribution ($V_{dist}$), e.g., reduced or targeted, relative to a composition lacking a delivery agent as described herein. The volume of distribution (Vdist) relates the amount of the drug in the body to the concentration of the drug in the blood or plasma. As used herein, the term "volume of distribution" refers to the fluid volume that would be required to contain the total amount of the drug in the body at the same concentration as in the blood or plasma: Vdist equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, Vdist can be used to determine a loading dose to achieve a steady state concentration. In some embodiments, the volume of distribution of the circP, circSP, circRNA or circRNA-SP when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Biological Effect

In one embodiment, the biological effect of the circP, circSP, circRNA or circRNA-SP delivered to the animals may be categorized by analyzing the protein expression in the animals. The protein expression may be determined from analyzing a biological sample collected from a mammal administered the circP, circSP, circRNA or circRNA-SP of the present invention. In one embodiment, the expression protein encoded by the circP, circSP, circRNA or circRNA-SP administered to the mammal of at least 50 pg/ml may be preferred. For example, a protein expression of 50-200 pg/ml for the protein encoded by the circP, circSP, circRNA or circRNA-SP delivered to the mammal may be seen as a therapeutically effective amount of protein in the mammal.

Detection of Circular Polynucleotides by Mass Spectrometry

Mass spectrometry (MS) is an analytical technique that can provide structural and molecular mass/concentration information on molecules after their conversion to ions. The molecules are first ionized to acquire positive or negative charges and then they travel through the mass analyzer to arrive at different areas of the detector according to their mass/charge (m/z) ratio. Methods of detecting polynucleotides are described in co-pending International Patent Publication No. WO2015038892, the contents of which is incorporated by reference in its entirety, such as, but not limited to, in paragraphs [0001055]-[0001067].

V. Uses of Circular Polynucleotides of the Invention

The circP, circSP, circRNA or circRNA-SP of the present invention are designed, in preferred embodiments, to provide for avoidance or evasion of deleterious bio-responses such as the immune response and/or degradation pathways, overcoming the threshold of expression and/or improving protein production capacity, improved expression rates or translation efficiency, improved drug or protein half-life and/or protein concentrations, optimized protein localization, to improve one or more of the stability and/or clearance in tissues, receptor uptake and/or kinetics, cellular access by the compositions, engagement with translational machinery, secretion efficiency (when applicable), accessibility to circulation, and/or modulation of a cell's status, function and/or activity.

Therapeutics
Therapeutic Agents

The circP, circSP, circRNA or circRNA-SP of the present invention and the proteins translated from them described herein can be used as therapeutic or prophylactic agents. They are provided for use in medicine. For example, a circP, circSP, circRNA or circRNA-SP described herein can be administered to a subject, wherein the circP, circRNA or circRNA-SP is translated in vivo to produce a therapeutic or prophylactic polypeptide in the subject. Provided are compositions, methods, kits, and reagents for diagnosis, treatment or prevention of a disease or condition in humans and other mammals. The active therapeutic agents of the invention include circP, circSP, circRNA or circRNA-SP, cells containing the circP, circSP, circRNA or circRNA-SP, or polypeptides translated from the circP, circRNA or circRNA-SP.

In certain embodiments, provided herein are combination therapeutics containing one or more circRNAs containing translatable regions that encode for a protein or proteins that boost a mammalian subject's immunity along with a protein that induces antibody-dependent cellular toxicity. For example, provided herein are therapeutics containing one or more nucleic acids that encode trastuzumab and granulocyte-colony stimulating factor (G-CSF). In particular, such combination therapeutics are useful in Her2+ breast cancer patients who develop induced resistance to trastuzumab. (See, e.g., Albrecht, Immunotherapy. 2(6):795-8 (2010)).

Provided herein are methods of inducing translation of a recombinant polypeptide in a cell population using the circP, circSP, circRNA or circRNA-SP described herein. Such translation can be in vivo, ex vivo, in culture, or in vitro. The cell population is contacted with an effective amount of a composition containing a circP, circSP, circRNA or circRNA-SP that may have at least one nucleoside modification. The circP, circRNA or circRNA-SP may also include at least one translatable region encoding the recombinant polypeptide. The population is contacted under conditions such that the circP, circSP, circRNA or circRNA-SP is localized into one or more cells of the cell population. The recombinant polypeptide is translated in the cell from the circP, circRNA or circRNA-SP.

An "effective amount" of the composition is provided based, at least in part, on the target tissue, target cell type, means of administration, physical characteristics of the circP, circSP, circRNA or circRNA-SP (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell.

Aspects of the invention are directed to methods of inducing in vivo translation of a recombinant polypeptide in a mammalian subject in need thereof. Therein, an effective amount of a composition containing a nucleic acid that has at least one structural or chemical modification and a translatable region encoding the recombinant polypeptide is administered to the subject using the delivery methods described herein. The nucleic acid is provided in an amount and under other conditions such that the nucleic acid is localized into a cell of the subject and the recombinant polypeptide is translated in the cell from the nucleic acid. The cell in which the nucleic acid is localized, or the tissue in which the cell is present, may be targeted with one or more than one rounds of nucleic acid administration.

In certain embodiments, the administered circP, circRNA or circRNA-SP directs production of one or more recombinant polypeptides that provide a functional activity which is substantially absent in the cell, tissue or organism in which the recombinant polypeptide is translated. For example, the missing functional activity may be enzymatic, structural, or gene regulatory in nature. In related embodiments, the administered circP, circRNA or circRNA-SP directs production of one or more recombinant polypeptides that increases (e.g., synergistically) a functional activity which is present but substantially deficient in the cell in which the recombinant polypeptide is translated.

In other embodiments, the administered circP, circRNA or circRNA-SP directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In some embodiments, the recombinant polypeptide increases the level of an endogenous protein in the cell to a desirable level; such an increase may bring the level of the endogenous protein from a subnormal level to a normal level or from a normal level to a super-normal level.

Alternatively, the recombinant polypeptide functions to antagonize the activity of an endogenous protein present in, on the surface of, or secreted from the cell. Usually, the activity of the endogenous protein is deleterious to the subject; for example, due to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, a protein toxin such as shiga and tetanus toxins, or a small molecule toxin such as botulinum, cholera, and diphtheria toxins. Additionally, the antagonized biological molecule may be an endogenous protein that exhibits an undesirable activity, such as a cytotoxic or cytostatic activity.

The recombinant proteins described herein may be engineered for localization within the cell, potentially within a specific compartment such as the nucleus, or are engineered for secretion from the cell or translocation to the plasma membrane of the cell.

In some embodiments, circP, circSP, circRNA or circRNA-SP may be used for treatment of any of a variety of diseases, disorders, and/or conditions, including but not limited to one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Diseases characterized by dysfunctional or aberrant protein activity include cystic fibrosis, sickle cell anemia, epidermolysis bullosa, amyotrophic lateral sclerosis, and glucose-6-phosphate dehydrogenase deficiency. The present invention provides a method for treating such conditions or diseases in a subject by introducing nucleic acid or cell-based therapeutics containing the circP, circSP, circRNA or circRNA-SP provided herein, wherein the circP, circRNA or circRNA-SP encodes for a protein that antagonizes or otherwise overcomes the aberrant protein activity present in the cell of the subject. Specific examples of a dysfunctional protein are the missense mutation variants of the cystic fibrosis transmembrane conductance regulator (CFTR) gene, which produce a dysfunctional protein variant of CFTR protein, which causes cystic fibrosis.

Diseases characterized by missing (or substantially diminished such that proper (normal or physiological protein function does not occur) protein activity include cystic fibrosis, Niemann-Pick type C, β thalassemia major, Duchenne muscular dystrophy, Hurler Syndrome, Hunter Syndrome, and Hemophilia A. Such proteins may not be present, or are essentially non-functional. The present invention provides a method for treating such conditions or diseases in a subject by introducing nucleic acid or cell-based therapeutics containing the circP, circSP, circRNA or circRNA-SP provided herein, wherein the circP, circRNA or circRNA-SP encodes for a protein that replaces the protein activity missing from the target cells of the subject. Specific examples of a dysfunctional protein are the nonsense mutation variants of the cystic fibrosis transmembrane conductance regulator (CFTR) gene, which produce a nonfunctional protein variant of CFTR protein, which causes cystic fibrosis.

Thus, provided are methods of treating cystic fibrosis in a mammalian subject by contacting a cell of the subject with a circRNA having a translatable region that encodes a functional CFTR polypeptide, under conditions such that an effective amount of the CTFR polypeptide is present in the cell. Preferred target cells are epithelial, endothelial and mesothelial cells, such as the lung, and methods of administration are determined in view of the target tissue; i.e., for lung delivery, the RNA molecules are formulated for administration by inhalation.

In another embodiment, the present invention provides a method for treating hyperlipidemia in a subject, by introducing into a cell population of the subject with a circRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. Nature 2010; 466: 714-721).

In another embodiment, the present invention provides a method for treating hematopoietic disorders, cardiovascular disease, oncology, diabetes, cystic fibrosis, neurological diseases, inborn errors of metabolism, skin and systemic disorders, and blindness. The identity of molecular targets to treat these specific diseases has been described (Templeton ed., Gene and Cell Therapy: Therapeutic Mechanisms and Strategies, $3^{rd}$ Edition, Bota Raton, Fla.: CRC Press; herein incorporated by reference in its entirety).

Provided herein, are methods to prevent infection and/or sepsis in a subject at risk of developing infection and/or sepsis, the method comprising administering to a subject in need of such prevention a composition comprising a circRNA precursor encoding an anti-microbial polypeptide (e.g., an anti-bacterial polypeptide), or a partially or fully processed form thereof in an amount sufficient to prevent infection and/or sepsis. In certain embodiments, the subject at risk of developing infection and/or sepsis may be a cancer patient. In certain embodiments, the cancer patient may have undergone a conditioning regimen. In some embodiments, the conditioning regiment may include, but is not limited to, chemotherapy, radiation therapy, or both. As a non-limiting example, a circRNA can encode Protein C, its zymogen or prepro-protein, the activated form of Protein C (APC) or variants of Protein C which are known in the art. The circP, circSP, circRNA or circRNA-SP may be chemically modified and delivered to cells. Non-limiting examples of polypeptides which may be encoded by the circP, circRNA or circRNA-SP of the present invention include those taught in U.S. Pat. Nos. 7,226,999; 7,498,305; 6,630,138 each of which is incorporated herein by reference in its entirety. These patents teach Protein C like molecules, variants and derivatives, any of which may be encoded within the chemically modified molecules of the present invention.

Further provided herein, are methods to treat infection and/or sepsis in a subject, the method comprising administering to a subject in need of such treatment a composition comprising a circP, circRNA or circRNA-SP precursor encoding an anti-microbial polypeptide (e.g., an anti-bacterial polypeptide), e.g., an anti-microbial polypeptide described herein, or a partially or fully processed form thereof in an amount sufficient to treat an infection and/or sepsis. In certain embodiments, the subject in need of treatment is a cancer patient. In certain embodiments, the cancer patient has undergone a conditioning regimen. In some embodiments, the conditioning regiment may include, but is not limited to, chemotherapy, radiation therapy, or both.

In certain embodiments, the subject may exhibits acute or chronic microbial infections (e.g., bacterial infections). In certain embodiments, the subject may have received or may be receiving a therapy. In certain embodiments, the therapy may include, but is not limited to, radiotherapy, chemotherapy, steroids, ultraviolet radiation, or a combination thereof. In certain embodiments, the patient may suffer from a microvascular disorder. In some embodiments, the microvascular disorder may be diabetes. In certain embodiments, the patient may have a wound. In some embodiments, the wound may be an ulcer. In a specific embodiment, the wound may be a diabetic foot ulcer. In certain embodiments, the subject may have one or more burn wounds. In certain embodiments, the administration may be local or systemic. In certain embodiments, the administration may be subcutaneous. In certain embodiments, the administration may be intravenous. In certain embodiments, the administration may be oral. In certain embodiments, the administration may be topical. In certain embodiments, the administration may be by inhalation. In certain embodiments, the administration may be rectal. In certain embodiments, the administration may be vaginal.

Other aspects of the present disclosure relate to transplantation of cells containing circP, circSP, circRNA or circRNA-SP to a mammalian subject. Administration of cells to mammalian subjects is known to those of ordinary skill in the art, and include, but is not limited to, local implantation (e.g., topical or subcutaneous administration), organ delivery or systemic injection (e.g., intravenous injection or inhalation), and the formulation of cells in pharmaceutically acceptable carrier. Such compositions containing circP, circSP, circRNA or circRNA-SP can be formulated for administration intramuscularly, transarterially, intraperitoneally, intravenously, intranasally, subcutaneously, endoscopically, transdermally, or intrathecally. In some embodiments, the composition may be formulated for extended release.

The subject to whom the therapeutic agent may be administered suffers from or may be at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

Wound Management

The circP, circSP, circRNA or circRNA-SP of the present invention may be used for wound treatment, e.g. of wounds exhibiting delayed healing. Methods comprising the administration of circP, circSP, circRNA or circRNA-SP in order to manage the treatment of wounds are described in co-pending International Patent Publication No. WO2015038892, the contents of which is incorporated by reference in its entirety, such as, but not limited to, in paragraphs [0001089]-[0001092].

Production of Antibodies

In one embodiment of the invention, the circP, circRNA or circRNA-SP may encode antibodies and fragments of such antibodies such as those described in co-pending International Patent Publication No. WO2015038892, the contents of which is incorporated by reference in its entirety, such as, but not limited to, in paragraphs [0001093]-[0001095].

Managing Infection

In one embodiment, provided are methods for treating or preventing a microbial infection (e.g., a bacterial infection) and/or a disease, disorder, or condition associated with a microbial or viral infection, or a symptom thereof, in a subject, by administering a circP, circRNA or circRNA-SP encoding an anti-microbial polypeptide. Said administration may be in combination with an anti-microbial agent (e.g., an anti-bacterial agent), e.g., an anti-microbial polypeptide or a small molecule anti-microbial compound described herein. The anti-microbial agents include, but are not limited to, anti-bacterial agents, anti-viral agents, anti-fungal agents, anti-protozoal agents, anti-parasitic agents, and anti-prion agents as well as compositions, delivery and methods of use of the polynucleotides herein are described in co-pending International Patent Publication No. WO2015038892, the contents of which is incorporated by reference in its entirety, such as, but not limited to, in paragraphs [0001096]-[0001116].

Modulation of the Immune Response

Avoidance of the Immune Response

As described herein, a useful feature of the circP, circSP, circRNA or circRNA-SP of the invention is the capacity to reduce, evade or avoid the innate immune response of a cell. In one aspect, provided herein are circP, circSP, circRNA or circRNA-SP which when delivered to cells, results in a reduced immune response from the host as compared to the response triggered by a reference compound, e.g. a linear polynucleotide corresponding to a circRNA of the invention, or a different circRNA of the invention. As used herein, a "reference compound" is any molecule or substance which when administered to a mammal, results in an innate immune response having a known degree, level or amount of immune stimulation. A reference compound need not be a nucleic acid molecule and it need not be any of the circP, circSP, circRNA or circRNA-SP of the invention. Hence, the measure of a circP, circSP, circRNA or circRNA-SP avoidance, evasion or failure to trigger an immune response can be expressed in terms relative to any compound or substance which is known to trigger such a response.

The term "innate immune response" includes a cellular response to exogenous single stranded nucleic acids, generally of viral or bacterial origin, which involves the induction of cytokine expression and release, particularly the interferons, and cell death. As used herein, the innate immune response or interferon response operates at the single cell level causing cytokine expression, cytokine release, global inhibition of protein synthesis, global destruction of cellular RNA, upregulation of major histocompatibility molecules, and/or induction of apoptotic death, induction of gene transcription of genes involved in apoptosis, anti-growth, and innate and adaptive immune cell activation. Some of the genes induced by type I IFNs include PKR, ADAR (adenosine deaminase acting on RNA), OAS (2',5'-oligoadenylate synthetase), RNase L, and Mx proteins. PKR and ADAR lead to inhibition of translation initiation and RNA editing, respectively. OAS is a dsRNA-dependent synthetase that activates the endoribonuclease RNase L to degrade ssRNA.

In some embodiments, the innate immune response comprises expression of a Type I or Type II interferon, and the expression of the Type I or Type II interferon is not increased more than two-fold compared to a reference from a cell which has not been contacted with a circP, circSP, circRNA or circRNA-SP of the invention.

In some embodiments, the innate immune response comprises expression of one or more IFN signature genes and where the expression of the one of more IFN signature genes is not increased more than three-fold compared to a reference from a cell which has not been contacted with the circP, circSP, circRNA or circRNA-SP of the invention.

While in some circumstances, it might be advantageous to eliminate the innate immune response in a cell, the invention provides circP, circSP, circRNA-SP, circRNA that upon administration result in a substantially reduced (significantly less) the immune response, including interferon signaling, without entirely eliminating such a response.

In some embodiments, the immune response is lower by 10%, 20%, 30%, 40%, 50%, 60%, 70%, 80%, 90%, 95%, 99%, 99.9%, or greater than 99.9% as compared to the immune response induced by a reference compound. The immune response itself may be measured by determining the expression or activity level of Type 1 interferons or the expression of interferon-regulated genes such as the toll-like receptors (e.g., TLR7 and TLR8). Reduction of innate immune response can also be measured by measuring the level of decreased cell death following one or more administrations to a cell population; e.g., cell death is 10%, 25%, 50%, 75%, 85%, 90%, 95%, or over 95% less than the cell death frequency observed with a reference compound. Moreover, cell death may affect fewer than 50%, 40%, 30%, 20%, 10%, 5%, 1%, 0.1%, 0.01% or fewer than 0.01% of cells contacted with the circP, circSP, circRNA-SP and the circRNA.

In another embodiment, the circP, circSP, circRNA or circRNA-SP of the present invention is significantly less immunogenic than a linear RNA molecule with the same sequence or a reference compound. As used herein, "significantly less immunogenic" refers to a detectable decrease in immunogenicity. In another embodiment, the term refers to a fold decrease in immunogenicity. In another embodiment, the term refers to a decrease such that an effective amount of the circP, circSP, circRNA or circRNA-SP can be administered without triggering a detectable immune response. In another embodiment, the term refers to a decrease such that the circP, circSP, circRNA or circRNA-SP can be repeatedly administered without eliciting an immune response sufficient to detectably reduce expression of the recombinant protein. In another embodiment, the decrease is such that the circP, circSP, circRNA or circRNA-SP can be repeatedly administered without eliciting an immune response sufficient to eliminate detectable expression of the recombinant protein.

In another embodiment, the circP, circSP, circRNA or circRNA-SP is 2-fold less immunogenic than its unmodified linear counterpart or reference compound. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a fold factor. In another embodiment, immunogenicity is reduced by a 50-fold factor. In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

Methods of determining immunogenicity are well known in the art, and include, e.g. measuring secretion of cytokines (e.g. IL-12, IFNalpha, TNF-alpha, RANTES, MIP-1alpha or beta, IL-6, IFN-beta, or IL-8), measuring expression of DC activation markers (e.g. CD83, HLA-DR, CD80 and CD86), or measuring ability to act as an adjuvant for an adaptive immune response.

The circP, circSP, circRNA or circRNA-SP of the invention, including the combination of modifications taught herein may have superior properties making them more suitable as therapeutic modalities.

It has been determined that the "all or none" model in the art is sorely insufficient to describe the biological phenomena associated with the therapeutic utility of circP, circSP, circRNA or circRNA-SP. The present inventors have determined that to improve protein production, one may consider the nature of the modification, or combination of modifications, the percent modification and survey more than one cytokine or metric to determine the efficacy and risk profile of a particular circP, circSP, circRNA or circRNA-SP.

In one aspect of the invention, methods of determining the effectiveness of a circRNA as compared to the unmodified linear counterpart involves the measure and analysis of one or more cytokines whose expression is triggered by the administration of the exogenous nucleic acid of the invention. These values are compared to administration of an unmodified nucleic acid or to a standard metric such as cytokine response, PolyIC, R-848 or other standard known in the art.

One example of a standard metric developed herein is the measure of the ratio of the level or amount of encoded polypeptide (protein) produced in the cell, tissue or organism to the level or amount of one or more (or a panel) of cytokines whose expression is triggered in the cell, tissue or organism as a result of administration or contact with the modified nucleic acid (e.g., modified circP, circSP, circRNA or circRNA-SP). Such ratios are referred to herein as the Protein:Cytokine Ratio or "PC" Ratio. The higher the PC ratio, the more efficacious the circP, circRNA or circRNA-SP (polynucleotide encoding the protein measured). Preferred PC Ratios, by cytokine, of the present invention may be greater than 1, greater than 10, greater than 100, greater than 1000, greater than 10,000 or more.

The PC ratio may be further qualified by the percent modification present in the polynucleotide. For example, normalized to a 100% modified nucleic acid, the protein production as a function of cytokine (or risk) or cytokine profile can be determined.

In one embodiment, the present invention provides a method for determining, across chemistries, cytokines or percent modification, the relative efficacy of any particular circRNA by comparing the PC Ratio of the circP, circSP, circRNA or circRNA-SP.

Modified circP, circSP, circRNA or circRNA-SP containing varying levels of nucleobase substitutions could be produced that maintain increased protein production and decreased immunostimulatory potential. The relative percentage of any modified nucleotide to its naturally occurring nucleotide counterpart can be varied during the IVT reaction (for instance, 100, 50, 25, 10, 5, 2.5, 1, 0.1, 0.01% 5 methyl cytidine usage versus cytidine; 100, 50, 25, 10, 5, 2.5, 1, 0.1, 0.01% pseudouridine or N1-methyl-pseudouridine usage versus uridine). Modified circP, circSP, circRNA or circRNA-SP can also be made that utilize different ratios using 2 or more different nucleotides to the same base (for instance, different ratios of pseudouridine and N1-methylpseudouridine). Modified circRNA can also be made with mixed ratios at more than 1 "base" position, such as ratios of 5 methyl cytidine/cytidine and pseudouridine/N1-methylpseudouridine/uridine at the same time. Use of modified circP, circSP, circRNA or circRNA-SP with altered ratios of modified nucleotides can be beneficial in reducing potential exposure to chemically modified nucleotides. Lastly, positional introduction of modified nucleotides into the circP, circSP, circRNA or circRNA-SP which modulate either protein production or immunostimulatory potential or both is also possible. The ability of such circP, circSP, circRNA or circRNA-SP to demonstrate these improved properties can be assessed in vitro (using assays such as the PBMC assay described herein), and can also be assessed in vivo through measurement of both circP, circRNA or circRNA-SP-encoded protein production and mediators of innate immune recognition such as cytokines.

In another embodiment, the relative immunogenicity of the circP, circSP, circRNA or circRNA-SP and its linear counterpart are determined by determining the quantity of the circP, circSP, circRNA or circRNA-SP required to elicit one of the above responses to the same degree as a given quantity of the unmodified nucleotide or reference compound. For example, if twice as much circP, circSP, circRNA or circRNA-SP is required to elicit the same response, than the circP, circSP, circRNA or circRNA-SP is two-fold less immunogenic than the unmodified nucleotide or the reference compound.

In another embodiment, the relative immunogenicity of the circP, circSP, circRNA or circRNA-SP and its linear counterpart are determined by determining the quantity of cytokine (e.g. IL-12, IFNalpha, TNF-alpha, RANTES, MIP-1alpha or beta, IL-6, IFN-beta, or IL-8) secreted in response to administration of the circP, circSP, circRNA or circRNA-SP, relative to the same quantity of the unmodified linear nucleotide or reference compound. For example, if one-half as much cytokine is secreted, than the circP, circSP, circRNA or circRNA-SP is two-fold less immunogenic than the unmodified linear nucleotide. In another embodiment, background levels of stimulation are subtracted before calculating the immunogenicity in the above methods.

Provided herein are also methods for performing the titration, reduction or elimination of the immune response in a cell or a population of cells. In some embodiments, the cell is contacted with varied doses of the same circP, circSP, circRNA or circRNA-SP and dose response is evaluated. In some embodiments, a cell is contacted with a number of different circP, circSP, circRNA or circRNA-SP at the same or different doses to determine the optimal composition for producing the desired effect. Regarding the immune response, the desired effect may be to avoid, evade or reduce the immune response of the cell. The desired effect may also be to alter the efficiency of protein production.

The circP, circSP, circRNA or circRNA-SP of the present invention may be used to reduce the immune response using the method described in International Publication No. WO2013003475, herein incorporated by reference in its entirety.

Activation of the Immune Response: Vaccines

According to the present invention, the circP, circSP, circRNA or circRNA-SP disclosed herein, may encode one or more vaccines. As used herein, a "vaccine" is a biological preparation that improves immunity to a particular disease or infectious agent. A vaccine introduces an antigen into the tissues or cells of a subject and elicits an immune response, thereby protecting the subject from a particular disease or pathogen infection. The circP, circRNA or circRNA-SP of the present invention may encode an antigen and when the circP, circRNA or circRNA-SP are expressed in cells, a desired immune response is achieved.

The use of RNA as a vaccine overcomes the disadvantages of conventional genetic vaccination involving incorporating DNA into cells in terms of safeness, feasibility, applicability, and effectiveness to generate immune responses. RNA molecules are considered to be significantly safer than DNA vaccines, as RNAs are more easily degraded. They are cleared quickly out of the organism and cannot integrate into the genome and influence the cell's gene expression in an uncontrollable manner. It is also less likely for RNA vaccines to cause severe side effects like the generation of autoimmune disease or anti-DNA antibodies (Bringmann A. et al., Journal of Biomedicine and Biotechnology (2010), vol. 2010, article ID623687). Transfection with RNA requires only insertion into the cell's cytoplasm, which is easier to achieve than into the nucleus. However, RNA is susceptible to RNase degradation and other natural decomposition in the cytoplasm of cells. Various attempts to increase the stability and shelf life of RNA vaccines. US 2005/0032730 to Von Der Mulbe et al. discloses improving the stability of mRNA vaccine compositions by increasing G(guanosine)/C(cytosine) content of the mRNA molecules. U.S. Pat. No. 5,580,859 to Felgner et al. teaches incorporating polynucleotide sequences coding for regulatory proteins that binds to and regulates the stabilities of mRNA. While not wishing to be bound by theory, it is believed that the circP, circRNA or circRNA-SP vaccines of the invention will result in improved stability and therapeutic efficacy due at least in part to the specificity, purity and selectivity of the construct designs.

Additionally, certain modified nucleosides, or combinations thereof, when introduced into the circP, circSP, circRNA or circRNA-SP of the invention will activate the innate immune response. Such activating molecules are useful as adjuvants when combined with polypeptides and/or other vaccines. In certain embodiments, the activating molecules contain a translatable region which encodes for a polypeptide sequence useful as a vaccine, thus providing the ability to be a self-adjuvant.

In one embodiment, the circP, circSP, circRNA or circRNA-SP of the present invention may be used in the prevention, treatment and diagnosis of diseases and physical disturbances caused by antigens or infectious agents. The circP, circRNA or circRNA- of the present invention may encode at least one polypeptide of interest (e.g. antibody or antigen) and may be provided to an individual in order to stimulate the immune system to protect against the disease-causing agents. As a non-limiting example, the biological activity and/or effect from an antigen or infectious agent may be inhibited and/or abolished by providing one or more circP, circSP, circRNA or circRNA-which have the ability to bind and neutralize the antigen and/or infectious agent.

In one embodiment, the circP, circRNA or circRNA-SP of the invention may encode an immunogen. The delivery of the circP, circRNA or circRNA-SP encoding an immunogen may activate the immune response. As a non-limiting example, the circP, circRNA or circRNA-SP encoding an immunogen may be delivered to cells to trigger multiple innate response pathways (see International Pub. No. WO2012006377 and US Patent Publication No. US20130177639; herein incorporated by reference in its entirety). As another non-limiting example, the circP, circRNA or circRNA-SP of the present invention encoding an immunogen may be delivered to a vertebrate in a dose amount large enough to be immunogenic to the vertebrate (see International Pub. No. WO2012006372 and WO2012006369 and US Publication No. US20130149375 and US20130177640; the contents of each of which are herein incorporated by reference in their entirety). A non-limiting list of infectious disease that the circP, circRNA or circRNA-SP vaccine may treat includes, viral infectious diseases such as AIDS (HIV), hepatitis A, B or C, herpes, herpes zoster (chicken pox), German measles (rubella virus), yellow fever, dengue fever etc. (flavi viruses), flu (influenza viruses), haemorrhagic infectious diseases (Marburg or Ebola viruses), bacterial infectious diseases such as Legionnaires' disease (*Legionella*), gastric ulcer (*Helicobacter*), cholera (*Vibrio*), *E. coli* infections, staphylococcal infections, *salmonella* infections or streptococcal infections, tetanus (*Clostridium tetani*), or protozoan infectious diseases (malaria, sleeping sickness, leishmaniasis, toxoplasmosis, i.e. infections caused by *plasmodium*, trypanosomes, *leishmania* and *toxoplasma*).

In one embodiment, the circP, circRNA or circRNA-SP of the invention may encode a tumor antigen to treat cancer. A non-limiting list of tumor antigens includes, 707-AP, AFP, ART-4, BAGE, .beta.-catenin/m, Bcr-abl, CAMEL, CAP-1, CASP-8, CDC27/m, CDK4/m, CEA, CT, Cyp-B, DAM, ELF2M, ETV6-AML1, G250, GAGE, GnT-V, Gp100, HAGE, HER-2/neu, HLA-A*0201-R170I, HPV-E7, HSP70-2M, HAST-2, hTERT (or hTRT), iCE, KIAA0205, LAGE, LDLR/FUT, MAGE, MART-1/melan-A, MC1R, myosin/m, MUC1, MUM-1, -2, -3, NA88-A, NY-ESO-1, p190 minor bcr-abl, Pml/RAR.alpha., PRAME, PSA, PSM, RAGE, RU1 or RU2, SAGE, SART-1 or SART-3, TEUAML1, TPI/m, TRP-1, TRP-2, TRP-2/INT2 and WT1.

The circP, circRNA or circRNA-SP of invention may encode a polypeptide sequence for a vaccine and may further comprise an inhibitor. The inhibitor may impair antigen presentation and/or inhibit various pathways known in the art. As a non-limiting example, the circP, circRNA or circRNA-SP of the invention may be used for a vaccine in combination with an inhibitor which can impair antigen presentation (see International Pub. No. WO2012089225 and WO2012089338; each of which is herein incorporated by reference in their entirety).

In one embodiment, the circP, circRNA or circRNA-SP of the invention may be self-replicating RNA. Self-replicating RNA molecules can enhance efficiency of RNA delivery and expression of the enclosed gene product. In one embodiment, the circP, circSP, circRNA or circRNA-SP may comprise at least one modification described herein and/or known in the art. In one embodiment, the self-replicating RNA can be designed so that the self-replicating RNA does not induce production of infectious viral particles. As a non-limiting example the self-replicating RNA may be designed by the methods described in US Pub. No. US20110300205 and International Pub. No. WO2011005799 and WO2013055905, the contents of each of which are herein incorporated by reference in their entirety.

In one embodiment, the self-replicating circP, circRNA or circRNA-SP of the invention may encode a protein which may raise the immune response. As a non-limiting example, the circP, circRNA or circRNA-SP may be self-replicating mRNA may encode at least one antigen (see US Pub. No. US20110300205, US20130171241, US20130177640 and US2013177639 and International Pub. Nos. WO2011005799, WO2012006372, WO2012006377, WO2013006838, WO2013006842, WO2012006369 and WO2013055905; the contents of each of which is herein incorporated by reference in their entirety). In one aspect, the self-replicating RNA may be administered to mammals at a large enough dose to raise the immune response in a large mammal (see e.g., International Publication No. WO2012006369, herein incorporated by reference in its entirety).

In one embodiment, the self-replicating circP, circRNA or circRNA-SP of the invention may be formulated using methods described herein or known in the art. As a non-limiting example, the self-replicating RNA may be formulated for delivery by the methods described in Geall et al (Nonviral delivery of self-amplifying RNA vaccines, PNAS 2012; PMID: 22908294; the contents of which is herein incorporated by reference in its entirety).

As another non-limiting example, the circP, circRNA or circRNA-SP of the present invention (e.g., nucleic acid molecules encoding an immunogen such as self-replicating RNA) may be substantially encapsulated within a PEGylated liposome (see International Patent Application No. WO2013033563; herein incorporated by reference in its entirety). In yet another non-limiting example, the self-replicating RNA may be formulated as described in International Application No. WO2013055905, herein incorporated by reference in its entirety. In one non-limiting example, the self-replicating RNA may be formulated using biodegradable polymer particles as described in International Publication No WO2012006359 or US Patent Publication No. US20130183355, the contents of each of which are herein incorporated by reference in its entirety.

In one embodiment, the self-replicating RNA may be formulated in virion-like particles. As a non-limiting example, the self-replicating RNA is formulated in virion-like particles as described in International Publication No WO2012006376, herein incorporated by reference in its entirety.

In another embodiment, the self-replicating RNA may be formulated in a liposome. As a non-limiting example, the self-replicating RNA may be formulated in liposomes as described in International Publication No. WO20120067378, herein incorporated by reference in its entirety. In one aspect, the liposomes may comprise lipids which have a pKa value which may be advantageous for delivery of circP, circRNA or circRNA-SP such as, but not limited to, mRNA. In another aspect, the liposomes may have an essentially neutral surface charge at physiological pH and may therefore be effective for immunization (see e.g., the liposomes described in International Publication No. WO20120067378, herein incorporated by reference in its entirety).

In yet another embodiment, the self-replicating RNA may be formulated in a cationic oil-in-water emulsion. As a non-limiting example, the self-replicating RNA may be formulated in the cationic oil-in-water emulsion described in International Publication No. WO2012006380, herein incorporated by reference in its entirety. The cationic oil-in-water emulsions which may be used with the self-replicating RNA described herein (e.g., circP, circRNA or circRNA-SP) may be made by the methods described in International Publication No. WO2012006380, herein incorporated by reference in its entirety.

In one embodiment, the circP, circRNA or circRNA-SP of the present invention may encode amphipathic and/or immunogenic amphipathic peptides.

In on embodiment, a formulation of the circP, circRNA or circRNA-SP of the present invention may further comprise an amphipathic and/or immunogenic amphipathic peptide. As a non-limiting example, the circP, circRNA or circRNA- SP comprising an amphipathic and/or immunogenic amphipathic peptide may be formulated as described in US. Pub. No. US20110250237 and International Pub. Nos. WO2010009277 and WO2010009065; each of which is herein incorporated by reference in their entirety.

In one embodiment, the circP, circRNA or circRNA-SP of the present invention may be immunostimulatory. As a non-limiting example, the circP, circRNA or circRNA-SP may encode all or a part of a positive-sense or a negative-sense stranded RNA virus genome (see International Pub No. WO2012092569 and US Pub No. US20120177701, each of which is herein incorporated by reference in their entirety). In another non-limiting example, the immunostimulatory circP, circRNA or circRNA-SP of the present invention may be formulated with an excipient for administration as described herein and/or known in the art (see International Pub No. WO2012068295 and US Pub No. US20120213812, each of which is herein incorporated by reference in their entirety). The circP, circRNA or circRNA-SP may further comprise a sequence region encoding a cytokine that promotes the immune response, such as a monokine, lymphokine, interleukin or chemokine, such as IL-1, IL-2, IL-3, IL-4, IL-5, IL-6, IL-7, IL-8, IL-9, IL-10, IL-12, INF-α, INF-γ, GM-CFS, LT-α, or growth factors such as hGH.

In one embodiment, the response of the vaccine formulated by the methods described herein may be enhanced by the addition of various compounds to induce the therapeutic effect. As a non-limiting example, the vaccine formulation may include a MHC II binding peptide or a peptide having a similar sequence to a MHC II binding peptide (see International Pub Nos. WO2012027365, WO2011031298 and US Pub No. US20120070493, US20110110965, each of which is herein incorporated by reference in their entirety). As another example, the vaccine formulations may comprise modified nicotinic compounds which may generate an antibody response to nicotine residue in a subject (see International Pub No. WO2012061717 and US Pub No. US20120114677, each of which is herein incorporated by reference in their entirety).

In one embodiment, the circP, circRNA or circRNA-SP may encode at least one antibody or a fragment or portion thereof. The antibodies may be broadly neutralizing antibodies which may inhibit and protect against a broad range of infectious agents. As a non-limiting example, the circP, circRNA or circRNA-SP encoding at least one antibody or fragment or portion thereof are provided to protect a subject against an infection disease and/or treat the disease. As another non-limiting example, the circP, circRNA or circRNA-SP encoding two or more antibodies or fragments or portions thereof which are able to neutralize a wide spectrum of infectious agents are provided to protect a subject against an infection disease and/or treat the disease.

In one embodiment, the circP, circRNA or circRNA-SP may encode an antibody heavy chain or an antibody light chain. The optimal ratio of circP, circRNA and/or circRNA-SP encoding antibody heavy chain and antibody light chain may be evaluated to determine the ratio that produces the maximal amount of a functional antibody and/or desired response. The circP, circRNA or circRNA-SP may also encode a single svFv chain of an antibody.

According to the present invention, the circP, circRNA or circRNA-SP which encode one or more broadly neutralizing antibodies may be administrated to a subject prior to exposure to infectious viruses.

In one embodiment, the effective amount of the circP, circRNA or circRNA-SP provided to a cell, a tissue or a subject may be enough for immune prophylaxis.

In some embodiment, the circP, circRNA or circRNA-SP encoding cancer cell specific proteins may be formulated as a cancer vaccines. As a non-limiting example, the cancer vaccines comprising at least one circP, circRNA or circRNA-SP of the present invention may be used prophylactically to prevent cancer. The vaccine may comprise an adjuvant and/or a preservative. As a non-limiting example, the adjuvant may be squalene. As another non-limiting example, the preservative may be thimerosal.

In one embodiment, the present invention provides immunogenic compositions containing circP, circRNA or circRNA-SP which encode one or more antibodies, and/or other anti-infection reagents. These immunogenic compositions may comprise an adjuvant and/or a preservative. As a non-limiting example, the antibodies may be broadly neutralizing antibodies.

In another instance, the present invention provides antibody therapeutics containing the circP, circRNA or circRNA-SP which encode one or more antibodies, and/or other anti-infectious reagents.

In one embodiment, the circP, circRNA or circRNA-SP compositions of the present invention may be administrated with other prophylactic or therapeutic compounds. As a non-limiting example, the prophylactic or therapeutic compound may be an adjuvant or a booster. As used herein, when referring to a prophylactic composition, such as a vaccine, the term "booster" refers to an extra administration of the pr prophylactic ophalytic composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years.

In one embodiment, the circP, circRNA or circRNA-SP may be administered intranasally similar to the administration of live vaccines. In another aspect the circP, circRNA or circRNA-SP may be administered intramuscularly or intradermally similarly to the administration of inactivated vaccines known in the art.

In one embodiment, the circP, circRNA or circRNA-SP may be used to protect against and/or prevent the transmission of an emerging or engineered threat which may be known or unknown.

In another embodiment, the circP, circRNA or circRNA-SP may be formulated by the methods described herein. The formulations may comprise circP, circRNA and/or circRNA-SP for more than one antibody or vaccine. In one aspect, the formulation may comprise circP, circRNA or circRNA-SP which can have a therapeutic and/or prophylactic effect on more than one disease, disorder or condition. As a non-limiting example, the formulation may comprise circP, circRNA or circRNA-SP encoding an antigen, antibody or viral protein.

In addition, the antibodies of the present invention may be used for research in many applications, such as, but not limited to, identifying and locating intracellular and extracellular proteins, protein interaction, signal pathways and cell biology.

In another embodiment, the circP, circRNA or circRNA-SP may be used in a vaccine such as, but not limited to, the modular vaccines described in International Publication No. WO2013093629, the contents of which are herein incorporated by reference in its entirety. As a non-limiting example, the circP, circRNA or circRNA-SP encode at least one antigen, at least one subcellular localization element and at least one CD4 helper element. In one aspect, the subcellular localization element may be a signal peptide of protein sequence that results in the exportation of the antigen from the cytosol. In another aspect the CD4 helper element may be, but is not limited to, P30, NEF, P23TT, P32TT, P21TT, PfT3, P2TT, HBVnc, HA, HBsAg and MT (International Publication No. WO2013093629, the contents of which are herein incorporated by reference in its entirety).

In one embodiment, the circP, circRNA or circRNA-SP may be used in the prevention or treatment of RSV infection or reducing the risk of RSV infection. Vaishnaw et al. in US Patent Publication No. US20131065499, the contents of which are herein incorporated by reference in its entirety, describe using a composition comprising a siRNA to treat and/or prevent a RSV infection. As a non-limiting example, the circP, circRNA or circRNA-SP may be formulated for intranasal administration for the prevention and/or treatment of RSV (see e.g., US Patent Publication No. US20130165499, the contents of which are herein incorporated by reference in its entirety).

In another embodiment, the circP, circRNA or circRNA-SP may be used in to reduce the risk or inhibit the infection of influenza viruses such as, but not limited to, the highly pathogenic avian influenza virus (such as, but not limited to, H5N1 subtype) infection and human influenza virus (such as, but not limited to, H1N1 subtype and H3N2 subtype) infection. The circP, circRNA or circRNA-SP described herein which may encode any of the protein sequences described in U.S. Pat. No. 8,470,771, the contents of which are herein incorporated by reference in its entirety, may be used in the treatment or to reduce the risk of an influenza infection.

In one embodiment, the circP, circRNA or circRNA-SP may be used to as a vaccine or modulating the immune response against a protein produced by a parasite. Bergmann-Leitner et al. in U.S. Pat. No. 8,470,560, the contents of which are herein incorporated by reference in its entirety, describe a DNA vaccine against the circumsporozoite protein (CSP) of malaria parasites. As a non-limiting example, the circP, circRNA and/or circRNA-SP may encode the CR2 binding motif of C3d and may be used a vaccine or therapeutic to modulate the immune system against the CSP of malaria parasites.

In one embodiment, the circP, circRNA or circRNA-SP may be used to produce a virus which may be labeled with alkyne-modified biomolecules such as, but not limited to, those described in International Patent Publication No. WO2013112778 and WO2013112780, the contents of each of which are herein incorporated by reference in its entirety. The labeled viruses may increase the infectivity of the virus and thus may be beneficial in making vaccines. The labeled viruses may be produced by various methods including those described in International Patent Publication No. WO2013112778 and WO2013112780, the contents of each of which are herein incorporated by reference in its entirety.

In one embodiment, the circP, circRNA or circRNA-SP may be used as a vaccine and may further comprise an adjuvant which may enable the vaccine to elicit a higher immune response. As a non-limiting example, the adjuvant could be a sub-micron oil-in-water emulsion which can elicit a higher immune response in human pediatric populations (see e.g., the adjuvanted vaccines described in US Patent Publication No. US20120027813 and U.S. Pat. No. 8,506,966, the contents of each of which are herein incorporated by reference in its entirety).

In another embodiment, the circP, circRNA or circRNA-SP may be used to as a vaccine and may also comprise 5' cap analogs to improve the stability and increase the expression of the vaccine. Non-limiting examples of 5' cap analogs are described in US Patent Publication No. US20120195917, the contents of which are herein incorporated by reference in its entirety.

Naturally Occurring Mutants

In another embodiment, the circP, circRNA or circRNA-SP can be utilized to express variants of naturally occurring proteins that have an improved disease modifying activity, including increased biological activity, improved patient outcomes, or a protective function, etc., as described in co-pending International Patent Publication No. WO2015038892, the contents of which is incorporated by reference in its entirety, such as, but not limited to, in paragraphs [0001174]-[0001175].

Major Groove Interacting Partners

As described herein, the phrase "major groove interacting partner" refers to RNA recognition receptors that detect and respond to RNA ligands through interactions, e.g. binding, with the major groove face of a nucleotide or nucleic acid. As such, RNA ligands comprising modified nucleotides or nucleic acids such as the circP, circSP, circRNA or circRNA-SP as described herein decrease interactions with major groove binding partners, and therefore decrease an innate immune response.

Example major groove interacting, e.g. binding, partners include, but are not limited to the following nucleases and helicases. Within membranes, TLRs (Toll-like Receptors) 3, 7, and 8 can respond to single- and double-stranded RNAs. Within the cytoplasm, members of the superfamily 2 class of DEX(D/H) helicases and ATPases can sense RNAs to initiate antiviral responses. These helicases include the RIG-I (retinoic acid-inducible gene I) and MDA5 (melanoma differentiation-associated gene 5). Other examples include laboratory of genetics and physiology 2 (LGP2), HIN-200 domain containing proteins, or Helicase-domain containing proteins.

Targeting of Pathogenic Organisms or Diseased Cells

Provided herein are methods for targeting pathogenic microorganisms, such as bacteria, yeast, protozoa, helminthes and the like, or diseased cells such as cancer cells using circP, circRNA or circRNA-SP that encode cytostatic or cytotoxic polypeptides. In one embodiment, the circP, circRNA or circRNA-SP introduced may contains modified nucleosides or other nucleic acid sequence modifications that are translated exclusively, or preferentially, in the target pathogenic organism, to reduce possible off-target effects of the therapeutic. Such methods are useful for removing pathogenic organisms or killing diseased cells found in any biological material, including blood, semen, eggs, and transplant materials including embryos, tissues, and organs.

Bioprocessing

The methods provided herein may be useful for enhancing protein product yield in a cell culture process as described in co-pending International Patent Publication No. WO2015038892, the contents of which is incorporated by reference in its entirety, such as, but not limited to, in paragraphs [0001176]-[0001187].

Cells

In one embodiment, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells may be from an established cell line, including, but not limited to, HeLa, NS0, SP2/0, KEK 293T, Vero, Caco, Caco-2, MDCK, COS-1, COS-7, K562, Jurkat, CHO-K1, DG44, CHOK1SV, CHO-S, Huvec, CV-1, Huh-7, NIH3T3, HEK293, 293, A549, HepG2, IMR-90, MCF-7, U-20S, Per.C6, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, *Dictyostelium* cells, *Candida* cells, *Saccharomyces* cells, *Schizosaccharomyces* cells, and *Penicillium* cells.

In certain embodiments, the cells are bacterial cells such as, but not limited to, *E. coli, B. subtilis*, or BL21 cells. Primary and secondary cells to be transfected by the methods of the invention can be obtained from a variety of tissues and include, but are not limited to, all cell types which can be maintained in culture. For examples, primary and secondary cells which can be transfected by the methods of the invention include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells may also be obtained from a donor of the same species or from another species (e.g., mouse, rat, rabbit, cat, dog, pig, cow, bird, sheep, goat, horse).

Purification and Isolation

Those of ordinary skill in the art should be able to make a determination of the methods to use to purify or isolate of a protein of interest from cultured cells. Generally, this is done through a capture method using affinity binding or non-affinity purification. If the protein of interest is not secreted by the cultured cells, then a lysis of the cultured cells should be performed prior to purification or isolation. One may use unclarified cell culture fluid containing the protein of interest along with cell culture media components as well as cell culture additives, such as anti-foam compounds and other nutrients and supplements, cells, cellular debris, host cell proteins, DNA, viruses and the like in the present invention. The process may be conducted in the bioreactor itself. The fluid may either be preconditioned to a desired stimulus such as pH, temperature or other stimulus characteristic or the fluid can be conditioned upon the addition of polymer(s) or the polymer(s) can be added to a carrier liquid that is properly conditioned to the required parameter for the stimulus condition required for that polymer to be solubilized in the fluid. The polymer may be allowed to circulate thoroughly with the fluid and then the stimulus may be applied (change in pH, temperature, salt concentration, etc.) and the desired protein and polymer(s) precipitate can out of the solution. The polymer and the desired protein(s) can be separated from the rest of the fluid and optionally washed one or more times to remove any trapped or loosely bound contaminants. The desired protein may then be recovered from the polymer(s) by, for example, elution and the like. Preferably, the elution may be done under a set of conditions such that the polymer remains in its precipitated form and retains any impurities to it during the selected elution of the desired protein. The polymer and protein as well as any impurities may be solubilized in a new fluid such as water or a buffered solution and the protein may be recovered by a means such as affinity, ion exchanged, hydrophobic, or some other type of chromatography that has a preference and selectivity for the protein over that of the polymer or impurities. The eluted protein may then be recovered and may be subjected to additional processing steps, either batch like steps or continuous flow through steps if appropriate.

In another embodiment, it may be useful to optimize the expression of a specific polypeptide in a cell line or collection of cell lines of potential interest, particularly a polypeptide of interest such as a protein variant of a reference protein having a known activity. In one embodiment, provided is a method of optimizing expression of a polypeptide of interest in a target cell, by providing a plurality of target cell types, and independently contacting with each of the plurality of target cell types a circRNA encoding a polypeptide. Additionally, culture conditions may be altered to increase protein production efficiency. Subsequently, the presence and/or level of the polypeptide of interest in the plurality of target cell types is detected and/or quantitated, allowing for the optimization of a polypeptide of interest's expression by selection of an efficient target cell and cell culture conditions relating thereto. Such methods may be useful when the polypeptide of interest contains one or more post-translational modifications or has substantial tertiary structure, which often complicate efficient protein production.

Protein Recovery

The protein of interest may be preferably recovered from the culture medium as a secreted polypeptide, or it can be recovered from host cell lysates if expressed without a secretory signal. It may be necessary to purify the protein of interest from other recombinant proteins and host cell proteins in a way that substantially homogenous preparations of the protein of interest are obtained. The cells and/or particulate cell debris may be removed from the culture medium or lysate. The product of interest may then be purified from contaminant soluble proteins, polypeptides and nucleic acids by, for example, fractionation on immunoaffinity or ion-exchange columns, ethanol precipitation, reverse phase HPLC (RP-HPLC), SEPHADEX® chromatography, chromatography on silica or on a cation exchange resin such as DEAE. Methods of purifying a protein heterologous expressed by a host cell are well known in the art.

Methods and compositions described herein may be used to produce proteins which are capable of attenuating or blocking the endogenous agonist biological response and/or antagonizing a receptor or signaling molecule in a mammalian subject. For example, IL-12 and IL-23 receptor signaling may be enhanced in chronic autoimmune disorders such as multiple sclerosis and inflammatory diseases such as rheumatoid arthritis, psoriasis, lupus erythematosus, ankylosing spondylitis and Chron's disease (Kikly K, Liu L, Na S, Sedgwich J D (2006) Cur. Opin. Immunol. 18(6): 670-5). In another embodiment, a nucleic acid encodes an antagonist for chemokine receptors. Chemokine receptors CXCR-4 and CCR-5 are required for HIV entry into host cells (Arenzana-Seisdedos F et al, (1996) Nature. October 3; 383 (6599): 400).

Gene Silencing

The circP, circSP, circRNA or circRNA-SP described herein are useful to silence (i.e., prevent or substantially reduce) expression of one or more target genes in a cell population. A circP, circRNA or circRNA-SP encoding a polypeptide of interest capable of directing sequence-specific histone H3 methylation is introduced into the cells in the population under conditions such that the polypeptide is translated and reduces gene transcription of a target gene via histone H3 methylation and subsequent heterochromatin formation. In some embodiments, the silencing mechanism is performed on a cell population present in a mammalian subject. By way of non-limiting example, a useful target gene is a mutated Janus Kinase-2 family member, wherein the mammalian subject expresses the mutant target gene suffers from a myeloproliferative disease resulting from aberrant kinase activity.

Co-administration of circP, circSP, circRNA or circRNA-SP and RNAi agents are also provided herein.

Modulation of Biological Pathways

The rapid translation circP, circSP, circRNA or circRNA-SP introduced into cells provides a desirable mechanism of modulating target biological pathways. Such modulation includes antagonism or agonism of a given pathway. In one embodiment, a method is provided for antagonizing a biological pathway in a cell by contacting the cell with an effective amount of a composition comprising a circP, circRNA or circRNA-SP encoding a polypeptide of interest, under conditions such that the circP, circRNA or circRNA-SP is localized into the cell and the polypeptide is capable of being translated in the cell from the circP, circRNA or circRNA-SP, wherein the polypeptide inhibits the activity of a polypeptide functional in the biological pathway. Exemplary biological pathways are those defective in an autoimmune or inflammatory disorder such as multiple sclerosis, rheumatoid arthritis, psoriasis, lupus erythematosus, ankylosing spondylitis colitis, or Crohn's disease; in particular, antagonism of the IL-12 and IL-23 signaling pathways are of particular utility. (See Kikly K, Liu L, Na S, Sedgwick J D (2006) Curr. Opin. Immunol. 18 (6): 670-5).

Further, provided are circP, circRNA or circRNA-SP encoding an antagonist for chemokine receptors; chemokine receptors CXCR-4 and CCR-5 are required for, e.g., HIV entry into host cells (Arenzana-Seisdedos F et al, (1996) Nature. October 3; 383(6599):400).

Alternatively, provided are methods of agonizing a biological pathway in a cell by contacting the cell with an effective amount of a circP, circRNA or circRNA-SP encoding a recombinant polypeptide under conditions such that the nucleic acid is localized into the cell and the recombinant polypeptide is capable of being translated in the cell from the nucleic acid, and the recombinant polypeptide induces the activity of a polypeptide functional in the biological pathway. Exemplary agonized biological pathways include pathways that modulate cell fate determination. Such agonization is reversible or, alternatively, irreversible.

Expression of Ligand or Receptor on Cell Surface

In some aspects and embodiments of the aspects described herein, the circP, circRNA or circRNA-SP described herein can be used to express a ligand or ligand receptor on the surface of a cell (e.g., a homing moiety). A ligand or ligand receptor moiety attached to a cell surface can permit the cell to have a desired biological interaction with a tissue or an agent in vivo. A ligand can be an antibody, an antibody fragment, an aptamer, a peptide, a vitamin, a carbohydrate, a protein or polypeptide, a receptor, e.g., cell-surface receptor, an adhesion molecule, a glycoprotein, a sugar residue, a therapeutic agent, a drug, a glycosaminoglycan, or any combination thereof. For example, a ligand can be an antibody that recognizes a cancer-cell specific antigen, rendering the cell capable of preferentially interacting with tumor cells to permit tumor-specific localization of a modified cell. A ligand can confer the ability of a cell composition to accumulate in a tissue to be treated, since a preferred ligand may be capable of interacting with a target molecule on the external face of a tissue to be treated. Ligands having limited cross-reactivity to other tissues are generally preferred.

In some cases, a ligand can act as a homing moiety which permits the cell to target to a specific tissue or interact with a specific ligand. Such homing moieties can include, but are not limited to, any member of a specific binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((SCFV)2 fragments), diabodies, tribodies or tetrabodies, which typically are covalently linked or otherwise stabilized (i.e., leucine zipper or helix stabilized) scFv fragments; and other homing moieties include for example, aptamers, receptors, and fusion proteins.

In some embodiments, the homing moiety may be a surface-bound antibody, which can permit tuning of cell targeting specificity. This is especially useful since highly specific antibodies can be raised against an epitope of interest for the desired targeting site. In one embodiment, multiple antibodies are expressed on the surface of a cell, and each antibody can have a different specificity for a desired target. Such approaches can increase the avidity and specificity of homing interactions.

A skilled artisan can select any homing moiety based on the desired localization or function of the cell, for example an estrogen receptor ligand, such as tamoxifen, can target cells to estrogen-dependent breast cancer cells that have an increased number of estrogen receptors on the cell surface. Other non-limiting examples of ligand/receptor interactions include CCRI (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), VLA-4/VCAM-1 (e.g., targeting to endothelium). In general, any receptor involved in targeting (e.g., cancer metastasis) can be harnessed for use in the methods and compositions described herein.

Stem Cells

In some embodiments of the present invention, circP, circRNA or circRNA-SP encoding various factors related to altering cell fate such as, but not limited to cell phenotype altering factors, transdifferentiation factors, differentiation factors and dedifferentiation factors, are utilized to alter cell phenotype, which is useful in the field of personal regenerative medicine, cell therapy and therapies for other diseases.

Altering the phenotype of cells in order to express a protein of interest or to change a cell to a different cell phenotype has been used in different clinical, therapeutic and research settings. Altering a phenotype of a cell is currently accomplished by expressing protein from DNA or viral vectors.

Currently there are studies being done to evaluate the use of human embryonic stem cells as a treatment option for various diseases such as Parkinson's disease and diabetes and injuries such as a spinal cord injury. Embryonic stem cells have the ability to grow indefinitely while maintaining pluripotency. However, there are ethical difficulties regarding the use of human embryos combined with the problem of tissue rejection following transplantation of the human embryonic stem cells into patients.

To avoid these ethical and rejection issues, induced pluripotent stem cells (iPSC) can be generated using the patient's own cells. Induction of iPSC was achieved by Takahashi and Yamanaka (*Cell*, 2006. 126(4):663-76; herein incorporated by reference in its entirety) using viral vectors to express KLF4, c-MYC, OCT4 and SOX2 otherwise collectively known as KMOS. Excisable lentiviral and transposon vectors, repeated application of transient plasmid, episomal and adenovirus vectors have also been used to try to derive iPSC (Chang, C.-W., et al., *Stem Cells*, 2009. 27(5):1042-1049; Kaji, K., et al., *Nature*, 2009. 458(7239):771-5; Okita, K., et al., *Science*, 2008. 322(5903):949-53; Stadtfeld, M., et al., *Science*, 2008. 322(5903):945-9; Woltjen, K., et al., *Nature*, 2009; Yu, J., et al., *Science*, 2009:1172482; Fusaki, N., et al., *Proc Jpn Acad Ser B Phys Biol Sci*, 2009. 85(8):348-62; each of which is herein incorporated by reference in its entirety). DNA-free methods to generate human iPSC has also been derived using serial protein transduction with recombinant proteins incorporating cell-penetrating peptide moieties (Kim, D., et al., *Cell Stem Cell*, 2009. 4(6):472-476; Zhou, H., et al., *Cell Stem Cell*, 2009. 4(5):381-4; each of which is herein incorporated by reference in its entirety), and infectious transgene delivery using the Sendai virus (Fusaki, N., et al., *Proc Jpn Acad Ser B Phys Biol Sci*, 2009. 85(8): p. 348-62; herein incorporated by reference in its entirety).

However, the clinical application of iPSC is limited by the low efficiency of deriving iPSC and the fact that in order to have cellular cell phenotype altering the genome needs to be modified. The present invention provides cell phenotype altering circRNAs encoding cell phenotype altering polypeptides of interest which have been designed to improve one or more of the stability and/or clearance in tissues, receptor uptake and/or kinetics, cellular access by the compositions, engagement with translational machinery, mRNA half-life, translation efficiency, immune evasion, protein production capacity, secretion efficiency (when applicable), accessibility to circulation, protein half-life and/or modulation of a cell's status, function and/or activity.

According to the present invention, these circP, circRNA or circRNA-SP may be modified as to avoid the deficiencies of other polypeptide-encoding molecules of the art.

In another aspect, the present disclosure provides chemical modifications located on the sugar moiety of the nucleotide.

In another aspect, the present disclosure provides chemical modifications located on the phosphate backbone of the cell phenotype altering circP, circRNA or circRNA-SP.

In another aspect, the present disclosure provides cell phenotype altering circP, circRNA or circRNA-SP which may contain chemical modifications, wherein the cell phenotype altering circP, circRNA or circRNA-SP reduces the cellular innate immune response, as compared to the cellular innate immune induced by a corresponding unmodified linear nucleic acid.

In another aspect, the present disclosure provides compositions comprising a compound as described herein. In some embodiments, the composition is a reaction mixture. In some embodiments, the composition is a pharmaceutical composition. In some embodiments, the composition is a cell culture. In some embodiments, the composition further comprises an RNA polymerase and a cDNA template. In some embodiments, the composition further comprises a nucleotide selected from the group consisting of adenosine, cytosine, guanosine, and uracil.

In a further aspect, the present disclosure provides methods of making a pharmaceutical formulation comprising a physiologically active secreted protein, comprising transfecting a first population of human cells with the pharmaceutical nucleic acid made by the methods described herein, wherein the secreted protein is active upon a second population of human cells.

In some embodiments, the secreted protein is capable of interacting with a receptor on the surface of at least one cell present in the second population. Non-limiting examples of secreted proteins include OCT such as OCT 4, SOX such as SOX1, SOX2, SOX3, SOX15 and SOX18, NANOG, KLF such as KLF1, KLF2, KLF4 and KLF5, NR5A2, MYC such as c-MYC and n-MYC, REM2, TERT and LIN28.

In some embodiments, the second population contains myeloblast cells that express the receptor for the secreted protein.

In certain embodiments, provided herein are combination therapeutics containing one or more cell phenotype altering cell phenotype altering circP, circRNA or circRNA-SP containing translatable regions that encode for a cell phenotype altering protein or proteins which may be used to produce induced pluripotent stem cells from somatic cells.

Modulation of Cell Lineage

Provided are methods of inducing an alteration in cell fate in a target mammalian cell. The target mammalian cell may be a precursor cell and the alteration may involve driving differentiation into a lineage, or blocking such differentiation. Alternatively, the target mammalian cell may be a differentiated cell, and the cell fate alteration includes driving de-differentiation into a pluripotent precursor cell, or blocking such de-differentiation, such as the dedifferentiation of cancer cells into cancer stem cells. In situations where a change in cell fate is desired, effective amounts of circP, circRNA or circRNA-SP encoding a cell fate inductive polypeptide is introduced into a target cell under conditions such that an alteration in cell fate is induced. In some embodiments, the circP, circRNA or circRNA-SP are useful to reprogram a subpopulation of cells from a first phenotype to a second phenotype. Such a reprogramming may be temporary or permanent. Optionally, the reprogramming induces a target cell to adopt an intermediate phenotype.

Additionally, the methods of the present invention are particularly useful to generate induced pluripotent stem cells (iPS cells) because of the high efficiency of transfection, the ability to re-transfect cells, and the tenability of the amount of recombinant polypeptides produced in the target cells. Further, the use of iPS cells generated using the methods described herein is expected to have a reduced incidence of teratoma formation.

Also provided are methods of reducing cellular differentiation in a target cell population. For example, a target cell population containing one or more precursor cell types is contacted with a composition having an effective amount of a circP, circRNA or circRNA-SP encoding a polypeptide, under conditions such that the polypeptide is translated and reduces the differentiation of the precursor cell. In non-limiting embodiments, the target cell population contains injured tissue in a mammalian subject or tissue affected by a surgical procedure. The precursor cell is, e.g., a stromal precursor cell, a neural precursor cell, or a mesenchymal precursor cell.

In a specific embodiment, provided are circP, circRNA or circRNA-SP that encode one or more differentiation factors Gata4, Mef2c and Tbx4. These circRNA-generated factors are introduced into fibroblasts and drive the reprogramming into cardiomyocytes. Such a reprogramming can be performed in vivo, by contacting a circP, circRNA or circRNA-SP-containing patch or other material to damaged cardiac tissue to facilitate cardiac regeneration. Such a process promotes cardiomyocyte genesis as opposed to fibrosis.

Mediation of Cell Death

In one embodiment, circP, circSP, circRNA or circRNA-SP compositions can be used to induce apoptosis in a cell (e.g., a cancer cell). In one aspect, compositions comprising circP, circRNA or circRNA-SP may be used to increase the expression of a death receptor, a death receptor ligand or a combination thereof. This method can be used to induce cell death in any desired cell and has particular usefulness in the treatment of cancer where cells escape natural apoptotic signals.

Apoptosis can be induced by multiple independent signaling pathways that converge upon a final effector mechanism consisting of multiple interactions between several "death receptors" and their ligands, which belong to the tumor necrosis factor (TNF) receptor/ligand superfamily. The best-characterized death receptors are CD95 ("Fas"), TNFRI (p55), death receptor 3 (DR3 or Apo3/TRAMO), DR4 and DR5 (apo2-TRAIL-R2). The final effector mechanism of apoptosis may be the activation of a series of proteinases designated as caspases. The activation of these caspases results in the cleavage of a series of vital cellular proteins and cell death. The molecular mechanism of death receptors/ligands-induced apoptosis is well known in the art. For example, Fas/FasL-mediated apoptosis is induced by binding of three FasL molecules which induces trimerization of Fas receptor via C-terminus death domains (DDs), which in turn recruits an adapter protein FADD (Fas-associated protein with death domain) and Caspase-8. The oligomerization of this trimolecular complex, Fas/FAIDD/caspase-8, results in proteolytic cleavage of proenzyme caspase-8 into active caspase-8 that, in turn, initiates the apoptosis process by activating other downstream caspases through proteolysis, including caspase-3. Death ligands in general are apoptotic when formed into trimers or higher order of structures. As monomers, they may serve as antiapoptotic agents by competing with the trimers for binding to the death receptors.

In one embodiment, the circP, circRNA or circRNA-SP composition encodes for a death receptor (e.g., Fas, TRAIL, TRAMO, TNFR, TLR etc.). Cells made to express a death receptor by transfection of circRNA become susceptible to death induced by the ligand that activates that receptor. Similarly, cells made to express a death ligand, e.g., on their surface, will induce death of cells with the receptor when the transfected cell contacts the target cell. In another embodiment, the circP, circRNA or circRNA-SP composition encodes for a death receptor ligand (e.g., FasL, TNF, etc.). In another embodiment, the circP, circRNA or circRNA-SP composition encodes a caspase (e.g., caspase 3, caspase 8, caspase 9 etc.). Where cancer cells often exhibit a failure to properly differentiate to a non-proliferative or controlled proliferative form, in another embodiment, the circP, circRNA or circRNA-SP composition encodes for both a death receptor and its appropriate activating ligand. In another embodiment, the circP, circRNA or circRNA-SP composition encodes for a differentiation factor that when expressed in the cancer cell, such as a cancer stem cell, will induce the cell to differentiate to a non-pathogenic or nonself-renewing phenotype (e.g., reduced cell growth rate, reduced cell division etc.) or to induce the cell to enter a dormant cell phase (e.g., $G_0$ resting phase).

One of skill in the art will appreciate that the use of apoptosis-inducing techniques may require that the circP, circSP, circRNA or circRNA-SP are appropriately targeted to e.g., tumor cells to prevent unwanted wide-spread cell death. Thus, one can use a delivery mechanism (e.g., attached ligand or antibody, targeted liposome etc.) that recognizes a cancer antigen such that the circP, circSP, circRNA or circRNA-SP are found only in cancer cells.

Cosmetic Applications

In one embodiment, the circP, circSP, circRNA or circRNA-SP may be used in the treatment, amelioration or prophylaxis of cosmetic conditions. Such conditions include acne, rosacea, scarring, wrinkles, eczema, shingles, psoriasis, age spots, birth marks, dry skin, calluses, rash (e.g., diaper, heat), scabies, hives, warts, insect bites, vitiligo, dandruff, freckles, and general signs of aging.

VI. Kits and Devices

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments.

In one aspect, the present invention provides kits comprising the molecules (circP, circSP, circRNA or circRNA-SP) of the invention. In one embodiment, the kit comprises one or more functional antibodies or function fragments thereof.

Said kits can be for protein production, comprising a first circP, circSP, circRNA or circRNA-SP comprising a translatable region. The kit may further comprise packaging and instructions and/or a delivery agent to form a formulation composition. The delivery agent may comprise a saline, a buffered solution, a lipidoid or any delivery agent disclosed herein.

In one embodiment, the buffer solution may include sodium chloride, calcium chloride, phosphate and/or EDTA. In another embodiment, the buffer solution may include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See e.g., U.S. Pub. No. 20120258046; herein incorporated by reference in its entirety). In a further embodiment, the buffer solutions may be precipitated or it may be lyophilized. The amount of each component may be varied to enable consistent, reproducible higher concentration saline or simple buffer formulations. The components may also be varied in order to increase the stability of circP, circSP, circRNA or circRNA-SP in the buffer solution over a period of time and/or under a variety of conditions. In one aspect, the present invention provides kits for protein production, comprising: a circP, circSP, circRNA or circRNA-SP comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a circP, circSP, circRNA or circRNA-SP comprising a translatable region, wherein the polynucleotide exhibits reduced degradation by a cellular nuclease, and packaging and instructions.

In one aspect, the present invention provides kits for protein production, comprising a circP, circRNA or circRNA-SP comprising a translatable region, wherein the circP, circRNA or circRNA-SP exhibits reduced degradation by a cellular nuclease, and a mammalian cell suitable for translation of the translatable region of the first nucleic acid.

In one embodiment, the levels of Protein C may be measured by immunoassay. The assay may be purchased and is available from any number of suppliers including BioMerieux, Inc. (Durham, N.C.), Abbott Laboratories (Abbott Park, Ill.), Siemens Medical Solutions USA, Inc. (Malvern, Pa.), BIOPORTO® Diagnostics A/S (Gentofte, Denmark), USCN® Life Science Inc. (Houston, Tex.) or Roche Diagnostic Corporation (Indianapolis, Ind.). In this embodiment, the assay may be used to assess levels of Protein C or its activated form or a variant delivered as or in response to administration of a circP, circSP, circRNA or circRNA-SP molecule.

Devices

The present invention provides for devices which may incorporate circP, circSP, circRNA or circRNA-SP. These devices contain in a stable formulation the reagents to synthesize a polynucleotide in a formulation available to be immediately delivered to a subject in need thereof, such as a human patient. The devices may be used to deliver circP, circRNA or circRNA-SP encoding a polypeptide of interest. Non-limiting examples of such a polypeptide of interest include a growth factor and/or angiogenesis stimulator for wound healing, a peptide antibiotic to facilitate infection control, and an antigen to rapidly stimulate an immune response to a newly identified virus.

Devices may also be used in conjunction with the present invention. In one embodiment, a device is used to assess levels of a protein which has been administered in the form of a circP, circRNA or circRNA-SP. The device may comprise a blood, urine or other biofluidic test. It may be as large as to include an automated central lab platform or a small decentralized bench top device. It may be point of care or a handheld device. In this embodiment, for example, Protein C or APC may be quantitated before, during or after treatment with a circP, circRNA or circRNA-SP encoding Protein C (its zymogen), APC or any variants thereof. Protein C, also known as autoprothrombin IIA and blood coagulation factor XIV is a zymogen, or precursor, of a serine protease which plays an important role in the regulation of blood coagulation and generation of fibrinolytic activity in vivo. It is synthesized in the liver as a single-chain polypeptide but undergoes posttranslational processing to give rise to a two-chain intermediate. The intermediate form of Protein C is converted via thrombin-mediated cleavage of a 12-residue peptide from the amino-terminus of the heavy chain to of the molecule to the active form, known as "activated protein C" (APC). The device may be useful in drug discovery efforts as a companion diagnostic test associated with Protein C, or APC treatment such as for sepsis or severe sepsis. In early studies it was suggested that APC had the ability to reduce mortality in severe sepsis. Following this line of work, clinical studies lead to the FDA approval of one compound, activated drotrecogin alfa (recombinant protein C). However, in late 2011, the drug was withdrawn from sale in all markets following results of the PROWESS-SHOCK study, which showed the study did not meet the primary endpoint of a statistically significant reduction in 28-day all-cause mortality in patients with septic shock. The present invention provides circP, circSP, circRNA or circRNA-SP which may be used in the diagnosis and treatment of sepsis, severe sepsis and septicemia which overcome prior issues or problems associated with increasing protein expression efficiencies in mammals.

In some embodiments the device is self-contained, and is optionally capable of wireless remote access to obtain instructions for synthesis and/or analysis of the generated circRNA. The device is capable of mobile synthesis of at least one circP, circSP, circRNA or circRNA-SP and preferably an unlimited number of different circP, circSP, circRNA or circRNA-SP. In certain embodiments, the device is capable of being transported by one or a small number of individuals. In other embodiments, the device is scaled to fit on a benchtop or desk. In other embodiments, the device is scaled to fit into a suitcase, backpack or similarly sized object. In another embodiment, the device may be a point of care or handheld device. In further embodiments, the device is scaled to fit into a vehicle, such as a car, truck or ambulance, or a military vehicle such as a tank or personnel carrier. The information necessary to generate a circP, circRNA or circRNA-SP encoding polypeptide of interest is present within a computer readable medium present in the device.

In one embodiment, a device may be used to assess levels of a protein which has been administered in the form of a circP, circRNA or circRNA-SP. The device may comprise a blood, urine or other biofluidic test.

In some embodiments, the device is capable of communication (e.g., wireless communication) with a database of nucleic acid and polypeptide sequences. The device contains at least one sample block for insertion of one or more sample vessels. Such sample vessels are capable of accepting in liquid or other form any number of materials such as template DNA, nucleotides, enzymes, buffers, and other reagents. The sample vessels are also capable of being heated and cooled by contact with the sample block. The sample block is generally in communication with a device base with one or more electronic control units for the at least one sample block. The sample block preferably contains a heating module, such heating molecule capable of heating and/or cooling the sample vessels and contents thereof to temperatures between about −20 C and above +100 C. The device base is in communication with a voltage supply such as a battery or external voltage supply. The device also contains means for storing and distributing the materials for RNA synthesis.

Optionally, the sample block contains a module for separating the synthesized nucleic acids. Alternatively, the device contains a separation module operably linked to the sample block. Preferably the device contains a means for analysis of the synthesized nucleic acid. Such analysis includes sequence identity (demonstrated such as by hybridization), absence of non-desired sequences, measurement of integrity of synthesized circP, circSP, circRNA or circRNA-SP (such has by microfluidic viscometry combined with spectrophotometry), and concentration and/or potency of circP, circSP, circRNA or circRNA-SP (such as by spectrophotometry).

In certain embodiments, the device is combined with a means for detection of pathogens present in a biological material obtained from a subject, e.g., the IBIS PLEX-ID system (Abbott, Abbott Park, Ill.) for microbial identification.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662; each of which is herein incorporated by reference in their entirety. Intradermal compositions may be administered by devices which limit the effective penetration length of a needle into the skin, such as those described in PCT publication WO 99/34850 (herein incorporated by reference in its entirety) and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537; each of which are herein incorporated by reference in their entirety. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

In some embodiments, the device may be a pump or comprise a catheter for administration of compounds or compositions of the invention across the blood brain barrier. Such devices include but are not limited to a pressurized olfactory delivery device, iontophoresis devices, multi-layered microfluidic devices, and the like. Such devices may be portable or stationary. They may be implantable or externally tethered to the body or combinations thereof.

Devices for administration may be employed to deliver the circP, circSP, circRNA or circRNA-SP of the present invention according to single, multi- or split-dosing regimens taught herein. Such devices are described below.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices may be utilized to deliver the single, multi- or split doses contemplated herein. Such devices are taught for example in, International Application PCT/US2013/30062 filed Mar. 9, 2013, the contents of which are incorporated herein by reference in their entirety.

In one embodiment, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

Methods of delivering therapeutic agents using solid biodegradable microneedles are described by O'hagan et al. in US Patent Publication No. US20130287832, the contents of which are herein incorporated by reference in its entirety. The microneedles are fabricated from the therapeutic agent (e.g., influenza vaccine) in combination with at least one solid excipient. After penetrating the skin, the microneedles dissolve in situ and release the therapeutic agent to the subject. As a non-limiting example, the therapeutic agents used in the fabrication of the microneedles are the polynucleotides described herein.

A microneedle assembly for transdermal drug delivery is described by Ross et al. in U.S. Pat. No. 8,636,696, the contents of which are herein incorporated by reference in its entirety. The assembly has a first surface and a second surface where the microneedles project outwardly from the second surface of the support. The assembly may include a channel and aperture to form a junction which allows fluids (e.g., therapeutic agents or drugs) to pass.

Methods and Devices Utilizing Catheters and/or Lumens

Methods and devices using catheters and lumens may be employed to administer the circP, circSP, circRNA or circRNA-SP of the present invention on a single, multi- or split dosing schedule. Such methods and devices are described in International Application PCT/US2013/30062 filed Mar. 9, 2013, the contents of which are incorporated herein by reference in their entirety.

Methods and Devices Utilizing Electrical Current

Methods and devices utilizing electric current may be employed to deliver the circP, circSP, circRNA or circRNA-SP of the present invention according to the single, multi- or split dosing regimens taught herein. Such methods and devices are described in International Application PCT/US2013/30062 filed Mar. 9, 2013, the contents of which are incorporated herein by reference in their entirety.

VII. Definitions

At various places in the present specification, substituents of compounds of the present disclosure are disclosed in groups or in ranges. It is specifically intended that the present disclosure include each and every individual sub-combination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

About: As used herein, the term "about" means+/−10% of the recited value.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Adjuvant: As used herein, the term "adjuvant" means a substance that enhances a subject's immune response to an antigen.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Antibody Fragment: As used herein, the term "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies; nanobodies; single-chain antibody molecules and multispecific antibodies formed from antibody fragments.

Antigen: As used herein, the term "antigen" refers to the substance that binds specifically to the respective antibody. An antigen may originate either from the body, such as cancer antigen used herein, or from the external environment, for instance, from infectious agents.

Antigens of interest or desired antigens: As used herein, the terms "antigens of interest" or "desired antigens" include those proteins and other biomolecules provided herein that are immunospecifically bound by the antibodies and fragments, mutants, variants, and alterations thereof described herein. Examples of antigens of interest include, but are not limited to, insulin, insulin-like growth factor, hGH, tPA, cytokines, such as interleukins (IL), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL; G-CSF, GM-CSF, M-CSF, MCP-1 and VEGF.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may effect the same outcome or a different outcome. The structure that produces the function may be the same or different. For example, bifunctional circP, circRNA or circRNA-SP of the present invention may encode a cytotoxic peptide (a first function) while those nucleosides which comprise the encoding RNA are, in and of themselves, cytotoxic (second function). In this example, delivery of the bifunctional circP, circRNA or circRNA-SP to a cancer cell would produce not only a peptide or protein molecule which may ameliorate or treat the cancer but would also deliver a cytotoxic payload of nucleosides to the cell should degradation, instead of translation of the circP, circRNA or circRNA-SP, occur.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a circRNA of the present invention may be considered biologically active if even a portion of the circP, circSP, circRNA or circRNA-SP is biologically active or mimics an activity considered biologically relevant.

Cancer stem cells: As used herein, "cancer stem cells" are cells that can undergo self-renewal and/or abnormal proliferation and differentiation to form a tumor.

Chemical terms: The following provides the definition of various chemical terms from "acyl" to "thiol."

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, trifluoroacetyl, propionyl, butanoyl and the like. Exemplary unsubstituted acyl groups include from 1 to 7, from 1 to 11, or from 1 to 21 carbons. In some embodiments, the alkyl group is further substituted with 1, 2, 3, or 4 substituents as described herein.

Non-limiting examples of optionally substituted acyl groups include, alkoxycarbonyl, alkoxycarbonylacyl, arylalkoxycarbonyl, aryloyl, carbamoyl, carboxyaldehyde, (heterocyclyl) imino, and (heterocyclyl)oyl:

The "alkoxycarbonyl" group, which as used herein, represents an alkoxy, as defined herein, attached to the parent molecular group through a carbonyl atom (e.g., —C(O)—OR, where R is H or an optionally substituted $C_{1-6}$, $C_{1-10}$, or $C_{1-20}$ alkyl group). Exemplary unsubstituted alkoxycarbonyl include from 1 to 21 carbons (e.g., from 1 to 11 or from 1 to 7 carbons). In some embodiments, the alkoxy group is further substituted with 1, 2, 3, or 4 substituents as described herein.

The "alkoxycarbonylacyl" group, which as used herein, represents an acyl group, as defined herein, that is substituted with an alkoxycarbonyl group, as defined herein (e.g., —C(O)-alkyl-C(O)—OR, where R is an optionally substituted $C_{1-6}$, $C_{1-10}$, or $C_{1-20}$ alkyl group). Exemplary unsubstituted alkoxycarbonylacyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ acyl, $C_{1-10}$ alkoxycarbonyl-$C_{1-10}$ acyl, or $C_{1-20}$ alkoxycarbonyl-$C_{1-20}$ acyl). In some embodiments, each alkoxy and alkyl group is further independently substituted with 1, 2, 3, or 4 substituents, as described herein (e.g., a hydroxy group) for each group.

The "arylalkoxycarbonyl" group, which as used herein, represents an arylalkoxy group, as defined herein, attached to the parent molecular group through a carbonyl (e.g., —C(O)—O-alkyl-aryl). Exemplary unsubstituted arylalkoxy groups include from 8 to 31 carbons (e.g., from 8 to 17 or from 8 to 21 carbons, such as $C_{6-10}$ aryl-$C_{1-6}$ alkoxy-carbonyl, $C_{6-10}$ aryl-$C_{1-10}$ alkoxy-carbonyl, or $C_{6-10}$ aryl-$C_{1-20}$ alkoxy-carbonyl). In some embodiments, the arylalkoxycarbonyl group can be substituted with 1, 2, 3, or 4 substituents as defined herein.

The "aryloyl" group, which as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The "carbamoyl" group, which as used herein, represents —C(O)—N($R^{N1}$)$_2$, where the meaning of each $R^{N1}$ is found in the definition of "amino" provided herein.

The "carboxyaldehyde" group, which as used herein, represents an acyl group having the structure —CHO.

The "(heterocyclyl) imino" group, which as used herein, represents a heterocyclyl group, as defined herein, attached to the parent molecular group through an imino group. In some embodiments, the heterocyclyl group can be substituted with 1, 2, 3, or 4 substituent groups as defined herein.

The "(heterocyclyl)oyl" group, which as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "alkyl," as used herein, is inclusive of both straight chain and branched chain saturated groups from 1 to 20 carbons (e.g., from 1 to 10 or from 1 to 6), unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH$_2$) or a substituted amino (i.e., —N($R^{N1}$)$_2$, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy, optionally substituted with an O-protecting group; (9) nitro; (10) oxo (e.g., carboxyaldehyde or acyl); (11) $C_{1-7}$ spirocyclyl; (12) thioalkoxy; (13) thiol; (14) —CO$_2$$R^{A'}$, optionally substituted with an O-protecting group and where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)NR$^{B'}$R$^{C'}$, where each of R$^{B'}$ and R$^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO$_2$R$^{D'}$, where R$^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO$_2$NR$^{E'}$R$^{F'}$, where each of R$^{E'}$ and R$^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)R$^{G'}$, where R$^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH$_2$)$_{s2}$(OCH$_2$CH$_2$)$_{s1}$(CH$_2$)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —NR$^{H'}$C(O)R$^{I'}$, wherein R$^{H'}$ is selected from the group consisting of (a1) hydrogen and (b1) $C_{1-6}$ alkyl, and R$^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —NR$^{J'}$C(O)OR$^{K'}$, wherein R$^{J'}$ is selected from the group consisting of (a1) hydrogen and (b1) $C_{1-6}$ alkyl, and R$^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH$_2$)$_{s2}$(OCH$_2$CH$_2$)$_{s1}$(CH$_2$)OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —NR$^{N1}$(CH$_2$)$_{s2}$(CH$_2$CH$_2$O)$_{s1}$(CH$_2$)$_{s3}$NR$^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein. For example, the alkylene group of a $C_1$-alkaryl can be further substituted with an oxo group to afford the respective aryloyl substituent.

The term "alkylene," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_{1-6}$, $C_{1-10}$, $C_{2-26}$, $C_{2-6}$, $C_{2-10}$, or $C_{2-20}$ alkylene). In some embodiments, the alkylene can be further substituted with 1, 2, 3, or 4 substituent groups as defined herein for an alkyl group. Similarly, the suffix "-ene" appended to any group indicates that the group is a divalent group.

Non-limiting examples of optionally substituted alkyl and alkylene groups include acylaminoalkyl, acyloxyalkyl, alkoxyalkyl, alkoxycarbonylalkyl, alkylsulfinyl, alkylsulfinylalkyl, aminoalkyl, carbamoylalkyl, carboxyalkyl, carboxyaminoalkyl, haloalkyl, hydroxyalkyl, perfluoroalkyl, and sulfoalkyl:

The "acylaminoalkyl" group, which as used herein, represents an acyl group, as defined herein, attached to an amino group that is in turn attached to the parent molecular group through an alkylene group, as defined herein (i.e., -alkyl-N($R^{N1}$)—C(O)—R, where R is H or an optionally substituted $C_{1-6}$, $C_{1-10}$, or $C_{1-26}$ alkyl group (e.g., haloalkyl) and $R^{N1}$ is as defined herein). Exemplary unsubstituted acylaminoalkyl groups include from 1 to 41 carbons (e.g., from 1 to 7, from 1 to 13, from 1 to 21, from 2 to 7, 2 to 13, from 2 to 21, or from 2 to 41 carbons). In some embodiments, the alkylene group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}{}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "acyloxyalkyl" group, which as used herein, represents an acyl group, as defined herein, attached to an oxygen atom that in turn is attached to the parent molecular group though an alkylene group (i.e., -alkyl-O—C(O)—R, where R is H or an optionally substituted $C_{1-6}$, $C_{1-10}$, or $C_{1-20}$ alkyl group). Exemplary unsubstituted acyloxyalkyl groups include from 1 to 21 carbons (e.g., from 1 to 7 or from 1 to 11 carbons). In some embodiments, the alkylene group is, independently, further substituted with 1, 2, 3, or 4 substituents as described herein.

The "alkoxyalkyl" group, which as used herein, represents an alkyl group that is substituted with an alkoxy group. Exemplary unsubstituted alkoxyalkyl groups include between 2 to 40 carbons (e.g., from 2 to 12 or from 2 to 20 carbons, such as $C_{1-6}$ alkoxy-$C_{1-6}$ alkyl, $C_{1-10}$ alkoxy-$C_{1-10}$ alkyl, or $C_{1-20}$ alkoxy-$C_{1-20}$ alkyl). In some embodiments, the alkyl and the alkoxy each can be further substituted with 1, 2, 3, or 4 substituent groups as defined herein for the respective group.

The "alkoxycarbonylalkyl" group, which as used herein, represents an alkyl group, as defined herein, that is substituted with an alkoxycarbonyl group, as defined herein (e.g., -alkyl-C(O)—OR, where R is an optionally substituted $C_{1-20}$, $C_{1-10}$, or $C_{1-6}$ alkyl group). Exemplary unsubstituted alkoxycarbonylalkyl include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkyl, $C_{1-10}$ alkoxycarbonyl-$C_{1-10}$ alkyl, or $C_{1-20}$ alkoxycarbonyl-$C_{1-20}$ alkyl). In some embodiments, each alkyl and alkoxy group is further independently substituted with 1, 2, 3, or 4 substituents as described herein (e.g., a hydroxy group).

The "alkylsulfinylalkyl" group, which as used herein, represents an alkyl group, as defined herein, substituted with an alkylsulfinyl group. Exemplary unsubstituted alkylsulfinylalkyl groups are from 2 to 12, from 2 to 20, or from 2 to 40 carbons. In some embodiments, each alkyl group can be further substituted with 1, 2, 3, or 4 substituent groups as defined herein.

The "aminoalkyl" group, which as used herein, represents an alkyl group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "carbamoylalkyl" group, which as used herein, represents an alkyl group, as defined herein, substituted with a carbamoyl group, as defined herein. The alkyl group can be further substituted with 1, 2, 3, or 4 substituent groups as described herein.

The "carboxyalkyl" group, which as used herein, represents an alkyl group, as defined herein, substituted with a carboxy group, as defined herein. The alkyl group can be further substituted with 1, 2, 3, or 4 substituent groups as described herein, and the carboxy group can be optionally substituted with one or more 0-protecting groups.

The "carboxyaminoalkyl" group, which as used herein, represents an aminoalkyl group, as defined herein, substituted with a carboxy, as defined herein. The carboxy, alkyl, and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group, and/or an O-protecting group).

The "haloalkyl" group, which as used herein, represents an alkyl group, as defined herein, substituted with a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —$CF_3$), —$CHF_2$, —$CH_2F$, —$CCl_3$, —$CH_2CH_2Br$, —$CH_2CH(CH_2CH_2Br)CH_3$, and —$CHICH_3$. In some embodiments, the haloalkyl group can be further substituted with 1, 2, 3, or 4 substituent groups as described herein for alkyl groups.

The "hydroxyalkyl" group, which as used herein, represents an alkyl group, as defined herein, substituted with one to three hydroxy groups, with the proviso that no more than one hydroxy group may be attached to a single carbon atom of the alkyl group, and is exemplified by hydroxymethyl, dihydroxypropyl, and the like. In some embodiments, the hydroxyalkyl group can be substituted with 1, 2, 3, or 4 substituent groups (e.g., O-protecting groups) as defined herein for an alkyl.

The "perfluoroalkyl" group, which as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The "sulfoalkyl" group, which as used herein, represents an alkyl group, as defined herein, substituted with a sulfo group of —$SO_3H$. In some embodiments, the alkyl group can be further substituted with 1, 2, 3, or 4 substituent groups as described herein, and the sulfo group can be further substituted with one or more O-protecting groups (e.g., as described herein).

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, 2-butenyl, and the like. Alkenyls include both cis and trans isomers. Alkenyl groups may be optionally substituted with 1, 2, 3, or 4 substituent groups that are selected, independently, from amino, aryl, cycloalkyl, or heterocyclyl (e.g., heteroaryl), as defined herein, or any of the exemplary alkyl substituent groups described herein.

Non-limiting examples of optionally substituted alkenyl groups include, alkoxycarbonylalkenyl, aminoalkenyl, and hydroxyalkenyl:

The "alkoxycarbonylalkenyl" group, which as used herein, represents an alkenyl group, as defined herein, that is substituted with an alkoxycarbonyl group, as defined herein (e.g., -alkenyl-C(O)—OR, where R is an optionally substituted $C_{1-20}$, $C_{1-10}$, or $C_{1-6}$ alkyl group). Exemplary unsubstituted alkoxycarbonylalkenyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkenyl, $C_{1-10}$ alkoxycarbonyl-$C_{2-10}$ alkenyl, or $C_{1-20}$ alkoxycarbonyl-$C_{2-20}$ alkenyl). In some embodiments, each alkyl, alkenyl, and alkoxy group is further independently substituted with 1, 2, 3, or 4 substituents as described herein (e.g., a hydroxy group).

The "aminoalkenyl" group, which as used herein, represents an alkenyl group, as defined herein, substituted with an amino group, as defined herein. The alkenyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkenyl" group, which as used herein, represents an alkenyl group, as defined herein, substituted with one to three hydroxy groups, with the proviso that no more than one hydroxy group may be attached to a single carbon atom of the alkyl group, and is exemplified by dihydroxypropenyl, hydroxyisopentenyl, and the like. In some embodiments, the hydroxyalkenyl group can be substituted with 1, 2, 3, or 4 substituent groups (e.g., O-protecting groups) as defined herein for an alkyl.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

Non-limiting examples of optionally substituted alkynyl groups include alkoxycarbonylalkynyl, aminoalkynyl, and hydroxyalkynyl:

The "alkoxycarbonylalkynyl" group, which as used herein, represents an alkynyl group, as defined herein, that is substituted with an alkoxycarbonyl group, as defined herein (e.g., -alkynyl-C(O)—OR, where R is an optionally substituted $C_{1-20}$, $C_{1-10}$, or $C_{1-6}$ alkyl group). Exemplary unsubstituted alkoxycarbonylalkynyl include from 4 to 41 carbons (e.g., from 4 to 10, from 4 to 13, from 4 to 17, from 4 to 21, or from 4 to 31 carbons, such as $C_{1-6}$ alkoxycarbonyl-$C_{2-6}$ alkynyl, $C_{1-10}$ alkoxycarbonyl-$C_{240}$ alkynyl, or $C_{1-20}$ alkoxycarbonyl-$C_{2-20}$ alkynyl). In some embodiments, each alkyl, alkynyl, and alkoxy group is further independently substituted with 1, 2, 3, or 4 substituents as described herein (e.g., a hydroxy group).

The "aminoalkynyl" group, which as used herein, represents an alkynyl group, as defined herein, substituted with an amino group, as defined herein. The alkynyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy, and/or an N-protecting group).

The "hydroxyalkynyl" group, which as used herein, represents an alkynyl group, as defined herein, substituted with one to three hydroxy groups, with the proviso that no more than one hydroxy group may be attached to a single carbon atom of the alkyl group. In some embodiments, the hydroxyalkynyl group can be substituted with 1, 2, 3, or 4 substituent groups (e.g., 0-protecting groups) as defined herein for an alkyl.

The term "amino," as used herein, represents $-N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, carboxyalkyl (e.g., optionally substituted with an O-protecting group, such as optionally substituted arylalkoxycarbonyl groups or any described herein), sulfoalkyl, acyl (e.g., acetyl, trifluoroacetyl, or others described herein), alkoxycarbonylalkyl (e.g., optionally substituted with an O-protecting group, such as optionally substituted arylalkoxycarbonyl groups or any described herein), heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., $-NH_2$) or a substituted amino (i.e., $-N(R^{N1})_2$). In a preferred embodiment, amino is $-NH_2$ or $-NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, carboxyalkyl, sulfoalkyl, acyl (e.g., acetyl, trifluoroacetyl, or others described herein), alkoxycarbonylalkyl (e.g., t-butoxycarbonylalkyl) or aryl, and each $R^{N2}$ can be H, $C_{1-20}$ alkyl (e.g., $C_{1-6}$ alkyl), or $C_{6-10}$ aryl.

Non-limiting examples of optionally substituted amino groups include acylamino and carbamyl:

The "acylamino" group, which as used herein, represents an acyl group, as defined herein, attached to the parent molecular group though an amino group, as defined herein (i.e., $N(R^{N1})$—C(O)—R, where R is H or an optionally substituted $C_{1-6}$, $C_{1-10}$, or $C_{1-20}$ alkyl group (e.g., haloalkyl) and $R^{N1}$ is as defined herein). Exemplary unsubstituted acylamino groups include from 1 to 41 carbons (e.g., from 1 to 7, from 1 to 13, from 1 to 21, from 2 to 7, from 2 to 13, from 2 to 21, or from 2 to 41 carbons). In some embodiments, the alkyl group is further substituted with 1, 2, 3, or 4 substituents as described herein, and/or the amino group is $-NH_2$ or $-NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, aryl, acyl (e.g., acetyl, trifluoroacetyl, or others described herein), or alkoxycarbonylalkyl, and each $R^{N2}$ can be H, alkyl, or aryl.

The "carbamyl" group, which as used herein, refers to a carbamate group having the structure $-NR^{N1}C(=O)OR$ or $-OC(=O)N(R^{N1})_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "amino acid," as described herein, refers to a molecule having a side chain, an amino group, and an acid group (e.g., a carboxy group of $-CO_2H$ or a sulfo group of —SO₃H), wherein the amino acid is attached to the parent molecular group by the side chain, amino group, or acid group (e.g., the side chain). In some embodiments, the amino acid is attached to the parent molecular group by a carbonyl group, where the side chain or amino group is attached to the carbonyl group. Exemplary side chains include an optionally substituted alkyl, aryl, heterocyclyl, alkaryl, alkheterocyclyl, aminoalkyl, carbamoylalkyl, and carboxyalkyl. Exemplary amino acids include alanine, arginine, asparagine, aspartic acid, cysteine, glutamic acid, glutamine, glycine, histidine, hydroxynorvaline, isoleucine, leucine, lysine, methionine, norvaline, ornithine, phenylalanine, proline, pyrrolysine, selenocysteine, serine, taurine, threonine, tryptophan, tyrosine, and valine. Amino acid groups may be optionally substituted with one, two, three, or, in the case of amino acid groups of two carbons or more, four substituents independently selected from the group consisting of: (1) $C_{1-6}$ alkoxy; (2) $C_{1-6}$ alkylsulfinyl; (3) amino, as defined herein (e.g., unsubstituted amino (i.e., —NH₂) or a substituted amino (i.e., —N(R^{N1})₂, where $R^{N1}$ is as defined for amino); (4) $C_{6-10}$ aryl-$C_{1-6}$ alkoxy; (5) azido; (6) halo; (7) ($C_{2-9}$ heterocyclyl)oxy; (8) hydroxy; (9) nitro; (10) oxo (e.g., carboxaldehyde or acyl); (11) $C_{1-7}$ spirocyclyl; (12) thioalkoxy; (13) thiol; (14) —CO₂$R^{A'}$, where $R^{A'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH₂)$_{s2}$(OCH₂CH₂)$_{s1}$(CH₂)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}$(CH₂)$_{s2}$(CH₂CH₂O)$_{s1}$(CH₂)$_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (15) —C(O)$NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —SO₂$R^{D'}$, where $R^{D'}$ is selected from the group consisting of (a) $C_{1-6}$ alkyl, (b) $C_{6-10}$ aryl, (c) $C_{1-6}$ alk-$C_{6-10}$ aryl, and (d) hydroxy; (17) —SO₂$NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl; (18) —C(O)$R^{G'}$, where $R^{G'}$ is selected from the group consisting of (a) $C_{1-20}$ alkyl (e.g., $C_{1-6}$ alkyl), (b) $C_{2-20}$ alkenyl (e.g., $C_{2-6}$ alkenyl), (c) $C_{6-10}$ aryl, (d) hydrogen, (e) $C_{1-6}$ alk-$C_{6-10}$ aryl, (f) amino-$C_{1-20}$ alkyl, (g) polyethylene glycol of —(CH₂)$_{s2}$(OCH₂CH₂)$_{s1}$(CH₂)$_{oR}$', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h) amino-polyethylene glycol of —$NR^{N1}$(CH₂)$_{s2}$(CH₂CH₂O)$_{s1}$(CH₂)$_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (19) —$NR^{H'}$C(O)R^{I'}, wherein $R^{H'}$ is selected from the group consisting of (a1) hydrogen and (b1) $C_{1-6}$ alkyl, and $R^{I'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH₂)$_{s2}$(OCH₂CH₂)$_{s1}$(CH₂)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}$(CH₂)$_{s2}$(CH₂CH₂O)$_{s1}$(CH₂)$_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; (20) —$NR^{J'}$C(O)O$R^{K'}$, wherein $R^{K'}$ is selected from the group consisting of (a1) hydrogen and (b1) $C_{1-6}$ alkyl, and $R^{K'}$ is selected from the group consisting of (a2) $C_{1-20}$ alkyl (e.g., $C_{1-6}$ alkyl), (b2) $C_{2-20}$ alkenyl (e.g., $C_{2-6}$ alkenyl), (c2) $C_{6-10}$ aryl, (d2) hydrogen, (e2) $C_{1-6}$ alk-$C_{6-10}$ aryl, (f2) amino-$C_{1-20}$ alkyl, (g2) polyethylene glycol of —(CH₂)$_{s2}$(OCH₂CH₂)$_{s1}$(CH₂)$_{s3}$OR', wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and R' is H or $C_{1-20}$ alkyl, and (h2) amino-polyethylene glycol of —$NR^{N1}$(CH₂)$_{s2}$(CH₂CH₂O)$_{s1}$(CH₂)$_{s3}NR^{N1}$, wherein s1 is an integer from 1 to 10 (e.g., from 1 to 6 or from 1 to 4), each of s2 and s3, independently, is an integer from 0 to 10 (e.g., from 0 to 4, from 0 to 6, from 1 to 4, from 1 to 6, or from 1 to 10), and each $R^{N1}$ is, independently, hydrogen or optionally substituted $C_{1-6}$ alkyl; and (21) amidine. In some embodiments, each of these groups can be further substituted as described herein.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, anthracenyl, phenanthrenyl, fluorenyl, indanyl, indenyl, and the like, and may be optionally substituted with 1, 2, 3, 4, or 5 substituents independently selected from the group consisting of: (1) $C_{1-2}$ acyl (e.g., carboxaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —(CH₂)$_q$CO₂$R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH₂)$_q$CONR$^{D'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH₂)$_q$SO₂$R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —(CH₂)$_q$SO₂$NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) $C_{2-20}$ alkenyl; and (27) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{1-6}$ alk-$C_{6-10}$ aryl, $C_{1-10}$ alk-$C_{6-10}$ aryl, or $C_{1-20}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "azido" represents an —$N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The term "boranyl," as used herein, represents —$B(R^{B1})_3$, where each $R^{B1}$ is, independently, selected from the group consisting of H and optionally substituted alkyl. In some embodiments, the boranyl group can be substituted with 1, 2, 3, or 4 substituents as defined herein for alkyl.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, cycloalkynyl, and aryl groups.

The term "carbonyl," as used herein, represents a C(O) group, which can also be represented as C=O.

The term "carboxy," as used herein, means —$CO_2H$.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicycle heptyl, and the like. When what would otherwise be a cycloalkyl group includes one or more carbon-carbon double bonds, the group is referred to as a "cycloalkenyl" group. For the purposes of this invention, cycloalkenyl excludes aryl groups. When what would otherwise be a cycloalkyl group includes one or more carbon-carbon triple bonds, the group is referred to as a "cycloalkynyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-16}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{6-16}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{6-10}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); (26) oxo; (27) $C_{2-20}$ alkenyl; and (28) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "cycloalkylalkyl" group, which as used herein, represents a cycloalkyl group, as defined herein, attached to the parent molecular group through an alkylene group, as defined herein (e.g., an alkylene group of from 1 to 4, from 1 to 6, from 1 to 10, or form 1 to 20 carbons). In some embodiments, the alkylene and the cycloalkyl each can be further substituted with 1, 2, 3, or 4 substituent groups as defined herein for the respective group.

The term "diastereomer," as used herein means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "heteroalkyl," as used herein, refers to an alkyl group, as defined herein, in which one or two of the constituent carbon atoms have each been replaced by nitrogen, oxygen, or sulfur. In some embodiments, the heteroalkyl group can be further substituted with 1, 2, 3, or 4 substituent groups as described herein for alkyl groups. The terms "heteroalkenyl" and heteroalkynyl," as used herein refer to alkenyl and alkynyl groups, as defined herein, respectively, in which one or two of the constituent carbon atoms have each been replaced by nitrogen, oxygen, or sulfur. In some embodiments, the heteroalkenyl and heteroalkynyl groups can be further substituted with 1, 2, 3, or 4 substituent groups as described herein for alkyl groups.

Non-limiting examples of optionally substituted heteroalkyl, heteroalkenyl, and heteroalkynyl groups include acyloxy, alkenyloxy, alkoxy, alkoxyalkoxy, alkoxycarbonylalkoxy, alkynyloxy, aminoalkoxy, arylalkoxy, carboxyalkoxy, cycloalkoxy, haloalkoxy, (heterocyclyl)oxy, perfluoroalkoxy, thioalkoxy, and thioheterocyclylalkyl:

The "acyloxy" group, which as used herein, represents an acyl group, as defined herein, attached to the parent molecular group though an oxygen atom (i.e., —O—C(O)—R, where R is H or an optionally substituted $C_{1-6}$, $C_{1-10}$, or $C_{1-20}$ alkyl group). Exemplary unsubstituted acyloxy groups include from 1 to 21 carbons (e.g., from 1 to 7 or from 1 to 11 carbons). In some embodiments, the alkyl group is further substituted with 1, 2, 3, or 4 substituents as described herein.

The "alkenyloxy" group, which as used here, represents a chemical substituent of formula —OR, where R is a $C_{2-20}$ alkenyl group (e.g., $C_{2-6}$ or $C_{2-10}$ alkenyl), unless otherwise specified. Exemplary alkenyloxy groups include ethenyloxy, propenyloxy, and the like. In some embodiments, the alkenyl group can be further substituted with 1, 2, 3, or 4 substituent groups as defined herein (e.g., a hydroxy group).

The "alkoxy" group, which as used herein, represents a chemical substituent of formula —OR, where R is a $C_{1-20}$ alkyl group (e.g., $C_{1-6}$ or $C_{1-10}$ alkyl), unless otherwise specified. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The "alkoxyalkoxy" group, which as used herein, represents an alkoxy group that is substituted with an alkoxy group. Exemplary unsubstituted alkoxyalkoxy groups include between 2 to 40 carbons (e.g., from 2 to 12 or from 2 to 20 carbons, such as $C_{1-6}$ alkoxy-$C_{1-6}$ alkoxy, $C_{1-10}$ alkoxy-$C_{1-10}$ alkoxy, or $C_{1-20}$ alkoxy-$C_{1-20}$ alkoxy). In some embodiments, the each alkoxy group can be further substituted with 1, 2, 3, or 4 substituent groups as defined herein.

The "alkoxycarbonylalkoxy" group, which as used herein, represents an alkoxy group, as defined herein, that is substituted with an alkoxycarbonyl group, as defined herein (e.g., —O-alkyl-C(O)—OR, where R is an optionally substituted $C_{1-6}$, $C_{1-10}$, or $C_{1-20}$ alkyl group). Exemplary unsubstituted alkoxycarbonylalkoxy include from 3 to 41 carbons (e.g., from 3 to 10, from 3 to 13, from 3 to 17, from 3 to 21, or from 3 to 31 carbons, such as $C_{1-6}$ alkoxycarbonyl-$C_{1-6}$ alkoxy, $C_{1-10}$ alkoxycarbonyl-$C_{1-10}$ alkoxy, or $C_{1-20}$ alkoxycarbonyl-$C_{1-20}$ alkoxy). In some embodiments, each alkoxy group is further independently substituted with 1, 2, 3, or 4 substituents, as described herein (e.g., a hydroxy group).

The "alkynyloxy" group, which as used herein, represents a chemical substituent of formula —OR, where R is a $C_{2-20}$ alkynyl group (e.g., $C_{2-6}$ or $C_{2-10}$ alkynyl), unless otherwise specified. Exemplary alkynyloxy groups include ethynyloxy, propynyloxy, and the like. In some embodiments, the alkynyl group can be further substituted with 1, 2, 3, or 4 substituent groups as defined herein (e.g., a hydroxy group).

The "aminoalkoxy" group, which as used herein, represents an alkoxy group, as defined herein, substituted with an amino group, as defined herein. The alkyl and amino each can be further substituted with 1, 2, 3, or 4 substituent groups as described herein for the respective group (e.g., $CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl, e.g., carboxy).

The "arylalkoxy" group, which as used herein, represents an alkaryl group, as defined herein, attached to the parent molecular group through an oxygen atom. Exemplary unsubstituted arylalkoxy groups include from 7 to 30 carbons (e.g., from 7 to 16 or from 7 to 20 carbons, such as $C_{6-10}$ aryl-$C_{1-6}$ alkoxy, $C_{6-10}$ aryl-$C_{1-10}$ alkoxy, or $C_{6-10}$ aryl-$C_{1-20}$ alkoxy). In some embodiments, the arylalkoxy group can be substituted with 1, 2, 3, or 4 substituents as defined herein.

The "aryloxy" group, which as used herein, represents a chemical substituent of formula —OR', where R' is an aryl group of 6 to 18 carbons, unless otherwise specified. In some embodiments, the aryl group can be substituted with 1, 2, 3, or 4 substituents as defined herein.

The "carboxyalkoxy" group, which as used herein, represents an alkoxy group, as defined herein, substituted with a carboxy group, as defined herein. The alkoxy group can be further substituted with 1, 2, 3, or 4 substituent groups as described herein for the alkyl group, and the carboxy group can be optionally substituted with one or more 0-protecting groups.

The "cycloalkoxy" group, which as used herein, represents a chemical substituent of formula —OR, where R is a $C_{3-8}$ cycloalkyl group, as defined herein, unless otherwise specified. The cycloalkyl group can be further substituted with 1, 2, 3, or 4 substituent groups as described herein. Exemplary unsubstituted cycloalkoxy groups are from 3 to 8 carbons. In some embodiment, the cycloalkyl group can be further substituted with 1, 2, 3, or 4 substituent groups as described herein.

The "haloalkoxy" group, which as used herein, represents an alkoxy group, as defined herein, substituted with a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —$OCF_3$), —$OCHF_2$, —$OCH_2F$, —$OCCl_3$, —$OCH_2CH_2Br$, —$OCH_2CH(CH_2CH_2Br)CH_3$, and —$OCHICH_3$. In some embodiments, the haloalkoxy group can be further substituted with 1, 2, 3, or 4 substituent groups as described herein for alkyl groups.

The "(heterocyclyl)oxy" group, which as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The "perfluoroalkoxy" group, which as used herein, represents an alkoxy group, as defined herein, where each hydrogen radical bound to the alkoxy group has been replaced by a fluoride radical. Perfluoroalkoxy groups are exemplified by trifluoromethoxy, pentafluoroethoxy, and the like.

The "alkylsulfinyl" group, which as used herein, represents an alkyl group attached to the parent molecular group through an —S(O)— group. Exemplary unsubstituted alkylsulfinyl groups are from 1 to 6, from 1 to 10, or from 1 to 20 carbons. In some embodiments, the alkyl group can be further substituted with 1, 2, 3, or 4 substituent groups as defined herein.

The "thioarylalkyl" group, which as used herein, represents a chemical substituent of formula —SR, where R is an arylalkyl group. In some embodiments, the arylalkyl group can be further substituted with 1, 2, 3, or 4 substituent groups as described herein.

The "thioalkoxy" group as used herein, represents a chemical substituent of formula —SR, where R is an alkyl group, as defined herein. In some embodiments, the alkyl group can be further substituted with 1, 2, 3, or 4 substituent groups as described herein.

The "thioheterocyclylalkyl" group, which as used herein, represents a chemical substituent of formula —SR, where R is an heterocyclylalkyl group. In some embodiments, the heterocyclylalkyl group can be further substituted with 1, 2, 3, or 4 substituent groups as described herein.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heteroarylalkyl" refers to a heteroaryl group, as defined herein, attached to the parent molecular group through an alkylene group, as defined herein. Exemplary unsubstituted heteroarylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heteroaryl, $C_{1-10}$ alk-$C_{1-12}$ heteroaryl, or $C_{1-20}$ alk-$C_{1-12}$ heteroaryl). In some embodiments, the alkylene and the heteroaryl each can be further substituted with 1, 2, 3, or 4 substituent groups as defined herein for the respective group. Heteroarylalkyl groups are a subset of heterocyclylalkyl groups.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2,3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3,4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3,4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxo-pyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo,4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2,3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

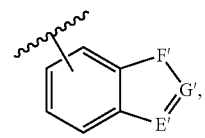

where

E' is selected from the group consisting of —N— and —CH—; F' is selected from the group consisting of —N=CH—, —NH—CH$_2$—, —NH—C(O)—, —NH—, —CH=N—, —CH$_2$—NH—, —C(O)—NH—, —CH=CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-20}$ alkyl (e.g., $C_{1-6}$ alkyl, $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-20}$ alkoxy (e.g., $C_{1-6}$ alkoxy, such as perfluoroalkoxy); (4) $C_{1-6}$ alkylsulfinyl; (5) $C_{6-10}$ aryl; (6) amino; (7) $C_{1-6}$ alk-$C_{6-10}$ aryl; (8)

azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-20}$ thioalkoxy (e.g., $C_{1-6}$ thioalkoxy); (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —$(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) $C_{1-6}$ alkyl, (b) $C_{6-10}$ aryl, and (c) $C_{1-6}$ alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; (27) ($C_{1-12}$ heterocyclyl)imino; (28) $C_{2-20}$ alkenyl; and (29) $C_{2-20}$ alkynyl. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The "heterocyclylalkyl" group, which as used herein, represents a heterocyclyl group, as defined herein, attached to the parent molecular group through an alkylene group, as defined herein. Exemplary unsubstituted heterocyclylalkyl groups are from 2 to 32 carbons (e.g., from 2 to 22, from 2 to 18, from 2 to 17, from 2 to 16, from 3 to 15, from 2 to 14, from 2 to 13, or from 2 to 12 carbons, such as $C_{1-6}$ alk-$C_{1-12}$ heterocyclyl, $C_{1-10}$ alk-$C_{1-12}$ heterocyclyl, or $C_{1-20}$ alk-$C_{1-12}$ heterocyclyl). In some embodiments, the alkylene and the heterocyclyl each can be further substituted with 1, 2, 3, or 4 substituent groups as defined herein for the respective group.

The term "hydrocarbon," as used herein, represents a group consisting only of carbon and hydrogen atoms.

The term "hydroxy," as used herein, represents an —OH group.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups, such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "O-protecting group," as used herein, represents those groups intended to protect an oxygen containing (e.g., phenol, hydroxyl, or carbonyl) group against undesirable reactions during synthetic procedures. Commonly used O-protecting groups are disclosed in Greene, "Protective Groups in Organic Synthesis," $3^{rd}$ Edition (John Wiley & Sons, New York, 1999), which is incorporated herein by reference. Exemplary O-protecting groups include acyl, aryloyl, or carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl; alkylcarbonyl groups, such as acyl, acetyl, propionyl, pivaloyl, and the like; optionally substituted arylcarbonyl groups, such as benzoyl; silyl groups, such as trimethylsilyl (TMS), tert-butyldimethylsilyl (TBDMS), tri-iso-propylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxycarbonyl, fluorenylmethyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); substituted alkyl, aryl, and alkaryl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2,2-trichloroethyl; 2-(trimethylsilyl)ethyl; vinyl, allyl, nitrophenyl; benzyl; methoxybenzyl; 3,4-dimethoxybenzyl; and nitrobenzyl); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; and oxazoline groups.

The term "oxo" as used herein, represents =O.

The prefix "perfluoro," as used herein, represents any group, as defined herein, where each hydrogen radical bound to the alkyl group has been replaced by a fluoride radical. For example, perfluoroalkyl groups are exemplified by trifluoromethyl, pentafluoroethyl, and the like.

The term "phosphoryl," as used herein, refers to

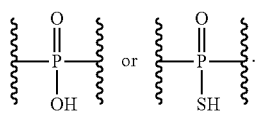

The term "protected hydroxyl," as used herein, refers to an oxygen atom bound to an O-protecting group.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —S(O)$_2$— group.

The term "thiol," as used herein represents an —SH group.

Circular: As used herein, the terms "circular", "cyclic", or "cyclized", refer to the presence of a continuous loop. Circular does not indicate a particular shape or configuration of the molecule. Circular molecules have an unbroken chain of subunits. Circular molecules such as the circP, circSP, circRNA or circRNA-SP of the present invention may be single units or multimers or comprise one or more components of a complex or higher order structure.

Circular Polynucleotide: As used herein, the terms "circular polynucleotide" or "circP" mean a single stranded circular polynucleotide which acts substantially like, and has the properties of, an RNA.

Circular RNA: As used herein, the terms "circular RNA" or "circRNA" mean a circular polynucleotide that can encode at least one polypeptide of interest.

Circular RNA Sponge: As used herein, the terms "circular RNA sponges" or "circular RNA-SP" mean a circular polynucleotide which comprises at least one sensor sequence and at least one region encoding at least one polypeptide of interest.

Circular Sponge: As used herein, the term "circular sponge," "circular polynucleotide sponge" or "circSP" means a circular polynucleotide which comprises at least one sensor sequence but does not encode a polypeptide of interest.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Committed: As used herein, the term "committed" means, when referring to a cell, when the cell is far enough into the differentiation pathway where, under normal circumstances, it will continue to differentiate into a specific cell type or subset of cell type instead of into a different cell type or reverting to a lesser differentiated cell type.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: Please see "circular".

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a circP, circSP, circRNA or circRNA-SP to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Developmental Potential: As used herein, "developmental potential" or "developmental potency" refers to the total of all developmental cell fates or cell types that can be achieved by a cell upon differentiation.

Developmental Potential Altering Factor: As used herein, "developmental potential altering factor" refers to a protein or RNA which can alter the developmental potential of a cell.

Digest: As used herein, the term "digest" means to break apart into smaller pieces or components. When referring to polypeptides or proteins, digestion results in the production of peptides.

Differentiated cell: As used herein, the term "differentiated cell" refers to any somatic cell that is not, in its native form, pluripotent. Differentiated cell also encompasses cells that are partially differentiated.

Differentiation: As used herein, the term "differentiation factor" refers to a developmental potential altering factor such as a protein, RNA or small molecule that can induce a cell to differentiate to a desired cell-type.

Differentiate: As used herein, "differentiate" refers to the process where an uncommitted or less committed cell acquires the features of a committed cell.

Distal: As used herein, the term "distal" means situated away from the center or away from a point or region of interest.

Dosing regimen: As used herein, a "dosing regimen" is a schedule of administration or physician determined regimen of treatment, prophylaxis, or palliative care.

Dose splitting factor (DSF)-ratio of PUD of dose split treatment divided by PUD of total daily dose or single unit dose. The value is derived from comparison of dosing regimens groups.

Embryonic stem cell: As used herein, the term "embryonic stem cell" refers to naturally occurring pluripotent stem cells of the inner cell mass of the embryonic blastocyst.

Encapsulate: As used herein, the term "encapsulate" means to enclose, surround or encase.

Encoded protein cleavage signal: As used herein, "encoded protein cleavage signal" refers to the nucleotide sequence which encodes a protein cleavage signal.

Engineered: As used herein, embodiments of the invention are "engineered" when they are designed to have a feature or property, whether structural or chemical, that varies from a starting point, wild type or native molecule.

Exosome: As used herein, "exosome" is a vesicle secreted by mammalian cells or a complex involved in RNA degradation.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a circP, circSP, circRNA or circRNA-SP and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

Immunoglobin: As used herein, the term "immunoglobin" (Ig) can be used interchangeably with "antibody."

Infectious Agent: As used herein, the phrase "infectious agent" means an agent capable of producing an infection.

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

Infectious agent: As used herein, an "infectious agent" refers to any microorganism, virus, infectious substance, or biological product that may be engineered as a result of biotechnology, or any naturally occurring or bioengineered component of any such microorganism, virus, infectious substance, or biological product, can cause emerging and contagious disease, death or other biological malfunction in a human, an animal, a plant or another living organism.

Influenza: As used herein, "influenza" or "flu" is an infectious disease of birds and mammals caused by RNA viruses of the family Orthomyxoviridae, the influenza viruses.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form circRNA multimers (e.g., through linkage of two or more circP, circSP, circRNA or circRNA-SP) or circular polynucleotide conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

MicroRNA (miRNA) binding site: As used herein, a microRNA (miRNA) binding site represents a nucleotide location or region of a nucleic acid transcript to which at least the "seed" region of a miRNA binds.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Monoclonal Antibody: As used herein the term "monoclonal antibody" refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site.

Mucus: As used herein, "mucus" refers to the natural substance that is viscous and comprises mucin glycoproteins.

Multipotent: As used herein, "multipotent" or "partially differentiated cell" when referring to a cell refers to a cell that has a developmental potential to differentiate into cells of one or more germ layers, but not all three germ layers.

Naturally occurring: As used herein, "naturally occurring" means existing in nature without artificial aid.

Neutralizing antibody: As used herein, a "neutralizing antibody" refers to an antibody which binds to its antigen and defends a cell from an antigen or infectious agent by neutralizing or abolishing any biological activity it has.

Non-human vertebrate: As used herein, a "non human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Oligopotent: As used herein, "oligopotent" when referring to a cell means to give rise to a more restricted subset of cell lineages than multipotent stem cells.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

Peptide: As used herein, "peptide" is less than or equal to 50 amino acids long, e.g., about 5, 10, 15, 20, 25, 30, 35, 40, 45, or 50 amino acids long.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained professional for a particular disease or condition.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Pluripotent: As used herein, "pluripotent" refers to a cell with the developmental potential, under different conditions, to differentiate to cell types characteristic of all three germ layers.

Pluripotency: As used herein, "pluripotency" or "pluripotent state" refers to the developmental potential of a cell where the cell has the ability to differentiate into all three embryonic germ layers (endoderm, mesoderm and ectoderm).

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Progenitor cell: As used herein, the term "progenitor cell" refers to cells that have greater developmental potential relative to a cell which it can give rise to by differentiation.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine ($\psi m$).

Purified: As used herein, "purify," "purified," "purification" means to make substantially pure or clear from unwanted components, material defilement, admixture or imperfection.

Repeated transfection: As used herein, the term "repeated transfection" refers to transfection of the same cell culture with a polynucleotide, primary construct or mmRNA a plurality of times. The cell culture can be transfected at least twice, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times at least 18 times, at least 19 times, at least 20 times, at least 25 times, at least 30 times, at least 35 times, at least 40 times, at least 45 times, at least 50 times or more.

Reprogramming: As used herein, "reprogramming" refers to a process that reverses the developmental potential of a cell or population of cells.

Reprogramming factor: As used herein, the term "reprogramming factor" refers to a developmental potential altering factor such as a protein, RNA or small molecule, the expression of which contributes to the reprogramming of a cell to a less differentiated or undifferentiated state.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Sensor Sequence: As used herein, the phrase "sensor sequence" means a receptor or pseudo-receptor for endogenous nucleic acid binding molecules.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Somatic cell: As used herein, "somatic cells" refers to any cell other than a germ cell, a cell present in or obtained from a pre-implantation embryo, or a cell resulting from proliferation of such a cell in vitro.

Somatic stem cell: As used herein, a "somatic stem cell" refers to any pluripotent or multipotent stem cell derived from non-embryonic tissue including fetal, juvenile and adult tissue.

Somatic pluripotent cell: As used herein, a "somatic pluripotent cell" refers to a somatic cell that has had its developmental potential altered to that of a pluripotent state.

Split dose: As used herein, a "split dose" is the division of a single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Stem cell: As used herein, the term "stem cell" refers to a cell in an undifferentiated or partially differentiated state that has the property of self-renewal and has the developmental potential to differentiate into multiple cell types, without a specific developmental potential. A stem cell may be able capable of proliferation and giving rise to more such stem cells while maintaining its developmental potential.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Totipotency: As used herein, "totipotency" refers to a cell with a developmental potential to make all of the cells found in the adult body as well as the extra-embryonic tissues, including the placenta.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Transcription: As used herein, the term "transcription" refers to methods to introduce exogenous nucleic acids into a cell. Methods of transfection include, but are not limited to, chemical methods, physical treatments and cationic lipids or mixtures.

Transdifferentiation: As used herein, "transdifferentiation" refers to the capacity of differentiated cells of one type to lose identifying characteristics and to change their phenotype to that of other fully differentiated cells.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Unipotent: As used herein, "unipotent" when referring to a cell means to give rise to a single cell lineage.

Vaccine: As used herein, the phrase "vaccine" refers to a biological preparation that improves immunity to a particular disease.

Viral protein: As used herein, the phrase "viral protein" means any protein originating from a virus.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1. Linear Modified mRNA Production

Linear modified mRNAs (mmRNAs) that can be cyclized to produce the circular RNA (circRNAs) of the present invention may be made using standard laboratory methods and materials. The methods described herein to make modified mRNA may be used to produce molecules of all sizes including long molecules. The open reading frame (ORF) of the gene of interest may be flanked by a 5' untranslated region (UTR) which may contain a strong Kozak translational initiation signal and/or an alpha-globin 3' UTR which may include an oligo(dT) sequence for templated addition of a poly-A tail. The modified mRNAs may be modified to reduce the cellular innate immune response. The modifications to reduce the cellular response may include pseudouridine (ψ) and 5-methyl-cytidine (5meC, 5mc or m$^5$C). (See, Kariko K et al. Immunity 23:165-75 (2005), Kariko K et al. Mol Ther 16:1833-40 (2008), Anderson B R et al. NAR (2010); each of which are herein incorporated by reference in their entireties).

The ORF may also include various upstream or downstream additions (such as, but not limited to, β-globin, tags, etc.) may be ordered from an optimization service such as, but not limited to, DNA2.0 (Menlo Park, Calif.) and may contain multiple cloning sites which may have XbaI recognition. Upon receipt of the construct, it may be reconstituted and transformed into chemically competent E. coli.

For the present invention, NEB DH5-alpha Competent *E. coli* are used. Transformations are performed according to NEB instructions using 100 ng of plasmid. The protocol is as follows:
1. Thaw a tube of NEB 5-alpha Competent *E. coli* cells on ice for 10 minutes.
2. Add 1-5 μl containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 μl of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.

Spread 50-100 μl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 μg), a maxi prep is performed using the Invitrogen PURELINK™ HiPure Maxiprep Kit (Carlsbad, Calif.), following the manufacturer's instructions.

In order to generate cDNA for In Vitro Transcription (IVT), the plasmid is first linearized using a restriction enzyme such as XbaI. A typical restriction digest with XbaI will comprise the following: Plasmid 1.0 μg; 10× Buffer 1.0 μl; XbaI 1.5 μl; dH$_2$O up to 10 μl; incubated at 37° C. for 1 hr. If performing at lab scale (<5 μg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the NanoDrop and analyzed to confirm linearization using agarose gel electrophoresis.

Example 2. PCR for cDNA Production

PCR procedures for the preparation of cDNA are performed using 2×KAPA HIFI™ HotStart ReadyMix by Kapa Biosystems (Woburn, Mass.). This system includes 2×KAPA ReadyMix 12.5 μl; Forward Primer (10 uM) 0.75 μl; Reverse Primer (10 uM) 0.75 μl; Template cDNA –100 ng; and dH$_2$O diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-T$_{120}$ (SEQ ID NO: 50) for a poly-A$_{120}$ (SEQ ID NO: 49) in the mRNA. Other reverse primers with longer or shorter poly(T) tracts can be used to adjust the length of the poly(A) tail in the polynucleotide mRNA.

The reaction is cleaned up using Invitrogen's PURELINK™ PCR Micro Kit (Carlsbad, Calif.) per manufacturer's instructions (up to 5 ng). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 3. In Vitro Transcription (IVT)

The in vitro transcription reaction generates polynucleotides containing uniformly modified polynucleotides. Such uniformly modified polynucleotides may comprise a region or part of the chimeric polynucleotides of the invention. The input nucleotide triphosphate (NTP) mix is made in-house using natural and un-natural NTPs.

A typical in vitro transcription reaction includes the following:

| 1 | Template cDNA | 1.0 μg |
|---|---|---|
| 2 | 10x transcription buffer (400 mM Tris-HCl pH 8.0, 190 mM MgCl$_2$, 50 mM DTT, 10 mM Spermidine) | 2.0 μl |
| 3 | Custom NTPs (25 mM each) | 7.2 μl |
| 4 | RNase Inhibitor | 20 U |
| 5 | T7 RNA polymerase | 3000 U |
| 6 | dH$_2$0 | Up to 20.0 μl. and |
| 7 | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 4. Enzymatic Capping of mRNA

Capping of a polynucleotide is performed as follows where the mixture includes: IVT RNA 60 μg-180 μg and dH$_2$O up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl$_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); dH$_2$O (Up to 28 μl); and incubation at 37° C. for 30 minutes for 60 μg RNA or up to 2 hours for 180 μg of RNA.

The polynucleotide is then purified using Ambion's MEGACLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 5. PolyA Tailing Reaction

Without a poly-T in the cDNA, a poly-A tailing reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$O up to 123.5 µl and incubation at 37° C. for 30 min. If the poly-A tail is already in the transcript, then the tailing reaction may be skipped and proceed directly to cleanup with Ambion's MEGA-CLEAR™ kit (Austin, Tex.) (up to 500 µg). Poly-A Polymerase is preferably a recombinant enzyme expressed in yeast.

It should be understood that the processivity or integrity of the polyA tailing reaction may not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6. Natural 5' Caps and 5' Cap Analogues

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 7. Capping

A. Protein Expression Assay

Synthetic mRNAs encoding human G-CSF (mRNA sequence fully modified with 5-methylcytosine at each cytosine and pseudouridine replacement at each uridine site shown in SEQ ID NO: 23 with a polyA tail approximately 160 nucleotides in length not shown in sequence) containing the ARCA (3' O-Me-m7G(5')ppp(5')G) cap analog or the Cap1 structure can be transfected into human primary keratinocytes at equal concentrations. 6, 12, 24 and 36 hours post-transfection the amount of G-CSF secreted into the culture medium can be assayed by ELISA. Synthetic mRNAs that secrete higher levels of G-CSF into the medium would correspond to a synthetic mRNA with a higher translationally-competent Cap structure.

B. Purity Analysis Synthesis

Synthetic mRNAs encoding human G-CSF (mRNA sequence fully modified with 5-methylcytosine at each cytosine and pseudouridine replacement at each uridine site shown in SEQ ID NO: 23 with a polyA tail approximately 160 nucleotides in length not shown in sequence) containing the ARCA cap analog or the Cap1 structure crude synthesis products can be compared for purity using denaturing Agarose-Urea gel electrophoresis or HPLC analysis. Synthetic mRNAs with a single, consolidated band by electrophoresis correspond to the higher purity product compared to a synthetic mRNA with multiple bands or streaking bands. Synthetic mRNAs with a single HPLC peak would also correspond to a higher purity product. The capping reaction with a higher efficiency would provide a more pure mRNA population.

C. Cytokine Analysis

Synthetic mRNAs encoding human G-CSF (mRNA sequence fully modified with 5-methylcytosine at each cytosine and pseudouridine replacement at each uridine site shown in SEQ ID NO: 23 with a polyA tail approximately 160 nucleotides in length not shown in sequence) containing the ARCA cap analog or the Cap1 structure can be transfected into human primary keratinocytes at multiple concentrations. 6, 12, 24 and 36 hours post-transfection the amount of pro-inflammatory cytokines such as TNF-alpha and IFN-beta secreted into the culture medium can be assayed by ELISA. Synthetic mRNAs that secrete higher levels of pro-inflammatory cytokines into the medium would correspond to a synthetic mRNA containing an immune-activating cap structure.

D. Capping Reaction Efficiency

Synthetic mRNAs encoding human G-CSF (mRNA sequence fully modified with 5-methylcytosine at each cytosine and pseudouridine replacement at each uridine site shown in SEQ ID NO: 23 with a polyA tail approximately 160 nucleotides in length not shown in sequence) containing the ARCA cap analog or the Cap1 structure can be analyzed for capping reaction efficiency by LC-MS after capped mRNA nuclease treatment. Nuclease treatment of capped mRNAs would yield a mixture of free nucleotides and the capped 5'-5-triphosphate cap structure detectable by LC-MS. The amount of capped product on the LC-MS spectra can be expressed as a percent of total mRNA from the reaction and would correspond to capping reaction efficiency. The cap structure with higher capping reaction efficiency would have a higher amount of capped product by LC-MS.

Example 8. Agarose Gel Electrophoresis of Modified RNA or RT PCR Products

Individual modified RNAs (200-400 ng in a 20 µl volume) or reverse transcribed PCR products (200-400 ng) are loaded into a well on a non-denaturing 1.2% Agarose E-Gel (Invitrogen, Carlsbad, Calif.) and run for 12-15 minutes according to the manufacturer protocol.

Example 9. Nanodrop Modified RNA Quantification and UV Spectral Data

Modified RNAs in TE buffer (1 µl) are used for Nanodrop UV absorbance readings to quantitate the yield of each modified RNA from an in vitro transcription reaction.

Example 10. Method of Screening for Protein Expression

A. Electrospray Ionization

A biological sample which may contain proteins encoded by modified RNA administered to the subject is prepared and analyzed according to the manufacturer protocol for electrospray ionization (ESI) using 1, 2, 3 or 4 mass analyzers. A biologic sample may also be analyzed using a tandem ESI mass spectrometry system.

Patterns of protein fragments, or whole proteins, are compared to known controls for a given protein and identity is determined by comparison.

B. Matrix-Assisted Laser Desorption/Ionization

A biological sample which may contain proteins encoded by modified RNA administered to the subject is prepared and analyzed according to the manufacturer protocol for matrix-assisted laser desorption/ionization (MALDI).

Patterns of protein fragments, or whole proteins, are compared to known controls for a given protein and identity is determined by comparison.

C. Liquid Chromatography-Mass Spectrometry-Mass Spectrometry

A biological sample, which may contain proteins encoded by modified RNA, may be treated with a trypsin enzyme to digest the proteins contained within. The resulting peptides are analyzed by liquid chromatography-mass spectrometry-mass spectrometry (LC/MS/MS). The peptides are fragmented in the mass spectrometer to yield diagnostic patterns that can be matched to protein sequence databases via computer algorithms. The digested sample may be diluted to achieve 1 ng or less starting material for a given protein. Biological samples containing a simple buffer background (e.g. water or volatile salts) are amenable to direct in-solution digest; more complex backgrounds (e.g. detergent, non-volatile salts, glycerol) require an additional clean-up step to facilitate the sample analysis.

Patterns of protein fragments, or whole proteins, are compared to known controls for a given protein and identity is determined by comparison.

Example 11. CircRNA Constructs

Any of the circP, circSP, circRNA or circRNA-SP described herein may be synthesized from the linear polynucleotides described herein by the methods described herein and/or known in the art.

A non-limiting example of a linear cDNA sequence encoding G-CSF which may be made into circRNA is described in Table 8. This construct includes a split IRES sequence, shown in bold italics in Table 8, an ASC1 site in the 3'UTR and a polyA tail of 80 nucleotides and does not include a Kozak sequence. The start codon of the sequence is underlined.

TABLE 8

Split IRES Construct

| Description | Sequence | SEQ ID NO: |
|---|---|---|
| G-CSF sequence with a split IRES and no Kozak sequence | TAATACGACTCACTATA GGGAAATAAGAGAGAAAAGAAGAGTAAGAAGAAATATAAGA *GGGTCTTTCCCCTCTCGCCAAAGGAATGCAAGGTCTGTTGAATGTC GTGAAGGAAGCAGTTCCTCTGGAAGCTTCTTGAAGACAAACAACGT CTGTAGCGACCCTTTGCAGGCAGCGGAACCCCCCACCTGGCGACAG GTGCCTCTGCGGCCAAAAGCCACGTGTATAAGATACACCTGCAAAG GCGGCACAACCCCAGTGCCACGTTGTGAGTTGGATAGTTGTGGAAA GAGTCAAATGGCTCACCTCAAGCGTATTCAACAAGGGGCTGAAGGA TGCCCAGAAGGTACCCCATTGTATGGGATCTGATCTGGGGCCTCGG TGCACATGCTTTACATGTGTTTAGTCGAGGTTAAAAAACGTCTAGGC CCCCCGAACCACGGGGACGTGGTTTTCCTTTGAAAAACACGATGAT AAT* ATGGCCGGTCCCGCGACCCAAAGCCCCATGAAACTTATGGCCCTG CAGTTGCTGCTTTGGCACTCGGCCCTCTGGACAGTCCAAGAAGCG ACTCCTCTCGGACCTGCCTCATCGTTGCCGCAGTCATTCCTTTTGA AGTGTCTGGAGCAGGTGCGAAAGATTCAGGGCGATGGAGCCGCAC TCCAAGAGAAGCTCTGCGCGACATACAAACTTTGCCATCCCGAGG AGCTCGTACTGCTCGGGCACAGCTTGGGGATTCCCTGGGCTCCTCT CTCGTCCTGTCCGTCGCAGGCTTTGCAGTTGGCAGGGTGCCTTTCC CAGCTCCACTCCGGTTTGTTCTTGTATCAGGGACTGCTGCAAGCCC TTGAGGGAATCTCGCCAGAATTGGGCCCGACGCTGGACACGTTGC AGCTCGACGTGGCGGATTTCGCAACAACCATCTGGCAGCAGATGG AGGAACTGGGGATGGCACCCGCGCTGCAGCCCACGCAGGGGGCA ATGCCGGCCTTTGCGTCCGCGTTTCAGCGCAGGGCGGGTGGAGTC CTCGTAGCGAGCCACCTTCAATCATTTTTGGAAGTCTCGTACCGGG TGCTGAGACATCTTGCGCAGCCGTGATAATAGGCTGGAGCCTCGG TGGCCATGCTTCTTGCCCCTTGGGCCTCCCCCCAGCCCCTCCTCCCC TTCCTGCACCCGTACCCCCGTGGTCTTTGAATAAAGTCTGAGTGGG CGGCAAAAAAAAAAAAAAAAAAAAAAAAAAAAAAAAAAAAAAA AAAAAAAAAAAAAAAAAAAAAAAAAAAAAAAAAAAAAAAGG CGCGCC *TCGTGAGGATCTATTTCCGGTGAATTCCTCGAGACTAGTTCTAGAGC GGCCGCGGATCCCGCCCCTCTCCCTCCCCCCCCCCTAACGTTACTG GCCGAAGCCGCTTGGAATAAGGCCGGTGTGCGTTTGTCTATATGTT ATTTTCCACCATATTGCCGTCTTTTGGCAATGTGAGGGCCCGGAAAC CTGGCCCTGTCTTCTTGACGAGCATTCCTAG* | 24 |

Further, circRNA of the present invention may be made using the linear constructs described in Table 9. In Table 9, the start codon of the sequences is underlined and the IRES sequence is in bold italics if included in the construct.

TABLE 9

Constructs

| | Sequence | SEQ ID NO: |
|---|---|---|
| G-CSF with Kozak sequence and IRES and human alpha-globin 3'UTR | Optimized G-CSF cDNA sequence containing a T7 polymerase site, kozak sequence, IRES and XbaI restriction site:<br>TAATACGACTCACTATA<br>GGGAAATAAGAGAGAAAAGAAGAGTAAGAAGAAATATAAGAGCC<br>ACC<br>*TCGTGAGGATCTATTTCCGGTGAATTCCTCGAGACTAGTTCTAGAGC*<br>*GGCCGCGGATCCCGCCCCTCTCCCTCCCCCCCCCCTAACGTTACTG*<br>*GCCGAAGCCGCTTGGAATAAGGCCGGTGTGCGTTTGTCTATATGTT*<br>*ATTTTCCACCATATTGCCGTCTTTTGGCAATGTGAGGGCCCGGAAAC*<br>*CTGGCCCTGTCTTCTTGACGAGCATTCCTAGGGGTCTTTCCCCTCTC*<br>*GCCAAAGGAATGCAAGGTCTGTTGAATGTCGTGAAGGAAGCAGTTC*<br>*CTCTGGAAGCTTCTTGAAGACAAACAACGTCTGTAGCGACCCTTTGC*<br>*AGGCAGCGGAACCCCCCACCTGGCGACAGGTGCCTCTGCGGCCAAA*<br>*AGCCACGTGTATAAGATACACCTGCAAAGGCGGCACAACCCCAGTG*<br>*CCACGTTGTGAGTTGGATAGTTGTGGAAAGAGTCAAATGGCTCACC*<br>*TCAAGCGTATTCAACAAGGGGCTGAAGGATGCCCAGAAGGTACCCC*<br>*ATTGTATGGGATCTGATCTGGGGCCTCGGTGCACATGCTTTACATGT*<br>*GTTTAGTCGAGGTTAAAAAACGTCTAGGCCCCCCGAACCACGGGGA*<br>*CGTGGTTTTCCTTTGAAAAACACGATGATAAT*<br>ATGGCCGGTCCCGCGACCCAAAGCCCCATGAAACTTATGGCCCTG<br>CAGTTGCTGCTTTGGCACTCGGCCCTCTGGACAGTCCAAGAAGCG<br>ACTCCTCTCGGACCTGCCTCATCGTTGCCGCAGTCATTCCTTTTGA<br>AGTGTCTGGAGCAGGTGCGAAAGATTCAGGGCGATGGAGCCGCAC<br>TCCAAGAGAAGCTCTGCGCGACATACAAACTTTGCCATCCCGAGG<br>AGCTCGTACTGCTCGGGCACAGCTTGGGGATTCCCTGGGCTCCTCT<br>CTCGTCCTGTCCGTCGCAGGCTTTGCAGTTGGCAGGGTGCCTTTCC<br>CAGCTCCACTCCGGTTTGTTCTTGTATCAGGGACTGCTGCAAGCCC<br>TTGAGGGAATCTCGCCAGAATTGGGCCCGACGCTGGACACGTTGC<br>AGCTCGACGTGGCGGATTTCGCAACAACCATCTGGCAGCAGATGG<br>AGGAACTGGGGATGGCACCCGCGCTGCAGCCCACGCAGGGGGCA<br>ATGCCGGCCTTTGCGTCCGCGTTTCAGCGCAGGGCGGGTGGAGTC<br>CTCGTAGCGAGCCACCTTCAATCATTTTTGGAAGTCTCGTACCGGG<br>TGCTGAGACATCTTGCGCAGCCG<br>TGATAATAG<br>GCTGGAGCCTCGGTGGCCATGCTTCTTGCCCCTTGGGCCTCCCCCC<br>AGCCCCTCCTCCCCTTCCTGCACCCGTACCCCCGTGGTCTTTGAAT<br>AAAGTCTGAGTGGGCGGCTCTAGA | 25 |
| | mRNA sequence (transcribed):<br>GGGAAAUAAGAGAGAAAAGAAGAGUAAGAAGAAAUAUAAGAGC<br>CACC<br><br>*UCGUGAGGAUCUAUUUCCGGUGAAUUCCUCGAGACUAGUUCUAG*<br>*AGCGGCCGCGGAUCCCGCCCCUCUCCCUCCCCCCCCCCUAACGUU*<br>*ACUGGCCGAAGCCGCUUGGAAUAAGGCCGGUGUGCGUUUGUCUA*<br>*UAUGUUAUUUUCCACCAUAUUGCCGUCUUUUGGCAAUGUGAGGG*<br>*CCCGGAAACCUGGCCCUGUCUUCUUGACGAGCAUUCCUAGGGGUC*<br>*UUUCCCCUCUCGCCAAAGGAAUGCAAGGUCUGUUGAAUGUCGUG*<br>*AAGGAAGCAGUUCCUCUGGAAGCUUCUUGAAGACAAACAACGUCU*<br>*GUAGCGACCCUUUGCAGGCAGCGGAACCCCCCACCUGGCGACAGG*<br>*UGCCUCUGCGGCCAAAAGCCACGUGUAUAAGAUACACCUGCAAAG*<br>*GCGGCACAACCCCAGUGCCACGUUGUGAGUUGGAUAGUUGUGGA*<br>*AAGAGUCAAAUGGCUCACCUCAAGCGUAUUCAACAAGGGGCUGAA*<br>*GGAUGCCCAGAAGGUACCCCAUUGUAUGGGAUCUGAUCUGGGGC*<br>*CUCGGUGCACAUGCUUUACAUGUGUUUAGUCGAGGUUAAAAAAC*<br>*GUCUAGGCCCCCCGAACCACGGGGACGUGGUUUUCCUUUGAAAAA*<br>*CACGAUGAUAAU* | 26 |

TABLE 9-continued

Constructs

| | Sequence | SEQ ID NO: |
|---|---|---|
| | <u>AUG</u>GCCGGUCCCGCGACCCAAAGCCCCAUGAAACUUAUGGCCCU<br>GCAGUUGCUGCUUUGGCACUCGGCCCUCUGGACAGUCCAAGAAG<br>CGACUCCUCUCGGACCUGCCUCAUCGUUGCCGCAGUCAUUCCUU<br>UUGAAGUGUCUGGAGCAGGUGCGAAAGAUUCAGGGCGAUGGAG<br>CCGCACUCCAAGAGAAGCUCUGCGCGACAUACAAACUUUGCCAU<br>CCCGAGGAGCUCUACUGCUCGGGCACAGCUUGGGGAUUCCCUG<br>GCUCCUCUCUCGUCCUGUCCGUCGCAGGCUUUGCAGUUGGCAG<br>GGUGCCUUUCCCAGCUCCACUCCGGUUUGUUCUUGUAUCAGGGA<br>CUGCUGCAAGCCCUUGAGGGAAUCUCGCCAGAAUUGGGCCCGAC<br>GCUGGACACGUUGCAGCUCGACGUGGCGGAUUUCGCAACAACCA<br>UCUGGCAGCAGAUGGAGGAACUGGGGAUGGCACCCGCGCUGCAG<br>CCCACGCAGGGGCAAUGCCGGCCUUUGCGUCCGCGUUUCAGCG<br>CAGGGCGGGUGGAGUCCUCGUAGCGAGCCACCUUCAAUCAUUUU<br>UGGAAGUCUCGUACCGGGUGCUGAGACAUCUUGCGCAGCCG<br>UGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGC | |
| G-CSF without a Kozak sequence and with an IRES and human alpha-globin 3'UTR | Optimized G-CSF cDNA sequence containing a T7 polymerase site, IRES and Xba1 restriction site:<br>TAATACGACTCACTATA<br>GGGAAATAAGAGAGAAAAGAAGAGTAAGAAGAAATATAAGA<br>*TCGTGAGGATCTATTTCCGGTGAATTCCTCGAGACTAGTTCTAGAGC<br>GGCCGCGGATCCCGCCCCTCTCCCTCCCCCCCCCCTAACGTTACTG<br>GCCGAAGCCGCTTGGAATAAGGCCGGTGTGCGTTTGTCTATATGTT<br>ATTTTCCACCATATTGCCGTCTTTTGGCAATGTGAGGGCCCGGAAAC<br>CTGGCCCTGTCTTCTTGACGAGCATTCCTAGGGGTCTTTCCCCTCTC<br>GCCAAAGGAATGCAAGGTCTGTTGAATGTCGTGAAGGAAGCAGTTC<br>CTCTGGAAGCTTCTTGAAGACAAACAACGTCTGTAGCGACCCTTTGC<br>AGGCAGCGGAACCCCCCACCTGGCGACAGGTGCCTCTGCGGCCAAA<br>AGCCACGTGTATAAGATACACCTGCAAAGGCGGCACAACCCCAGTG<br>CCACGTTGTGAGTTGGATAGTTGTGGAAAGAGTCAAATGGCTCACC<br>TCAAGCGTATTCAACAAGGGGCTGAAGGATGCCCAGAAGGTACCCC<br>ATTGTATGGGATCTGATCTGGGGCCTCGGTGCACATGCTTTACATGT<br>GTTTAGTCGAGGTTAAAAAACGTCTAGGCCCCCCGAACCACGGGGA<br>CGTGGTTTTCCTTTGAAAAACACGATGATAAT*<br><br><u>ATG</u>GCCGGTCCCGCGACCCAAAGCCCCATGAAACTTATGGCCCTG<br>CAGTTGCTGCTTTGGCACTCGGCCCTCTGGACAGTCCAAGAAGCG<br>ACTCCTCTCGGACCTGCCTCATCGTTGCCGCAGTCATTCCTTTTGA<br>AGTGTCTGGAGCAGGTGCGAAAGATTCAGGGCGATGGAGCCGCAC<br>TCCAAGAGAAGCTCTGCGCGACATACAAACTTTGCCATCCCGAGG<br>AGCTCGTACTGCTCGGGCACAGCTTGGGGATTCCCTGGGCTCCTCT<br>CTCGTCCTGTCCGTCGCAGGCTTTGCAGTTGGCAGGGTGCCTTTCC<br>CAGCTCCACTCCGGTTTGTTCTTGTATCAGGGACTGCTGCAAGCCC<br>TTGAGGGAATCTCGCCAGAATTGGGCCCGACGCTGGACACGTTGC<br>AGCTCGACGTGGCGGATTTCGCAACAACCATCTGGCAGCAGATGG<br>AGGAACTGGGGATGGCACCCGCGCTGCAGCCCACGCAGGGGGCA<br>ATGCCGGCCTTTGCGTCCGCGTTTCAGCGCAGGGCGGGTGGAGTC<br>CTCGTAGCGAGCCACCTTCAATCATTTTTGGAAGTCTCGTACCGGG<br>TGCTGAGACATCTTGCGCAGCCG<br>TGATAATAG<br>GCTGGAGCCTCGGTGGCCATGCTTCTTGCCCCTTGGGCCTCCCCC<br>AGCCCCTCCTCCCCTTCCTGCACCCGTACCCCCGTGGTCTTTGAAT<br>AAAGTCTGAGTGGGCGGCTCTAGA | 27 |

TABLE 9-continued

Constructs

| | Sequence | SEQ ID NO: |
|---|---|---|
| | mRNA sequence (transcribed):<br>GGGAAAUAAGAGAGAAAAGAAGAGUAAGAAGAAAUAUAAGA<br><br>*UCGUGAGGAUCUAUUUCCGGUGAAUUCCUCGAGACUAGUUCUAG<br>AGCGGCCGCGGAUCCCGCCCCUCUCCCUCCCCCCCCCUAACGUU<br>ACUGGCCGAAGCCGCUUGGAAUAAGGCCGGUGUGCGUUUGUCUA<br>UAUGUUAUUUUCCACCAUAUUGCCGUCUUUUGGCAAUGUGAGGG<br>CCCGGAAACCUGGCCCUGUCUUCUUGACGAGCAUUCCUAGGGGUC<br>UUUCCCCUCUCGCCAAAGGAAUGCAAGGUCUGUUGAAUGUCGUG<br>AAGGAAGCAGUUCCUCUGGAAGCUUCUUGAAGACAAACAACGUCU<br>GUAGCGACCCUUUGCAGGCAGCGGAACCCCCCACCUGGCGACAGG<br>UGCCUCUGCGGCCAAAAGCCACGUGUAUAAGAUACACCUGCAAAG<br>GCGGCACAACCCCAGUGCCACGUUGUGAGUUGGAUAGUUGUGGA<br>AAGAGUCAAAUGGCUCACCUCAAGCGUAUUCAACAAGGGGCUGAA<br>GGAUGCCCAGAAGGUACCCCAUUGUAUGGGAUCUGAUCUGGGGC<br>CUCGGUGCACAUGCUUUACAUGUGUUUAGUCGAGGUUAAAAAAC<br>GUCUAGGCCCCCCGAACCACGGGGACGUGGUUUUCCUUUGAAAAA<br>CACGAUGAUAAU*<br><br>AUGGCCGGUCCCGCGACCCAAAGCCCCAUGAAACUUAUGGCCCU<br>GCAGUUGCUGCUUUGGCACUCGGCCCUCUGGACAGUCCAAGAAG<br>CGACUCCUCUCGGACCUGCCUCAUCGUUGCCGCAGUCAUUCCUU<br>UUGAAGUGUCUGGAGCAGGUGCGAAAGAUUCAGGGCGAUGGAG<br>CCGCACUCCAAGAGAAGCUCUGCGCGACAUACAAACUUUGCCAU<br>CCCGAGGAGCUCGUACUGCUCGGGCACAGCUUGGGGAUUCCCUG<br>GGCUCCUCUCUCGUCCUGUCCGUCGCAGGCUUUGCAGUUGGCAG<br>GGUGCCUUUCCCAGCUCCACUCCGGUUUGUUCUUGUAUCAGGGA<br>CUGCUGCAAGCCCUUGAGGGAAUCUCGCCAGAAUUGGGCCCCGAC<br>GCUGGACACGUUGCAGCUCGACGUGGCGGAUUUCGCAACAACCA<br>UCUGGCAGCAGAUGGAGGAACUGGGGAUGGCACCCGCGCUGCAG<br>CCCACGCAGGGGCAAUGCCGGCCUUUGCGUCCGCGUUUCAGCG<br>CAGGGCGGGUGGAGUCCUCGUAGCGAGCCACCUUCAAUCAUUUU<br>UGGAAGUCUCGUACCGGGUGCUGAGACAUCUUGCGCAGCCG<br>UGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGC | 28 |
| G-CSF without a Kozak<br>sequence and with a human<br>alpha-globin 3'UTR | Optimized G-CSF cDNA sequence containing a T7<br>polymerase site, a Kozak sequence and XbaI<br>restriction site:<br>TAATACGACTCACTATA<br>GGGAAATAAGAGAGAAAAGAAGAGTAAGAAGAAATATAAGA<br><br><u>ATG</u>GCCGGTCCCGCGACCCAAAGCCCCATGAAACTTATGGCCCTG<br>CAGTTGCTGCTTTGGCACTCGGCCCTCTGGACAGTCCAAGAAGCG<br>ACTCCTCTCGGACCTGCCTCATCGTTGCCGCAGTCATTCCTTTTGA<br>AGTGTCTGGAGCAGGTGCGAAAGATTCAGGGCGATGGAGCCGCAC<br>TCCAAGAGAAGCTCTGCGCGACATACAAACTTTGCCATCCCGAGG<br>AGCTCGTACTGCTCGGGCACAGCTTGGGGATTCCCTGGGCTCCTCT<br>CTCGTCCTGTCCGTCGCAGGCTTTGCAGTTGGCAGGGTGCCTTTCC<br>CAGCTCCACTCCGGTTTGTTCTTGTATCAGGGACTGCTGCAAGCCC<br>TTGAGGGAATCTCGCCAGAATTGGGCCCGACGCTGGACACGTTGC<br>AGCTCGACGTGGCGGATTTCGCAACAACCATCTGGCAGCAGATGG<br>AGGAACTGGGGATGGCACCCGCGCTGCAGCCCACGCAGGGGGCA<br>ATGCCGGCCTTTGCGTCCGCGTTTCAGCGCAGGGCGGGTGGAGTC<br>CTCGTAGCGAGCCACCTTCAATCATTTTTGGAAGTCTCGTACCGGG<br>TGCTGAGACATCTTGCGCAGCCG<br>TGATAATAG<br>GCTGGAGCCTCGGTGGCCATGCTTCTTGCCCCTTGGGCCTCCCCC<br>AGCCCCTCCTCCCCTTCCTGCACCCGTACCCCCGTGGTCTTTGAAT<br>AAAGTCTGAGTGGGCGGCTCTAGA | 29 |

TABLE 9-continued

Constructs

| | Sequence | SEQ ID NO: |
|---|---|---|
| | mRNA sequence (transcribed):<br>GGGAAAUAAGAGAGAAAAGAAGAGUAAGAAGAAAUAUAAGA<br><u>AUG</u>GCCGGUCCCGCGACCCAAAGCCCCAUGAAACUUAUGGCCCU<br>GCAGUUGCUGCUUUGGCACUCGGCCCUCUGGACAGUCCAAGAAG<br>CGACUCCUCUCGGACCUGCCUCAUCGUUGCCGCAGUCAUUCCUU<br>UUGAAGUGUCUGGAGCAGGUGCGAAAGAUUCAGGGCGAUGGAG<br>CCGCACUCCAAGAGAAGCUCUGCGCGACAUACAAACUUUGCCAU<br>CCCGAGGAGCUCGUACUGCUCGGGCACAGCUUGGGGAUUCCCUG<br>GGCUCCUCUCUCGUCCUGUCCGUCGCAGGCUUUGCAGUUGGCAG<br>GGUGCCUUUCCCAGCUCCACUCCGGUUUGUUCUUGUAUCAGGGA<br>CUGCUGCAAGCCCUUGAGGGAAUCUCGCCAGAAUUGGGCCCGAC<br>GCUGGACACGUUGCAGCUCGACGUGGCGGAUUUCGCAACAACCA<br>UCUGGCAGCAGAUGGAGGAACUGGGGAUGGCACCCGCGCUGCAG<br>CCCACGCAGGGGGCAAUGCCGGCCUUUGCGUCCGCGUUUCAGCG<br>CAGGGCGGGUGGAGUCCUCGUAGCGAGCCACCUUCAAUCAUUUU<br>UGGAAGUCUCGUACCGGGUGCUGAGACAUCUUGCGCAGCCG<br>UGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGC | 30 |
| G-CSF with an IRES, a human alpha-globin 3'UTR and a polyA tail of 80 nucleotides | Optimized G-CSF cDNA sequence containing a T7 polymerase site, IRES, a polyA tail of 80 nucleotides and Asc1 restriction site:<br>TAATACGACTCACTATA<br>GGGAAATAAGAGAGAAAAGAAGAGTAAGAAGAAATATAAGAGCC<br>ACC<br>*TCGTGAGGATCTATTTCCGGTGAATTCCTCGAGACTAGTTCTAGAGC*<br>*GGCCGCGGATCCCGCCCCTCTCCCTCCCCCCCCCCTAACGTTACTG*<br>*GCCGAAGCCGCTTGGAATAAGGCCGGTGTGCGTTTGTCTATATGTT*<br>*ATTTTCCACCATATTGCCGTCTTTTGGCAATGTGAGGGCCCGGAAAC*<br>*CTGGCCCTGTCTTCTTGACGAGCATTCCTAGGGGTCTTTCCCCTCTC*<br>*GCCAAAGGAATGCAAGGTCTGTTGAATGTCGTGAAGGAAGCAGTTC*<br>*CTCTGGAAGCTTCTTGAAGACAAACAACGTCTGTAGCGACCCTTTGC*<br>*AGGCAGCGGAACCCCCCACCTGGCGACAGGTGCCTCTGCGGCCAAA*<br>*AGCCACGTGTATAAGATACACCTGCAAAGGCGGCACAACCCCAGTG*<br>*CCACGTTGTGAGTTGGATAGTTGTGGAAAGAGTCAAATGGCTCACC*<br>*TCAAGCGTATTCAACAAGGGGCTGAAGGATGCCCAGAAGGTACCCC*<br>*ATTGTATGGGATCTGATCTGGGGCCTCGGTGCACATGCTTTACATGT*<br>*GTTTAGTCGAGGTTAAAAAACGTCTAGGCCCCCCGAACCACGGGGA*<br>*CGTGGTTTTCCTTTGAAAAACACGATGATAAT*<br><u>ATG</u>GCCGGTCCCGCGACCCAAAGCCCCATGAAACTTATGGCCCTG<br>CAGTTGCTGCTTTGGCACTCGGCCCTCTGGACAGTCCAAGAAGCG<br>ACTCCTCTCGGACCTGCCTCATCGTTGCCGCAGTCATTCCTTTTGA<br>AGTGTCTGGAGCAGGTGCGAAAGATTCAGGGCGATGGAGCCGCAC<br>TCCAAGAGAAGCTCTGCGCGACATACAAACTTTGCCATCCCGAGG<br>AGCTCGTACTGCTCGGGCACAGCTTGGGGATTCCCTGGGCTCCTCT<br>CTCGTCCTGTCCGTCGCAGGCTTTGCAGTTGGCAGGGTGCCTTTCC<br>CAGCTCCACTCCGGTTTGTTCTTGTATCAGGGACTGCTGCAAGCCC<br>TTGAGGGAATCTCGCCAGAATTGGGCCCGACGCTGGACACGTTGC<br>AGCTCGACGTGGCGGATTTCGCAACAACCATCTGGCAGCAGATGG<br>AGGAACTGGGGATGGCACCCGCGCTGCAGCCCACGCAGGGGGCA<br>ATGCCGGCCTTTGCGTCCGCGTTTCAGCGCAGGGCGGGTGGAGTC<br>CTCGTAGCGAGCCACCTTCAATCATTTTTGGAAGTCTCGTACCGGG<br>TGCTGAGACATCTTGCGCAGCCG<br>TGATAATAG<br>GCTGGAGCCTCGGTGGCCATGCTTCTTGCCCCTTGGGCCTCCCCC<br>AGCCCCTCCTCCCCTTCCTGCACCCGTACCCCCGTGGTCTTTGAAT<br>AAAGTCTGAGTGGGCGGCAAAAAAAAAAAAAAAAAAAAAAAA<br>AAAAAAAAAAAAAAAAAAAAAAAAAAAAAAAAAAAAAAA<br>AAAAAAAAAAAGGCGCGCC | 31 |
| | mRNA sequence (transcribed):<br>GGGAAAUAAGAGAGAAAAGAAGAGUAAGAAGAAAUAUAAGAGCC<br>ACC | 32 |

TABLE 9-continued

Constructs

| Sequence | SEQ ID NO: |
|---|---|
| UCGUGAGGAUCUAUUUCCGGUGAAUUCCUCGAGACUAGUUCUAG AGCGGCCGCGGAUCCCGCCCCUCUCCCUCCCCCCCCCUAACGUU ACUGGCCGAAGCCGCUUGGAAUAAGGCCGGUGUGCGUUUGUCUA UAUGUUAUUUUCCACCAUAUUGCCGUCUUUUGGCAAUGUGAGGG CCCGGAAACCUGGCCCUGUCUUCUUGACGAGCAUUCCUAGGGGUC UUUCCCCUCUCGCCAAAGGAAUGCAAGGUCUGUUGAAUGUCGUG AAGGAAGCAGUUCCUCUGGAAGCUUCUUGAAGACAAACAACGUCU GUAGCGACCCUUUGCAGGCAGCGGAACCCCCCACCUGGCGACAGG UGCCUCUGCGGCCAAAAGCCACGUGUAUAAGAUACACCUGCAAAG GCGGCACAACCCCAGUGCCACGUUGUGAGUUGGAUAGUUGUGGA AAGAGUCAAAUGGCUCACCUCAAGCGUAUUCAACAAGGGGCUGAA GGAUGCCCAGAAGGUACCCCAUUGUAUGGGAUCUGAUCUGGGGC CUCGGUGCACAUGCUUUACAUGUGUUUAGUCGAGGUUAAAAAAC GUCUAGGCCCCCCGAACCACGGGGACGUGGUUUUCCUUUGAAAAA CACGAUGAUAAU | |
| AUGGCCGGUCCCGCGACCCAAAGCCCCAUGAAACUUAUGGCCCU GCAGUUGCUGCUUUGGCACUCGGCCCUCUGGACAGUCCAAGAAG CGACUCCUCUCGGACCUGCCUCAUCGUUGCCGCAGUCAUUCCUU UUGAAGUGUCUGGAGCAGGUGCGAAAGAUUCAGGGCGAUGGAG CCGCACUCCAAGAGAAGCUCUGCGCGACAUACAAACUUUGCCAU CCCGAGGAGCUCGUACUGCUCGGGCACAGCUUGGGGAUUCCCUG GGCUCCUCUCUCGUCCUGUCCGUCGCAGGCUUUGCAGUUGGCAG GGUGCCUUUCCCAGCUCCACUCCGGUUUGUUCUUGUAUCAGGGA CUGCUGCAAGCCCUUGAGGGAAUCUCGCCAGAAUUGGGCCCGAC GCUGGACACGUUGCAGCUCGACGUGGCGGAUUUCGCAACAACCA UCUGGCAGCAGAUGGAGGAACUGGGGAUGGCACCCGCGCUGCAG CCCACGCAGGGGGCAAUGCCGGCCUUUGCGUCCGCGUUUCAGCG CAGGGCGGGUGGAGUCCUCGUAGCGAGCCACCUUCAAUCAUUUU UGGAAGUCUCGUACCGGGUGCUGAGACAUCUUGCGCAGCCG UGAUAAUAG GCUGGAGCCUCGGUGGCCAUGCUUCUUGCCCCUUGGGCCUCCCC CCAGCCCUCCUCCCCUUCCUGCACCCGUACCCCCGUGGUCUUUG AAUAAAGUCUGAGUGGGCGGC AAAAAAAAAAAAAAAAAAAAAAAAAAAAAAAAAAAAAAAAAA AAAAAAAAAAAAAAAAAAAAAAAAAAAAAAAA | |
| G-CSF without a Kozak sequence and with an IRES, a human alpha-globin 3'UTR and a polyA tail of 80 nucleotides | Optimized G-CSF cDNA sequence containing a T7 polymerase site, an IRES sequence, a polyA tail of 80 nucleotides and Asc1 restriction site:<br>TAATACGACTCACTATA GGGAAATAAGAGAGAAAAGAAGAGTAAGAAGAAATATAAGA TCGTGAGGATCTATTTCCGGTGAATTCCTCGAGACTAGTTCTAGAGC GGCCGCGGATCCCGCCCCTCTCCCTCCCCCCCCCCTAACGTTACTG GCCGAAGCCGCTTGGAATAAGGCCGGTGTGCGTTTGTCTATATGTT ATTTTCCACCATATTGCCGTCTTTTGGCAATGTGAGGGCCCGGAAAC CTGGCCCTGTCTTCTTGACGAGCATTCCTAGGGGTCTTTCCCCTCTC GCCAAAGGAATGCAAGGTCTGTTGAATGTCGTGAAGGAAGCAGTTC CTCTGGAAGCTTCTTGAAGACAAACAACGTCTGTAGCGACCCTTTGC AGGCAGCGGAACCCCCCACCTGGCGACAGGTGCCTCTGCGGCCAAA AGCCACGTGTATAAGATACACCTGCAAAGGCGGCACAACCCCAGTG CCACGTTGTGAGTTGGATAGTTGTGGAAAGAGTCAAATGGCTCACC TCAAGCGTATTCAACAAGGGGCTGAAGGATGCCCAGAAGGTACCCC ATTGTATGGGATCTGATCTGGGGCCTCGGTGCACATGCTTTACATGT GTTTAGTCGAGGTTAAAAAACGTCTAGGCCCCCCGAACCACGGGGA CGTGGTTTTCCTTTGAAAAACACGATGATAAT | 33 |

TABLE 9-continued

Constructs

| Sequence | SEQ ID NO: |
|---|---|

ATGGCCGGTCCCGCGACCCAAAGCCCCATGAAACTTATGGCCCTG
CAGTTGCTGCTTTGGCACTCGGCCCTCTGGACAGTCCAAGAAGCG
ACTCCTCTCGGACCTGCCTCATCGTTGCCGCAGTCATTCCTTTTGA
AGTGTCTGGAGCAGGTGCGAAAGATTCAGGGCGATGGAGCCGCAC
TCCAAGAGAAGCTCTGCGCGACATACAAACTTTGCCATCCCGAGG
AGCTCGTACTGCTCGGGCACAGCTTGGGGATTCCCTGGGCTCCTCT
CTCGTCCTGTCCGTCGCAGGCTTTGCAGTTGGCAGGGTGCCTTTCC
CAGCTCCACTCCGGTTTGTTCTTGTATCAGGGACTGCTGCAAGCCC
TTGAGGGAATCTCGCCAGAATTGGGCCCGACGCTGGACACGTTGC
AGCTCGACGTGGCGGATTTCGCAACAACCATCTGGCAGCAGATGG
AGGAACTGGGGATGGCACCCGCGCTGCAGCCCACGCAGGGGGCA
ATGCCGGCCTTTGCGTCCGCGTTTCAGCGCAGGGCGGGTGGAGTC
CTCGTAGCGAGCCACCTTCAATCATTTTTGGAAGTCTCGTACCGGG
TGCTGAGACATCTTGCGCAGCCG
TGATAATAG
GCTGGAGCCTCGGTGGCCATGCTTCTTGCCCCTTGGGCCTCCCCC
AGCCCCTCCTCCCCTTCCTGCACCCGTACCCCCGTGGTCTTTGAAT
AAAGTCTGAGTGGGCGGCAAAAAAAAAAAAAAAAAAAAAAAAAA
AAAAAAAAAAAAAAAAAAAAAAAAAAAAAAAAAAAAAAAAAAAA
AAAAAAAAAAAGGCGCGCC

| mRNA sequence (transcribed): | 34 |
|---|---|

GGGAAAUAAGAGAGAAAAGAAGAGUAAGAAGAAAUAUAAGA
UCGUGAGGAUCUAUUUCCGGUGAAUUCCUCGAGACUAGUUCUAG
AGCGGCCGCGGAUCCCGCCCCUCUCCCUCCCCCCCCCCUAACGUU
ACUGGCCGAAGCCGCUUGGAAUAAGGCCGGUGUGCGUUUGUCUA
UAUGUUAUUUUCCACCAUAUUGCCGUCUUUUGGCAAUGUGAGGG
CCCGGAAACCUGGCCCUGUCUUCUUGACGAGCAUUCCUAGGGGUC
UUUCCCCUCUCGCCAAAGGAAUGCAAGGUCUGUUGAAUGUCGUG
AAGGAAGCAGUUCCUCUGGAAGCUUCUUGAAGACAAACAACGUCU
GUAGCGACCCUUUGCAGGCAGCGGAACCCCCCACCUGGCGACAGG
UGCCUCUGCGGCCAAAAGCCACGUGUAUAAGAUACACCUGCAAAG
GCGGCACAACCCCAGUGCCACGUUGUGAGUUGGAUAGUUGUGGA
AAGAGUCAAAUGGCUCACCUCAAGCGUAUUCAACAAGGGGCUGAA
GGAUGCCCAGAAGGUACCCCAUUGUAUGGGAUCUGAUCUGGGGC
CUCGGUGCACAUGCUUUACAUGUGUUUAGUCGAGGUUAAAAAAC
GUCUAGGCCCCCGAACCACGGGGACGUGGUUUUCCUUUGAAAAA
CACGAUGAUAAU

AUGGCCGGUCCCGCGACCCAAAGCCCCAUGAAACUUAUGGCCCU
GCAGUUGCUGCUUUGGCACUCGGCCCUCUGGACAGUCCAAGAAG
CGACUCCUCUCGGACCUGCCUCAUCGUUGCCGCAGUCAUUCCUU
UUGAAGUGUCUGGAGCAGGUGCGAAAGAUUCAGGGCGAUGGAG
CCGCACUCCAAGAGAAGCUCUGCGCGACAUACAAACUUUGCCAU
CCCGAGGAGCUCGUACUGCUCGGGCACAGCUUGGGGAUUCCCUG
GGCUCCUCUCUCGUCCUGUCCGUCGCAGGCUUUGCAGUUGGCAG
GGUGCCUUUCCCAGCUCCACUCCGGUUUGUUCUUGUAUCAGGGA
CUGCUGCAAGCCCUUGAGGGAAUCUCGCCAGAAUUGGGCCCGAC
GCUGGACACGUUGCAGCUCGACGUGGCGGAUUUCGCAACAACCA
UCUGGCAGCAGAUGGAGGAACUGGGGAUGGCACCCGCGCUGCAG
CCCACGCAGGGGCAAUGCCGGCCUUUGCGUCCGCGUUUCAGCG
CAGGGCGGGUGGAGUCCUCGUAGCGAGCCACCUUCAAUCAUUUU
UGGAAGUCUCGUACCGGGUGCUGAGACAUCUUGCGCAGCCG
UGAUAAUAG
GCUGGAGCCUCGGUGGCCAUGCUUCUUGCCCCUUGGGCCUCCCC
CCAGCCCCUCCUCCCCUUCCUGCACCCGUACCCCCGUGGUCUUUG
AAUAAAGUCUGAGUGGGCGGCAAAAAAAAAAAAAAAAAAAAAA
AAAAAAAAAAAAAAAAAAAAAAAAAAAAAAAAAAAAAAAAAAA
AAAAAAAAAAAAA

| G-CSF with a human alpha-globin 3'UTR and a polyA tail of 80 nucleotides | Optimized G-CSF cDNA sequence containing a T7 polymerase site, a polyA tail of 80 nucleotides and Asc1 restriction site:<br>TAATACGACTCACTATA<br>GGGAAATAAGAGAGAAAAGAAGAGTAAGAAGAAATATAAGAGCC<br>ACC | 35 |

TABLE 9-continued

Constructs

| | Sequence | SEQ ID NO: |
|---|---|---|
| | ATGGCCGGTCCCGCGACCCAAAGCCCCATGAAACTTATGGCCCTG<br>CAGTTGCTGCTTTGGCACTCGGCCCTCTGGACAGTCCAAGAAGCG<br>ACTCCTCTCGGACCTGCCTCATCGTTGCCGCAGTCATTCCTTTTGA<br>AGTGTCTGGAGCAGGTGCGAAAGATTCAGGGCGATGGAGCCGCAC<br>TCCAAGAGAAGCTCTGCGCGACATACAAACTTTGCCATCCCGAGG<br>AGCTCGTACTGCTCGGGCACAGCTTGGGGATTCCCTGGGCTCCTCT<br>CTCGTCCTGTCCGTCGCAGGCTTTGCAGTTGGCAGGGTGCCTTTCC<br>CAGCTCCACTCCGGTTTGTTCTTGTATCAGGGACTGCTGCAAGCCC<br>TTGAGGGAATCTCGCCAGAATTGGGCCCGACGCTGGACACGTTGC<br>AGCTCGACGTGGCGGATTTCGCAACAACCATCTGGCAGCAGATGG<br>AGGAACTGGGGATGGCACCCGCGCTGCAGCCCACGCAGGGGGCA<br>ATGCCGGCCTTTGCGTCCGCGTTTCAGCGCAGGGCGGGTGGAGTC<br>CTCGTAGCGAGCCACCTTCAATCATTTTTGGAAGTCTCGTACCGGG<br>TGCTGAGACATCTTGCGCAGCCG<br>TGATAATAG<br>GCTGGAGCCTCGGTGGCCATGCTTCTTGCCCCTTGGGCCTCCCCC<br>AGCCCCTCCTCCCCTTCCTGCACCCGTACCCCCGTGGTCTTTGAAT<br>AAAGTCTGAGTGGGCGGCAAAAAAAAAAAAAAAAAAAAAAAA<br>AAAAAAAAAAAAAAAAAAAAAAAAAAAAAAAAAAAAAAAA<br>AAAAAAAAAAAGGCGCGCC | |
| | mRNA sequence (transcribed):<br>GGGAAAUAAGAGAGAAAAGAAGAGUAAGAAGAAAUAUAAGAGC<br>CACC<br>AUGGCCGGUCCCGCGACCCAAAGCCCCAUGAAACUUAUGGCCCU<br>GCAGUUGCUGCUUUGGCACUCGGCCCUCUGGACAGUCCAAGAAG<br>CGACUCCUCUCGGACCUGCCUCAUCGUUGCCGCAGUCAUUCCUU<br>UUGAAGUGUCUGGAGCAGGUGCGAAAGAUUCAGGGCGAUGGAG<br>CCGCACUCCAAGAGAAGCUCUGCGCGACAUACAAACUUUGCCAU<br>CCCGAGGAGCUCGUACUGCUCGGGCACAGCUUGGGGAUUCCCUG<br>GCUCCUCUCUCGUCCUGUCCGUCGCAGGCUUUGCAGUUGGCAG<br>GGUGCCUUUCCCAGCUCCACUCCGGUUUGUUCUUGUAUCAGGGA<br>CUGCUGCAAGCCCUUGAGGGAAUCUCGCCAGAAUUGGGCCCGAC<br>GCUGGACACGUUGCAGCUCGACGUGGCGGAUUUCGCAACAACCA<br>UCUGGCAGCAGAUGGAGGAACUGGGGAUGGCACCCGCGCUGCAG<br>CCCACGCAGGGGCAAUGCCGGCCUUUGCGUCCGCGUUUCAGCG<br>CAGGGCGGGUGGAGUCCUCGUAGCGAGCCACCUUCAAUCAUUUU<br>UGGAAGUCUCGUACCGGGUGCUGAGACAUCUUGCGCAGCCG<br>UGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGCAAAAAAAAAAAAAAAAAAAAAA<br>AAAAAAAAAAAAAAAAAAAAAAAAAAAAAAAAAAAAAAAA<br>AAAAAAAAAAAAAA | 36 |
| G-CSF without a kozak sequence and with a human alpha-globin 3′UTR and a polyA tail of 80 nucleotides | Optimized G-CSF cDNA sequence containing a T7 polymerase site, a polyA tail of 80 nucleotides and Asc1 restriction site:<br>TAATACGACTCACTATA<br>GGGAAATAAGAGAGAAAAGAAGAGTAAGAAGAAATATAAGA<br>ATGGCCGGTCCCGCGACCCAAAGCCCCATGAAACTTATGGCCCTG<br>CAGTTGCTGCTTTGGCACTCGGCCCTCTGGACAGTCCAAGAAGCG<br>ACTCCTCTCGGACCTGCCTCATCGTTGCCGCAGTCATTCCTTTTGA<br>AGTGTCTGGAGCAGGTGCGAAAGATTCAGGGCGATGGAGCCGCAC<br>TCCAAGAGAAGCTCTGCGCGACATACAAACTTTGCCATCCCGAGG<br>AGCTCGTACTGCTCGGGCACAGCTTGGGGATTCCCTGGGCTCCTCT<br>CTCGTCCTGTCCGTCGCAGGCTTTGCAGTTGGCAGGGTGCCTTTCC<br>CAGCTCCACTCCGGTTTGTTCTTGTATCAGGGACTGCTGCAAGCCC<br>TTGAGGGAATCTCGCCAGAATTGGGCCCGACGCTGGACACGTTGC<br>AGCTCGACGTGGCGGATTTCGCAACAACCATCTGGCAGCAGATGG<br>AGGAACTGGGGATGGCACCCGCGCTGCAGCCCACGCAGGGGGCA<br>ATGCCGGCCTTTGCGTCCGCGTTTCAGCGCAGGGCGGGTGGAGTC<br>CTCGTAGCGAGCCACCTTCAATCATTTTTGGAAGTCTCGTACCGGG<br>TGCTGAGACATCTTGCGCAGCCG<br>TGATAATAG<br>GCTGGAGCCTCGGTGGCCATGCTTCTTGCCCCTTGGGCCTCCCCC<br>AGCCCCTCCTCCCCTTCCTGCACCCGTACCCCCGTGGTCTTTGAAT<br>AAAGTCTGAGTGGGCGGCAAAAAAAAAAAAAAAAAAAAAAAA<br>AAAAAAAAAAAAAAAAAAAAAAAAAAAAAAAAAAAAAAAA<br>AAAAAAAAAAAGGCGCGCC | 37 |

TABLE 9-continued

Constructs

| Sequence | SEQ ID NO: |
|---|---|
| mRNA sequence (transcribed):<br>GGGAAAUAAGAGAGAAAAGAAGAGUAAGAAGAAAUAUAAGA<br>AUGGCCGGUCCCGCGACCCAAAGCCCCAUGAAACUUAUGGCCCU<br>GCAGUUGCUGCUUUGGCACUCGGCCCUCUGGACAGUCCAAGAAG<br>CGACUCCUCUCGGACCUGCCUCAUCGUUGCCGCAGUCAUUCCUU<br>UUGAAGUGUCUGGAGCAGGUGCGAAAGAUUCAGGGCGAUGGAG<br>CCGCACUCCAAGAGAAGCUCUGCGCGACAUACAAACUUUGCCAU<br>CCCGAGGAGCUCGUACUGCUCGGGCACAGCUUGGGGAUUCCCUG<br>GGCUCCUCUCUCGUCCUGUCCGUCGCAGGCUUUGCAGUUGGCAG<br>GGUGCCUUUCCCAGCUCCACUCCGGUUUGUUCUUGUAUCAGGGA<br>CUGCUGCAAGCCCUUGAGGGAAUCUCGCCAGAAUUGGGCCCGAC<br>GCUGGACACGUUGCAGCUCGACGUGGCGGAUUUCGCAACAACCA<br>UCUGGCAGCAGAUGGAGGAACUGGGGAUGGCACCCGCGCUGCAG<br>CCCACGCAGGGGCAAUGCCGGCCUUUGCGUCCGCGUUUCAGCG<br>CAGGGCGGGUGGAGUCCUCGUAGCGAGCCACCUUCAAUCAUUUU<br>UGGAAGUCUCGUACCGGGUGCUGAGACAUCUUGCGCAGCCG<br>UGAUAAUAG<br>GCUGGAGCCUCGGUGGCCAUGCUUCUUGCCCCUUGGGCCUCCCC<br>CCAGCCCCUCCUCCCCUUCCUGCACCCGUACCCCCGUGGUCUUUG<br>AAUAAAGUCUGAGUGGGCGGCAAAAAAAAAAAAAAAAAAAAA<br>AAAAAAAAAAAAAAAAAAAAAAAAAAAAAAAAAAAAAAAA<br>AAAAAAAAAAAAAAA | 38 |

Example 12. Effect of Kozak Sequence on Expression of Modified Nucleic Acids

HeLa cells were seeded at a density of 17000 per well in 100 ul cell culture medium (DMEM+10% FBS). G-CSF mRNA having an IRES sequence and Kozak sequence (G-CSF IRES Kozak; mRNA sequence shown in SEQ ID NO: 25; polyA tail of approximately 140 nucleotides not shown in sequence; 5' cap, Cap1), G-CSF mRNA having an IRES sequence but not a Kozak sequence (G-CSF IRES; mRNA sequence shown in SEQ ID NO: 27; polyA tail of approximately 140 nucleotides not shown in sequence; 5' cap, Cap1), G-CSF mRNA without an IRES or Kozak sequence (GCSF no Kozak; mRNA sequence shown in SEQ ID NO: 29; polyA tail of approximately 140 nucleotides not shown in sequence; 5' cap, Cap1) or a G-CSF sequence having a Kozak sequence (G-CSF Kozak; mRNA sequence shown in SEQ ID NO: 31; polyA tail of approximately 140 nucleotides not shown in sequence; 5' cap, Cap1) were fully modified with fully modified with 5-methylcytosine and 1-methylpseudouridine and tested at a concentration of 75 ng per well in 24 well plates. 24 hours after transfection, the expression of G-CSF was measured by ELISA, and the results are shown in Table 10.

TABLE 10

G-CSF expression

| Description | Protein Expression (ng/ml) |
|---|---|
| G-CSF IRES Kozak | 2.01 |
| G-CSF IRES | 1.64 |
| G-CSF no Kozak | 795.53 |
| G-CSF Kozak | 606.28 |

Example 13. Cyclization and/or Concatemerization

According to the present invention, a chimeric polynucleotide may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the nucleic acid contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase may be used to enzymatically link a 5'-phosphorylated nucleic acid molecule to the 3'-hydroxyl group of a nucleic acid forming a new phosphorodiester linkage. In an example reaction, 1 μg of a nucleic acid molecule is incubated at 37° C. for 1 hour with 1-10 units of T4 RNA ligase (New England Biolabs, Ipswich, Mass.) according to the manufacturer's protocol. The ligation reaction may occur in the presence of a split polynucleotide capable of base-pairing with both the 5'- and 3'-region in juxtaposition to assist the enzymatic ligation reaction.

In the third route, either the 5'- or 3'-end of the cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

Example 14. Chimeric Synthesis of RNA

Chimeric RNA molecules may be designed and/or synthesized prior to circularization.

A. Capping

The RNA (220 µL) eluted from the IVT step is denatured by heating to 65° C. for 15 minutes followed by cooling on ice for at least 2 min. The capping reaction is performed in 300 µL with the denatured RNA (220 µL), GTP (1 mM), SAM (0.5 mM), RNase Inhibitor (1 U/µL), 1× Capping buffer, and Vaccinia capping complex (0.4 U/µL) (NEB). These reactions are incubated at 37° C. for 2 hr on the thermomixer. The reactions are purified using MEGAclear spin columns (Ambion) and eluted in 250 µL water. The eluted mRNA was analyzed by CE (Agilent 2100 Bioanalyzer) and quantified by UV absorbance.

B. Incorporation of 3'-azido-2',3'-dideoxyadenosine-5'-triphosphate (3'-azido-ddATP)

3'-azido-ddATP is incorporated into the 3'-end of tailless RNA using yeast poly(A) polymerase as depicted in the following scheme (Scheme 1), which illustrates the general synthesis of 3'-azido RNA by incorporation of 3'-azido ddATP onto the 3'-end of RNA using yeast poly(A) polymerase.

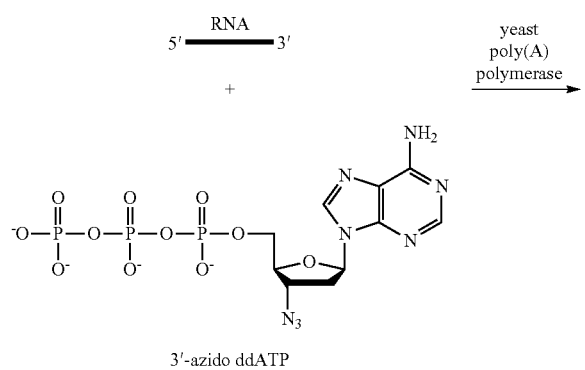

3'-azido ddATP

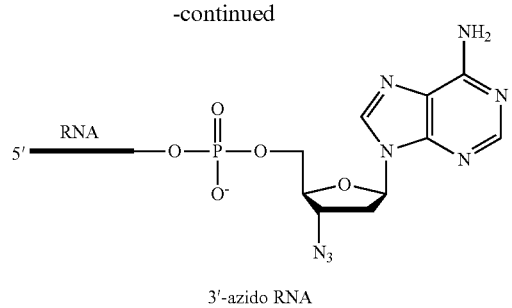

3'-azido RNA

In 100 µL reactions, RNA transcript (0.2 µM), 3'-azido-ddATP (500 µM), murine RNase inhibitor (NEB) (1 U/µL), 1x reaction buffer (20 mM Tris-HCl, pH 7.0, 0.6 mM $MnCl_2$, 20 µM EDTA, 0.2 mM DTT, 100 µg/mL acetylated BSA, 10% glycerol), and yeast poly(A) polymerase (2400 U, Affymetrix) are incubated at 37° C. for 1 hr, followed by ethanol precipitation. The RNA is dissolved in 100 µL DEPC-treated $H_2O$ and further purified by gel filtration using an illustra NICK column or illustra MicroSpin G-25 column (GE Healthcare).

The RNA is concentrated, if necessary, by ultrafiltration using an Amicon Ultra-0.5 centrifugal device (100K NMWL), quantified by UV absorbance, and analyzed by capillary electrophoresis (CE) (Agilent 2100 Bioanalyzer). The RNA obtained at this point is a mixture of unmodified and 3'-azido RNA which cannot be distinguished by CE, and this mixture is used without further purification in subsequent reactions.

C. Synthesis of 5'-Bicyclo[6.1.0]Nonyne (BCN) Poly(A) Tails 1-6

5'-bicyclo[6.1.0]nonyne (BCN) poly(A) tails 1-6 are synthesized for generating RNA-poly(A) tail conjugates using strain-promoted azide-alkyne cycloaddition (SPAAC) chemistry. The following scheme (Scheme 2) shows the structures of 5'-BCN poly(A) tails 1-6. Tails 1-3 are stabilized on the 3' end with two 2'-OMe A's and an inverted T. Tails 4-6 contain only A.

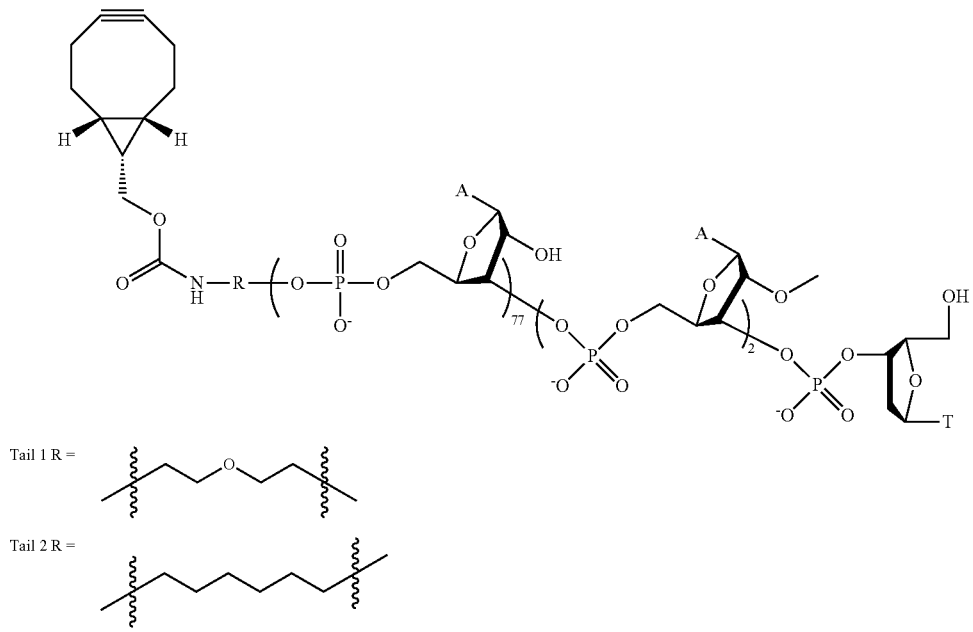

-continued
Tail 3 R = 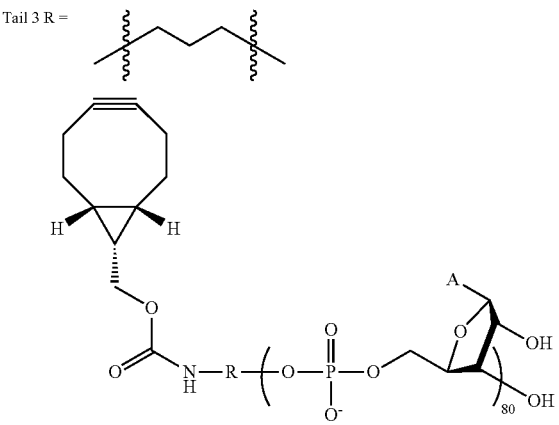
Tail 4 R = 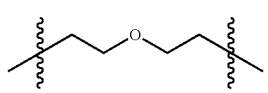
Tail 5 R = 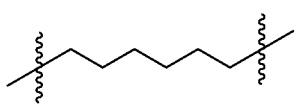
Tail 6 R = 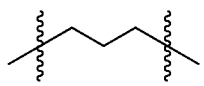
Tail 7
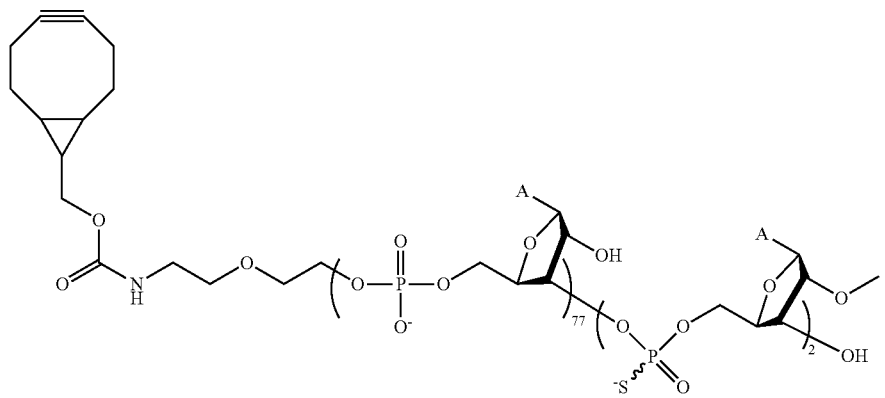
Tail 8
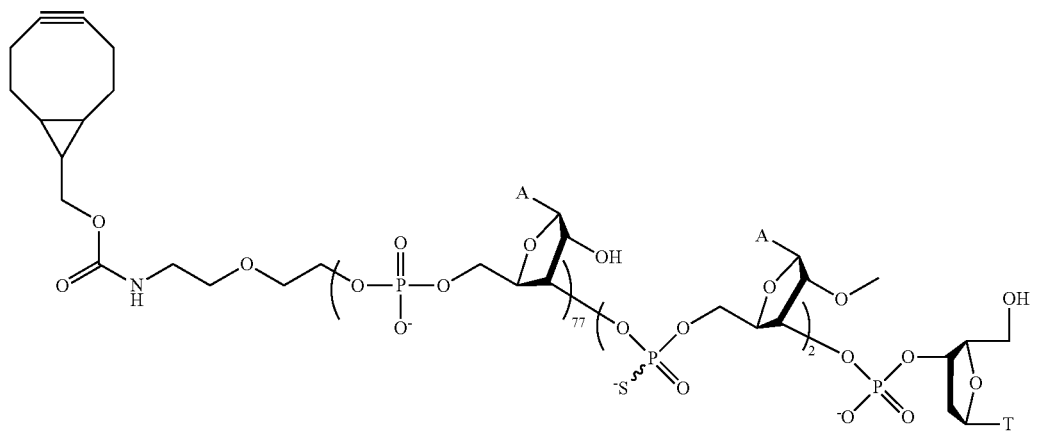

While tails 1 and 4 could be synthesized directly by solid phase phosphoramidite oligomerization technology, tails 2, 3, 5, and 6 are first synthesized as the 5'-amino derivatives (tails 2a, 3a, 5a, and 6a) which are then coupled to the reactive BCN group via NHS chemistry. The following scheme (Scheme 3) illustrates the synthesis of tails 2, 3, 5, and 6 by coupling the corresponding 5'-amino oligoribonucleotides to the BCN N-hydroxysuccinimide ester I.

Freiburg, Germany) Buffer A was 100 mM triethylammonium acetate (Biosolve, Valkenswaard, The Netherlands) and buffer B contained 95% acetonitrile in buffer A. A flow rate of 15 mL/min is employed. UV traces at 260 and 280 were recorded. A gradient of 5% B to 45% B within 57 column volumes was employed. Appropriate fractions are pooled and precipitated with 3M NaOAc, pH=5.2 and 70% ethanol. The pellet is isolated by centrifugation, dissolved in Scheme 3

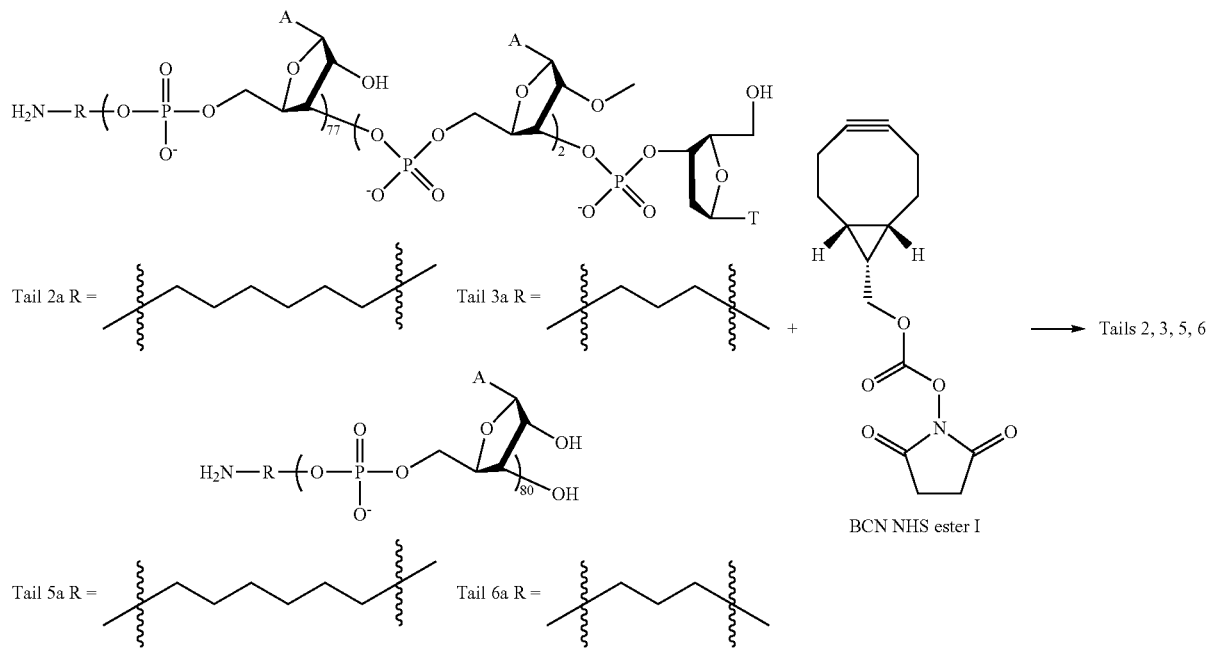

Tails 1, 2a, 3a, 4, 5a, 6a, 7 and 8 are assembled on an Expedite 8909 DNA/RNA synthesizer (Perseptive) employing solid phase phosphoramidite oligomerization technology. Syntheses are initiated on a solid support made of controlled pore glass (CPG, 1000Å) with either immobilized 3'-O-dimethoxytrityl-thymidine at a loading of 31 µmol/g (obtained from Prime Synthesis, Aston, Pa., USA) generating a 3'-3'-linkage at the 3'-end or immobilized 5'-0-dimethoxytrityl-adenosine loaded at 32 µmol/g (Chemgenes, Wilmington, Mass.; USA).

In order to introduce an amino-linker at the 5'-end either a trifluoracetyl (TFA)-protected aminohexyl phosphoramidite (SAFC Proligo, Hamburg, Germany) or the corresponding propyl derivative from Glen Research (Sterling, Va., USA) is employed. All amidites are dissolved in anhydrous acetonitrile (100 mM) and molecular sieves (3 Å) are added. 5-Ethyl thiotetrazole (ETT, 500 mM in acetonitrile) is used as activator solution. Coupling times are 5 minutes for the nucleoside phosphoramidites and 12 minutes for the linker amidites. Ancillary reagents for RNA synthesis are purchased from SAFC Proligo (Hamburg, Germany). After finalization of the solid phase synthesis, the dried solid support is transferred to a 15 mL polypropylene tube and the RNA is cleaved from the solid support and deprotected by methods known in the field (Wincott F., et al, Nucleic Acid Res., 1995, 23, 2677-84).

Crude oligomers are purified by RP HPLC using an XBridge C18 19×50 mm column (Waters, Eschborn, Germany) on an AKTA Explorer system (GE Healthcare, water and the concentration of the solution is determined by absorbance measurement at 260 nm in a UV photometer (Eppendorf, Germany).

For the coupling step to produce tails 2, 3, 5, and 6 by NHS chemistry as depicted in Scheme 3 above, the respective amine-modified oligoribonucleotide is dissolved in 100 mM sodium borate/KCl buffer (pH 8.5) to yield a concentration of 500 µM. Click-Easy® BCN N-hydroxysuccinimide ester I (5 mg, Berry & Associates, Inc., Dexter; MI, USA) is dissolved in 50 µL DMSO. The reaction is initiated by addition of about 3 equivalents BCN derivative to the RNA solution. The progress of the reaction is monitored by the change of retention time on an anion exchange HPLC column (Dionex DNA Pac PA200, 4×250 mm, Dionex, Idstein, Germany). After completion of the reaction the oligoribonucleotide conjugate is precipitated using 3 M NaOAc (pH 5.2)/EtOH and purified on a C18 XBridge reversed phase HPLC column (Waters, Eschborn, Germany).

D. Poly(A) Tail Conjugation Using Strain-Promoted Azide-Alkyne Cycloaddition (SPAAC)

RNA transcripts modified on the 3'-end with 3'-azido-ddATP are ligated to 80 nt 5'-BCN poly(A) tails using strain-promoted azide-alkyne cycloaddition (SPAAC) to give RNA-poly(A) tail conjugates of the general form shown in the following scheme (Scheme 4). The scheme shows the general synthesis of RNA-poly(A) tail conjugates by SPAAC with 3'-azido RNA and 5'-BCN poly(A) tail.

Scheme 4

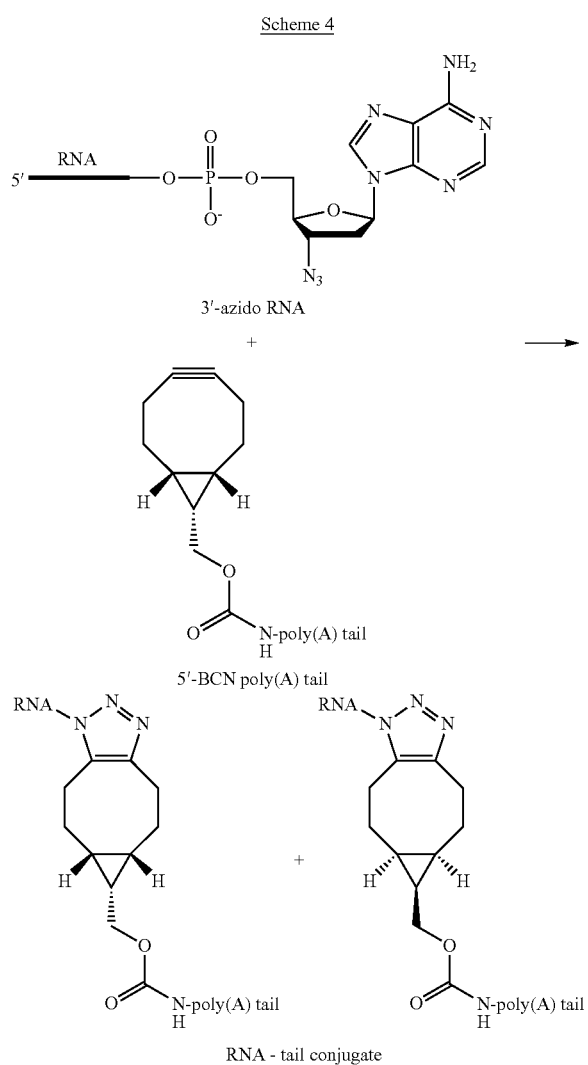

RNA - tail conjugate

3'-azido RNA and tail 1 are mixed in at least a 1:50 molar ratio, respectively, in water and diluted with ethanol to a final concentration of 70% ethanol. Generally, the concentration of 3'-azido RNA is between 150-400 nM in the reaction mixture. The reactions are shaken at room temperature for 1 hr, diluted with water to 200 μL if necessary, ethanol precipitated, and dissolved in DEPC-treated water.

Alternatively, the reactions are purified by MEGAclear kit (Ambion) and eluted in water. The RNA reaction mixture is analyzed by CE (Agilent 2100 Bioanalyzer).

Conjugates may also be made in this manner with RNA which already contain a poly(A) tail through transcription by T7 RNA polymerase, and tails 1 and 4.

In order to remove excess unreacted 5'-BCN tail, the reaction mixture is reacted with biotin azide (500 μM) in 10% DMSO by shaking for 1 hr at room temperature, followed by a MEGAclear purification.

The reaction mixture is then subjected to streptavidin capture with M-280 Streptavidin Dynabeads (Life Technologies). The beads (200 μL, 2 mg) are washed with a high salt buffer (10 mM Tris-HCl, pH 7.4, 0.5 M NaCl, and 1 mM EDTA) three times and resuspended in 200 μL high salt buffer. The reaction mixture, which contains approximately 1.3 nmol 5'-BCN tail, is diluted to 200 μL for a final concentration of 1× high salt buffer, and added to the beads. The sample and beads are mixed at room temperature for 15 min. This supernatant is saved and ethanol precipitated.

CE was used to confirm that the 5'-biotin-tails were removed from the reaction mixtures. The purity of the clicked constructs after this procedure are greater than 80%.

E. DNA Splint-Templated Poly(A) Tail Conjugation Using SPAAC

A DNA splint complementary to the 3'-end of the RNA and to the poly(A) tail is used to template the SPAAC reaction. RNA-poly(A) tail conjugates are synthesized by mixing 3'-azido RNA, 5'-BCN poly(A) tail, and splint in a molar ratio of 1:3:3 with final concentrations of 100 nM: 300 nM: 300 nM, respectively, in a 100 μL reaction containing 1 M NaCl. The RNA and DNA splint mixture is heated to 70° C. for 5 min, cooled at 1° C./min until reaching 25° C., and maintained at 25° C. overnight. Salts are removed by ultrafiltration (Amicon Ultra-0.5 centrifugal device 100K NMWL).

The DNA splint is removed by digestion with TURBO DNase (Ambion) in 50 μL reactions containing no more than 200 ng/μL of the reaction mixture, 1× reaction buffer, and TURBO DNase (2 U). These reactions are incubated for 30 min at 37° C. and terminated by the addition of 2 μL of 0.5 M EDTA. The buffer components are again removed by ultrafiltration. The RNA-poly(A) tail conjugates are purified from unmodified and unreacted 3'-azido RNA using oligo(T) Dynabeads (Ambion). The oligo(T) purification is performed as directed by the manufacturer's protocol, except the beads were washed and the RNA sample prepared in a high salt buffer containing 10 mM Tris-HCl, pH 7.4, 0.5 M NaCl, and 1 mM EDTA, the beads are washed after binding with a low salt buffer containing 10 mM Tris-HCl, pH 7.4, 0.1 M NaCl, and 1 mM EDTA, and the RNA-poly(A) tail conjugates are eluted in 10 mM Tris-HCl, pH 7.4, and 1 mM EDTA.

All steps in the click reaction and purification are analyzed by CE (Agilent 2100 Bioanalyzer).

F. Analysis of 3'-azido-ddATP Incorporation

Since 3'-azido RNA and RNA-tail conjugates are blocked on the 3'-end for poly(A) extension by poly(A) polymerase, only the unmodified RNA is a substrate for enzymatic tailing. The percentage of unmodified RNA, and therefore 3'-azido RNA, can be determined by calculating the % difference in the area of the peak corresponding to the unmodified RNA and 3'-azido RNA mixture after removal of the unmodified RNA and normalization to the area of the RNA-tail 1 conjugate peak.

In many cases, the click reaction goes to completion under the conditions described, allowing for a determination of azide incorporation simply by determining the % yield of the RNA-tail conjugate.

In 10 μL, the RNA mixture after the SPAAC reaction in 70% ethanol is treated with $E.\ coli$ poly(A) polymerase (NEB) (5 U) in a reaction containing the RNA reaction mixture (300-400 ng/μL), ATP (1 mM), and 1× reaction buffer (50 mM Tris-HCl, pH 7.9, 250 mM NaCl, 10 mM $MgCl_2$). Reactions containing no enzyme are also used for comparative controls. Controls where unmodified RNA is mixed with tail and treated with poly(A) polymerase may also be performed to ensure that all unmodified RNA would become tailed. Salts are removed from the reactions by ultrafiltration, and the reactions are analyzed by CE.

In the control reactions, all unmodified RNA is lengthened by treatment with PAP. In all these cases, after the SPAAC reaction and treatment with PAP, no RNA is left in the peak representing the putative mixture of unmodified RNA and 3'-azido RNA, indicating the click reactions went to completion and azide incorporation could be determined from % yield of the RNA-tail conjugate.

G. Total Area Under the Curve of mCherry Fluorescence

The mRNA (50 ng) generated are transfected using LIPO-FECTAMINE2000™ into HeLa cells. The cells are placed in the Incucyte kinetic imaging system (Essen Bioscience) where mCherry fluorescence was measured every 2 hrs for 142 hrs. Each transfection is performed in triplicate. The total area under the curve is integrated using GraphPad Prism.

H. Activity in HeLa Cells

The mRNA (25 ng) generated are transfected in triplicate using LIPOFECTAMINE2000™ into HeLa cells. After incubation overnight, the cells are lysed in GLO lysis buffer (Promega). NanoGlo substrate is added and luminescent signal is quantified using Synergy MicroPlate Reader (BioTek).

I. Expression in HeLa Cells

The mRNA (250 ng) generated are transfected in triplicate using LIPOFECTAMINE2000™ into HeLa cells. After incubation overnight, the supernatant is collected and used to measure the levels of protein (R&D Systems).

J. IFNβ Levels in Supernatant of BJ Fibroblasts Transfected with mRNA

The mRNA generated (500 ng) is transfected in triplicate using LIPOFECTAMINE2000™ into BJ fibroblasts. After incubation for 48 hrs, the supernatant is collected and used to measure the levels of human Interferon-β (R&D Systems).

Example 15. Generation of RNA Transcripts for Circularization

A. Transcription of RNA

In general, linear RNA molecules are transcribed using the methods known in the art and/or described in Example 1 and Example 3. The in vitro transcription reaction generates polynucleotides which may contain modified nucleotides. Such polynucleotides are uniformly modified or comprise a region or part of the polynucleotides of the invention which comprise modified nucleotides. The input nucleotide triphosphate (NTP) mix can be made in-house or assembled from commercial reagents using natural and non-natural NTPs.

B. Generation of RNA Transcript 5' End Functionality

For circularization, the 5' end and 3' end of the linear RNA (e.g., RNA transcript) is modified to provide suitable functionalities for circularization. At the 5' end, modified guanosine (e.g., 5'-amino guanosine, 5' azide guanosine, also known as 5' azido guanosine, and the like) (collectively "5'Gmod") or 5' guanosine monophosphate (GMP) is incorporated into the 5'-end of RNA using T7 RNA polymerase. In an IVT reaction, 5'-amino guanosine, 5' azide guanosine or GMP is incorporated at a specified (e.g., a 10:1) ratio to guanosine triphosphate (GTP). Incorporation of GMP facilitates, for example, enzymatic ligation of the ends of linear RNA using T4 RNA (or DNA) ligase. Incorporation of modified guanosine facilitates, for example, certain click chemistry ligations, etc.

In preliminary studies to determine how well GMP is incorporated into transcripts, mCherry RNA is transcribed with guanosine monophosphate (GMP) and a nucleotide triphosphate mix to form a 5'-monophosphate mCherry RNA. The ratio of GMP to GTP was 1:1, 4:1 or 10:1 and the 5'-monophosphate mCherry RNA was fully modified with 1-methylpseudouridine. A capping reaction was performed after the mCherry RNA was transcribed. For the mCherry RNA with GTP, CTP, ATP and modified UTP (N1-methylpseudouridine, 98% capping was achieved. For the mCherry transcribed with CTP, ATP, modified UTP and a 2:1 ratio of GMP:GTP, 16.71% capping observed indicating that >80% of molecules have a GMP at 5' end and will be a substrate for T4 ligase. For the mCherry transcribed with CTP, ATP, modified UTP and a 4:1 ratio of GMP:GTP, 11% capping observed indicating that up to 90% of molecules have a GMP at 5' end and will be a substrate for T4 ligase. For the mCherry transcribed with CTP, ATP, modified UTP and a 4:1 ratio of GMP:GTP, 5.5% capping indicating that up to 94% of the molecules have a GMP at 5' end and will be a substrate for T4 ligase.

An alternative method for generating 5'GMP transcription product is to treat the GTP, CTP, UTP, ATP transcription product, post purification with 5' pyrophosphohydrolase (NEB) to remove the gamma and beta phosphates from the 5' termini of the transcribed RNA, leaving a monophosphate at the 5' end. The reaction is carried out in 1× reaction buffer (50 mM NaCl, 10 mM Tris-HCl pH 7.9, 10 mM $MgCl_2$, 1 mM DTT) at 37° C. for 2 hours and then purified using MirVana™ or MegaClear™ clean-up kits.

C. Generation of RNA Transcript 3' End Functionality

To generate 3' end functionality, a 3'-azido-2',3'-dideoxyadenosine-5'-triphosphate (3'-azido-ddATP) was incorporated as follows. In 100 µL reactions, RNA transcript (0.2 µM), 3'-azido-ddATP (500 µM), murine RNase inhibitor (NEB) (1 U/µL), 1× reaction buffer (20 mM Tris-HCl, pH 7.0, 0.6 mM $MnCl_2$, 20 µM EDTA, 0.2 mM DTT, 100 µg/mL acetylated BSA, 10% glycerol), and yeast poly(A) polymerase (2400 U, Affymetrix) are incubated at 37° C. for 1 hr, followed by ethanol precipitation. The RNA is dissolved in 100 µL DEPC-treated $H_2O$ and further purified by gel filtration using an illustra NICK column or illustra MicroSpin G-25 column (GE Healthcare). The RNA is concentrated, if necessary, by ultrafiltration using an Amicon Ultra-0.5 centrifugal device (100K NMWL), quantified by UV absorbance, and analyzed by capillary electrophoresis (CE) (Agilent 2100 Bioanalyzer) to confirm the absence of degradation. The RNA obtained at this point is a mixture of unmodified and 3' azido RNA which cannot be distinguished by CE, and this mixture can be used without further purification in subsequent reactions.

Scheme 1. General synthesis of 3'-azido RNA by incorporation of 3'-azido ddATP onto the 3'-end of RNA using yeast poly(A) polymerase.

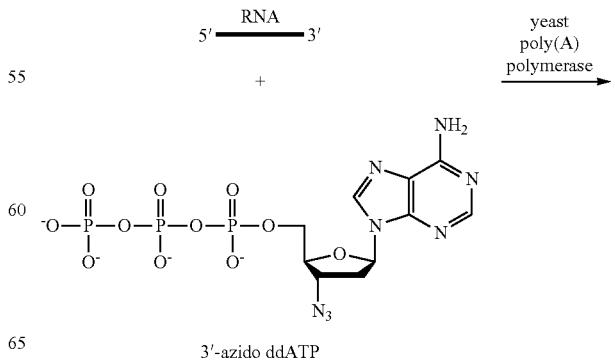

3'-azido ddATP

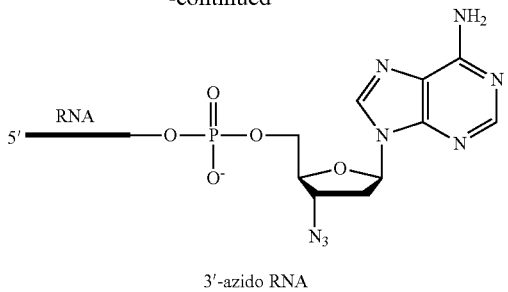

3'-azido RNA

To determine the extent of 3' azide incorporation, a diagnostic click reaction can be used to characterize transcript 3' ends. Briefly, an aliquot of RNA transcripts modified on the 3'-end with 3'-azido-ddATP are ligated to short (e.g., 80 nt) 5'-bicyclo[6.1.0]nonyne (BCN) poly(A) tails using strain-promoted azide-alkyne cycloaddition (SPAAC) to give RNA-poly(A) tail conjugates After the SPAAC reactions in 70% ethanol, a mixture of RNA species is produced which presumably includes unmodified RNA, unreacted 3'-azido RNA, and the desired RNA-tail conjugate. However, this only corresponds to two distinct peaks in the CE electropherogram, as unmodified RNA and 3'-azido RNA are indistinguishable. Since 3'-azido RNA and RNA-tail conjugates are blocked on the 3'-end for poly(A) extension by poly(A) polymerase, only the unmodified RNA is a substrate for enzymatic tailing. The percentage of unmodified RNA, and therefore 3'-azido RNA, can be determined by calculating the % difference in the area of the peak corresponding to the unmodified RNA and 3'-azido RNA mixture after removal of the unmodified RNA and normalization to the area of the RNA-tail conjugate peak. In many cases, the click reaction goes to completion under the conditions described, allowing for a determination of azide incorporation simply by determining the % yield of the RNA-tail conjugate.

In 10 µL, the RNA mixture after the SPAAC reaction in 70% ethanol was treated with E. coli poly(A) polymerase (NEB) (5 U) in a reaction containing the RNA reaction mixture (300-400 ng/µL), ATP (1 mM), and 1× reaction buffer (50 mM Tris-HCl, pH 7.9, 250 mM NaCl, 10 mM $MgCl_2$). Reactions containing no enzyme were also used for comparative controls. Controls where unmodified RNA was mixed with 5'-BCN tail and treated with poly(A) polymerase were also performed to ensure that all unmodified RNA would become tailed. Salts were removed from the reactions by ultrafiltration, and the reactions were analyzed by CE. In the control reactions, all unmodified RNA is lengthened by treatment with PAP. In all these cases, after the SPAAC reaction and treatment with PAP, no RNA is left in the peak representing the putative mixture of unmodified RNA and 3'-azido RNA, indicating the diagnostic click reactions went to completion and azide incorporation could be determined from % yield of the RNA-tail conjugate.

D. Formulation

Any of the linear polynucleotides or circular polynucleotides described herein may be formulated as described herein. Non-limiting examples and methods for formulating polynucleotides are described in International Patent Publication No. WO2013090648 and International Publication No. WO2014152211, the contents of each of which are herein incorporated by reference in its entirety.

Example 16. Circularization of Linear RNA

A. Circularization Using DNAzyme

In one method, linear RNA is transcribed with guanosine triphosphate (GTP) and a nucleotide triphosphate mix to form a 5'-triphosphate RNA. Ligation is performed using methods known in the art and/or described herein (Whitney et al., Journal of American Chemical Society (2005), 127. pp 13124-13125.). DNAzyme is designed to anneal to the 5' and 3' termini of the linear RNA DNAzyme 1 shown here (TTCTCTCTTATTTCCGTAGGGTTGGTAGACCAGGT-TGAGCCGGCGTCCTTGTTTATTT TCTAGAGC-CCGCCC; SEQ ID NO: 41). The two oligos are exposed to elevated temperatures (>65° C.) for a brief period of time to not exceed 5 minutes and allowed to cool to room temperature in the reaction buffer containing Hepes pH 7.5 and NaCl. Once the reaction has cooled zinc chloride is added to catalyze the reaction. Circularization of the RNA is shown using DNAzyme digest.

DNAzymes can have the sequences as described herein, for example, the sequences set forth as SEQ ID NO: 41. Such DNAzyme sequences have a structural composition as follows: nucleotides complementary to the 5' end of the molecule (e.g., RNA molecule to be circularized)—core of the DNAzyme—nucleotides complementary to the 3' end of the molecule (e.g., RNA molecule to be circularized).

In exemplary constructs, the DNAzyme comprises about 15 nucleotides complementary to the 5' end of the molecule (e.g., RNA molecule to be circularized) and about 15 nucleotides complementary to the 3' end of the molecule (e.g., RNA molecule to be circularized) flanking the core. In exemplary constructs, the DNAzyme comprises about 10 to about 20 or about 12 to about 25 nucleotides complementary to the 5' end of the molecule (e.g., RNA molecule to be circularized) and about 10 to about 20 or about 12 to about 25 nucleotides complementary to the 3' end of the molecule (e.g., RNA molecule to be circularized) flanking the core. In an exemplary DNAzyme (SEQ ID NO: 41), nucleotides 1-15 are complementary to the 5' end of the molecule, nucleotides 16-55 comprise the core, and nucleotides 56-72 are complementary to the 3' end of the molecule.

Further description of exemplary core sequences can be found, for example, in Whitney et al. (2005) 127, 13124-13125.

Generic DNAzyme sequences can be constructed that maintain the core but vary in the base composition of the complementary sequences. For the complementary flanking regions, length and base composition can vary as long as base pairing between the RNA of interest in maintained.

In another method, linear RNA with a 5' GMP terminus, installed either through transcription with a ratio of GMP: GTP or generated by treatment of GTP transcribed RNA with pyrophosphohydrolase to generate the GMP, is ligated using T4 DNA ligase or T4 RNA ligase facilitated with a splint to join the 3' and 5' termini. Splint ligation is performed using methods known in the art and/or described herein (Moore and Sharp. Science (1992) vol. 256 No. 5059. p. 992-997 and Stark et al., RNA. November 2006; 12(11): 2014-2019). As an example, Splint 1 (TTCTCTCTTATTTC-CCTTTTTCTAGAGCCCGCC; SEQ ID NO: 39) or Splint 2 (TCTTTTCTCTCTTATTTCCCTTTTTCTAGAGC-CCGCCCACTC; SEQ ID NO: 40) are annealed to the 5' and 3' termini of the linear RNA. Prior to annealing the RNA is denatured at elevate temperatures (>65° C.) for short periods of time (<10 mins) in water. Once the RNA has been denatured the splint is added in excess in a buffered solution, annealing is promoted by heating this mixture to elevated temperatures and allowing to cool to room temperature. After the annealed mixture reaches room temperature, the reaction is transferred to reaction buffer (50 mM Tris-HCl pH 7.5, 10 mM MgCl2, 1 mM ATP, 10 mM DTT, 10% PEG, 50 mM NaCl) and allowed to cool to room temperature. T4 DNA ligase is added to the cooled mixture and the reaction is allowed to proceed 4 hours- to overnight at 25° C. The ligation reaction is then purified using MIRVANA™ Total RNA Isolation protocol. The purified reaction is then treated with DNAse I to digest the DNA splint and again purified. Circularization of the RNA is shown using DNAzyme digest.

Splint sequences (e.g., for the T4 RNA Ligase, T4 DNA Ligase or chemical dumbbell approaches described herein) can have the sequences as described herein, for example, the sequences set forth as SEQ ID NOs: 39 and 40. Such splint sequences have a structural composition as follows: nucleotides complementary to the 5' most nucleotides of the RNA to be circularized—nucleotides complementary to the 3' most nucleotides of the RNA to be circularized In exemplary embodiments, the splint comprises nucleotides which are complementary to the about 15-25 5' most nucleotides of the RNA to be circularized and nucleotides complementary to the about 15-25 3' most nucleotides of the RNA to be circularized.

Splint 1 (SEQ ID NO: 39), for example, comprises 16 nucleotides complementary to the 16 5' most bases of the RNA to be circularized (nucleotides 1-16 of SEQ ID NO: 39) and 17 nucleotides complementary to the 17 3' most nucleotides of the RNA to be circularized (nucleotides 17-33 of SEQ ID NO: 39). Splint 2 (SEQ ID NO: 40), for example, comprises 20 nucleotides complementary to the 20 5' most nucleotides of the RNA to be circularized (nucleotides 1-20 of SEQ ID NO: 40) and 22 nucleotides complementary to the 22 3' most nucleotides of the RNA to be circularized (nucleotides 21-42 of SEQ ID NO: 40). Generic splints for any RNA/mRNA of interest can be designed in the same manner such. Base composition of splints for any RNA/mRNA will have various base compositions depending on the nucleotide sequence of the RNA/mRNA to be circularized.

In another method, linear RNA with a 5' GMP terminus, installed either through transcription with a ratio of GMP: GTP or generated by treatment of GTP transcribed RNA with pyrophosphohydrolase to generate the GMP, is ligated using T4 RNA ligase without the use of a splint. bug of RNA is denatured by heating to 65° C. for 10 minutes in a thermocycler. The reaction is allowed to cool at room temperature for 10 minutes. A ligation master mix of 1× T4 RNA ligation buffer (50 mM Tris-HCl, 10 mM MgCl$_2$, 1 mM DTT, pH 7.5), 50 μM ATP, 10% PEG8000, 20 units of RNAse inhibitor (NEB) is added. 1 μl (10 units) of T4 RNA Ligase (NEB) is added. The reaction is incubated at 25° C. for 2 hours or at 16° C. overnight. The reaction is terminated by adding 50 mM EDTA. Ligation is purified by adding 1.5 volumes of 100% ethanol to reaction and following the mirVana™ Total RNA Isolation protocol. Ligation product is eluted off of the column twice in 50 μl of 95° C. water. Circularization of the RNA is shown using PolyA polymerase extension (Example 18 A) DNAzyme digest (Example 18 B).

In any of the above methods, the resulting RNA may comprise a cap and a DNAzyme digestion assay (as described in detail below) can be used to verify ligation of transcript ends.

B. Circularization Using Chemical Dumbbell and Click

In one method, linear RNA is transcribed with Guanosine-5'-(6-aminohexyl)-Monophosphate. A PAP reaction (polyA polymerase reaction) is conducted on the 3' end of the RNA and then purified to add the azide at the 3' end as described above. The 5' amine is then functionalized with a chemical dumbbell through a NHS-conjugation reaction in a sodium bicarbonate solution with a pH of 7 or greater. The chemical dumbbell can be a dibenzocyclooctyne (DBCO)-Sulfo-NHS Ester or DBCO-N-hydroxysuccinimidyl ester. This reaction is allowed to proceed for at least 2 hours. After the NHS ester conjugation reaction is complete, the reaction mixture is buffer exchanged and any unreacted chemical dumbbell is removed. The bifunctionalized RNA is mix with a splint that is complementary to the 3' and 5' termini and will bring the cyclooctyne (5' end and azide (3' end) functional groups together. Splint 1 (TTCTCTCTTATTTCCCTTTTTCTA-GAGCCCGCC; SEQ ID NO: 39) or Splint 2 (TCTTTTCTCTCTTATTTCCCTTTTTCTAGAGCCCGC-CCACTC; SEQ ID NO: 40) are annealed in a concentrated solution with the RNA and the copper free click reaction is allowed to proceed. Circularization can be shown with DNAzyme digestion.

C. Circularization Using Oligo Dumbbell and Click

In one method, linear RNA is transcribed with 5' azido guanosine. A PAP reaction (polyA polymerase reaction) is conducted on the 3' end of the RNA to install the 3' azide as described above. The functionalized linear RNA is evaluated using UPLC®. The linear, functionalize RNA is circularized using the oligo DBCOdT ACACACACACACAC dTDBCO (SEQ ID NO: 43) and Splint 3 (TCTTTTCTCTCTTATTTC-CCAGTGTGTGTGTGTGTATTTTTCTAGAGCCCGC-CCACT C; SEQ ID NO: 44) or Splint 4 (TTCTCTTATTTC-CCAGTGTGTGTGTGTGTATTTTTCTAGAGCCGCC; SEQ ID NO: 45) using click methods.

Example 17. RNAs for Circularization

Linear RNA shown in Table 11 are circularized using the methods known in the art and/or are described herein. In Table 11, the first "G" in Construct 1 and Construct 2 is where a modified G such as GMP, 5'-azido guanosine, 5'-amino guanosine, may be located. For construct 1, the first 47 bolded nucleotides are the 5' UTR sequence, the bolded and italicized nucleotides in the 5'UTR are the binding site of the DNAzyme which may be used for a diagnostic cleavage assay, the underlined, bolded and italicized G in the 5'UTR is the actual site of cleavage. The bolded text in nucleotides 48-513 of construct 1 is a miR-122-5p sequence. Nucleotides 514-569, which are bolded, are the 3'UTR sequence and the italicized nucleotides are the binding site of the DNAzyme and the underlined, bolded and italicized G in the 3'UTR is the actual site of cleavage. At the end of construct 1, nucleotides 570-575 (UCUAGA sequence), is an XbaI site sequence transcribed from plasmid template, and the AAAA at the end of the sequence is to facilitate the PAP reaction. Construct 2 has the same features as construct 1 with an "NH" at the 5' end of the 5'UTR. The "NH" in construct No. 2 represents an amino-modified functionality at the 5' end of the RNA. Alternatively, an N3 can replace NH representing an azide-modified functionality at the 5' end of the RNA.

TABLE 11

Linear RNA for Circularization

| Construct No. | Sequence | SEQ ID NO |
|---|---|---|
| 1 | GGGAAAUAAGAGAGAAAAGAAGAGUAAGAAGAAAUAUAAGAGCCA<br>CC<br>GCACGAGUGUCCCGCGUGGUUGUGGUUGCUGCUGUCGCUCAAACACCAU<br>UGUCACACUCCAGCCUGUGCUGGGGGCACCACCCAGAUUGAUCUGCGAC<br>UCCAAACACCAUUGUCACACUCCAUCUUGAAGCCAAAGAAGCCGAAA<br>ACAUCACAACCGGAUGCAAACACCAUUGUCACACUCCAUGAGAACAU<br>UACUGUACCGGAUACAAAGGUCAAUUUCUACAAACACCAUUGUCACAC<br>UCCAAGGACAGCAGGCCGUCGAAGUGUGGCAGGGGCUCGCGCUCAAACA<br>CCAUUGUCACACUCCAGGGUCAGGCCCUCCUCGUCAACUCAUCACAGCC<br>GUGGGACAAACACCAUUGUCACACUCCAUAAAGCGGUGUCGGGGCUC<br>CGCAGCUUGACGACGUUGCUCAAACACCAUUGUCACACUCCACACGUU<br>UAGGAAGCUUUUUAGAGUGUACAGCAAUUUCCU<br>GAGAAAAGAAGAGUAAGAAGAAAUAGUGGUCUUUGAAUAAAGUCU<br>GAGUGGGCGGC<br>UCUAGAAAAA | 46 |
| 2 | NH-<br>GGGAAAUAAGAGAGAAAAGAAGAGUAAGAAGAAAUAUAAGAGCCA<br>CC<br>GCACGAGUGUCCCGCGUGGUUGUGGUUGCUGCUGUCGCUCAAACACCAU<br>UGUCACACUCCAGCCUGUGCUGGGGGCACCACCCAGAUUGAUCUGCGAC<br>UCCAAACACCAUUGUCACACUCCAUCUUGAAGCCAAAGAAGCCGAAA<br>ACAUCACAACCGGAUGCAAACACCAUUGUCACACUCCAUGAGAACAU<br>UACUGUACCGGAUACAAAGGUCAAUUUCUACAAACACCAUUGUCACAC<br>UCCAAGGACAGCAGGCCGUCGAAGUGUGGCAGGGGCUCGCGCUCAAACA<br>CCAUUGUCACACUCCAGGGUCAGGCCCUCCUCGUCAACUCAUCACAGCC<br>GUGGGACAAACACCAUUGUCACACUCCAUAAAGCGGUGUCGGGGCUC<br>CGCAGCUUGACGACGUUGCUCAAACACCAUUGUCACACUCCACACGUU<br>UAGGAAGCUUUUUAGAGUGUACAGCAAUUUCCU<br>GAGAAAAGAAGAGUAAGAAGAAAUAGUGGUCUUUGAAUAAAGUCU<br>GAGUGGGCGGC<br>UCUAGAAAAA | 47 |

In one method, the constructs in Table 11 are circularized using an enzymatic ligation, for example, T4 RNA ligase (or DNA ligase) ligation or DNAzyme ligation. As a non-limiting example, construct 1 is circularized using a GMP functionalized RNA and enzymatic ligation, for example T4 RNA ligation, or GTP-containing RNA and DNAzyme ligation (with a specialized DNAzyme).

In another method, the constructs in Table 11 are circularized using a click based chemical dumbbell 5'-3' linkage. As a non-limiting example, the 5' and 3' termini of construct 2 is circularized using a triazole linkage to connect the 5' and 3' termini of construct 2 (Cu-free click chemistry generates a triazole linkage).

In yet another method, the constructs in Table 11 are circularized using a click based oligonucleotide dumbbell that has been functionalized with double cyclooctyne. As a non-limiting example, the 5' and 3' termini of construct 1 is circularized using an oligonucleotide dumbbell ($NH_3UACACACACACACACUNH_3$; SEQ ID NO: 42) which has been functionalized with cyclooctyne groups on each end and generates triazole linkages with RNA transcripts containing 5' and 3' azides.

In yet another method, the constructs in Table 11 are circularized using a click based oligonucleotide dumbbell. As a non-limiting example, the 5' and 3' termini of construct 1 is circularized using an oligonucleotide dumbbell (DBCO dt ACACACACACAC DBCO dT; SEQ ID NO: 43) which has a triazole linkage on the 5' and 3' end.

Example 18. To Demonstrate Circularization

A. RNA T4 Ligation and PolyA Polymerase

Figure 9:
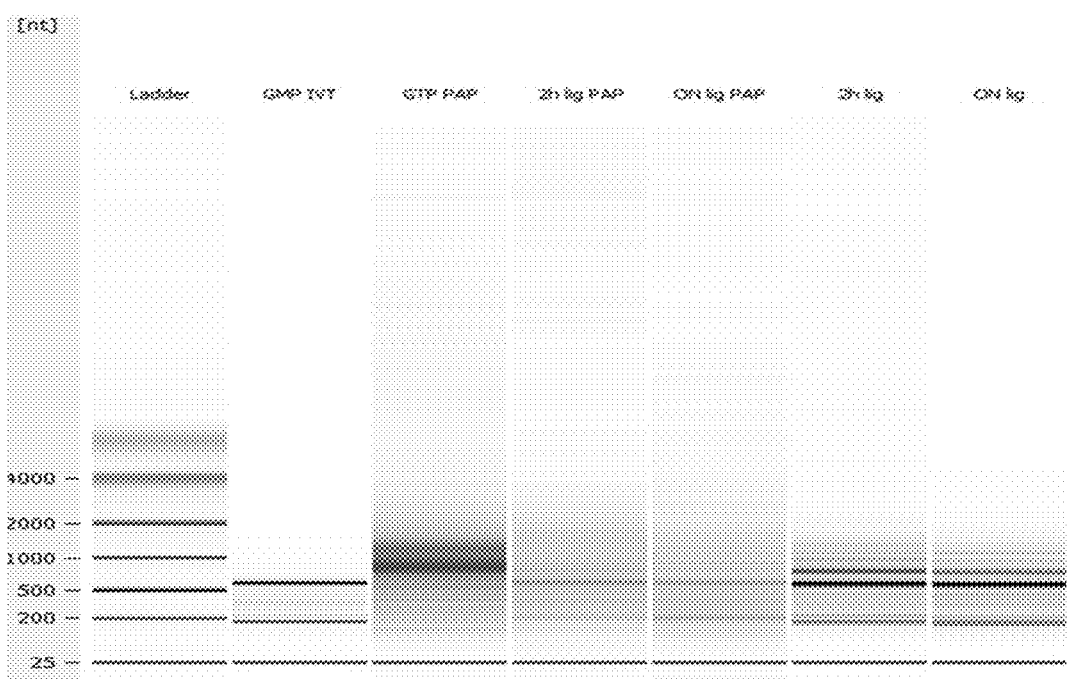
FIG. 9 is a gel profile showing RNA T4 ligation and PolyA polymerase treatment.

To determine the extent of circularization, reaction product can be subjected to diagnostic PAP reactions as follows. IVT generated material (linear RNA construct, Table 11) that has been transcribed with CTP, ATP, modified UTP and 10:1 GMP:GTP was ligated with T4 RNA ligase as described above). In FIG. 9, lane 1 (after the ladder lane) shows IVT generated material that has been transcribed with CTP, ATP, modified UTP and 10:1 GMP:GTP, lane 2 shows IVT generated material and exposed to polyA polymerase post-clean up, lane 3 shows 2 hour T4 RNA ligated material exposed to polyA polymerase, lane 4 shows overnight T4 RNA ligated material exposed to polyA polymerase, lane 5 shows 2 hour ligated material post clean up (w/o PAP) and lane 6 shows overnight ligated material post clean up (w/o PAP). The polyA polymerase will add a tail on the exposed 3' end of the molecule if the product is linear (shown in FIG. 9 by higher molecule band spearing) and if the molecule is circularized then the 3' end will not be exposed and the polyA polymerase reaction will not occur. Lanes 3 and 4 show no PAP reaction and lane 2 shows a complete PAP reaction.

B. DNAzyme Digestion 20 uL of the mRNA solution (~1 mg/mL) are mixed with 4 uL of each DNAzymes (50 uM solution in Water) and 8 uL of a 100 mM TRIS-Cl pH8, 10 mM EDTA, 200 mM NaCl solution. For the cleavage of the polyA-tail the DNAzyme X05714 (mouse 3'-UTR) or X05712 (human 3'-UTR) is used. For the cap-cleavage the DNAzyme X05709 is used. The mixture is heated for 10 min to 65° C. and subsequently cooled down to room temperature. This step is designed to anneal the DNAzyme with the mRNA. After the mixture is cooled to room temperature 2 uL of a 250 mM MgCl2 solution, 2 uL of Calf Intestinal Phosphatase (2 U/uL in storage buffer), 1 uL of CNPase (0.05 ug/ml in storage buffer) and 1 uL of an aqueous 500 mM DTT solution are added. (The components can be premixed to a master mix and then added in one step). The mixture is incubated for 4 hours at 37° C. The incubation reaction is stopped by addition of 5 uL of a 1M Triethylammonimacteate solution containing 250 mM EDTA. The results are analyzed by UHPLC.

Example 19. Effect of miR Sponge on Expression of Luciferase Encoded by Modified Messenger RNA Transcripts HeLa cells are seeded at a density of 17000 per well in 100 ul cell culture medium (DMEM+10% FBS). Primary hepatocytes are seeded at a density of 40,000 per well in 100 uL media (InvitroGRO CP+2.2% Torpedo Antibiotic mix) and maintained in HI media (InvitroGRO HI+2.2% Torpedo Antibiotic mix). The cells are transfected with 75 ng of Luciferase mRNA construct with no mir-142 or miR-122 complementary sites, Luciferase mRNA construct with miR-122 complementary site in the 3'UTR, or a Luciferase mRNA construct with miR-142 complementary site in the 3'UTR in the presence or absence of miR-sponge (at 75 ng or 150 ng), using Lipofectamine 2000. Luciferase mRNA transcripts are transcribed by T7 polymerase in-vitro transcription reactions using Adenosine Triphosphate, Guanosine Triphosphate, Cytosine Triphosphate and 1-Methyl-Pseudouridine Triphosphate nucleotides. Luciferase luminescence is measured 14 hours after transfection using a plate reader.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

We claim:
1. A single-stranded circular polynucleotide encoding a polypeptide, wherein said circular polynucleotide comprises a sequence of Formula II:

$$[A_n]\text{-}L^1\text{-}[B_o] \quad \text{Formula II}$$

wherein each A and each B independently comprises any nucleoside;
n and o are independently 15 to 1000; and
$L^1$ has the structure of Formula III:

Formula III

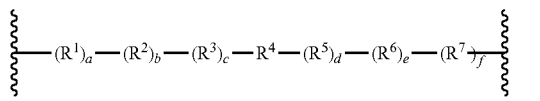

wherein a, b, c, d, e, and f are each, independently, 0 or 1;
each of $R^1$, $R^3$, $R^5$, and $R^7$, is, independently, selected from optionally substituted $C_1$-$C_6$ alkylene, optionally substituted $C_1$-$C_6$ heteroalkylene, O, S, and $NR^8$;
$R^2$ and $R^6$ are each, independently, selected from carbonyl, thiocarbonyl, sulfonyl, or phosphoryl;
$R^4$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_9$ heterocyclylene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^1)_a$—$(R^2)_b$—$(R^3)_c$ to $(R^5)_d$—$(R^6)_e$—$(R^7)_f$;
wherein if c, d, e, and f are 0, $R^4$ is not a bond; and
$R^8$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl;
wherein $L^1$ is attached to $[A_n]$ and $[B_o]$ at the sugar of one of said nucleosides; and
wherein said circular polynucleotide comprises a coding region, a 5' untranslated region (UTR) and a 3'UTR.

2. A single-stranded circular polynucleotide encoding a polypeptide, wherein said circular polynucleotide comprises a sequence of Formula II:

$$[A_n]\text{-}L^1\text{-}[B_o] \quad \text{Formula II}$$

wherein each A and B independently comprises any nucleoside;
n and o are, independently, 15 to 1000; and
$L^1$ is a bond or has the structure of Formula III:

Formula III

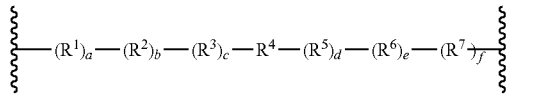

wherein a, b, c, d, e, and f are each, independently, 0 or 1;
each of $R^1$, $R^3$, $R^5$, and $R^7$, is, independently, selected from optionally substituted $C_1$-$C_6$ alkylene, optionally substituted $C_1$-$C_6$ heteroalkylene, O, S, and $NR^8$;
$R^2$ and $R^6$ are each, independently, selected from carbonyl, thiocarbonyl, sulfonyl, or phosphoryl;
$R^4$ is optionally substituted $C_1$-$C_{10}$ alkylene, optionally substituted $C_2$-$C_{10}$ alkenylene, optionally substituted $C_2$-$C_{10}$ alkynylene, optionally substituted $C_2$-$C_9$ heterocyclylene, optionally substituted $C_6$-$C_{12}$ arylene, optionally substituted $C_2$-$C_{100}$ polyethylene glycolene, or optionally substituted $C_1$-$C_{10}$ heteroalkylene, or a bond linking $(R^1)_a$—$(R^2)_b$—$(R^3)_c$ to $(R^5)_d$—$(R^6)_e$—$(R^7)_f$; and
$R^8$ is hydrogen, optionally substituted $C_1$-$C_4$ alkyl, optionally substituted $C_2$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl;
wherein $L^1$ is attached to $[A_n]$ and $[B_o]$ at the sugar of one of the nucleosides;
wherein at least one of $[A_n]$ and $[B_o]$ includes the structure of Formula IV or Formula XVIII:

Formula IV

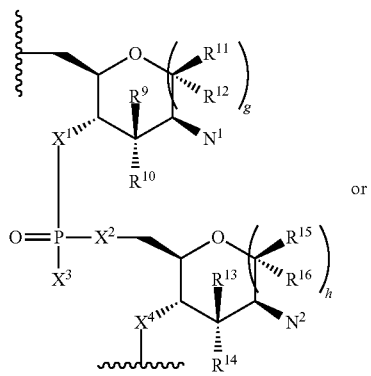

or

Formula XVIII

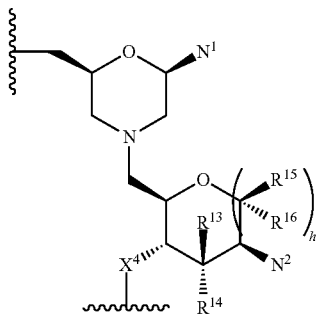

wherein each of $N^1$ and $N^2$ is independently a nucleobase;
each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;
each of g and h is, independently, 0 or 1;
each $X^1$ and $X^4$ is, independently, O, NH, or S; and
each $X^2$ is independently O, NH, or S; and
each $X^3$ is OH or SH, or a salt thereof;
wherein, for Formula IV, at least one of $X^1$, $X^2$, or $X^4$ is NH or S; and
wherein said circular polynucleotide comprises a coding region, a 5' untranslated region (UTR) and a 3' UTR.

3. The circular polynucleotide of claim 2, wherein $X^1$ is NH.

4. The circular polynucleotide of claim 2, wherein $X^4$ is NH.

5. The circular polynucleotide of claim 2, wherein $X^2$ is S.

6. The circular polynucleotide of claim 2, further comprising at least one 5' cap structure.

7. The circular polynucleotide of claim 6, further comprising a poly-A tail region.

8. The circular polynucleotide of claim 7, wherein the one of the coding region, the 5' UTR, the 3' UTR, the 5' cap structure, or the poly-A tail comprises $[A_n]$-L1-$[B_o]$.

9. The circular polynucleotide of claim 7, wherein one of the coding region, the 5' UTR, the 3' UTR, the 5' cap structure, or the poly-A tail comprises $[A_n]$ and another of the coding region, the 5' UTR, the 3' UTR, the 5' cap structure, or the poly-A tail comprises $[B_o]$.

10. The circular polynucleotide claim 2, wherein said 5' UTR comprises at least one Kozak sequence.

11. The circular polynucleotide of claim 2 wherein the circular polynucleotide comprises at least one modified nucleoside.

12. The circular polynucleotide of claim 11, wherein the modified nucleoside is 1 methyl-pseudouridine.

13. The circular polynucleotide of claim 2, wherein $R^4$ is optionally substituted $C_{2-9}$ heterocyclylene.

14. The circular polynucleotide of claim 13, wherein the optionally substituted $C_{2-9}$ heterocyclyl has the structure:

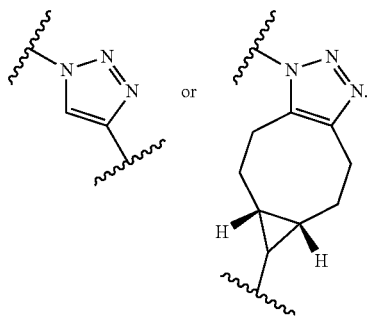 [SMILES: *c1cn(*)nn1 ; *C1[C@H]2CCc3nnn(*)c3CC[C@@H]12]

15. The circular polynucleotide of claim 2, wherein $L^1$ comprises the structure:

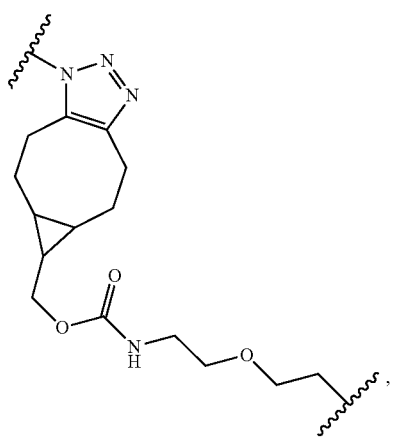

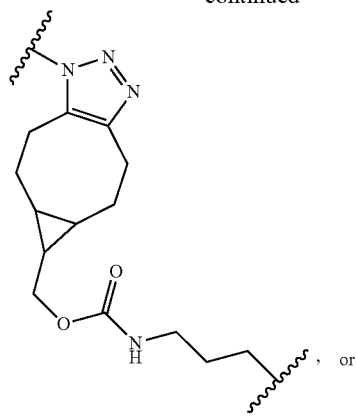

, or

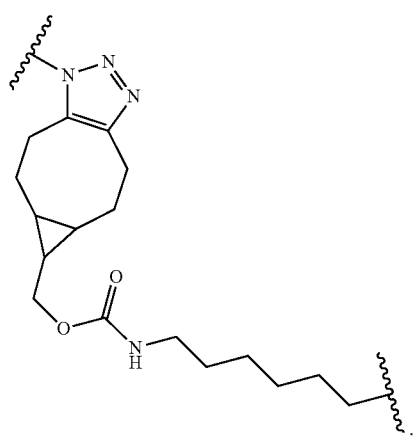

.

16. The circular polynucleotide of claim 2, wherein $L^1$ is attached to $[A_n]$ at the 3' or 4' position of the sugar of one of the nucleosides and to $[B_o]$ at the 5' or 6' position of the sugar of one of the nucleosides.

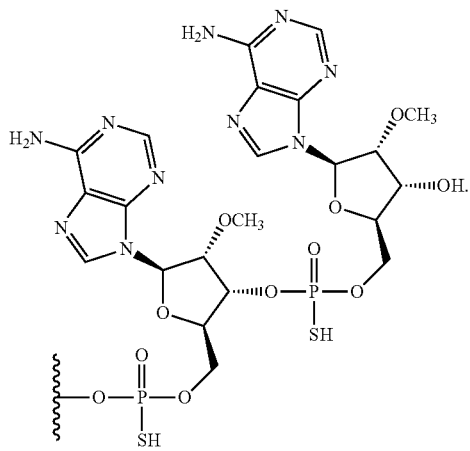 [SMILES: *OP(=O)(S)OC[C@H]1O[C@@H](n2cnc3c(N)ncnc32)[C@H](OC)[C@@H]1OP(=O)(S)OC[C@H]1O[C@@H](n2cnc3c(N)ncnc32)[C@H](OC)[C@@H]1O]

17. A method of producing a composition comprising the circular polynucleotide of claim 2 encoding a polypeptide, wherein the circular polynucleotide comprises the structure of Formula Va or Vb:

Formula Va

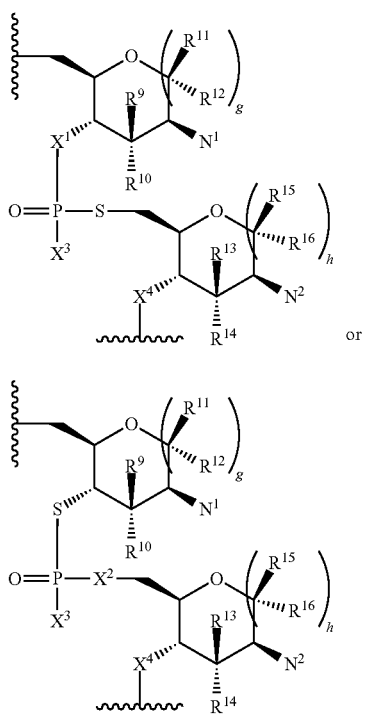

or

Formula Vb the method comprising reacting a compound having the structure of Formula VIa or VIb:

Formula VIa

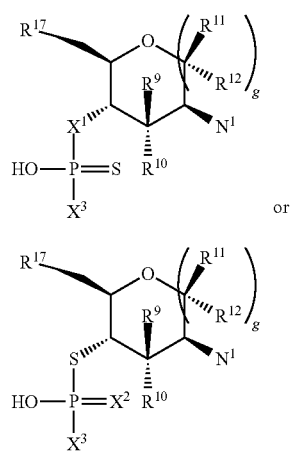

or

Formula VIb with a compound having the structure of Formula VII:

Formula VII

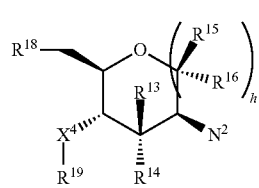

wherein each of N¹ and N² is independently a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, O, NH, or S; and each $X^2$ is O or S; and each $X^3$ is independently OH or SH, or a salt thereof;

each of $R^{17}$ and $R^{19}$ is, independently, a region of linked nucleosides; and $R^{18}$ is a halogen;

to produce a composition comprising a circular polynucleotide encoding a polypeptide, wherein the circular polynucleotide comprises the structure of Formula Va or Vb.

18. A method of producing a composition comprising the circular polynucleotide of claim 2 encoding a polypeptide, wherein the circular polynucleotide comprises the structure of Formula VIIIa or VIIIb:

Formula VIIIa

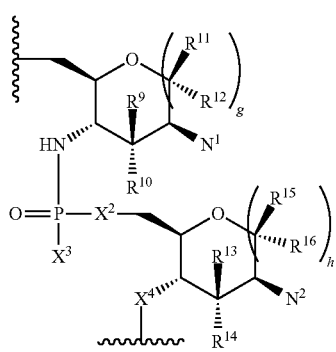

or

Formula VIIIb

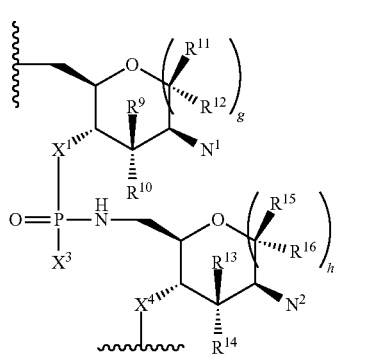

the method comprising reacting a compound having the structure of Formula IXa or IXb:

Formula IXa

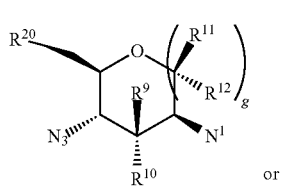

or

-continued

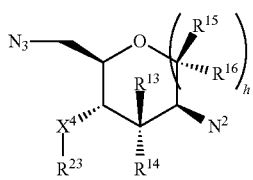
Formula IXb with a compound having the structure of Formula Xa or Xb:

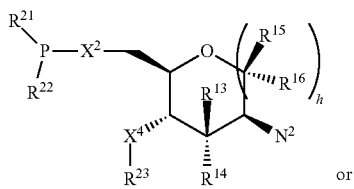
Formula Xa or

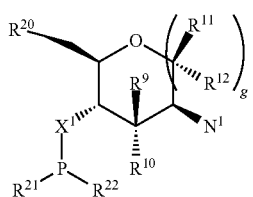
Formula Xb wherein each of $N^1$ and $N^2$ is independently a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^4$ is, independently, O, NH, or S; and each $X^1$ and $X^2$ is independently O or S;

each $X^3$ is independently OH, SH, or a salt thereof;

each of $R^{20}$ and $R^{23}$ is, independently, a region of linked nucleosides; and each of $R^{21}$ and $R^{22}$ is, independently, optionally substituted $C_1$-$C_6$ alkoxy;

to produce a composition comprising a circular polynucleotide encoding a polypeptide, wherein the circular polynucleotide comprises the structure of Formula VIIIa or VIIIb.

19. A method of producing a composition comprising the circular polynucleotide of claim 2 encoding a polypeptide, wherein the circular polynucleotide comprises the structure of Formula XIa, XIb, XIIa, or XIIb:

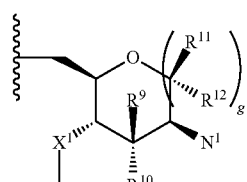
Formula XIa

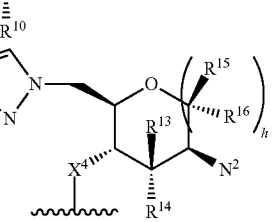

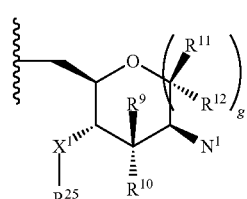
Formula XIb

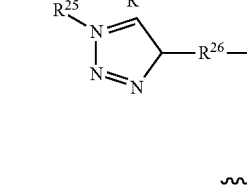

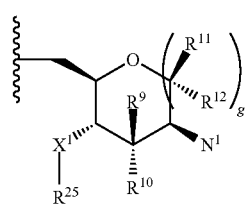
Formula XIIa

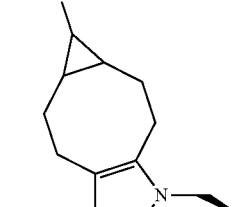

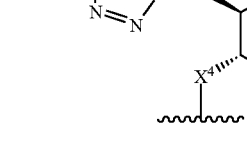
, or

-continued

Formula XIIb

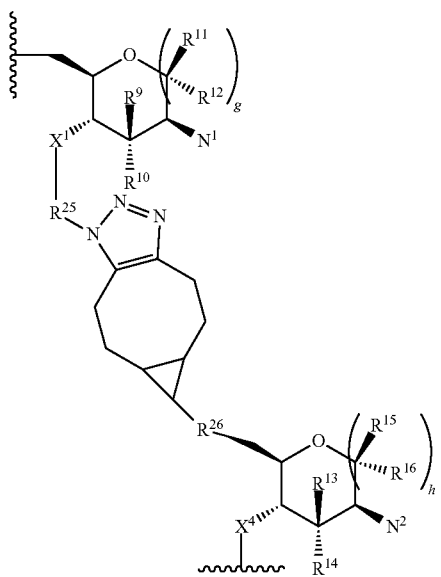

the method comprising reacting a compound having the structure of Formula XIIIa, XIIIb, XIVa, or XIVb:

Formula XIIIa

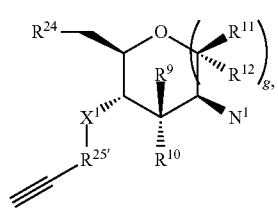

Formula XIIIb

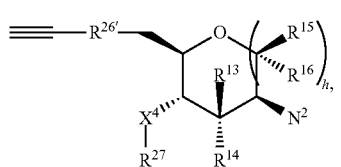

Formula XIVa

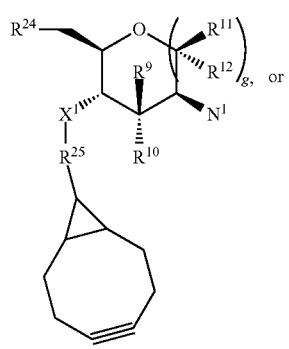

-continued

Formula XIVb

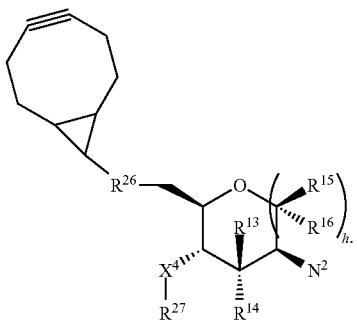

with a compound having the structure of Formula XVa or XVb:

Formula XVa

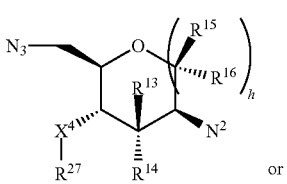

or

Formula XVb

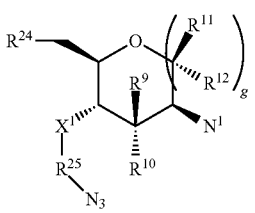

wherein each of $N^1$ and $N^2$ is independently a nucleobase;

each of $R^9$, $R^{10}$, $R^{11}$, $R^{12}$, $R^{13}$, $R^{14}$, $R^{15}$, and $R^{16}$ is, independently, H, halo, hydroxy, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

each of g and h is, independently, 0 or 1;

each $X^1$ and $X^4$ is, independently, absent, O, NH, or S; or a salt thereof;

each of $R^{24}$ and $R^{27}$ is, independently, a region of linked nucleosides; and each of $R^{25}$, $R^{25'}$, $R^{26}$, and $R^{26'}$ is, independently, absent, optionally substituted $C_1$-$C_6$ alkylene or optionally substituted $C_1$-$C_6$ heteroalkylene or $R^{25}$ or $R^{26'}$ and the alkynyl group together form optionally substituted cycloalkynyl;

to produce a composition comprising a circular polynucleotide encoding a polypeptide, wherein the circular polynucleotide comprises the structure of Formula XIa, XIb, XIIa, or XIIb.

20. A method of producing a composition comprising the circular polynucleotide of claim 2 encoding a polypeptide, wherein the circular polynucleotide has a sequence comprising Formula II:

$$[A_n]\text{-}L^1\text{-}[B_o]$$ Formula II the method comprising reacting a compound having the structure of Formula XVI:

$$[A_n]\text{-}(R^1)_a\text{---}(R^2)_b\text{---}(R^3)_c\text{---}N_3$$ Formula XVI with a compound having the structure of Formula XVII:

$$R^{27}\text{---}(R^5)_d\text{---}(R^6)_e\text{---}(R^7)_f\text{---}[B_o]$$ Formula XVII wherein each A and B is independently any nucleoside; n and o are, independently 15 to 1000; and $L^1$ has the structure of Formula III:

$$\{\text{---}(R^1)_a\text{---}(R^2)_b\text{---}(R^3)_c\text{---}R^4\text{---}(R^5)_d\text{---}(R^6)_e\text{---}(R^7)_f\text{---}\}$$ Formula III wherein a, b, c, d, e, and f are each, independently, 0 or 1;

each of $R^1$, $R^3$, $R^5$, and $R^7$, is, independently, selected from optionally substituted $C_1$-$C_6$ alkylene, optionally substituted $C_1$-$C_6$ heteroalkylene, O, S, and $NR^8$;

$R^2$ and $R^6$ are each, independently, selected from carbonyl, thiocarbonyl, sulfonyl, or phosphoryl;

$R^4$ is an optionally substituted triazolene; and $R^8$ is hydrogen, optionally substituted $C_1$-$C_4$ alkyl, optionally substituted $C_3$-$C_4$ alkenyl, optionally substituted $C_2$-$C_4$ alkynyl, optionally substituted $C_2$-$C_6$ heterocyclyl, optionally substituted $C_6$-$C_{12}$ aryl, or optionally substituted $C_1$-$C_7$ heteroalkyl; and $R^{27}$ is an optionally substituted $C_2$-$C_3$ alkynyl or an optionally substituted $C_8$-$C_{12}$ cycloalkynyl, wherein $L^1$ is attached to $[A_n]$ and $[B_o]$ at the sugar of one of the nucleosides;

to produce a composition comprising a circular polynucleotide encoding a polypeptide, wherein the circular polynucleotide has a sequence comprising Formula II.

21. A method of producing a composition comprising the circular polynucleotide claim 2 encoding a polypeptide, wherein the circular polynucleotide comprises the structure of Formula XVIII:

Formula XVIII the method comprising reacting a compound having the structure of Formula XIX:

Formula XIX with a compound having the structure of Formula XX:

Formula XX wherein each of $N^1$ and $N^2$ is, independently, a nucleobase;

each of $R^{13}$, $R^{14}$, $R^{15}$, and $R^{16}$ is, independently, H, halo, hydroxyl, thiol, optionally substituted $C_1$-$C_6$ alkyl, optionally substituted $C_1$-$C_6$ heteroalkyl, optionally substituted $C_2$-$C_6$ heteroalkenyl, optionally substituted $C_2$-$C_6$ heteroalkynyl, optionally substituted amino, azido, or optionally substituted $C_6$-$C_{10}$ aryl;

h is 0 or 1; and $X^4$ is O, NH, or S;

to produce a composition comprising a circular polynucleotide encoding a polypeptide, wherein the circular polynucleotide comprises the structure of Formula XVIII.

* * * * *